US012715894B2

(12) United States Patent
Hou et al.

(10) Patent No.: US 12,715,894 B2
(45) Date of Patent: Aug. 25, 2026

(54) TRIPTOLIDE CONJUGATES AND USES THEREOF

(71) Applicants: Reyoung Corporation, Gaithersburg, MD (US); Reyoung Drug Discovery Co., LTD., Shanghai (CN)

(72) Inventors: Frank Shujie Hou, Clarksburg, MD (US); Jian Xue, Shanghai (CN); Yushan Zhao, Potomic, MD (US); Dezu Miao, Yiyuan County (CN)

(73) Assignees: REYOUNG CORPORATION, Gaithersburg, MD (US); REYOUNG DRUG DISCOVERY CO., LTD., Shanghai (CN)

(*) Notice: Subject to any disclaimer, the term of this patent is extended or adjusted under 35 U.S.C. 154(b) by 691 days.

(21) Appl. No.: 18/022,110

(22) PCT Filed: Aug. 20, 2021

(86) PCT No.: PCT/US2021/046802

§ 371 (c)(1),
(2) Date: Feb. 17, 2023

(87) PCT Pub. No.: WO2022/040487

PCT Pub. Date: Feb. 24, 2022

(65) Prior Publication Data

US 2023/0303618 A1 Sep. 28, 2023

Related U.S. Application Data

(60) Provisional application No. 63/068,898, filed on Aug. 21, 2020.

(51) Int. Cl.

| | |
|---|---|
| ***C07J 73/00*** | (2006.01) |
| ***A61P 35/00*** | (2006.01) |
| *A61P 25/28* | (2006.01) |

(52) U.S. Cl.

CPC ............ *C07J 73/003* (2013.01); *A61P 35/00* (2018.01)

(58) Field of Classification Search

None

See application file for complete search history.

(56) References Cited

FOREIGN PATENT DOCUMENTS

| | | | | | |
|---|---|---|---|---|---|
| CN | 109464675 | A | | 3/2019 | |
| WO | WO-2009/082607 | A2 | | 7/2009 | |
| WO | WO-2012/016188 | A2 | | 2/2012 | |
| WO | WO-2017136739 | A1 | * | 8/2017 | ............ A61P 35/00 |
| WO | WO-2021178437 | A1 | * | 9/2021 | ............ C07H 15/26 |

OTHER PUBLICATIONS

Iyengar et al., Science & Society series on drugs and science, EMBO reports vol. 14 | No. 12 | 2013 (Year: 2013).*

STN, CAS 2121516-29-6 Registry, Entered STN: Aug. 28, 2017 (Year: 2017).*

Chen Anji et al: "Synthesis and characterization of pentaerythritol derived glycoconjugates as supramolecular gelators", Organic & Biomolecular Chemistry, vol. 17, No. 24, Jan. 1, 2019 (Jan. 1, 2019), pp. 6043-6056.

Qing-Li He et al: "Targeted Delivery and Sustained Antitumor Activity of Triptolide through Glucose Conjugation", Angewandte Chemie, vol. 128, No. 39, Aug. 30, 2016 (Aug. 30, 2016), pp. 12214-12218.

Xu F et al: "Design, synthesis, and biological evaluation of novel watersoluble triptolide derivatives: Antineoplastic activity against imatinibresistant CML cells bearing T3151 mutant Bcr-Abl", Bioorganic & Medicinal Chemistry, Elsevier, Amsterdam, NL, vol. 18, No. 5, Mar. 1, 2010 (Mar. 1, 2010), pp. 1806-1815.

Yu, et al., "Renal-targeting triptolide-glucosamine conjugate exhibits lower toxicity and superior efficacy in attenuation of ischemia/reperfusion renal injury in rats", Acta Pharmacologica Sinica, vol. 37, No. 11, Jul. 11, 2016 (Jul. 11, 2016), pp. 1467-1480.

Biesssen et al. "Cholesterol derivative of a new triantennary cluster galactoside directs low and high-density lipoproteins to the parenchymal liver cell" Biochem. J. vol. 382, pp. 283-289, dated Mar. 25, 1994 (7 pages).

He et al. "Targeted Delivery and Sustained Antitumor Activity of Triptolide through Glucose Conjugation" Angewandte Chemie, vol. 128 No. 39, pp. 12214-12218. Dated Aug. 30, 2016 (6 pages).

Kempen et al. "A Water-Soluble Cholesteryl-Containing Trisgalactoside: Synthesis, Properties, and Use in Directing-Lipid-Containing Particles to the Liver", Journal of Medicinal Chemistry, vol. 27 No. 10, pp. 1312-1316, dated Dec. 15, 1983. (8 pages).

Peter et al. "Synthesen von Galactose-Cluster-haltigen Steroid-Derivaten" Liebigs Ann. Chem. 1990 pp. 863-869, dated Mar. 23, 1990 (8 pages).

Rensen et al. "Design and Synthesis of Novel N-Acetylgalactosamine-Terminated Glycolipids for Targeting of Lipoproteins to the Hepatic Asialoglycoprotein Receptor" Journal of Medicinal Chemistry, No. 47, pp. 5798-5808, dated Oct. 6, 2004 (11 pages).

Rensen et al. "Determination of the Upper Size Limit for Uptake and Processing of Ligands by the Asialoglycoprotein Receptor on Hepatocytes in Vitro and in Vivo" The Journal of Biological Chemistry vol. 276 No. 40., p. 37577-37548, dated Oct. 5, 2001 (8 pages).

Sliedregt et al. "Design and Synthesis of Novel Amphiphilic Dendritic Galactosides for Selective Targeting of Liposomes to the Hepatic Asialoglycoprotein Receptor" Journal of Medicinal Chemistry, vol. 42, No. 4, pp. 609-618, dated 1999 (10 pages).

(Continued)

*Primary Examiner* — Kortney L. Klinkel
*Assistant Examiner* — Alison Azar Hastings
(74) *Attorney, Agent, or Firm* — Foley & Lardner LLP

(57) ABSTRACT

This disclosure provides triptolide-conjugates, methods of making such compounds, pharmaceutical compositions and medicaments comprising such compounds, as well methods of using such compounds in the treatment of conditions/diseases, such as those relating to cancer, immunomodulation and/or inflammation.

13 Claims, 4 Drawing Sheets

(56) References Cited

OTHER PUBLICATIONS

Van Berkel et al. "The Effect of a Water-soluble Tris-Galactoside-terminated Cholesterol Derivative on the Fate of Low Density Lipoproteins and Liposomes" The Journal of Biological Chemistry vol. 260 No. 5 pp. 2694-2699 dated Mar. 10, 1985.
Zhou et al. "Conjugating glucosamine to triptolide to enhance its protective effect against renal ischemiareperfusion injury and reduce its toxicity", Journal of Drug Targeting, vol. 22 No. 3 pp. 200-2010, dated Jan. 28, 2014 (12 pages).
EP Communication pursuant to Article 94(3) EPC on EP Appl. No. 21773180.1 dated Apr. 13, 2026 (4 pages).

* cited by examiner

TRIPTOLIDE CONJUGATES AND USES THEREOF

RELATED APPLICATIONS

This application claims the priority benefit of U.S. provisional application 63/068,898 filed Aug. 21, 2020, the entire contents of which are incorporated herein by reference.

BACKGROUND

Triptolide, a bioactive compound isolated from the plant of *Tripterygium wilfordii* Hook F, has been widely used in traditional medicine in China for treating diseases or disorders relating to immunomodulation and anti-inflammation. Triptolide has attracted attention from researches within the last decades due to its potential therapeutic application for immunosuppression, anti-inflammation, cancer treatment, and neuroprotection. [Ziaei S., Halaby R. *Immunosuppressive, anti-inflammatory and anti-cancer properties of triptolide: A mini review. Avicenna, J. Phytomed.* 2016, 6(2), 149-64; Yuan K., Li X., Lu Q. et al. *Application and mechanisms of triptolide in the treatment of inflammatory Diseases—a review. Front. Pharmacol.* 2019, 10, 1469; Noel P., Von Hoff D. D., Saluja A. K., et al. *Triptolide and its derivatives as cancer therapies. Trends in Pharmacol. Sci.* 2019, 40(5), 327-41; Zhang B., Song C., Feng B., Fan W. *Neuroprotection by triptolide against cerebral ischemia/reperfusion injury through the inhibition of NF-κB/PUMA signal in rats. Ther. Clin. Risk Manag.* 2106, 12, 817-824.]

However, there are several drawbacks associated with using triptolide that limits preclinical development and clinical applications, which include poor water solubility, narrow therapeutic index, and very short half-life time in vivo. [Patil S., Lis L. G., Schumacher R. J., et al. *Phosphonooxymethyl Prodrug of Triptolide: Synthesis, Physicochemical Characterization, and Efficacy in Human Colon Adenocarcinoma and Ovarian Cancer Xenografts. J Med. Chem.* 2015, 58, 9334-44; and Zhao Y., Miao D., Hou S., Huang Q. *Compositions of Schisandra Extracts and Methods Thereof.* WO2018/200143A2, 2018.] To address the poor aqueous solubility of triptolide, the following several prodrugs have been developed with the chemical moieties: carboxylic [Dai, D., Yuan, H., Musser, J. H. *Preparation of triptolide prodrugs having high aqueous solubility*. WO 02070472, 2002], amino acid [Musser, J. H. *Synthesis of triptolide prodrugs having high aqueous solubility for immunosuppressive and anti-inflammatory treatment*. WO 0012483, 2000], phosphonooxymethyl ester [Georg E. G., Patil S. P., Saluja A. K., Chugh R., Vickers S. M. *Triptolide Prodrugs*. WO2010129918A1, 2010], hydroquinone derived carboxylic acid ester [Peng Z., Liu M., Du Q., Yang Y., Song W., Chen Y. *Preparation of water-soluble triptolide derivatives useful as anticancer agents*. CN 110003304 A, 2019], polyethylene glycol [Lin Y., Huang X., Yan. D. *A water-soluble triptolide prodrug using polyethylene glycol as carrier, its preparation method and application*. CN 104629036 A, 2015] or carboxylated chitosan [Zeng H., Zhang Z., Yan M., et al. *Preparation method and application of triptolide-carboxylated chitosan conjugate in preparing drug for treating rheumatic arthritis, cancer and Alzheimer's disease*. CN 109464675 A, 2019.] These prodrugs have better aqueous solubility; however, their therapeutic indexes and/or half-life times are not significantly altered as compared with triptolide due to the prodrugs' lack of targeting and quick release of triptolide in blood. To increase the therapeutic targeting for cancer treatment, triptolide was recently conjugated with glucose, which would allow transport by tumors that overexpress glucose transporters [He Q., Minn L., Wang Q., et al. *Targeted Delivery and Sustained Antitumor Activity of Triptolide through Glucose Conjugation. Angew. Chem. Int. Ed. Engl.* 2016, 55(39), 12035-9; and Liu J., He Q., Minn L., Yu B., Wang Q. *Glucose Conjugate of Triptolide, Analogs and Uses Thereof.* WO2017/136739 A1, 2017] or a clinically available anti-EGFR monoclonal antibody to form an antibody drug conjugate [Zhang K., Ma Y., Guo Y., et al. Cetuximab-triptolide conjugate suppresses the growth of EGFR-overexpressing lung cancers through targeting RNA polymerase II. *Mol. Ther. Oncolytics* 2020, 18, 304-316.], both of which showed higher therapeutic index in preclinical models. Thus, there remains a need to develop triptolide conjugates that have good aqueous solubility, higher therapeutic index and/or longer half-life times.

This disclosure addresses this need by providing triptolide conjugates having good aqueous solubility, higher therapeutic index and/or longer half-life times; methods of making such compounds; pharmaceutical compositions and medicaments comprising such compounds; as well methods of using such compounds in the treatment of conditions/diseases.

SUMMARY

Provided in one aspect is a compound of Formula (I), or an enantiomer, an enantiomeric mixture, a diastereomer, a diastereomeric mixture, or a pharmaceutically acceptable salt thereof:

(I)

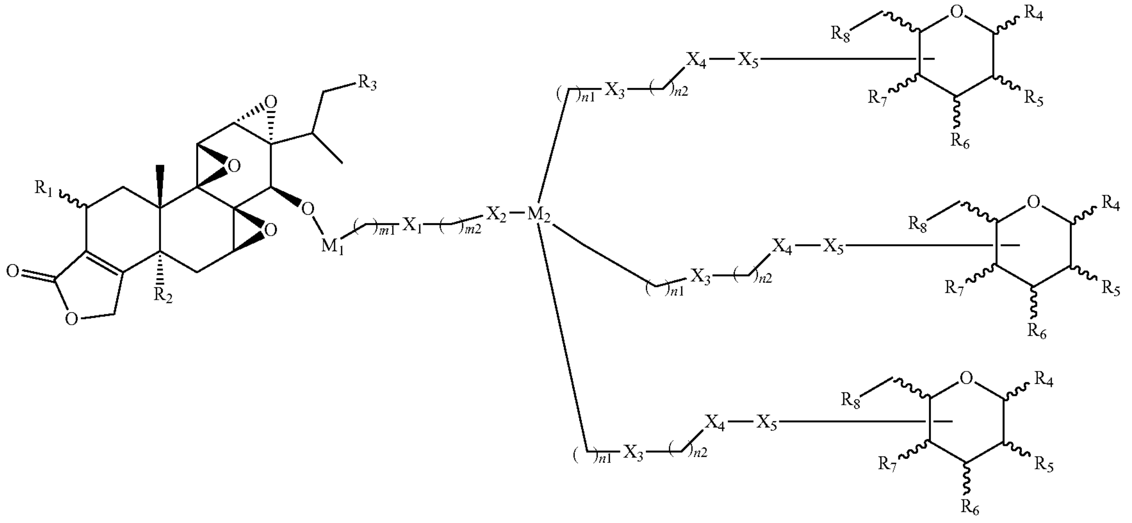

wherein $m_1$, $m_2$, $n_1$, $n_2$ are each independently 0-15;

$R_1$, $R_2$, and $R_3$ each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$M_1$ is selected from a bond, —C═O—, —$OPO_2$—, —$SO_2$—, —NH(CO)—, —(CO)NH—, —$CH_2OPO_2$—, —$CH_2OCO$—, and —$CH_2O$—;

$M_2$ is selected from C and Si;

$X_1$, $X_2$, $X_3$, $X_4$, and $X_5$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocyclene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocyclene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $X_5$ is attached to any one of $R_4$, $R_5$, $R_6$, $R_7$, and $R_8$; the remaining $R_4$, $R_5$, $R_6$, $R_7$, and $R_8$ that are not attached to $X_5$ are each independently H, OH, $O(CO)NH_2$, halo, $NH(C_1$-$C_{10}$ acyl), unsubstituted or substituted $O(C_1$-$C_{10}$ alkyl), unsubstituted or substituted $O(C_3$-$C_{10}$ cycloalkyl), unsubstituted or substituted $O(C_1$-$C_{10}$ acyl), unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide.

Provided in one aspect is a compound of Formula (II), or an enantiomer, an enantiomeric mixture, a diastereomer, a diastereomeric mixture, or a pharmaceutically acceptable salt thereof:

(II)

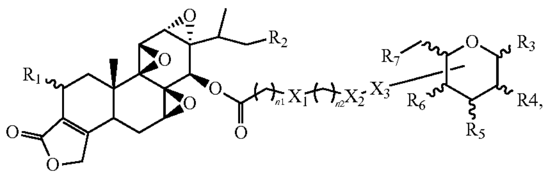

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, $L_2$-(CO)O, O(CO)-$L_2$, O, S, S—S, Se—Se—, NH, NR, NH(CO), (CO)NH, $L_2$-(CO)NH, (CO)NH-$L_2$, $L_2$-NH(CO), NH(CO)-$L_2$, NH(CO)-$L_2$-NH(CO), —NR-$L_2$-NR, $L_2$-O, O-$L_2$, $L_2$-NR, NR-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $X_3$ is attached to any one of $R_3$, $R_4$, $R_5$, $R_6$ and $R_7$ and the remaining $R_3$, $R_4$, $R_5$, $R_6$ and $R_7$ that are not attached to $X_3$ are each independently H, OH, $O(CO)NH_2$, halo, unsubstituted or substituted amino group, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide.

Provided in one aspect is a compound of Formula (III), or an enantiomer, an enantiomeric mixture, a diastereomer, a diastereomeric mixture, or a pharmaceutically acceptable salt thereof:

(III)

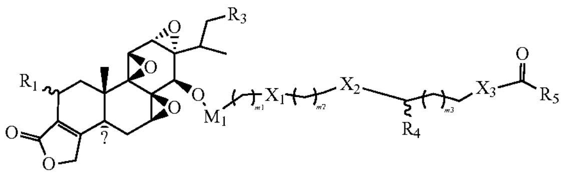

wherein $m_1$, $m_2$, and $m_3$ are each independently 0-15;

$M_1$ is selected from a bond, —CO—, —$OPO_2$—, —$SO_2$—, —$CH_2OPO_2$, —$CH_2OCO$—, and —$CH_2O$—;

$R_1$, $R_2$, and $R_3$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl;

$R_4$ is NHR', NHCOR', NHCOOR', CONHR', or COOR';

each R' is H, unsubstituted or substituted $C_1$-$C_{10}$ alkyl, unsubstituted or substituted $C_3$-$C_{10}$ cycloalkyl, unsubstituted or substituted $C_3$-$C_{10}$ cycloalkyl($C_1$-$C_{10}$ alkyl), unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, or unsubstituted or substituted $C_1$-$C_{10}$ heterocycyl($C_1$-$C_{10}$ alkyl); and $R_5$ is unsubstituted or substituted $C_1$-$C_{10}$ alkyl, unsubstituted or substituted $C_3$-$C_{10}$ cycloalkyl, unsubstituted or substituted aryl, unsubstituted or substituted heteroaryl, or unsubstituted or substituted $C_1$-$C_{10}$ heterocycyl.

Provided in one aspect is a compound of Formula (IV), or an enantiomer, an enantiomeric mixture, a diastereomer, a diastereomeric mixture, or a pharmaceutically acceptable salt thereof:

(IV)

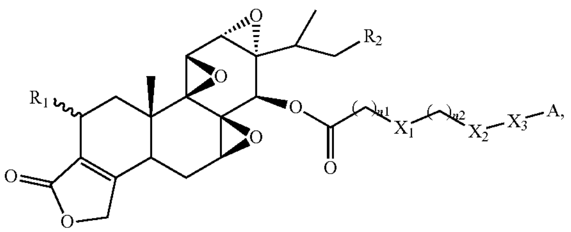

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, $L_2$-NH, NH-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and A is unsubstituted or substituted $C_3$-$C_{15}$ cycloalkyl, unsubstituted or substituted $C_1$-$C_{15}$ heterocyclyl, unsubstituted or substituted aryl, unsubstituted or substituted heteroaryl, or an oligosaccharide comprising 3-15 same or different monosaccharides.

Also provided herein in one aspect is pharmaceutical composition comprising any one of the compounds disclosed herein or an enantiomer, an enantiomeric mixture, a diastereomer, a diastereomeric mixture, or a pharmaceutically acceptable salt thereof, and at least one pharmaceutically acceptable excipient.

Also provided herein is a method for treating cancer in a subject in need thereof, comprising administering to the subject a therapeutically effective amount of any one of the compounds, or an enantiomer, an enantiomeric mixture, a diastereomer, a diastereomeric mixture, or a pharmaceutically acceptable salt thereof. In some embodiments, the cancer is heptacellular carcinoma (HCC), lung cancer, breast cancer, pancreatic cancer, biliary tract cancer, colorectal cancer, or glioblastoma.

Also provided herein is a method for treating a disease or disorder is related to immunomodulation and/or inflammation in a subject in need thereof, comprising administering to the subject a therapeutically effective amount of any one of the compounds, or an enantiomer, an enantiomeric mixture, a diastereomer, a diastereomeric mixture, or a pharmaceutically acceptable salt thereof. In some embodiments, the disease or disorder is related to inflammatory and/or autoimmune diseases. In some embodiments, the disease or disorder related to inflammation and/or inflammation is membranous nephropathy (MN), lupus nephritis, systemic lupus erythematosus, kidney transplantation, renal fibrosis, inflammatory bowel disease, Crohn's disease, intestinal fibrosis, liver fibrosis, asthma, acute lung injury, pulmonary arterial hypertension, pulmonary fibrosis, diabetic nephropathy, diabetic cardiomyopathy, rheumatoid arthritis, or psoriasis.

DETAILED DESCRIPTION

Figure 1:
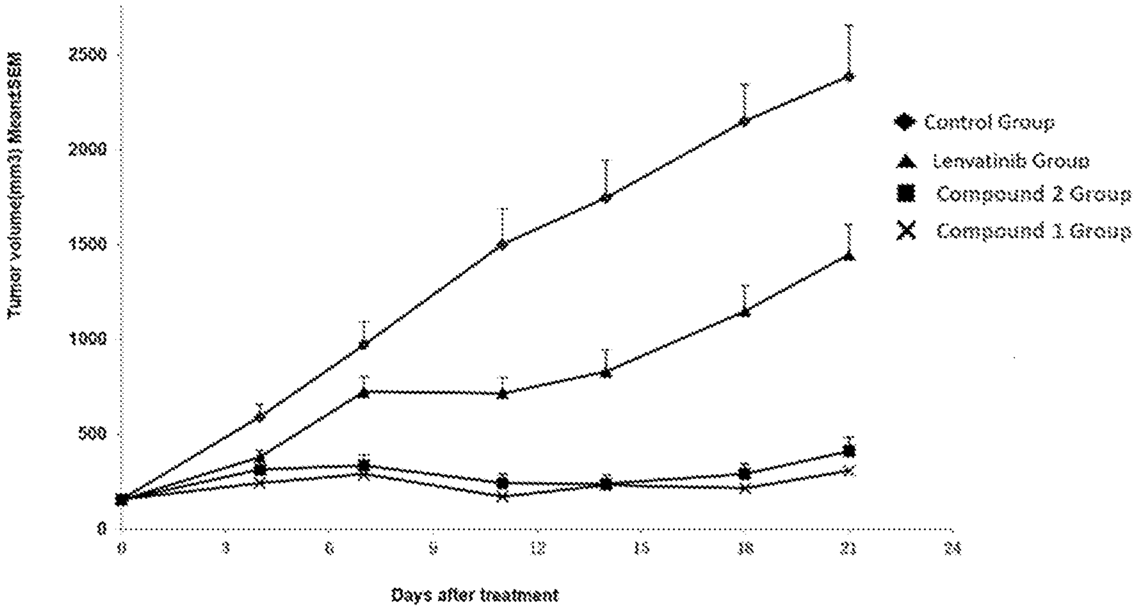
FIG. 1 shows the tumor growth-time of treatment curve for mice that were treated over a three week period: Group 1 (control group; i.p. 0.5% CMC-Na/carboxymethylcellulose sodium; once daily); Group 2 (Compound 1; 2.0 mg/kg, i.p.; once daily); Group 3 (Compound 2; 2.0 mg/kg, i.p.; once daily); and Group 4 (Lenvatinib; 5.0 mg/kg, oral; once daily).

This disclosure provides triptolide conjugates that may have any one of the following desirable properties for preclinical development and clinical applications, such as good aqueous solubility, higher therapeutic index, and/or longer half-life times. Also provided herein are methods of making such compounds, pharmaceutical compositions and medicaments comprising such compounds, as well methods of using such compounds in the treatment of conditions/diseases, such as those relating to cancer, immunomodulation and/or inflammation.

Compounds

Provided in one aspect is a compound of Formula (I), or an enantiomer, an enantiomeric mixture, a diastereomer, a diastereomeric mixture, or a pharmaceutically acceptable salt thereof:

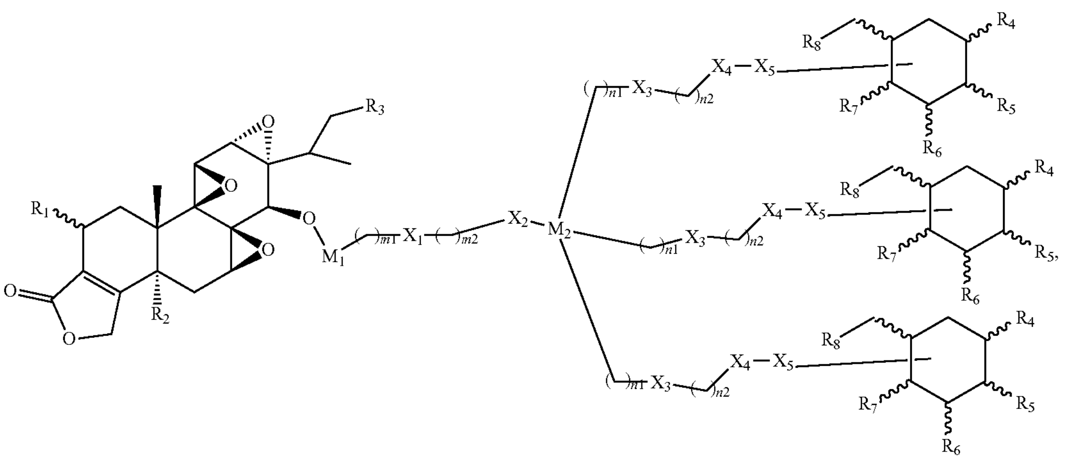

(I)

wherein $m_1$, $m_2$, $n_1$, $n_2$ are each independently 0-15;

$R_1$, $R_2$, and $R_3$ each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$M_1$ is selected from a bond, —C═O—, —$OPO_2$—, —$SO_2$—, —NH(CO)—, —(CO)NH—, —$CH_2OPO_2$—, —$CH_2OCO$—, and —$CH_2O$—;

$M_2$ is selected from C and Si;

$X_1$, $X_2$, $X_3$, $X_4$, and $X_5$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $X_5$ is attached to any one of $R_4$, $R_5$, $R_6$, $R_7$, and $R_8$; the remaining $R_4$, $R_5$, $R_6$, $R_7$, and $R_8$ that are not attached to $X_5$ are each independently H, OH, O(CO)$NH_2$, halo, NH($C_1$-$C_{10}$ acyl), unsubstituted or substituted O($C_1$-$C_{10}$ alkyl), unsubstituted or substituted O($C_3$-$C_{10}$ cycloalkyl), unsubstituted or substituted O($C_1$-$C_{10}$ acyl), unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide.

In some embodiments, $m_1$ is 0, 1, 2, 3, 4, 5, 6, 7, 8, 9, 10, 11, 12, 13, 14, or 15. In some embodiments, $m_1$ is 0. In some embodiments, $m_1$ is 1. In some embodiments, $m_1$ is 2. In some embodiments, $m_1$ is 3. In some embodiments, $m_1$ is 4. In some embodiments, $m_1$ is 5. In some embodiments, $m_1$ is 6. In some embodiments, $m_1$ is 7. In some embodiments, $m_1$ is 8. In some embodiments, $m_1$ is 9. In some embodiments, $m_1$ is 10. In some embodiments, $m_1$ is 11. In some embodiments, $m_1$ is 12. In some embodiments, $m_1$ is 13. In some embodiments, $m_1$ is 14. In some embodiments, $m_1$ is 15.

In some embodiments, $m_2$ is 0, 1, 2, 3, 4, 5, 6, 7, 8, 9, 10, 11, 12, 13, 14, or 15. In some embodiments, $m_2$ is 0. In some embodiments, $m_2$ is 1. In some embodiments, $m_2$ is 2. In some embodiments, $m_2$ is 3. In some embodiments, $m_2$ is 4. In some embodiments, $m_2$ is 5. In some embodiments, $m_2$ is 6. In some embodiments, $m_2$ is 7. In some embodiments, $m_2$ is 8. In some embodiments, $m_2$ is 9. In some embodiments, $m_2$ is 10. In some embodiments, $m_2$ is 11. In some embodiments, $m_2$ is 12. In some embodiments, $m_2$ is 13. In some embodiments, $m_2$ is 14. In some embodiments, $m_2$ is 15.

In some embodiments, $n_1$ is 0, 1, 2, 3, 4, 5, 6, 7, 8, 9, 10, 11, 12, 13, 14, or 15. In some embodiments, $n_1$ is 0. In some embodiments, $n_1$ is 1. In some embodiments, $n_1$ is 2. In some embodiments, $n_1$ is 3. In some embodiments, $n_1$ is 4. In some embodiments, $n_1$ is 5. In some embodiments, $n_1$ is 6. In some embodiments, $n_1$ is 7. In some embodiments, $n_1$ is 8. In some embodiments, $n_1$ is 9. In some embodiments, $n_1$ is 10. In some embodiments, $n_1$ is 11. In some embodiments, $n_1$ is 12. In some embodiments, $n_1$ is 13. In some embodiments, $n_1$ is 14. In some embodiments, $n_1$ is 15.

In some embodiments, $n_2$ is 0, 1, 2, 3, 4, 5, 6, 7, 8, 9, 10, 11, 12, 13, 14, or 15. In some embodiments, $n_2$ is 0. In some embodiments, $n_2$ is 1. In some embodiments, $n_2$ is 2. In some embodiments, $n_2$ is 3. In some embodiments, $n_2$ is 4. In some embodiments, $n_2$ is 5. In some embodiments, $n_2$ is 6. In some embodiments, $n_2$ is 7. In some embodiments, $n_2$ is 8. In some embodiments, $n_2$ is 9. In some embodiments, $n_2$ is 10. In some embodiments, $n_2$ is 11. In some embodiments, $n_2$ is 12. In some embodiments, $n_2$ is 13. In some embodiments, $n_2$ is 14. In some embodiments, $n_2$ is 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_1$ is OH. In some embodiments, $R_1$ is hydrogen. In some embodiments, $R_1$ is halo. In some embodiments, $R_1$ is unsubstituted or substituted $C_1$-$C_{10}$ alkyl. In some embodiments, $R_1$ is unsubstituted or substituted $C_3$-$C_{10}$ cycloalkyl. In some embodiments, $R_1$ is unsubstituted or substituted $C_1$-$C_{10}$ acyl. In some embodiments, $R_1$ is unsubstituted or substituted $C_1$-$C_{10}$ carboxyl ester. In some embodiments, $R_1$ is unsubstituted or substituted $C_1$-$C_{10}$ alkyl ketone. In some embodiments, $R_1$ unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_2$ is OH. In some embodiments, $R_2$ is hydrogen. In some embodiments, $R_2$ is halo. In some embodiments, $R_2$ is unsubstituted or substituted $C_1$-$C_{10}$ alkyl. In some embodiments, $R_2$ is unsubstituted or substituted $C_3$-$C_{10}$ cycloalkyl. In some embodiments, $R_2$ is unsubstituted or substituted $C_1$-$C_{10}$ acyl. In some embodiments, $R_2$ is unsubstituted or substituted $C_1$-$C_{10}$ carboxyl ester. In some embodiments, $R_2$ is unsubstituted or substituted $C_1$-$C_{10}$ alkyl ketone. In some embodiments, $R_2$ unsubstituted or substituted $C_1$-$C_{10}$ alkyl ether.

In some embodiments, $R_3$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_3$ is OH. In some embodiments, $R_3$ is hydrogen. In some embodiments, $R_3$ is halo. In some embodiments, $R_3$ is unsubstituted or substituted $C_1$-$C_{10}$ alkyl. In some embodiments, $R_3$ is unsubstituted or substituted $C_3$-$C_{10}$ cycloalkyl. In some embodiments, $R_3$ is unsubstituted or substituted $C_1$-$C_{10}$ acyl. In some embodiments, $R_3$ is unsubstituted or substituted $C_1$-$C_{10}$ carboxyl ester. In some embodiments, $R_3$ is unsubstituted or substituted $C_1$-$C_{10}$ alkyl ketone. In some embodiments, $R_3$ unsubstituted or substituted $C_1$-$C_{10}$ alkyl ether.

In some embodiments, $M_1$ is any one of the following: bond; —C═O—; —$OPO_2$—; —$SO_2$—; —NH(CO)— or —(CO)NH—; and —$CH_2OPO_2$—, —$CH_2OCO$—, or —$CH_2O$—. In some embodiments, $M_1$ is a bond. In some embodiments, $M_1$ is —C═O—. In some embodiments, $M_1$ is —$OPO_2$—. In some embodiments, $M_1$ is —$SO_2$—. In some embodiments, $M_1$ is NH(CO)— or —(CO)NH—. In some embodiments, $M_1$ is —$CH_2OPO_2$—, —$CH_2OCO$—, or —$CH_2O$—. In some embodiments, $M_1$ is —$CH_2OPO_2$. In some embodiments, $M_1$ is —$CH_2OCO$—. In some embodiments, $M_1$ is —$CH_2O$—.

In some embodiments, $M_2$ is any one of the following: C; and Si. In some embodiments, $M_2$ is C. In some embodiments, $M_2$ is Si.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), —NR-$L_2$-NR, $L_2$-O, or O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_1$ is a bond. In some embodiments, $X_1$ is C═O. In some embodiments, $X_1$ is (C═O)-$L_1$-(C═O). In some embodiments, $X_1$ is (C═O)-$L_1$. In some embodiments, $X_1$ is $L_1$-(C═O). In some embodiments, $X_1$ is O(CO). In some embodiments, $X_1$ is (CO)O. In some embodiments, $X_1$ is O. In some embodiments, $X_1$ is S. In some embodiments, $X_1$ is S—S. In some embodiments, $X_1$ is Se—Se—. In some embodiments, $X_1$ is NH. In some embodiments, $X_1$ is NR. In some embodiments, $X_1$ is NH(CO). In some embodiments, $X_1$ is (CO)NH. In some embodiments, $X_1$ is $L_2$-NH(CO). In some embodiments, $X_1$ is NH(CO)-$L_2$. In some embodiments, $X_1$ is $L_2$-(CO)NH. In some embodiments, $X_1$ is —(CO)NH-$L_2$. In some embodiments, $X_1$ is (CO)NH-$L_2$-NH(CO). In some embodiments, $X_1$ is —NR-$L_2$-NR. In some embodiments, $X_1$ is $L_2$-O. In some embodiments, $X_1$ is O-$L_2$. In some embodiments, $X_1$ is unsubstituted or substituted $C_1$-$C_{10}$ alkylene. In some embodiments, $X_1$ is unsubstituted or substituted $C_3$-$C_{10}$ cycloalkylene. In some embodiments, $X_1$ is unsubstituted or substituted arylene. In some embodiments, $X_1$ is unsubstituted or substituted heteroarylene. In some embodiments, $X_1$ is unsubstituted or substituted $C_1$-$C_{10}$ heterocycylene. In some embodiments, $X_1$ is unsubstituted or substituted peptide comprising 1, 2, 3, 4, 5, 6, 7, 8, 9, or 10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), —NR-$L_2$-NR, $L_2$-O, or O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_2$ is a bond. In some embodiments, $X_2$ is C═O. In some embodiments, $X_2$ is (C═O)-$L_1$-(C═O). In some embodiments, $X_2$ is (C═O)-$L_1$. In some embodiments, $X_2$ is $L_1$-(C═O). In some embodiments, $X_2$ is O(CO). In some embodiments, $X_2$ is (CO)O. In some embodiments, $X_2$ is O. In some embodiments, $X_2$ is S. In some embodiments, $X_2$ is S—S. In some embodiments, $X_2$ is Se—Se—. In some embodiments, $X_2$ is NH. In some embodiments, $X_2$ is NR. In some embodiments, $X_2$ is NH(CO). In some embodiments, $X_2$ is (CO)NH. In some embodiments, $X_2$ is $L_2$-NH(CO). In some embodiments, $X_2$ is NH(CO)-$L_2$. In some embodiments, $X_2$ is $L_2$-(CO)NH. In some embodiments, $X_2$ is —(CO)NH-$L_2$. In some embodiments, $X_2$ is (CO)NH-$L_2$-NH(CO). In some embodiments, $X_2$ is —NR-$L_2$-NR. In some embodiments, $X_2$ is $L_2$-O. In some embodiments, $X_2$ is O-$L_2$. In some embodiments, $X_2$ is unsubstituted or substituted $C_1$-$C_{10}$ alkylene. In some embodiments, $X_2$ is unsubstituted or substituted $C_3$-$C_{10}$ cycloalkylene. In some embodiments, $X_2$ is unsubstituted or substituted arylene. In some embodiments, $X_2$ is unsubstituted or substituted heteroarylene. In some embodiments, $X_2$ is unsubstituted or substituted $C_1$-$C_{10}$ heterocycylene. In some embodiments, $X_2$ is unsubstituted or substituted peptide comprising 1, 2, 3, 4, 5, 6, 7, 8, 9, or 10 natural amino acids.

In some embodiments, $X_3$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), —NR-$L_2$-NR, $L_2$-O, or O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_3$ is a bond. In some embodiments, $X_3$ is C═O. In some embodiments, $X_3$ is (C═O)-$L_1$-(C═O). In some embodiments, $X_3$ is (C═O)-$L_1$. In some embodiments, $X_3$ is $L_1$-(C═O). In some embodiments, $X_3$ is O(CO). In some embodiments, $X_3$ is (CO)O. In some embodiments, $X_3$ is O. In some embodiments, $X_3$ is S. In some embodiments, $X_3$ is S—S. In some embodiments, $X_3$ is Se—Se—. In some embodiments, $X_3$ is NH. In some embodiments, $X_3$ is NR. In some embodiments, $X_3$ is NH(CO). In some embodiments, $X_3$ is (CO)NH. In some embodiments, $X_3$ is $L_2$-NH(CO). In some embodiments, $X_3$ is NH(CO)-$L_2$. In some embodiments, $X_3$ is $L_2$-(CO)NH. In some embodiments, $X_3$ is —(CO)NH-$L_2$. In some embodiments, $X_3$ is (CO)NH-$L_2$-NH(CO). In some embodiments, $X_3$ is —NR-$L_2$-NR. In some embodiments, $X_3$ is $L_2$-O. In some embodiments, $X_3$ is O-$L_2$. In some embodiments, $X_3$ is unsubstituted or substituted $C_1$-$C_{10}$ alkylene. In some embodiments, $X_3$ is unsubstituted or substituted $C_3$-$C_{10}$ cycloalkylene. In some embodiments, $X_3$ is unsubstituted or substituted arylene. In some embodiments, $X_3$ is unsubstituted or substituted heteroarylene. In some embodiments, $X_3$ is unsubstituted or substituted $C_1$-$C_{10}$ heterocycylene. In some embodiments, $X_3$ is unsubstituted or substituted peptide comprising 1, 2, 3, 4, 5, 6, 7, 8, 9, or 10 natural amino acids.

In some embodiments, $X_4$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), —NR-$L_2$-NR, $L_2$-O, or O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_4$ is a bond. In some embodiments, $X_4$ is C═O. In some embodiments, $X_4$ is (C═O)-$L_1$-(C═O). In some embodiments, $X_4$ is (C═O)-$L_1$. In some embodiments, $X_4$ is $L_1$-(C═O). In some embodiments, $X_4$ is O(CO). In some embodiments, $X_4$ is (CO)O. In some embodiments, $X_5$ is O. In some embodiments, $X_4$ is S. In some embodiments, $X_4$ is S—S. In some embodiments, $X_4$ is Se—Se—. In some embodiments, $X_4$ is NH. In some embodiments, $X_4$ is NR. In some embodiments, $X_4$ is NH(CO). In some embodiments, $X_4$ is (CO)NH. In some embodiments, $X_4$ is $L_2$-NH(CO). In some embodiments, $X_4$ is NH(CO)-$L_2$. In some embodiments, $X_4$ is $L_2$-(CO)NH. In some embodiments, $X_4$ is —(CO)NH-$L_2$. In some embodiments, $X_4$ is (CO)NH-$L_2$-NH(CO). In some embodiments, $X_4$ is —NR-$L_2$-NR. In some embodiments, $X_4$ is $L_2$-O. In some embodiments, $X_4$ is O-$L_2$. In some embodiments, $X_4$ is unsubstituted or substituted $C_1$-$C_{10}$ alkylene. In some embodiments, $X_4$ is unsubstituted or substituted $C_3$-$C_{10}$ cycloalkylene. In some embodiments, $X_4$ is unsubstituted or substituted arylene. In some embodiments, $X_4$ is unsubstituted or substituted heteroarylene. In some embodiments, $X_4$ is unsubstituted or substituted $C_1$-$C_{10}$ heterocycylene. In some embodiments, $X_4$ is unsubstituted or substituted peptide comprising 1, 2, 3, 4, 5, 6, 7, 8, 9, or 10 natural amino acids.

In some embodiments, $X_5$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), —NR-$L_2$-NR, $L_2$-O, or O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_5$ is a bond. In some embodiments, $X_5$ is C═O. In some embodiments, $X_5$ is (C═O)-$L_1$-(C═O). In some embodiments, $X_5$ is (C═O)-$L_1$. In some embodiments, $X_5$ is $L_1$-(C═O). In some embodiments, $X_5$ is O(CO). In some embodiments, $X_5$ is (CO)O. In some embodiments, $X_5$ is O. In some embodiments, $X_5$ is S. In some embodiments, $X_5$ is S—S. In some embodiments, $X_5$ is Se—Se—. In some embodiments, $X_5$ is NH. In some embodiments, $X_5$ is NR. In some embodiments, $X_5$ is NH(CO). In some embodiments, $X_5$ is (CO)NH. In some embodiments, $X_5$ is $L_2$-NH(CO). In some embodiments, $X_5$ is NH(CO)-$L_2$. In some embodiments, $X_5$ is $L_2$-(CO)NH. In some embodiments, $X_5$ is —(CO)NH-$L_2$. In some embodiments, $X_5$ is (CO)NH-$L_2$-NH(CO). In some embodiments, $X_5$ is —NR-$L_2$-NR. In some embodiments, $X_5$ is $L_2$-O. In some embodiments, $X_5$ is O-$L_2$. In some embodiments, $X_5$ is unsubstituted or substituted $C_1$-$C_{10}$ alkylene. In some embodiments, $X_5$ is unsubstituted or substituted $C_3$-$C_{10}$ cycloalkylene. In some embodiments, $X_5$ is unsubstituted or substituted arylene. In some embodiments, $X_5$ is unsubstituted or substituted heteroarylene. In some embodiments, $X_5$ is unsubstituted or substituted $C_1$-$C_{10}$ heterocycylene. In some embodiments, $X_5$ is unsubstituted or substituted peptide comprising 1, 2, 3, 4, 5, 6, 7, 8, 9, or 10 natural amino acids.

In some embodiments, each $L_1$ is independently unsubstituted or substituted arylene; unsubstituted or substituted heteroarylene; or unsubstituted or substituted $C_1$-$C_{10}$ heterocycylene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocycylene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $X_5$ is attached to $R_4$; and $R_5$, $R_6$, $R_7$, and $R_8$ are each independently any one of the following: H; OH; O(CO)$NH_2$; halo; NH($C_1$-$C_{10}$ acyl); unsubstituted or substituted O($C_1$-$C_{10}$ alkyl); unsubstituted or substituted O($C_3$-$C_{10}$ cycloalkyl); unsubstituted or substituted O($C_1$-$C_{10}$ acyl); unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_5$ is attached to $R_4$; and $R_5$, $R_6$, $R_7$, and $R_8$ are each independently H. In some embodiments, $X_5$ is attached to $R_4$; and $R_5$, $R_6$, $R_7$, and $R_8$ are each independently OH. In some embodiments, $X_5$ is attached to $R_4$; and $R_5$, $R_6$, $R_7$, and $R_8$ are each independently O(CO)$NH_2$. In some embodiments, $X_5$ is attached to $R_4$; and $R_5$, $R_6$, $R_7$, and $R_8$ are each independently halo. In some embodiments, $X_5$ is attached to $R_4$; and $R_5$, $R_6$, $R_7$, and $R_8$ are each independently NH($C_1$-$C_{10}$ acyl). In some embodiments, $X_5$ is attached to $R_4$; and $R_5$, $R_6$, $R_7$, and $R_8$ are each independently unsubstituted or substituted O($C_1$-$C_{10}$ alkyl). In some embodiments, $X_5$ is attached to $R_4$; and $R_5$, $R_6$, $R_7$, and $R_8$ are each independently unsubstituted or substituted O($C_3$-$C_{10}$ cycloalkyl). In some embodiments, $X_5$ is attached to $R_4$; and $R_5$, $R_6$, $R_7$, and $R_8$ are each independently unsubstituted or substituted O($C_1$-$C_{10}$ acyl). In some embodiments, $X_5$ is attached to $R_4$; and $R_5$, $R_6$, $R_7$, and $R_8$ are each independently unsubstituted or substituted $C_1$-$C_{10}$ carboxyl ester. In some embodiments, $X_5$ is attached to $R_4$; and $R_5$, $R_6$, $R_7$, and $R_8$ are each independently unsubstituted or substituted $C_1$-$C_{10}$ alkyl ketone. In some embodiments, $X_5$ is attached to $R_4$; and $R_5$, $R_6$, $R_7$, and $R_8$ are each independently unsubstituted or substituted $C_1$-$C_{10}$ alkyl ether. In some embodiments, $X_5$ is attached to $R_4$; and $R_5$, $R_6$, $R_7$, and $R_8$ are each independently unsubstituted or substituted aryl. In some embodiments, $X_5$ is attached to $R_4$; and $R_5$, $R_6$, $R_7$, and $R_5$ are each independently unsubstituted or substituted heteroaryl. In some embodiments, $X_5$ is attached to $R_4$; and $R_5$, $R_6$, $R_7$, and $R_8$ are each independently unsubstituted or substituted $C_1$-$C_{10}$ heterocycyl. In some embodiments, $X_5$ is attached to $R_4$; and $R_5$, $R_6$, $R_7$, and $R_8$ are each independently unsubstituted or substituted peptide comprising 1, 2, 3, 4, 5, 6, 7, 8, 9, or 10 amino acids. In some embodiments, $X_5$ is attached to $R_4$; and $R_5$, $R_6$, $R_7$, and $R_8$ are each independently and forms a glycosidic bond with a natural monosaccharide.

In some embodiments, $X_5$ is attached to $R_6$; and $R_4$, $R_5$, $R_7$, and $R_8$ are each independently any one of the following: H; OH; O(CO)$NH_2$; halo; NH($C_1$-$C_{10}$ acyl); unsubstituted or substituted O($C_1$-$C_{10}$ alkyl); unsubstituted or substituted O($C_3$-$C_{10}$ cycloalkyl); unsubstituted or substituted O($C_1$-$C_{10}$ acyl); unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_5$ is attached to $R_6$; and $R_4$, $R_5$, $R_7$, and $R_8$ are each independently H. In some embodiments, $X_5$ is attached to $R_6$; and $R_4$, $R_5$, $R_7$, and $R_8$ are each independently OH. In some embodiments, $X_5$ is attached to $R_6$; and $R_4$, $R_5$, $R_7$, and $R_8$ are each independently O(CO)$NH_2$. In some embodiments, $X_5$ is attached to $R_6$; and $R_4$, $R_5$, $R_7$, and $R_8$ are each independently halo. In some embodiments, $X_5$ is attached to $R_6$; and $R_4$, $R_5$, $R_7$, and $R_8$ are each independently NH($C_1$-$C_{10}$ acyl). In some embodiments, $X_5$ is attached to $R_6$; and $R_4$, $R_5$, $R_7$, and $R_8$ are each independently unsubstituted or substituted O($C_1$-$C_{10}$ alkyl). In some embodiments, $X_5$ is attached to $R_6$; and $R_4$, $R_5$, $R_7$, and $R_8$ are each independently unsubstituted or substituted O($C_3$-$C_{10}$ cycloalkyl). In some embodiments, $X_5$ is attached to $R_6$; and $R_4$, $R_5$, $R_7$, and $R_8$ are each independently unsubstituted or substituted O($C_1$-$C_{10}$ acyl). In some embodiments, $X_5$ is attached to $R_6$; and $R_4$, $R_5$, $R_7$, and $R_8$ are each independently unsubstituted or substituted $C_1$-$C_{10}$ carboxyl ester. In some embodiments, $X_5$ is attached to $R_6$; and $R_4$, $R_5$, $R_7$, and $R_8$ are each independently unsubstituted or substituted $C_1$-$C_{10}$ alkyl ketone. In some embodiments, $X_5$ is attached to $R_6$; and $R_4$, $R_5$, $R_7$, and $R_8$ are each independently unsubstituted or substituted $C_1$-$C_{10}$ alkyl ether. In some embodiments, $X_5$ is attached to $R_6$; and $R_4$, $R_5$, $R_7$, and $R_8$ are each independently unsubstituted or substituted aryl. In some embodiments, $X_5$ is attached to $R_6$; and $R_4$, $R_5$, $R_7$, and $R_8$ are each independently unsubstituted or substituted heteroaryl. In some embodiments, $X_5$ is attached to $R_6$; and $R_4$, $R_5$, $R_7$, and $R_8$ are each independently unsubstituted or substituted $C_1$-$C_{10}$ heterocycyl. In some embodiments, $X_5$ is attached to $R_6$; and $R_4$, $R_5$, $R_7$, and $R_8$ are each independently unsubstituted or substituted peptide comprising 1, 2, 3, 4, 5, 6, 7, 8, 9, or 10 amino acids. In some embodiments, $X_5$ is attached to $R_6$; and $R_4$, $R_5$, $R_7$, and $R_8$ are each independently and forms a glycosidic bond with a natural monosaccharide.

In some embodiments, $X_5$ is attached to $R_7$; and $R_4$, $R_5$, $R_6$, and $R_8$ are each independently any one of the following: H; OH; O(CO)$NH_2$; halo; NH($C_1$-$C_{10}$ acyl); unsubstituted or substituted O($C_1$-$C_{10}$ alkyl); unsubstituted or substituted O($C_3$-$C_{10}$ cycloalkyl); unsubstituted or substituted O($C_1$-$C_{10}$ acyl); unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_5$ is attached to $R_7$; and $R_4$, $R_5$, $R_6$, and $R_8$ are each independently H. In some embodiments, $X_5$ is attached to $R_7$; and $R_4$, $R_5$, $R_6$, and $R_8$ are each independently OH. In some embodiments, $X_5$ is attached to $R_7$; and $R_4$, $R_5$, $R_6$, and $R_8$ are each independently O(CO)$NH_2$. In some embodiments, $X_5$ is attached to $R_7$; and $R_4$, $R_5$, $R_6$, and $R_8$ are each independently halo. In some embodiments, $X_5$ is attached to $R_7$; and $R_4$, $R_5$, $R_6$, and $R_8$ are each independently NH($C_1$-$C_{10}$ acyl). In some embodiments, $X_5$ is attached to $R_7$; and $R_4$, $R_5$, $R_6$, and $R_8$ are each independently unsubstituted or substituted O($C_1$-$C_{10}$ alkyl). In some embodiments, $X_5$ is attached to $R_7$; and $R_4$, $R_5$, $R_6$, and $R_8$ are each independently unsubstituted or substituted O($C_3$-$C_{10}$ cycloalkyl). In some embodiments, $X_5$ is attached to $R_7$; and $R_4$, $R_5$, $R_6$, and $R_8$ are each independently unsubstituted or substituted O($C_1$-$C_{10}$ acyl). In some embodiments, $X_5$ is attached to $R_7$; and $R_4$, $R_5$, $R_6$, and $R_8$ are each independently unsubstituted or substituted $C_1$-$C_{10}$ carboxyl ester. In some embodiments, $X_5$ is attached to $R_7$; and $R_4$, $R_5$, $R_6$, and $R_8$ are each independently unsubstituted or substituted $C_1$-$C_{10}$ alkyl ketone. In some embodiments, $X_5$ is attached to $R_7$; and $R_4$, $R_5$, $R_6$, and $R_8$ are each independently unsubstituted or substituted $C_1$-$C_{10}$ alkyl ether. In some embodiments, $X_5$ is attached to $R_7$; and $R_4$, $R_5$, $R_6$, and $R_8$ are each independently unsubstituted or substituted aryl. In some embodiments, $X_5$ is attached to $R_7$; and $R_4$, $R_5$, $R_6$, and $R_8$ are each independently unsubstituted or substituted heteroaryl. In some embodiments, $X_5$ is attached to $R_7$; and $R_4$, $R_5$, $R_6$, and $R_8$ are each independently unsubstituted or substituted $C_1$-$C_{10}$ heterocycyl. In some embodiments, $X_5$ is attached to $R_7$; and $R_4$, $R_5$, $R_6$, and $R_8$ are each independently unsubstituted or substituted peptide comprising 1, 2, 3, 4, 5, 6, 7, 8, 9, or 10 amino acids. In some embodiments, $X_5$ is attached to $R_7$; and $R_4$, $R_5$, $R_6$, and $R_8$ are each independently and forms a glycosidic bond with a natural monosaccharide.

In some embodiments, $X_5$ is attached to $R_8$; and $R_4$, $R_5$, $R_6$, and $R_7$ are each independently any one of the following: H; OH; $O(CO)NH_2$; halo; $NH(C_1$-$C_{10}$ acyl); unsubstituted or substituted $O(C_1$-$C_{10}$ alkyl); unsubstituted or substituted $O(C_3$-$C_{10}$ cycloalkyl); unsubstituted or substituted $O(C_1$-$C_{10}$ acyl); unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_5$ is attached to $R_8$; and $R_4$, $R_5$, $R_6$, and $R_7$ are each independently H. In some embodiments, $X_5$ is attached to $R_8$; and $R_4$, $R_5$, $R_6$, and $R_7$ are each independently OH. In some embodiments, $X_5$ is attached to $R_8$; and $R_4$, $R_5$, $R_6$, and $R_7$ are each independently O(CO) $NH_2$. In some embodiments, $X_5$ is attached to $R_8$; and $R_4$, $R_5$, $R_6$, and $R_7$ are each independently halo. In some embodiments, $X_5$ is attached to $R_8$; and $R_4$, $R_5$, $R_6$, and $R_7$ are each independently $NH(C_1$-$C_{10}$ acyl). In some embodiments, $X_5$ is attached to $R_8$; and $R_4$, $R_5$, $R_6$, and $R_7$ are each independently unsubstituted or substituted $O(C_1$-$C_{10}$ alkyl). In some embodiments, $X_5$ is attached to $R_8$; and $R_4$, $R_5$, $R_6$, and $R_7$ are each independently unsubstituted or substituted $O(C_3$-$C_{10}$ cycloalkyl). In some embodiments, $X_5$ is attached to $R_8$; and $R_4$, $R_5$, $R_6$, and $R_7$ are each independently unsubstituted or substituted $O(C_1$-$C_{10}$ acyl). In some embodiments, $X_5$ is attached to $R_8$; and $R_4$, $R_5$, $R_6$, and $R_7$ are each independently unsubstituted or substituted $C_1$-$C_{10}$ carboxyl ester. In some embodiments, $X_5$ is attached to $R_8$; and $R_4$, $R_5$, $R_6$, and $R_7$ are each independently unsubstituted or substituted $C_1$-$C_{10}$ alkyl ketone. In some embodiments, $X_5$ is attached to $R_8$; and $R_4$, $R_5$, $R_6$, and $R_7$ are each independently unsubstituted or substituted $C_1$-$C_{10}$ alkyl ether. In some embodiments, $X_5$ is attached to $R_8$; and $R_4$, $R_5$, $R_6$, and $R_7$ are each independently unsubstituted or substituted aryl. In some embodiments, $X_5$ is attached to $R_8$; and $R_4$, $R_5$, $R_6$, and $R_7$ are each independently unsubstituted or substituted heteroaryl. In some embodiments, $X_5$ is attached to $R_8$; and $R_4$, $R_5$, $R_6$, and $R_7$ are each independently unsubstituted or substituted $C_1$-$C_{10}$ heterocycyl. In some embodiments, $X_5$ is attached to $R_8$; and $R_4$, $R_5$, $R_6$, and $R_7$ are each independently unsubstituted or substituted peptide comprising 1, 2, 3, 4, 5, 6, 7, 8, 9, or 10 amino acids. In some embodiments, $X_5$ is attached to $R_8$; and $R_4$, $R_5$, $R_6$, and $R_7$ are each independently and forms a glycosidic bond with a natural monosaccharide.

In some embodiments of Formula I, $m_1$ and $m_2$ are each independently 0, 1, 2, 3, or 4. In some embodiments, $n_1$ and $n_2$ are each independently 0, 1, 2, 3, or 4. In some embodiments, $R_1$, $R_2$, and $R_3$ are each H. In some embodiments, $M_1$ is —C═O—, —NH(CO)—, or —(CO)NH—; and $M_2$ is C. In some embodiments, $X_1$ is a bond and $X_2$ is NH(CO) or (CO)NH. In some embodiments, $X_3$ is O; $X_4$ is (CO)NH-$L_2$-NH(CO); and $X_5$ is NH(CO)-$L_2$, $L_2$-(CO)NH, $L_2$-O, or O-$L_2$. In some embodiments, $X_5$ is attached to $R_4$; and $R_5$, $R_6$, $R_7$, and $R_8$ are each independently OH or $NH(C_1$-$C_{10}$ acyl). In some embodiments, $X_5$ is attached to $R_8$; and $R_4$, $R_6$, $R_7$, and $R_8$ are each independently OH or $NH(C_1$-$C_{10}$ acyl). In some embodiments, $X_5$ is attached to $R_8$; and $R_4$, $R_5$, $R_6$, and $R_7$ are each independently OH or $NH(C_1$-$C_{10}$ acyl).

Provided in one aspect is a compound of Formula (II), or an enantiomer, an enantiomeric mixture, a diastereomer, a diastereomeric mixture, or a pharmaceutically acceptable salt thereof:

(II)

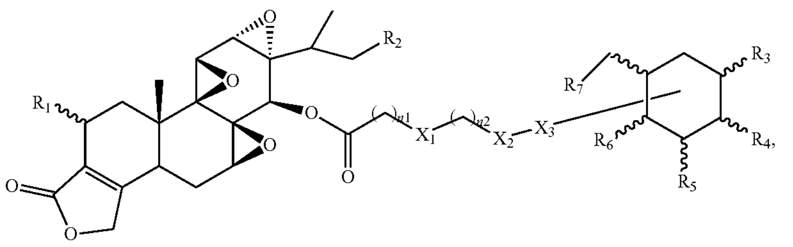

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether; $X_1$, $X_2$ and $X_3$ are each independently a bond, C═O, (C═O)-$L_1$-(C═O), (C═O)-$L_1$, $L_1$-(C═O), O(CO), (CO)O, $L_2$-(CO)O, O(CO)-$L_2$, O, S, S—S, Se—Se—, NH, NR, NH(CO), (CO)NH, $L_2$-(CO)NH, (CO)NH-$L_2$, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $X_3$ is attached to any one of $R_3$, $R_4$, $R_5$, $R_6$ and $R_7$ and the remaining $R_3$, $R_4$, $R_5$, $R_6$ and $R_7$ that are not attached to $X_3$ are each independently H, OH, $O(CO)NH_2$, halo, unsubstituted or substituted amino group, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide.

In some embodiments, $n_1$ is 0, 1, 2, 3, 4, 5, 6, 7, 8, 9, 10, 11, 12, 13, 14, or 15. In some embodiments, $n_1$ is 0. In some embodiments, $n_1$ is 1. In some embodiments, $n_1$ is 2. In some embodiments, $n_1$ is 3. In some embodiments, $n_1$ is 4. In some embodiments, $n_1$ is 5. In some embodiments, $n_1$ is 6. In some embodiments, $n_1$ is 7. In some embodiments, $n_1$ is 8. In some embodiments, $n_1$ is 9. In some embodiments, $n_1$ is 10. In some embodiments, $n_1$ is 11. In some embodiments, $n_1$ is 12. In some embodiments, $n_1$ is 13. In some embodiments, $n_1$ is 14. In some embodiments, $n_1$ is 15.

In some embodiments, $n_2$ is 0, 1, 2, 3, 4, 5, 6, 7, 8, 9, 10, 11, 12, 13, 14, or 15. In some embodiments, $n_2$ is 0. In some embodiments, $n_2$ is 1. In some embodiments, $n_2$ is 2. In some embodiments, $n_2$ is 3. In some embodiments, $n_2$ is 4. In some embodiments, $n_2$ is 5. In some embodiments, $n_2$ is 6. In some embodiments, $n_2$ is 7. In some embodiments, $n_2$ is 8. In some embodiments, $n_2$ is 9. In some embodiments, $n_2$ is 10. In some embodiments, $n_2$ is 11. In some embodiments, $n_2$ is 12. In some embodiments, $n_2$ is 13. In some embodiments, $n_2$ is 14. In some embodiments, $n_2$ is 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_1$ is OH. In some embodiments, $R_1$ is hydrogen. In some embodiments, $R_1$ is halo. In some embodiments, $R_1$ is unsubstituted or substituted $C_1$-$C_{10}$ alkyl. In some embodiments, $R_1$ is unsubstituted or substituted $C_3$-$C_{10}$ cycloalkyl. In some embodiments, $R_1$ is unsubstituted or substituted $C_1$-$C_{10}$ acyl. In some embodiments, $R_1$ is unsubstituted or substituted $C_1$-$C_{10}$ carboxyl ester. In some embodiments, $R_1$ is unsubstituted or substituted $C_1$-$C_{10}$ alkyl ketone. In some embodiments, $R_1$ unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_2$ is OH. In some embodiments, $R_2$ is hydrogen. In some embodiments, $R_2$ is halo. In some embodiments, $R_2$ is unsubstituted or substituted $C_1$-$C_{10}$ alkyl. In some embodiments, $R_2$ is unsubstituted or substituted $C_3$-$C_{10}$ cycloalkyl. In some embodiments, $R_2$ is unsubstituted or substituted $C_1$-$C_{10}$ acyl. In some embodiments, $R_2$ is unsubstituted or substituted $C_1$-$C_{10}$ carboxyl ester. In some embodiments, $R_2$ is unsubstituted or substituted $C_1$-$C_{10}$ alkyl ketone. In some embodiments, $R_2$ unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), (CO)O, $L_2$-(CO)O, or O(CO)-$L_2$; O, S, S—S, or Se—Se—; NH, NR, NH(CO), (CO)NH, $L_2$-(CO)NH, (CO)NH-$L_2$, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_1$ is a bond. In some embodiments, $X_1$ is C═O. In some embodiments, $X_1$ is (C═O)-$L_1$-(C═O). In some embodiments, $X_1$ is (C═O)-$L_1$. In some embodiments, $X_1$ is $L_1$-(C═O). In some embodiments, $X_1$ is O(CO). In some embodiments, $X_1$ is (CO)O. In some embodiments, $X_1$ is $L_2$-(CO)O. In some embodiments, $X_1$ is O(CO)-$L_2$. In some embodiments, $X_1$ is O. In some embodiments, $X_1$ is S. In some embodiments, $X_1$ is S—S. In some embodiments, $X_1$ is Se—Se—. In some embodiments, $X_1$ is NH. In some embodiments, $X_1$ is NR. In some embodiments, $X_1$ is NH(CO). In some embodiments, $X_1$ is (CO)NH. In some embodiments, $X_1$ is $L_2$-(CO)NH. In some embodiments, $X_1$ is (CO)NH-$L_2$. In some embodiments, $X_1$ is $L_2$-NH(CO). In some embodiments, $X_1$ is NH(CO)-$L_2$. In some embodiments, $X_1$ is —NR-$L_2$-NR. In some embodiments, $X_1$ is $L_2$-O. In some embodiments, $X_1$ is O-$L_2$. In some embodiments, $X_1$ is unsubstituted or substituted $C_1$-$C_{10}$ alkylene. In some embodiments, $X_1$ is unsubstituted or substituted $C_3$-$C_{10}$ cycloalkylene. In some embodiments, $X_1$ is unsubstituted or substituted arylene. In some embodiments, $X_1$ is unsubstituted or substituted heteroarylene. In some embodiments, $X_1$ is unsubstituted or substituted $C_1$-$C_{10}$ heterocycylene. In some embodiments, $X_1$ is unsubstituted or substituted peptide comprising 1, 2, 3, 4, 5, 6, 7, 8, 9, or 10 natural amino acids.

In some embodiments, $X_2$ is any one of the following: bond; C═O, (C═O)-$L_1$-(C═O), (C═O)-$L_1$, $L_1$-(C═O), O(CO), (CO)O, $L_2$-(CO)O, or O(CO)-$L_2$; O, S, S—S, or Se—Se—; NH, NR, NH(CO), (CO)NH, $L_2$-(CO)NH, (CO)NH-$L_2$, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_2$ is a bond. In some embodiments, $X_2$ is C═O. In some embodiments, $X_2$ is (C═O)-$L_1$-(C═O). In some embodiments, $X_2$ is (C═O)-$L_1$. In some embodiments, $X_2$ is $L_1$-(C═O). In some embodiments, $X_2$ is O(CO). In some embodiments, $X_2$ is (CO)O. In some embodiments, $X_2$ is $L_2$-(CO)O. In some embodiments, $X_2$ is O(CO)-$L_2$. In some embodiments, $X_2$ is O. In some embodiments, $X_2$ is S. In some embodiments, $X_2$ is S—S. In some embodiments, $X_2$ is Se—Se—. In some embodiments, $X_2$ is NH. In some embodiments, $X_2$ is NR. In some embodiments, $X_2$ is NH(CO). In some embodiments, $X_2$ is (CO)NH. In some embodiments, $X_2$ is $L_2$-(CO)NH. In some embodiments, $X_2$ is (CO)NH-$L_2$. In some embodiments, $X_2$ is $L_2$-NH(CO). In some embodiments, $X_2$ is $NH(CO)-L_2$. In some embodiments, $X_2$ is —NR-$L_2$-NR. In some embodiments, $X_2$ is $L_2$-O. In some embodiments, $X_2$ is O-$L_2$. In some embodiments, $X_2$ is unsubstituted or substituted $C_1$-$C_{10}$ alkylene. In some embodiments, $X_2$ is unsubstituted or substituted $C_3$-$C_{10}$ cycloalkylene. In some embodiments, $X_2$ is unsubstituted or substituted arylene. In some embodiments, $X_2$ is unsubstituted or substituted heteroarylene. In some embodiments, $X_2$ is unsubstituted or substituted $C_1$-$C_{10}$ heterocyclene. In some embodiments, $X_2$ is unsubstituted or substituted peptide comprising 1, 2, 3, 4, 5, 6, 7, 8, 9, or 10 natural amino acids.

In some embodiments, $X_3$ is any one of the following: bond; C═O, (C═O)-$L_1$-(C═O), (C═O)-$L_1$, $L_1$-(C═O), O(CO), (CO)O, $L_2$-(CO)O, or O(CO)-$L_2$; O, S, S—S, or Se—Se—; NH, NR, NH(CO), (CO)NH, $L_2$-(CO)NH, (CO) NH-$L_2$, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocyclene; and unsubstituted or substituted peptide comprising 1-10 natural amino acids. In some embodiments, $X_3$ is a bond. In some embodiments, $X_3$ is C═O. In some embodiments, $X_3$ is (C═O)-$L_1$-(C═O). In some embodiments, $X_3$ is (C═O)-$L_1$. In some embodiments, $X_3$ is $L_1$-(C═O). In some embodiments, $X_3$ is O(CO). In some embodiments, $X_3$ is (CO)O. In some embodiments, $X_3$ is $L_2$-(CO)O. In some embodiments, $X_3$ is O(CO)-$L_2$. In some embodiments, $X_3$ is O. In some embodiments, $X_3$ is S. In some embodiments, $X_3$ is S—S. In some embodiments, $X_3$ is Se—Se—. In some embodiments, $X_3$ is NH. In some embodiments, $X_3$ is NR. In some embodiments, $X_3$ is NH(CO). In some embodiments, $X_3$ is (CO)NH. In some embodiments, $X_3$ is $L_2$-(CO)NH. In some embodiments, $X_3$ is (CO)NH-$L_2$. In some embodiments, $X_3$ is $L_2$-NH(CO). In some embodiments, $X_3$ is NH(CO)-$L_2$. In some embodiments, $X_3$ is —NR-$L_2$-NR. In some embodiments, $X_3$ is $L_2$-O. In some embodiments, $X_3$ is O-$L_2$. In some embodiments, $X_3$ is unsubstituted or substituted $C_1$-$C_{10}$ alkylene. In some embodiments, $X_3$ is unsubstituted or substituted $C_3$-$C_{10}$ cycloalkylene. In some embodiments, $X_3$ is unsubstituted or substituted arylene. In some embodiments, $X_3$ is unsubstituted or substituted heteroarylene. In some embodiments, $X_3$ is unsubstituted or substituted $C_1$-$C_{10}$ heterocyclene. In some embodiments, $X_3$ is unsubstituted or substituted peptide comprising 1, 2, 3, 4, 5, 6, 7, 8, 9, or 10 natural amino acids.

In some embodiments, each $L_1$ is independently unsubstituted or substituted arylene; unsubstituted or substituted heteroarylene; or unsubstituted or substituted $C_1$-$C_{10}$ heterocyclene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocyclene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $X_3$ is attached to $R_3$; and $R_4$, $R_5$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_3$ is attached to $R_3$; and $R_4$, $R_5$, $R_6$ and $R_7$ are each independently H. In some embodiments, $X_3$ is attached to $R_3$; and $R_4$, $R_5$, $R_6$ and $R_7$ are each independently OH. In some embodiments, $X_3$ is attached to $R_3$; and $R_4$, $R_5$, $R_6$ and $R_7$ are each independently $O(CO)NH_2$. In some embodiments, $X_3$ is attached $R_3$; and $R_4$, $R_5$, $R_6$ and $R_7$ are each independently halo. In some embodiments, $X_3$ is attached to $R_3$; and $R_4$, $R_5$, $R_6$ and $R_7$ are each independently amino group. In some embodiments, $X_3$ is attached to $R_3$; and $R_4$, $R_5$, $R_6$ and $R_7$ are each independently unsubstituted or substituted $C_1$-$C_{10}$ alkyl. In some embodiments, $X_3$ is attached to $R_3$; and $R_4$, $R_5$, $R_6$ and $R_7$ are each independently unsubstituted or substituted $C_3$-$C_{10}$ cycloalkyl. In some embodiments, $X_3$ is attached to $R_3$; and $R_4$, $R_5$, $R_6$ and $R_7$ are each independently unsubstituted or substituted $C_1$-$C_{10}$ acyl. In some embodiments, $X_3$ is attached to $R_3$; and $R_4$, $R_5$, $R_6$ and $R_7$ are each independently unsubstituted or substituted $C_1$-$C_{10}$ carboxyl ester. In some embodiments, $X_3$ is attached to $R_3$; and $R_4$, $R_5$, $R_6$ and $R_7$ are each independently unsubstituted or substituted $C_1$-$C_{10}$ alkyl ketone. In some embodiments, $X_3$ is attached to $R_3$; and $R_4$, $R_5$, $R_6$ and $R_7$ are each independently unsubstituted or substituted $C_1$-$C_{10}$ alkyl ether. In some embodiments, $X_3$ is attached to $R_3$; and $R_4$, $R_5$, $R_6$ and $R_7$ are each independently unsubstituted or substituted aryl. In some embodiments, $X_3$ is attached to $R_3$; and $R_4$, $R_5$, $R_6$ and $R_7$ are each independently unsubstituted or substituted heteroaryl. In some embodiments, $X_3$ is attached to $R_3$; and $R_4$, $R_5$, $R_6$ and $R_7$ are each independently unsubstituted or substituted $C_1$-$C_{10}$ heterocycyl. In some embodiments, $X_3$ is attached to $R_3$; and $R_4$, $R_5$, $R_6$ and $R_7$ are each independently unsubstituted or substituted peptide comprising 1, 2, 3, 4, 5, 6, 7, 8, 9, or 10 amino acids. In some embodiments, $X_3$ is attached to $R_3$; and $R_4$, $R_5$, $R_6$ and $R_7$ are each independently and forms a glycosidic bond with a natural monosaccharide.

In some embodiments, $X_3$ is attached to $R_4$; and $R_3$, $R_5$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_3$ is attached to $R_4$; and $R_3$, $R_5$, $R_6$ and $R_7$ are each independently H. In some embodiments, $X_3$ is attached to $R_4$; and $R_3$, $R_5$, $R_6$ and $R_7$ are each independently OH. In some embodiments, $X_3$ is attached to $R_4$; and $R_3$, $R_5$, $R_6$ and $R_7$ are each independently $O(CO)NH_2$. In some embodiments, $X_3$ is attached to $R_4$; and $R_3$, $R_5$, $R_6$ and $R_7$ are each independently halo. In some embodiments, $X_3$ is attached to $R_4$; and $R_3$, $R_5$, $R_6$ and $R_7$ are each independently amino group. In some embodiments, $X_3$ is attached to $R_4$; and $R_3$, $R_5$, $R_6$ and $R_7$ are each independently unsubstituted or substituted $C_1$-$C_{10}$ alkyl. In some embodiments, $X_3$ is attached to $R_4$; and $R_3$, $R_5$, $R_6$ and $R_7$ are each independently unsubstituted or substituted $C_3$-$C_{10}$ cycloalkyl. In some embodiments, $X_3$ is attached to $R_4$; and $R_3$, $R_5$, $R_6$ and $R_7$ are each independently unsubstituted or substituted $C_1$-$C_{10}$ acyl. In some embodiments, $X_3$ is attached to $R_4$; and $R_3$, $R_5$, $R_6$ and $R_7$ are each independently unsubstituted or substituted $C_1$-$C_{10}$ carboxyl ester. In some embodiments, $X_3$ is attached to $R_4$; and $R_3$, $R_5$, $R_6$ and $R_7$ are each independently unsubstituted or substituted $C_1$-$C_{10}$ alkyl ketone. In some embodiments, $X_3$ is attached to $R_4$; and $R_3$, $R_5$, $R_6$ and $R_7$ are each independently unsubstituted or substituted $C_1$-$C_{10}$ alkyl ether. In some embodiments, $X_3$ is attached to $R_4$; and $R_3$, $R_5$, $R_6$ and $R_7$ are each independently unsubstituted or substituted aryl. In some embodiments, $X_3$ is attached to $R_4$; and $R_3$, $R_5$, $R_6$ and $R_7$ are each independently unsubstituted or substituted heteroaryl. In some embodiments, $X_3$ is attached to $R_4$; and $R_3$, $R_5$, $R_6$ and $R_7$ are each independently unsubstituted or substituted $C_1$-$C_{10}$ heterocycyl. In some embodiments, $X_3$ is attached to $R_4$; and $R_3$, $R_5$, $R_6$ and $R_7$ are each independently unsubstituted or substituted peptide comprising 1, 2, 3, 4, 5, 6, 7, 8, 9, or 10 amino acids. In some embodiments, $X_3$ is attached to $R_4$; and $R_3$, $R_5$, $R_6$ and $R_7$ are each independently and forms a glycosidic bond with a natural monosaccharide.

In some embodiments, $X_3$ is attached to $R_5$; and $R_3$, $R_4$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_3$ is attached to $R_5$; and $R_3$, $R_4$, $R_6$ and $R_7$ are each independently H. In some embodiments, $X_3$ is attached to $R_5$; and $R_3$, $R_4$, $R_6$ and $R_7$ are each independently OH. In some embodiments, $X_3$ is attached to $R_5$; and $R_3$, $R_4$, $R_6$ and $R_7$ are each independently $O(CO)NH_2$. In some embodiments, $X_3$ is attached to $R_5$; and $R_3$, $R_4$, $R_6$ and $R_7$ are each independently halo. In some embodiments, $X_3$ is attached to $R_5$; and $R_3$, $R_4$, $R_6$ and $R_7$ are each independently amino group. In some embodiments, $X_3$ is attached to $R_5$; and $R_3$, $R_4$, $R_6$ and $R_7$ are each independently unsubstituted or substituted $C_1$-$C_{10}$ alkyl. In some embodiments, $X_3$ is attached to $R_5$; and $R_3$, $R_4$, $R_6$ and $R_7$ are each independently unsubstituted or substituted $C_3$-$C_{10}$ cycloalkyl. In some embodiments, $X_3$ is attached to $R_5$; and $R_3$, $R_4$, $R_6$ and $R_7$ are each independently unsubstituted or substituted $C_1$-$C_{10}$ acyl. In some embodiments, $X_3$ is attached to $R_5$; and $R_3$, $R_4$, $R_6$ and $R_7$ are each independently unsubstituted or substituted $C_1$-$C_{10}$ carboxyl ester. In some embodiments, $X_3$ is attached to $R_5$; and $R_3$, $R_4$, $R_6$ and $R_7$ are each independently unsubstituted or substituted $C_1$-$C_{10}$ alkyl ketone. In some embodiments, $X_3$ is attached to $R_5$; and $R_3$, $R_4$, $R_6$ and $R_7$ are each independently unsubstituted or substituted $C_1$-$C_{10}$ alkyl ether. In some embodiments, $X_3$ is attached to $R_5$; and $R_3$, $R_4$, $R_6$ and $R_7$ are each independently unsubstituted or substituted aryl. In some embodiments, $X_3$ is attached to $R_5$; and $R_3$, $R_4$, $R_6$ and $R_7$ are each independently unsubstituted or substituted heteroaryl. In some embodiments, $X_3$ is attached to $R_5$; and $R_3$, $R_4$, $R_6$ and $R_7$ are each independently unsubstituted or substituted $C_1$-$C_{10}$ heterocycyl. In some embodiments, $X_3$ is attached to $R_5$; and $R_3$, $R_4$, $R_6$ and $R_7$ are each independently unsubstituted or substituted peptide comprising 1, 2, 3, 4, 5, 6, 7, 8, 9, or 10 amino acids. In some embodiments, $X_3$ is attached to $R_5$; and $R_3$, $R_4$, $R_6$ and $R_7$ are each independently and forms a glycosidic bond with a natural monosaccharide.

In some embodiments, $X_3$ is attached to $R_6$; and $R_3$, $R_4$, $R_5$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_3$ is attached to $R_6$; and $R_3$, $R_4$, $R_5$ and $R_7$ are each independently H. In some embodiments, $X_3$ is attached to $R_6$; and $R_3$, $R_4$, $R_5$ and $R_7$ are each independently OH. In some embodiments, $X_3$ is attached to $R_6$; and $R_3$, $R_4$, $R_5$ and $R_7$ are each independently $O(CO)NH_2$. In some embodiments, $X_3$ is attached to $R_6$; and $R_3$, $R_4$, $R_5$ and $R_7$ are each independently halo. In some embodiments, $X_3$ is attached to $R_6$; and $R_3$, $R_4$, $R_5$ and $R_7$ are each independently amino group. In some embodiments, $X_3$ is attached to $R_6$; and $R_3$, $R_4$, $R_5$ and $R_7$ are each independently unsubstituted or substituted $C_1$-$C_{10}$ alkyl. In some embodiments, $X_3$ is attached to $R_6$; and $R_3$, $R_4$, $R_5$ and $R_7$ are each independently unsubstituted or substituted $C_3$-$C_{10}$ cycloalkyl. In some embodiments, $X_3$ is attached to $R_6$; and $R_3$, $R_4$, $R_5$ and $R_7$ are each independently unsubstituted or substituted $C_1$-$C_{10}$ acyl. In some embodiments, $X_3$ is attached to $R_6$; and $R_3$, $R_4$, $R_5$ and $R_7$ are each independently unsubstituted or substituted $C_1$-$C_{10}$ carboxyl ester. In some embodiments, $X_3$ is attached to $R_6$; and $R_3$, $R_4$, $R_5$ and $R_7$ are each independently unsubstituted or substituted $C_1$-$C_{10}$ alkyl ketone. In some embodiments, $X_3$ is attached to $R_6$; and $R_3$, $R_4$, $R_5$ and $R_7$ are each independently unsubstituted or substituted $C_1$-$C_{10}$ alkyl ether. In some embodiments, $X_3$ is attached to $R_6$; and $R_3$, $R_4$, $R_5$ and $R_7$ are each independently unsubstituted or substituted aryl. In some embodiments, $X_3$ is attached to $R_6$; and $R_3$, $R_4$, $R_5$ and $R_7$ are each independently unsubstituted or substituted heteroaryl. In some embodiments, $X_3$ is attached to $R_6$; and $R_3$, $R_4$, $R_5$ and $R_7$ are each independently unsubstituted or substituted $C_1$-$C_{10}$ heterocycyl. In some embodiments, $X_3$ is attached to $R_6$; and $R_3$, $R_4$, $R_5$ and $R_7$ are each independently unsubstituted or substituted peptide comprising 1, 2, 3, 4, 5, 6, 7, 8, 9, or 10 amino acids. In some embodiments, $X_3$ is attached to $R_6$; and $R_3$, $R_4$, $R_5$ and $R_7$ are each independently and forms a glycosidic bond with a natural monosaccharide.

In some embodiments, $X_3$ is attached to $R_7$; and $R_3$, $R_4$, $R_5$ and $R_6$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide. In some embodiments, $X_3$ is attached to $R_7$; and $R_3$, $R_4$, $R_5$ and $R_6$ are each independently H. In some embodiments, $X_3$ is attached to $R_7$; and $R_3$, $R_4$, $R_5$ and $R_6$ are each independently OH. In some embodiments, $X_3$ is attached to $R_7$; and $R_3$, $R_4$, $R_5$ and $R_6$ are each independently $O(CO)NH_2$. In some embodiments, $X_3$ is attached to $R_7$; and $R_3$, $R_4$, $R_5$ and $R_6$ are each independently halo. In some embodiments, $X_3$ is attached to $R_7$; and $R_3$, $R_4$, $R_5$ and $R_6$ are each independently amino group. In some embodiments, $X_3$ is attached to $R_7$; and $R_3$, $R_4$, $R_5$ and $R_6$ are each independently unsubstituted or substituted $C_1$-$C_{10}$ alkyl. In some embodiments, $X_3$ is attached to $R_7$; and $R_3$, $R_4$, $R_5$ and $R_6$ are each independently unsubstituted or substituted $C_3$-$C_{10}$ cycloalkyl. In some embodiments, $X_3$ is attached to $R_7$; and $R_3$, $R_4$, $R_5$ and $R_6$ are each independently unsubstituted or substituted $C_1$-$C_{10}$ acyl. In some embodiments, $X_3$ is attached to $R_7$; and $R_3$, $R_4$, $R_5$ and $R_6$ are each independently unsubstituted or substituted $C_1$-$C_{10}$ carboxyl ester. In some embodiments, $X_3$ is attached to $R_7$; and $R_3$, $R_4$, $R_5$ and $R_6$ are each independently unsubstituted or substituted $C_1$-$C_{10}$ alkyl ketone. In some embodiments, $X_3$ is attached to $R_7$; and $R_3$, $R_4$, $R_5$ and $R_6$ are each independently unsubstituted or substituted $C_1$-$C_{10}$ alkyl ether. In some embodiments, $X_3$ is attached to $R_7$; and $R_3$, $R_4$, $R_5$ and $R_6$ are each independently unsubstituted or substituted aryl. In some embodiments, $X_3$ is attached to $R_7$; and $R_3$, $R_4$, $R_5$ and $R_6$ are each independently unsubstituted or substituted heteroaryl. In some embodiments, $X_3$ is attached to $R_7$; and $R_3$, $R_4$, $R_5$ and $R_6$ are each independently unsubstituted or substituted $C_1$-$C_{10}$ heterocycyl. In some embodiments, $X_3$ is attached to $R_7$; and $R_3$, $R_4$, $R_5$ and $R_6$ are each independently unsubstituted or substituted peptide comprising 1, 2, 3, 4, 5, 6, 7, 8, 9, or 10 amino acids. In some embodiments, $X_3$ is attached to $R_7$; and $R_3$, $R_4$, $R_5$ and $R_6$ are each independently and forms a glycosidic bond with a natural monosaccharide.

In some embodiments of Formula IL, $n_1$ and $n_2$ are each independently 0, 1, 2, 3, or 4. In some embodiments, $R_1$ and $R_2$ are each H. In some embodiments, $X_1$ is a bond, NH(CO), (CO)NH, (C═O)-$L_1$-(C═O), (C═O)-$L_1$, $L_1$-(C═O), and O; and $L_1$ is unsubstituted or substituted $C_1$-$C_{10}$ heterocycylene. In some embodiments, $X_2$ is a bond, C═O, NH(CO), (CO)NH, $L_2$-NH(CO), and NH(CO)-$L_2$. In some embodiments, $X_3$ is a bond, O(CO), (CO)O, $L_2$-(CO)O, O(CO)-$L_2$, O, S, $L_2$-NH(CO), or NH(CO)-$L_2$. In some embodiments, $X_3$ is attached to $R_4$; and $R_3$, $R_5$, $R_6$ and $R_7$ are each independently OH or halo. In some embodiments, $X_3$ is attached to $R_7$; and $R_3$, $R_4$, $R_5$ and $R_6$ are each independently OH or halo.

Provided in one aspect is a compound of Formula (III), or an enantiomer, an enantiomeric mixture, a diastereomer, a diastereomeric mixture, or a pharmaceutically acceptable salt thereof:

(III)

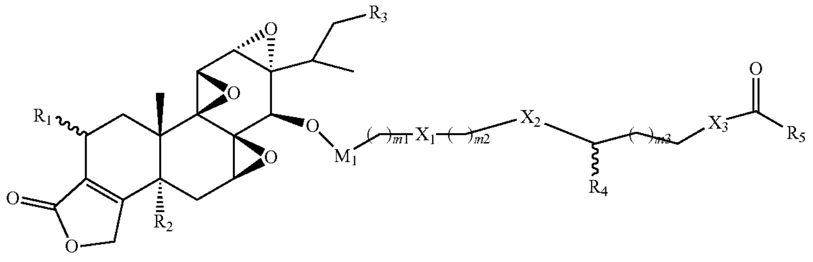

wherein $m_1$, $m_2$, and $m_3$ are each independently 0-15;

$M_1$ is selected from a bond, —CO—, —$OPO_2$—, —$SO_2$—, —$CH_2OPO_2$, —$CH_2OCO$—, and —$CH_2O$—;

$R_1$, $R_2$, and $R_3$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl;

$R_4$ is NHR', NHCOR', NHCOOR', CONHR', or COOR';

each R' is H, unsubstituted or substituted $C_1$-$C_{10}$ alkyl, unsubstituted or substituted $C_3$-$C_{10}$ cycloalkyl, unsubstituted or substituted $C_3$-$C_{10}$ cycloalkyl($C_1$-$C_{10}$ alkyl), unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, or unsubstituted or substituted $C_1$-$C_{10}$ heterocycyl($C_1$-$C_{10}$ alkyl); and $R_5$ is unsubstituted or substituted $C_1$-$C_{10}$ alkyl, unsubstituted or substituted $C_3$-$C_{10}$ cycloalkyl, unsubstituted or substituted aryl, unsubstituted or substituted heteroaryl, or unsubstituted or substituted $C_1$-$C_{10}$ heterocycyl.

In some embodiments, $m_1$ is 0, 1, 2, 3, 4, 5, 6, 7, 8, 9, 10, 11, 12, 13, 14, or 15. In some embodiments, $m_1$ is 0. In some embodiments, $m_1$ is 1. In some embodiments, $m_1$ is 2. In some embodiments, $m_1$ is 3. In some embodiments, $m_1$ is 4. In some embodiments, $m_1$ is 5. In some embodiments, $m_1$ is 6. In some embodiments, $m_1$ is 7. In some embodiments, $m_1$ is 8. In some embodiments, $m_1$ is 9. In some embodiments, $m_1$ is 10. In some embodiments, $m_1$ is 11. In some embodiments, $m_1$ is 12. In some embodiments, $m_1$ is 13. In some embodiments, $m_1$ is 14. In some embodiments, $m_1$ is 15.

In some embodiments, $m_2$ is 0, 1, 2, 3, 4, 5, 6, 7, 8, 9, 10, 11, 12, 13, 14, or 15. In some embodiments, $m_2$ is 0. In some embodiments, $m_2$ is 1. In some embodiments, $m_2$ is 2. In some embodiments, $m_2$ is 3. In some embodiments, $m_2$ is 4. In some embodiments, $m_2$ is 5. In some embodiments, $m_2$ is 6. In some embodiments, $m_2$ is 7. In some embodiments, $m_2$ is 8. In some embodiments, $m_2$ is 9. In some embodiments, $m_2$ is 10. In some embodiments, $m_2$ is 11. In some embodiments, $m_2$ is 12. In some embodiments, $m_2$ is 13. In some embodiments, $m_2$ is 14. In some embodiments, $m_2$ is 15.

In some embodiments, $m_3$ is 0, 1, 2, 3, 4, 5, 6, 7, 8, 9, 10, 11, 12, 13, 14, or 15. In some embodiments, $m_3$ is 0. In some embodiments, $m_3$ is 1. In some embodiments, $m_3$ is 2. In some embodiments, $m_3$ is 3. In some embodiments, $m_3$ is 4. In some embodiments, $m_3$ is 5. In some embodiments, $m_3$ is 6. In some embodiments, $m_3$ is 7. In some embodiments, $m_3$ is 8. In some embodiments, $m_3$ is 9. In some embodiments, $m_3$ is 10. In some embodiments, $m_3$ is 11. In some embodiments, $m_3$ is 12. In some embodiments, $m_3$ is 13. In some embodiments, $m_3$ is 14. In some embodiments, $m_3$ is 15.

In some embodiments, $M_1$ is any one of the following: bond; —C═O—; —$OPO_2$—; —$SO_2$—; —$CH_2OPO_2$, —$CH_2OCO$—, and —$CH_2O$—. In some embodiments, $M_1$ is a bond. In some embodiments, $M_1$ is —C═O—. In some embodiments, $M_1$ is —$OPO_2$—. In some embodiments, $M_1$ is —$SO_2$—. In some embodiments, $M_1$ is —$CH_2OPO_2$. In some embodiments, $M_1$ is —$CH_2OCO$—. In some embodiments, $M_1$ is —$CH_2O$—.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_1$ is OH. In some embodiments, $R_1$ is hydrogen. In some embodiments, $R_1$ is halo. In some embodiments, $R_1$ is unsubstituted or substituted $C_1$-$C_{10}$ alkyl. In some embodiments, $R_1$ is unsubstituted or substituted $C_3$-$C_{10}$ cycloalkyl. In some embodiments, $R_1$ is unsubstituted or substituted $C_1$-$C_{10}$ acyl. In some embodiments, $R_1$ is unsubstituted or substituted $C_1$-$C_{10}$ carboxyl ester. In some embodiments, $R_1$ is unsubstituted or substituted $C_1$-$C_{10}$ alkyl ketone. In some embodiments, $R_1$ unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_2$ is OH. In some embodiments, $R_2$ is hydrogen. In some embodiments, $R_2$ is halo. In some embodiments, $R_2$ is unsubstituted or substituted $C_1$-$C_{10}$ alkyl. In some embodiments, $R_2$ is unsubstituted or substituted $C_3$-$C_{10}$ cycloalkyl. In some embodiments, $R_2$ is unsubstituted or substituted $C_1$-$C_{10}$ acyl. In some embodiments, $R_2$ is unsubstituted or substituted $C_1$-$C_{10}$ carboxyl ester. In some embodiments, $R_2$ is unsubstituted or substituted $C_1$-$C_{10}$ alkyl ketone. In some embodiments, $R_2$ unsubstituted or substituted $C_1$-$C_{10}$ alkyl ether.

In some embodiments, $R_3$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_3$ is OH. In some embodiments, $R_3$ is hydrogen. In some embodiments, $R_3$ is halo. In some embodiments, $R_3$ is unsubstituted or substituted $C_1$-$C_{10}$ alkyl. In some embodiments, $R_3$ is unsubstituted or substituted $C_3$-$C_{10}$ cycloalkyl. In some embodiments, $R_3$ is unsubstituted or substituted $C_1$-$C_{10}$ acyl. In some embodiments, $R_3$ is unsubstituted or substituted $C_1$-$C_{10}$ carboxyl ester. In some embodiments, $R_3$ is unsubstituted or substituted $C_1$-$C_{10}$ alkyl ketone. In some embodiments, $R_3$ unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocyclene; and unsubstituted or substituted peptide comprising 1-10 natural amino acids. In some embodiments, $X_1$ is a bond. In some embodiments, $X_1$ is C═O. In some embodiments, $X_1$ is (C═O)-$L_1$-(C═O). In some embodiments, $X_1$ is (C═O)-$L_1$. In some embodiments, $X_1$ is $L_1$-(C═O). In some embodiments, $X_1$ is O(CO). In some embodiments, $X_1$ is (CO)O. In some embodiments, $X_1$ is O. In some embodiments, $X_1$ is S. In some embodiments, $X_1$ is S—S. In some embodiments, $X_1$ is Se—Se—. In some embodiments, $X_1$ is NH. In some embodiments, $X_1$ is NR. In some embodiments, $X_1$ is NH(CO). In some embodiments, $X_1$ is (CO)NH. In some embodiments, $X_1$ is $L_2$-NH(CO). In some embodiments, $X_1$ is NH(CO)-$L_2$. In some embodiments, $X_1$ is —NR-$L_2$-NR. In some embodiments, $X_1$ is $L_2$-O. In some embodiments, $X_1$ is O-$L_2$. In some embodiments, $X_1$ is unsubstituted or substituted $C_1$-$C_{10}$ alkylene. In some embodiments, $X_1$ is unsubstituted or substituted $C_3$-$C_{10}$ cycloalkylene. In some embodiments, $X_1$ is unsubstituted or substituted arylene. In some embodiments, $X_1$ is unsubstituted or substituted heteroarylene. In some embodiments, $X_1$ is unsubstituted or substituted $C_1$-$C_{10}$ heterocyclene. In some embodiments, $X_1$ is unsubstituted or substituted peptide comprising 1, 2, 3, 4, 5, 6, 7, 8, 9, or 10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene;

unsubstituted or substituted arylene; unsubstituted or substituted heteroarylene; unsubstituted or substituted $C_1$-$C_{10}$ heterocyclene; and unsubstituted or substituted peptide comprising 1-10 natural amino acids. In some embodiments, $X_2$ is a bond. In some embodiments, $X_2$ is C═O. In some embodiments, $X_2$ is (C═O)-$L_1$-(C═O). In some embodiments, $X_2$ is (C═O)-$L_1$. In some embodiments, $X_2$ is $L_1$-(C═O). In some embodiments, $X_2$ is O(CO). In some embodiments, $X_2$ is (CO)O. In some embodiments, $X_2$ is O. In some embodiments, $X_2$ is S. In some embodiments, $X_2$ is S—S. In some embodiments, $X_2$ is Se—Se—. In some embodiments, $X_2$ is NH. In some embodiments, $X_2$ is NR. In some embodiments, $X_2$ is NH(CO). In some embodiments, $X_2$ is (CO)NH. In some embodiments, $X_2$ is $L_2$-NH(CO). In some embodiments, $X_2$ is NH(CO)-$L_2$. In some embodiments, $X_2$ is —NR-$L_2$-NR. In some embodiments, $X_2$ is $L_2$-O. In some embodiments, $X_2$ is O-$L_2$. In some embodiments, $X_2$ is unsubstituted or substituted $C_1$-$C_{10}$ alkylene. In some embodiments, $X_2$ is unsubstituted or substituted $C_3$-$C_{10}$ cycloalkylene. In some embodiments, $X_2$ is unsubstituted or substituted arylene. In some embodiments, $X_2$ is unsubstituted or substituted heteroarylene. In some embodiments, $X_2$ is unsubstituted or substituted $C_1$-$C_{10}$ heterocyclene. In some embodiments, $X_2$ is unsubstituted or substituted peptide comprising 1, 2, 3, 4, 5, 6, 7, 8, 9, or 10 natural amino acids.

In some embodiments, $X_3$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocyclene; and unsubstituted or substituted peptide comprising 1-10 natural amino acids. In some embodiments, $X_3$ is a bond. In some embodiments, $X_3$ is C═O. In some embodiments, $X_3$ is (C═O)-$L_1$-(C═O). In some embodiments, $X_3$ is (C═O)-$L_1$. In some embodiments, $X_3$ is $L_1$-(C═O). In some embodiments, $X_3$ is O(CO). In some embodiments, $X_3$ is (CO)O. In some embodiments, $X_3$ is O. In some embodiments, $X_3$ is S. In some embodiments, $X_3$ is S—S. In some embodiments, $X_3$ is Se—Se—. In some embodiments, $X_3$ is NH. In some embodiments, $X_3$ is NR. In some embodiments, $X_3$ is NH(CO). In some embodiments, $X_3$ is (CO)NH. In some embodiments, $X_3$ is $L_2$-NH(CO). In some embodiments, $X_3$ is NH(CO)-$L_2$. In some embodiments, $X_3$ is —NR-$L_2$-NR. In some embodiments, $X_3$ is $L_2$-O. In some embodiments, $X_3$ is O-$L_2$. In some embodiments, $X_3$ is unsubstituted or substituted $C_1$-$C_{10}$ alkylene. In some embodiments, $X_3$ is unsubstituted or substituted $C_3$-$C_{10}$ cycloalkylene. In some embodiments, $X_3$ is unsubstituted or substituted arylene. In some embodiments, $X_3$ is unsubstituted or substituted heteroarylene. In some embodiments, $X_3$ is unsubstituted or substituted $C_1$-$C_{10}$ heterocyclene. In some embodiments, $X_3$ is unsubstituted or substituted peptide comprising 1, 2, 3, 4, 5, 6, 7, 8, 9, or 10 natural amino acids.

In some embodiments, each $L_1$ is independently unsubstituted or substituted arylene; unsubstituted or substituted heteroarylene; or unsubstituted or substituted $C_1$-$C_{10}$ heterocyclene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocyclene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $R_4$ is any one of the following: NHR'; NHCOR'; NHCOOR'; CONHR'; and COOR'. In some embodiments, $R_4$ is NHR'. In some embodiments, $R_4$ is NHCOR'. In some embodiments, $R_4$ is NHCOOR'. In some embodiments, $R_4$ is CONHR'. In some embodiments, $R_4$ is COOR'

In some embodiments, each R' is independently unsubstituted or substituted $C_1$-$C_{10}$ alkyl; unsubstituted or substituted $C_3$-$C_{10}$ cycloalkyl; unsubstituted or substituted $C_3$-$C_{10}$ cycloalkyl($C_1$-$C_{10}$ alkyl); unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; or unsubstituted or substituted $C_1$-$C_{10}$ heterocycyl($C_1$-$C_{10}$ alkyl). In some embodiments, each R' is independently unsubstituted or substituted $C_1$-$C_{10}$ alkyl. In some embodiments, each R' is independently unsubstituted or substituted $C_3$-$C_{10}$ cycloalkyl. In some embodiments, each R' is independently unsubstituted or substituted $C_3$-$C_{10}$ cycloalkyl ($C_1$-$C_{10}$ alkyl). In some embodiments, each R' is independently unsubstituted or substituted $C_1$-$C_{10}$ acyl. In some embodiments, each R' is independently unsubstituted or substituted $C_1$-$C_{10}$ carboxyl ester. In some embodiments, each R' is independently unsubstituted or substituted $C_1$-$C_{10}$ alkyl ketone. In some embodiments, each R' is independently unsubstituted or substituted $C_1$-$C_{10}$ alkyl ether. In some embodiments, each R' is independently unsubstituted or substituted aryl. In some embodiments, each R' is independently unsubstituted or substituted heteroaryl. In some embodiments, each R' is independently unsubstituted or substituted $C_1$-$C_{10}$ heterocycyl. In some embodiments, each R' is independently unsubstituted or substituted $C_1$-$C_{10}$ heterocycyl($C_1$-$C_{10}$ alkyl).

In some embodiments, $R_5$ is unsubstituted or substituted $C_1$-$C_{10}$ alkyl; unsubstituted or substituted $C_3$-$C_{10}$ cycloalkyl; unsubstituted or substituted aryl; unsubstituted or substituted heteroaryl; or unsubstituted or substituted $C_1$-$C_{10}$ heterocycyl. In some embodiments, $R_5$ is unsubstituted or substituted $C_1$-$C_{10}$ alkyl. In some embodiments, $R_5$ is unsubstituted or substituted $C_3$-$C_{10}$ cycloalkyl. In some embodiments, each $R_5$ is independently unsubstituted or substituted aryl. In some embodiments, each $R_5$ is independently unsubstituted or substituted heteroaryl. In some embodiments, each $R_5$ is independently unsubstituted or substituted $C_1$-$C_{10}$ heterocycyl.

In some embodiments of Formula III, $m_1$, $m_2$, and $m_3$ are each independently 0, 1, 2, 3, or 4. In some embodiments, $M_1$ is —C═O—. In some embodiments, $R_1$, $R_2$, and $R_3$ are each H. In some embodiments, $X_1$ is a bond. In some embodiments, $X_2$ is NH(CO) or (CO)NH. In some embodiments, $X_3$ is NH or NR. In some embodiments, $R_4$ is NHCOR' or NHCOOR'; and R' is unsubstituted or substituted $C_1$-$C_{10}$ alkyl or unsubstituted or substituted $C_3$-$C_{10}$ cycloalkyl. In some embodiments, $R_5$ is unsubstituted or substituted $C_1$-$C_{10}$ alkyl.

Provided in one aspect is a compound of Formula (IV), or an enantiomer, an enantiomeric mixture, a diastereomer, a diastereomeric mixture, or a pharmaceutically acceptable salt thereof:

(IV)

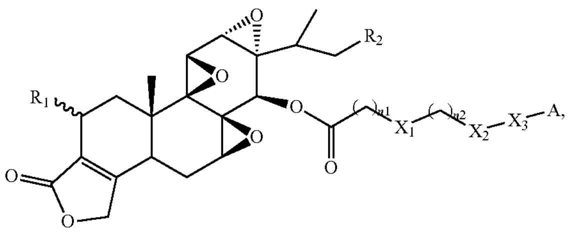

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, $L_2$-NH, NH-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and A is unsubstituted or substituted $C_3$-$C_{15}$ cycloalkyl, unsubstituted or substituted $C_1$-$C_{15}$ heterocyclyl, unsubstituted or substituted aryl, unsubstituted or substituted heteroaryl, or an oligosaccharide comprising 3-15 same or different monosaccharides.

In some embodiments, $n_1$ is 0, 1, 2, 3, 4, 5, 6, 7, 8, 9, 10, 11, 12, 13, 14, or 15. In some embodiments, $n_1$ is 0. In some embodiments, $n_1$ is 1. In some embodiments, $n_1$ is 2. In some embodiments, $n_1$ is 3. In some embodiments, $n_1$ is 4. In some embodiments, $n_1$ is 5. In some embodiments, $n_1$ is 6. In some embodiments, $n_1$ is 7. In some embodiments, $n_1$ is 8. In some embodiments, $n_1$ is 9. In some embodiments, $n_1$ is 10. In some embodiments, $n_1$ is 11. In some embodiments, $n_1$ is 12. In some embodiments, $n_1$ is 13. In some embodiments, $n_1$ is 14. In some embodiments, $n_1$ is 15.

In some embodiments, $n_2$ is 0, 1, 2, 3, 4, 5, 6, 7, 8, 9, 10, 11, 12, 13, 14, or 15. In some embodiments, $n_2$ is 0. In some embodiments, $n_2$ is 1. In some embodiments, $n_2$ is 2. In some embodiments, $n_2$ is 3. In some embodiments, $n_2$ is 4. In some embodiments, $n_2$ is 5. In some embodiments, $n_2$ is 6. In some embodiments, $n_2$ is 7. In some embodiments, $n_2$ is 8. In some embodiments, $n_2$ is 9. In some embodiments, $n_2$ is 10. In some embodiments, $n_2$ is 11. In some embodiments, $n_2$ is 12. In some embodiments, $n_2$ is 13. In some embodiments, $n_2$ is 14. In some embodiments, $n_2$ is 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_1$ is OH. In some embodiments, $R_1$ is hydrogen. In some embodiments, $R_1$ is halo. In some embodiments, $R_1$ is unsubstituted or substituted $C_1$-$C_{10}$ alkyl. In some embodiments, $R_1$ is unsubstituted or substituted $C_3$-$C_{10}$ cycloalkyl. In some embodiments, $R_1$ is unsubstituted or substituted $C_1$-$C_{10}$ acyl. In some embodiments, $R_1$ is unsubstituted or substituted $C_1$-$C_{10}$ carboxyl ester. In some embodiments, $R_1$ is unsubstituted or substituted $C_1$-$C_{10}$ alkyl ketone. In some embodiments, $R_1$ unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether. In some embodiments, $R_2$ is OH. In some embodiments, $R_2$ is hydrogen. In some embodiments, $R_2$ is halo. In some embodiments, $R_2$ is unsubstituted or substituted $C_1$-$C_{10}$ alkyl. In some embodiments, $R_2$ is unsubstituted or substituted $C_3$-$C_{10}$ cycloalkyl. In some embodiments, $R_2$ is unsubstituted or substituted $C_1$-$C_{10}$ acyl. In some embodiments, $R_2$ is unsubstituted or substituted $C_1$-$C_{10}$ carboxyl ester. In some embodiments, $R_2$ is unsubstituted or substituted $C_1$-$C_{10}$ alkyl ketone. In some embodiments, $R_2$ unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$, $L_2$-NH, or NH-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_1$ is a bond. In some embodiments, $X_1$ is C═O. In some embodiments, $X_1$ is (C═O)-$L_1$-(C═O). In some embodiments, $X_1$ is (C═O)-$L_1$. In some embodiments, $X_1$ is $L_1$-(C═O). In some embodiments, $X_1$ is O(CO). In some embodiments, $X_1$ is (CO)O. In some embodiments, $X_1$ is O. In some embodiments, $X_1$ is S. In some embodiments, $X_1$ is S—S. In some embodiments, $X_1$ is Se—Se—. In some embodiments, $X_1$ is NH. In some embodiments, $X_1$ is NR. In some embodiments, $X_1$ is NH(CO). In some embodiments, $X_1$ is (CO)NH. In some embodiments, $X_1$ is $L_2$-NH(CO). In some embodiments, $X_1$ is NH(CO)-$L_2$. In some embodiments, $X_1$ is —NR-$L_2$-NR. In some embodiments, $X_1$ is $L_2$-O. In some embodiments, $X_1$ is O-$L_2$. In some embodiments, $X_1$ is $L_2$-NH. In some embodiments, $X_1$ is NH-$L_2$. In some embodiments, $X_1$ is unsubstituted or substituted $C_1$-$C_{10}$ alkylene. In some embodiments, $X_1$ is unsubstituted or substituted $C_3$-$C_{10}$ cycloalkylene. In some embodiments, $X_1$ is unsubstituted or substituted arylene. In some embodiments, $X_1$ is unsubstituted or substituted heteroarylene. In some embodiments, $X_1$ is unsubstituted or substituted $C_1$-$C_{10}$ heterocycylene. In some embodiments, $X_1$ is unsubstituted or substituted peptide comprising 1, 2, 3, 4, 5, 6, 7, 8, 9, or 10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$, $L_2$-NH, or NH-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_2$ is a bond. In some embodiments, $X_2$ is C═O. In some embodiments, $X_2$ is (C═O)-$L_1$-(C═O). In some embodiments, $X_2$ is (C═O)-$L_1$. In some embodiments, $X_2$ is $L_1$-(C═O). In some embodiments, $X_2$ is O(CO). In some embodiments, $X_2$ is (CO)O. In some embodiments, $X_2$ is O. In some embodiments, $X_2$ is S. In some embodiments, $X_2$ is S—S. In some embodiments, $X_2$ is Se—Se—. In some embodiments, $X_2$ is NH. In some embodiments, $X_2$ is NR. In some embodiments, $X_2$ is NH(CO). In some embodiments, $X_2$ is (CO)NH. In some embodiments, $X_2$ is $L_2$-NH(CO). In some embodiments, $X_2$ is NH(CO)-$L_2$. In some embodiments, $X_2$ is —NR-$L_2$-NR. In some embodiments, $X_2$ is $L_2$-O. In some embodiments, $X_2$ is O-$L_2$. In some embodiments, $X_2$ is $L_2$-NH. In some embodiments, $X_2$ is NH-$L_2$. In some embodiments, $X_2$ is unsubstituted or substituted $C_1$-$C_{10}$ alkylene. In some embodiments, $X_2$ is unsubstituted or substituted $C_3$-$C_{10}$ cycloalkylene. In some embodiments, $X_2$ is unsubstituted or substituted arylene. In some embodiments, $X_2$ is unsubstituted or substituted heteroarylene. In some embodiments, $X_2$ is unsubstituted or substituted $C_1$-$C_{10}$ heterocycylene. In some embodiments, $X_2$ is unsubstituted or substituted peptide comprising 1, 2, 3, 4, 5, 6, 7, 8, 9, or 10 natural amino acids.

In some embodiments, $X_3$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$, $L_2$-NH, or NH-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids. In some embodiments, $X_3$ is a bond. In some embodiments, $X_3$ is C═O. In some embodiments, $X_3$ is (C═O)-$L_1$-(C═O). In some embodiments, $X_3$ is (C═O)-$L_1$. In some embodiments, $X_3$ is $L_1$-(C═O). In some embodiments, $X_3$ is O(CO). In some embodiments, $X_3$ is (CO)O. In some embodiments, $X_3$ is O. In some embodiments, $X_3$ is S. In some embodiments, $X_3$ is S—S. In some embodiments, $X_3$ is Se—Se—. In some embodiments, $X_3$ is NH. In some embodiments, $X_3$ is NR. In some embodiments, $X_3$ is NH(CO). In some embodiments, $X_3$ is (CO)NH. In some embodiments, $X_3$ is $L_2$-NH(CO). In some embodiments, $X_3$ is NH(CO)-$L_2$. In some embodiments, $X_3$ is —NR-$L_2$-NR. In some embodiments, $X_3$ is $L_2$-O. In some embodiments, $X_3$ is O-$L_2$. In some embodiments, $X_3$ is $L_2$-NH. In some embodiments, $X_3$ is NH-$L_2$. In some embodiments, $X_3$ is unsubstituted or substituted $C_1$-$C_{10}$ alkylene. In some embodiments, $X_3$ is unsubstituted or substituted $C_3$-$C_{10}$ cycloalkylene. In some embodiments, $X_3$ is unsubstituted or substituted arylene. In some embodiments, $X_3$ is unsubstituted or substituted heteroarylene. In some embodiments, $X_3$ is unsubstituted or substituted $C_1$-$C_{10}$ heterocycylene. In some embodiments, $X_3$ is unsubstituted or substituted peptide comprising 1, 2, 3, 4, 5, 6, 7, 8, 9, or 10 natural amino acids.

In some embodiments, each $L_1$ is independently unsubstituted or substituted arylene; unsubstituted or substituted heteroarylene; or unsubstituted or substituted $C_1$-$C_{10}$ heterocycylene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocycylene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, A is unsubstituted or substituted $C_3$-$C_{10}$ cycloalkyl; unsubstituted or substituted $C_1$-$C_{15}$ heterocyclyl; unsubstituted or substituted aryl; unsubstituted or substituted heteroaryl; and oligosaccharide comprising 3-15 same or different monosaccharides. In some embodiments, A is unsubstituted or substituted $C_3$-$C_{10}$ cycloalkyl. In some embodiments, A is unsubstituted or substituted $C_1$-$C_{15}$ heterocyclyl. In some embodiments, A is unsubstituted or substituted aryl. In some embodiments, A is unsubstituted or substituted heteroaryl. In some embodiments, unsubstituted or substituted heteroaryl is unsubstituted or substituted quinolinyl or unsubstituted or substituted acridinyl. In some embodiments, A is an oligosaccharide comprising 3, 4, 5, 6, 7, 8, 9, 10, 11, 12, 13, 14, or 15 same or different monosaccharides.

In some embodiments of Formula IV, $n_1$ and $n_2$ are each independently 0, 1, 2, 3, or 4. In some embodiments, $R_1$ and $R_2$ are each hydrogen. In some embodiments, $X_1$ is a bond, (C═O)-$L_1$, $L_1$-(C═O), and O; and $L_1$ is unsubstituted or substituted $C_1$-$C_{10}$ heterocycylene. In some embodiments, $X_2$ is bond. In some embodiments, $X_3$ is a bond, O, $L_2$-NH, or NH-$L_2$. In some embodiments, A is unsubstituted or substituted heteroaryl.

Provided in one aspect is a compound of Formula (V), or an enantiomer, an enantiomeric mixture, a diastereomer, a diastereomeric mixture, or a pharmaceutically acceptable salt thereof:

to $X_4$ are each independently H, OH, $O(CO)NH_2$, halo, unsubstituted or substituted amino group, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide;

$R_8$ is $OR_{10}$ or oligopeptide bond formed with a natural amino acid;

(V)

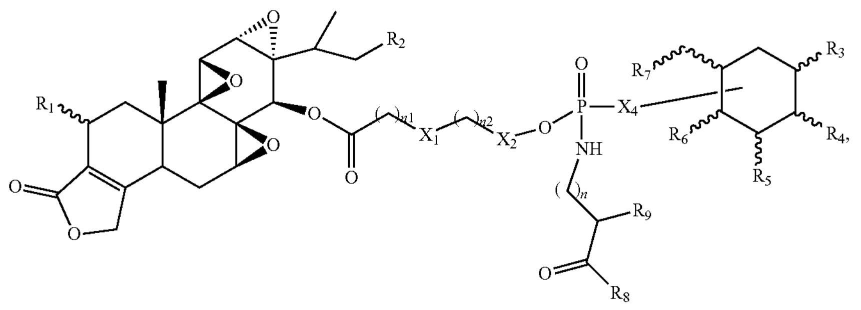

wherein n, $n_1$, and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_4$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl;

$X_4$ is attached to any one of $R_3$, $R_4$, $R_5$, $R_6$ and $R_7$ and the remaining $R_3$, $R_4$, $R_5$, $R_6$ and $R_7$ that are not attached $R_{10}$ is unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $R_9$ is H or a side chain of natural amino acid.

In some embodiments, n is 0, 1, 2, 3, 4, 5, 6, 7, 8, 9, 10, 11, 12, 13, 14, or 15. In some embodiments, $n_1$ is 0, 1, 2, 3, 4, 5, 6, 7, 8, 9, 10, 11, 12, 13, 14, or 15. In some embodiments, $n_2$ is 0, 1, 2, 3, 4, 5, 6, 7, 8, 9, 10, 11, 12, 13, 14, or 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_4$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, each $L_1$ is independently unsubstituted or substituted arylene; unsubstituted or substituted heteroarylene; or unsubstituted or substituted $C_1$-$C_{10}$ heterocycylene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocycylene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $X_4$ is attached to $R_3$; and $R_4$, $R_5$, $R_6$ and $R_7$ are each independently any one of the following: H; OH; O(CO)$NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_4$ is attached to $R_4$; and $R_3$, $R_5$, $R_6$ and $R_7$ are each independently any one of the following: H; OH; O(CO)$NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_4$ is attached to $R_5$; and $R_3$, $R_4$, $R_6$ and $R_7$ are each independently any one of the following: H; OH; O(CO)$NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_4$ is attached to $R_6$; and $R_3$, $R_4$, $R_5$ and $R_7$ are each independently any one of the following: H; OH; O(CO)$NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_4$ is attached to $R_7$; and $R_3$, $R_4$, $R_5$ and $R_6$ are each independently any one of the following: H; OH; O(CO)$NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $R_8$ is $OR_{10}$ or oligopeptide bond formed with a natural amino acid. In some embodiments, $R_8$ is $OR_{10}$. In some embodiments, $R_8$ is oligopeptide bond formed with a natural amino acid.

In some embodiments, $R_{10}$ is unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, $R_{10}$ is unsubstituted or substituted $C_1$-$C_{10}$ alkyl. In some embodiments, $R_{10}$ is unsubstituted or substituted $C_3$-$C_{10}$ cycloalkyl. In some embodiments, $R_{10}$ is unsubstituted or substituted $C_1$-$C_{10}$ acyl. In some embodiments, $R_{10}$ is unsubstituted or substituted $C_1$-$C_{10}$ carboxyl ester. In some embodiments, $R_{10}$ is unsubstituted or substituted $C_1$-$C_{10}$ alkyl ketone. In some embodiments, $R_{10}$ is unsubstituted or substituted $C_1$-$C_{10}$ alkyl ether. In some embodiments, $R_{10}$ is unsubstituted or substituted aryl. In some embodiments, $R_{10}$ is unsubstituted or substituted heteroaryl. In some embodiments, $R_{10}$ is unsubstituted or substituted $C_1$-$C_{10}$ heterocycyl.

In some embodiments, $R_9$ is H; or a side chain of natural amino acid. In some embodiments, $R_9$ is H. In some embodiments, $R_9$ is a side chain of natural amino acid.

Provided in one aspect is a compound of Formula (VI), or an enantiomer, an enantiomeric mixture, a diastereomer, a diastereomeric mixture, or a pharmaceutically acceptable salt thereof:

(VI)

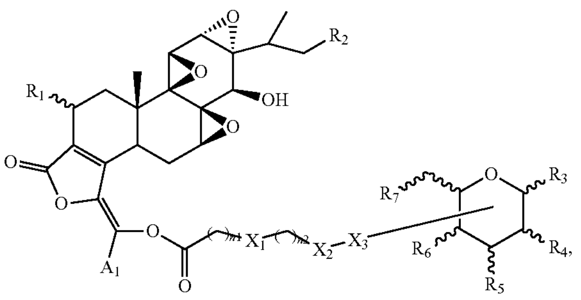

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl;

$X_3$ is attached to any one of $R_3$, $R_4$, $R_5$, $R_6$ and $R_7$ and the remaining $R_3$, $R_4$, $R_5$, $R_6$ and $R_7$ that are not attached to $X_3$ are each independently H, OH, $O(CO)NH_2$, halo, unsubstituted or substituted amino group, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide; and $A_1$ is unsubstituted or substituted $C_3$-$C_{15}$ cycloalkyl, unsubstituted or substituted $C_1$-$C_{15}$ heterocyclyl, unsubstituted or substituted aryl, or unsubstituted or substituted heteroaryl, or

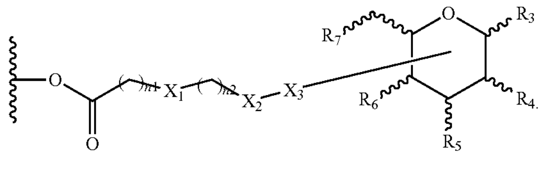

In some embodiments, $n_1$ is 0, 1, 2, 3, 4, 5, 6, 7, 8, 9, 10, 11, 12, 13, 14, or 15. In some embodiments, $n_2$ is 0, 1, 2, 3, 4, 5, 6, 7, 8, 9, 10, 11, 12, 13, 14, or 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_3$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, each $L_1$ is independently unsubstituted or substituted arylene; unsubstituted or substituted heteroarylene; or unsubstituted or substituted $C_1$-$C_{10}$ heterocycylene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocycylene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $X_3$ is attached to $R_3$; and $R_4$, $R_5$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_3$ is attached to $R_4$; and $R_3$, $R_5$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_3$ is attached to $R_5$; and $R_3$, $R_4$, $R_6$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_3$ is attached to $R_6$; and $R_3$, $R_4$, $R_5$ and $R_7$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $X_3$ is attached to $R_7$; and $R_3$, $R_4$, $R_5$ and $R_6$ are each independently any one of the following: H; OH; $O(CO)NH_2$; halo; amino group; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; unsubstituted or substituted $C_1$-$C_{10}$ heterocycyl; unsubstituted or substituted peptide comprising 1-10 amino acids; and forms a glycosidic bond with a natural monosaccharide.

In some embodiments, $A_1$ is unsubstituted or substituted $C_3$-$C_{15}$ cycloalkyl; unsubstituted or substituted $C_1$-$C_{15}$ heterocycyl; unsubstituted or substituted aryl; unsubstituted or substituted heteroaryl; or

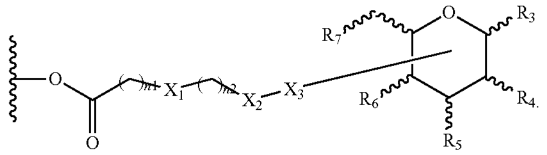

In some embodiments, $A_1$ is unsubstituted or substituted $C_3$-$C_{15}$ cycloalkyl. In some embodiments, $A_1$ is unsubstituted or substituted $C_1$-$C_{15}$ heterocycyl. In some embodiments, $A_1$ is unsubstituted or substituted aryl. In some embodiments, $A_1$ is unsubstituted or substituted heteroaryl. In some embodiments, $A_1$ is

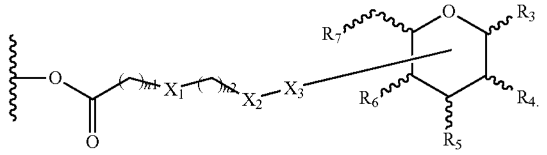

Provided in one aspect is a compound of Formula (VII), or an enantiomer, an enantiomeric mixture, a diastereomer, a diastereomeric mixture, or a pharmaceutically acceptable salt thereof:

(VII)

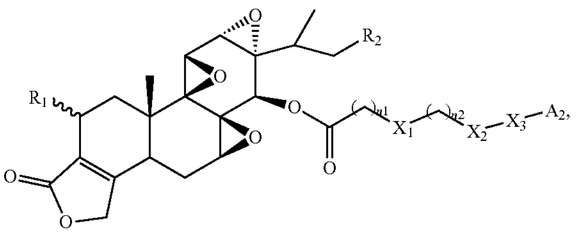

wherein $n_1$ and $n_2$ are each independently is 0-15;

$R_1$ and $R_2$ are each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$X_1$, $X_2$ and $X_3$ are each independently a bond, C═O, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, —NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocycylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocycylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $A_2$ is linear- or star-shaped poly (d-glutamic acid), poly (1-glutamic acid), or poly (dl-glutamic acid).

In some embodiments, $n_1$ is 0, 1, 2, 3, 4, 5, 6, 7, 8, 9, 10, 11, 12, 13, 14, or 15. In some embodiments, $n_2$ is 0, 1, 2, 3, 4, 5, 6, 7, 8, 9, 10, 11, 12, 13, 14, or 15.

In some embodiments, $R_1$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $R_2$ is OH; hydrogen; halo; unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; or unsubstituted or substituted $C_1$-$C_{10}$ alkyl ether.

In some embodiments, $X_1$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_2$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, $X_3$ is any one of the following: bond; C═O, (C═O)-$L_1$-(C═O), (C═O)-$L_1$, $L_1$-(C═O), O(CO), or (CO)O; O, S, S—S, or Se—Se—; NH, NR, NH(CO), (CO)NH, $L_2$-NH(CO), NH(CO)-$L_2$, —NR-$L_2$-NR, $L_2$-O, O-$L_2$; unsubstituted or substituted $C_1$-$C_{10}$ alkylene, unsubstituted or substituted $C_3$-$C_{10}$ cycloalkylene; unsubstituted or substituted arylene; unsubstituted or substituted heteroarylene; unsubstituted or substituted $C_1$-$C_{10}$ heterocycylene; and unsubstituted or substituted peptide comprising 1-10 natural amino acids.

In some embodiments, each $L_1$ is independently unsubstituted or substituted arylene; unsubstituted or substituted heteroarylene; or unsubstituted or substituted $C_1$-$C_{10}$ heterocycylene. In some embodiments, each $L_1$ is independently unsubstituted or substituted arylene. In some embodiments, each $L_1$ is independently unsubstituted or substituted heteroarylene. In some embodiments, each $L_1$ is independently unsubstituted or substituted $C_1$-$C_{10}$ heterocycylene.

In some embodiments, each R is independently unsubstituted or substituted $C_1$-$C_{10}$ alkyl; unsubstituted or substituted $C_3$-$C_{10}$ cycloalkyl; unsubstituted or substituted $C_1$-$C_{10}$ acyl; unsubstituted or substituted $C_1$-$C_{10}$ carboxyl ester; unsubstituted or substituted $C_1$-$C_{10}$ alkyl ketone; unsubstituted or substituted $C_1$-$C_{10}$ alkyl ether; unsubstituted or substituted aryl; unsubstituted or substituted heteroaryl; or unsubstituted or substituted $C_1$-$C_{10}$ heterocycyl. In some embodiments, each R is independently unsubstituted or substituted $C_1$-$C_{10}$ alkyl. In some embodiments, each R is independently unsubstituted or substituted $C_3$-$C_{10}$ cycloalkyl. In some embodiments, each R is independently unsubstituted or substituted $C_1$-$C_{10}$ acyl. In some embodiments, each R is independently unsubstituted or substituted $C_1$-$C_{10}$ carboxyl ester. In some embodiments, each R is independently unsubstituted or substituted $C_1$-$C_{10}$ alkyl ketone. In some embodiments, each R is independently unsubstituted or substituted $C_1$-$C_{10}$ alkyl ether. In some embodiments, each R is independently unsubstituted or substituted aryl. In some embodiments, each R is independently unsubstituted or substituted heteroaryl. In some embodiments, each R is independently unsubstituted or substituted $C_1$-$C_{10}$ heterocycyl.

In some embodiments, $A_2$ is linear- or star-shaped poly (d-glutamic acid); linear- or star-shaped poly (l-glutamic acid); or linear- or star-shaped poly (dl-glutamic acid). In some embodiments, $A_2$ is linear- or star-shaped poly (d-glutamic acid). In some embodiments, $A_2$ is linear- or star-shaped poly (l-glutamic acid). In some embodiments, $A_2$ is or linear- or star-shaped poly (dl-glutamic acid).

In any of the embodiments disclosed herein, the compound is any one of the compounds disclosed in any on the following tables.

TABLE 1
| Compound No. | Structure |
| --- | --- |
| Compound 1 | 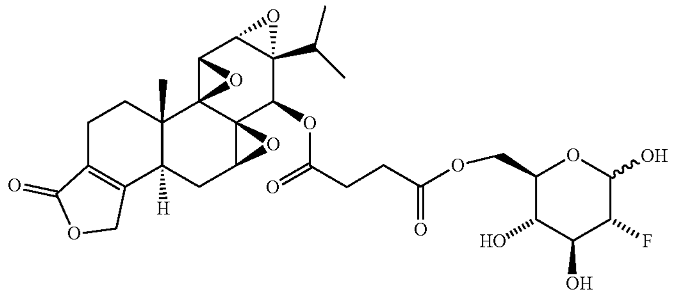 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)OC[C@H]1OC(O)[C@H](F)[C@@H](O)[C@@H]1O] |
| Compound 2 | 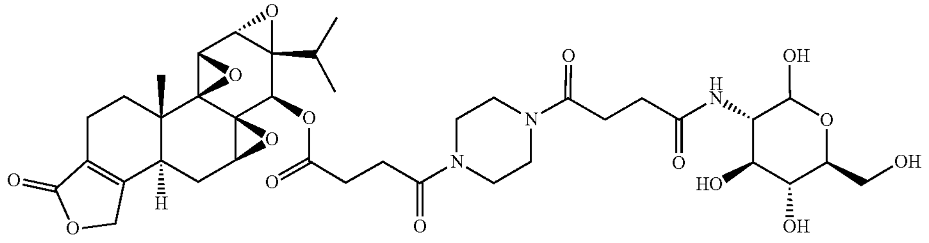 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(C(=O)CCC(=O)N[C@@H]2C(O)O[C@@H](CO)[C@H](O)[C@H]2O)CC1] |
| Compound 3 | 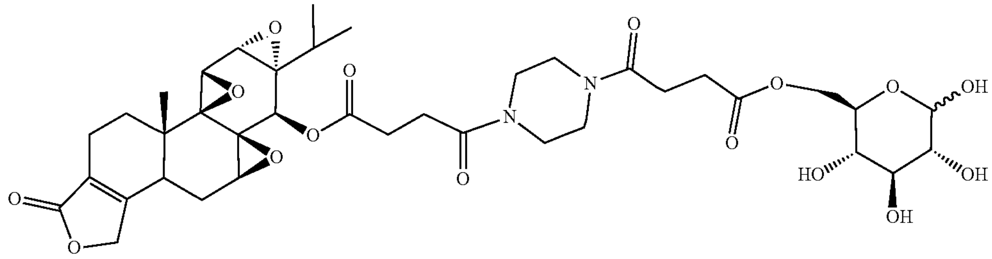 |
| Compound 4 | 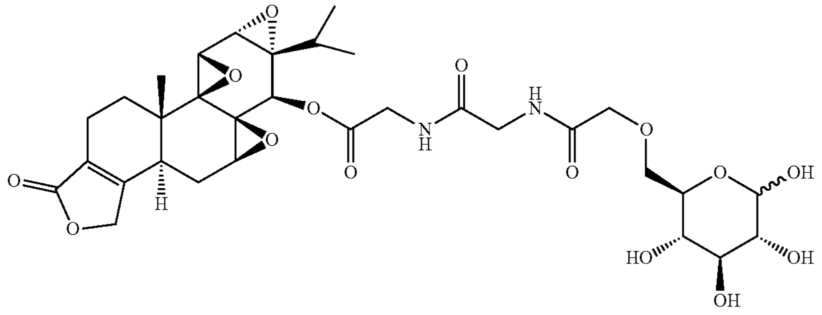 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CNC(=O)CNC(=O)COC[C@H]1OC(O)[C@H](O)[C@@H](O)[C@@H]1O] |
| Compound 5 | 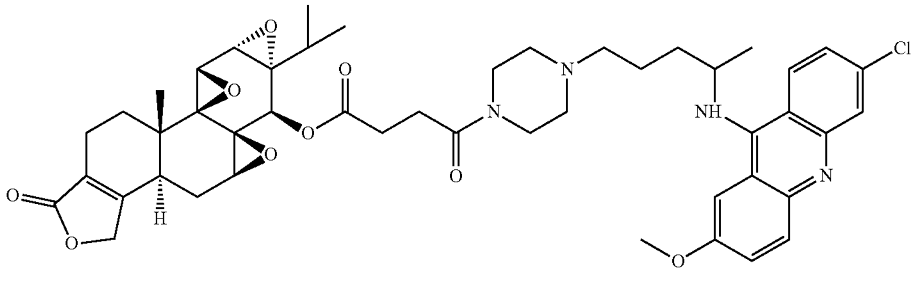 [SMILES: COc1ccc2nc3cc(Cl)ccc3c(NC(C)CCCN3CCN(C(=O)CCC(=O)O[C@@H]4[C@@]5(C(C)C)O[C@H]5[C@@H]5O[C@]56[C@]45O[C@H]5C[C@H]4C5=C(CC[C@@]46C)C(=O)OC5)CC3)c2c1] |

TABLE 1-continued
| Compound No. | Structure |
| --- | --- |
| Compound 6 | 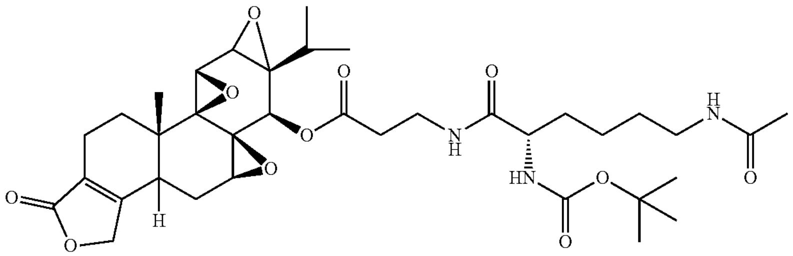 [SMILES: CC(=O)NCCCC[C@H](NC(=O)OC(C)(C)C)C(=O)NCCC(=O)O[C@@H]1[C@@]2(C(C)C)OC2[C@@H]2O[C@]23[C@]12O[C@H]2CC1C2=C(CC[C@@]13C)C(=O)OC2] |
| Compound 7 | 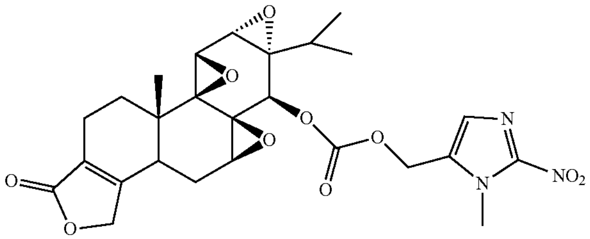 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)OCc1cnc([N+](=O)[O-])n1C] |
| Compound 8 | 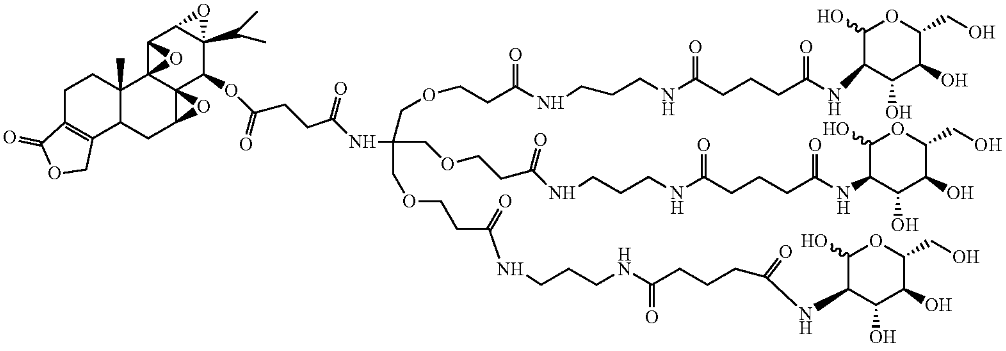 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC(COCCC(=O)NCCCNC(=O)CCCC(=O)N[C@H]1C(O)O[C@H](CO)[C@@H](O)[C@@H]1O)(COCCC(=O)NCCCNC(=O)CCCC(=O)N[C@H]1C(O)O[C@H](CO)[C@@H](O)[C@@H]1O)COCCC(=O)NCCCNC(=O)CCCC(=O)N[C@H]1C(O)O[C@H](CO)[C@@H](O)[C@@H]1O] |
| Compound 9 | 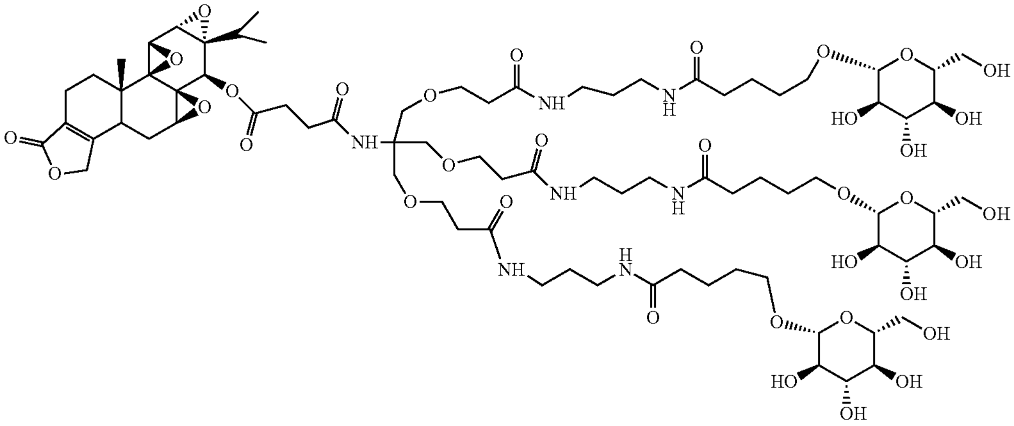 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC(COCCC(=O)NCCCNC(=O)CCCCO[C@@H]1O[C@H](CO)[C@@H](O)[C@H](O)[C@H]1O)(COCCC(=O)NCCCNC(=O)CCCCO[C@@H]1O[C@H](CO)[C@@H](O)[C@H](O)[C@H]1O)COCCC(=O)NCCCNC(=O)CCCCO[C@@H]1O[C@H](CO)[C@@H](O)[C@H](O)[C@H]1O] |

TABLE 1-continued
| Compound No. | Structure |
| --- | --- |
| Compound 10 | 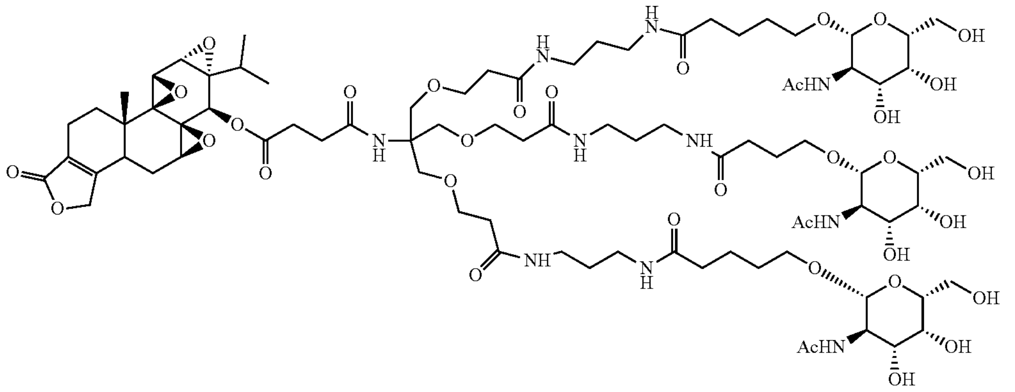 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O] |
| Compound 11 | 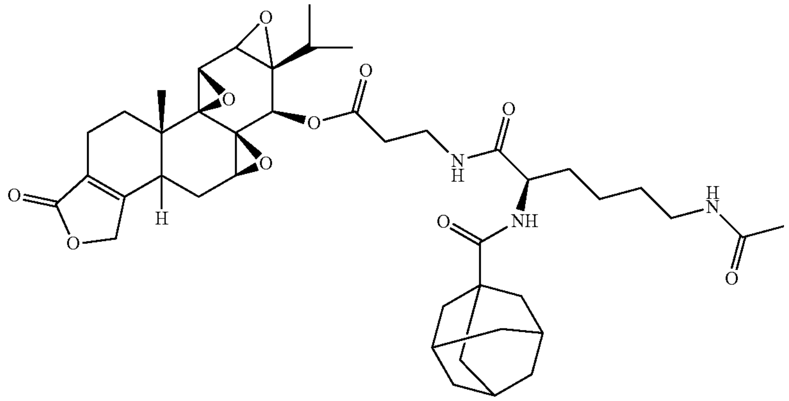 [SMILES: CC(=O)NCCCC[C@@H](NC(=O)C12CC3CC(CC(C3)C1)C2)C(=O)NCCC(=O)O[C@@H]1[C@@]2(C(C)C)OC2[C@@H]2O[C@]23[C@]12O[C@H]2CC1C2=C(CC[C@@]13C)C(=O)OC2] |
| Compound 12 | 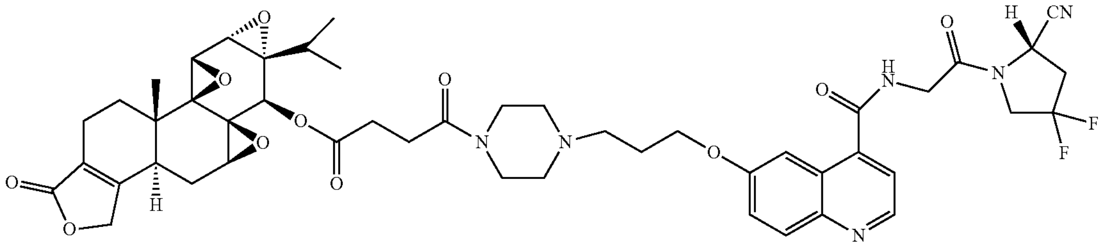 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(CCCOc2ccc3nccc(C(=O)NCC(=O)N4CC(F)(F)C[C@H]4C#N)c3c2)CC1] |
| Compound 13 | 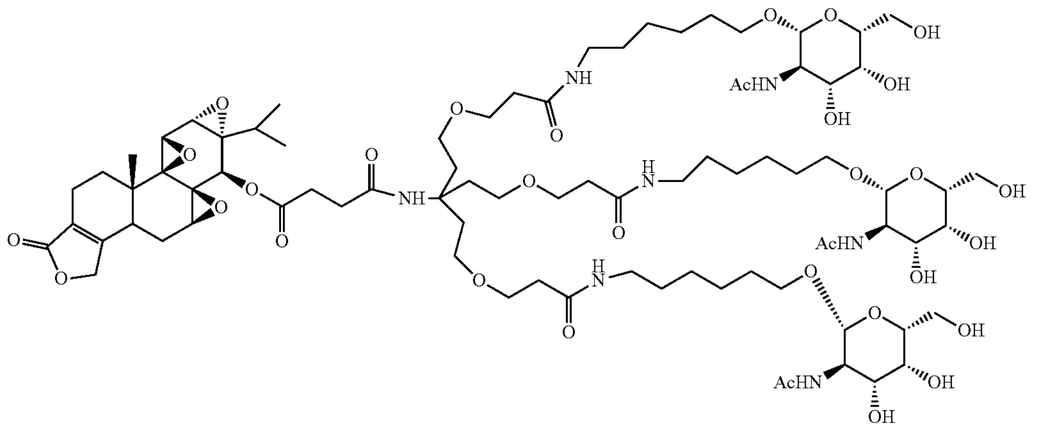 [SMILES: CC(=O)N[C@H]1[C@H](OCCCCCCNC(=O)CCOCCC(CCOCCC(=O)NCCCCCCO[C@@H]2O[C@H](CO)[C@H](O)[C@H](O)[C@H]2NC(C)=O)(CCOCCC(=O)NCCCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O] |

TABLE 1-continued
| Compound No. | Structure |
|---|---|
| Compound 14 | 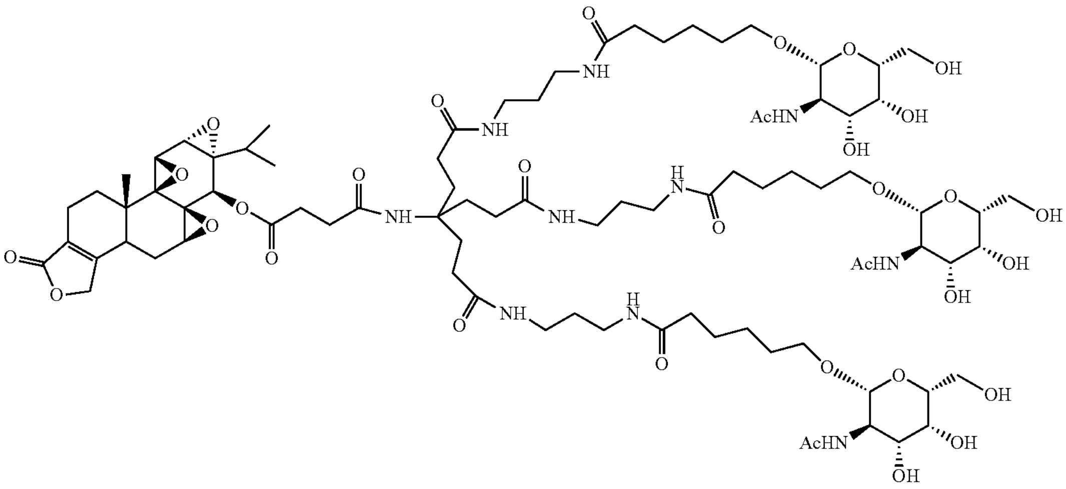 [SMILES: CC(=O)N[C@H]1[C@H](OCCCCCC(=O)NCCCNC(=O)CCC(CCC(=O)NCCCNC(=O)CCCCCO[C@@H]2O[C@H](CO)[C@H](O)[C@H](O)[C@H]2NC(C)=O)(CCC(=O)NCCCNC(=O)CCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O] |
TABLE 2
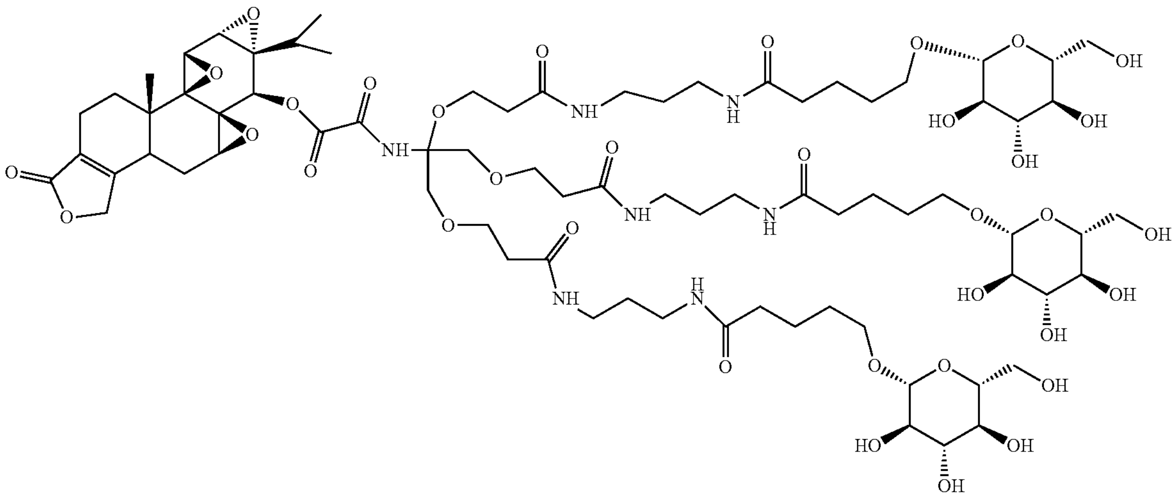 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)C(=O)NC(COCCC(=O)NCCCNC(=O)CCCCO[C@@H]1O[C@H](CO)[C@@H](O)[C@H](O)[C@H]1O)(COCCC(=O)NCCCNC(=O)CCCCO[C@@H]1O[C@H](CO)[C@@H](O)[C@H](O)[C@H]1O)OCCC(=O)NCCCNC(=O)CCCCO[C@@H]1O[C@H](CO)[C@@H](O)[C@H](O)[C@H]1O]

TABLE 2-continued
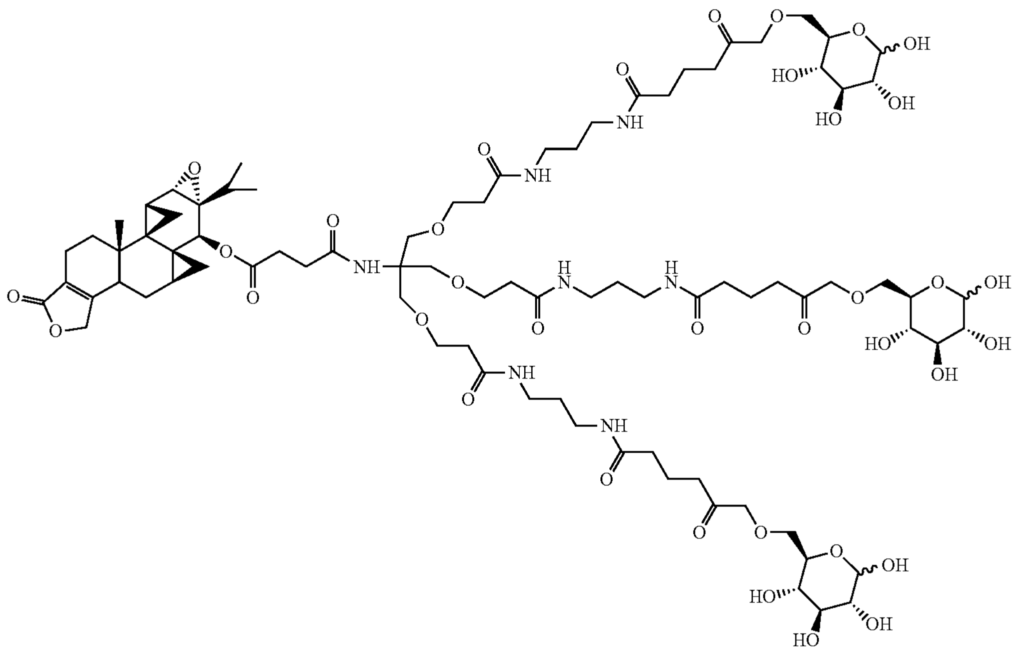 [SMILES: CC(C)[C@]12O[C@H]1[C@@H]1C[C@]13[C@]1(C[C@H]1CC1C4=C(CC[C@@]13C)C(=O)OC4)[C@@H]2OC(=O)CCC(=O)NC(COCCC(=O)NCCCNC(=O)CCCC(=O)COC[C@H]1OC(O)[C@H](O)[C@@H](O)[C@@H]1O)(COCCC(=O)NCCCNC(=O)CCCC(=O)COC[C@H]1OC(O)[C@H](O)[C@@H](O)[C@@H]1O)COCCC(=O)NCCCNC(=O)CCCC(=O)COC[C@H]1OC(O)[C@H](O)[C@@H](O)[C@@H]1O]
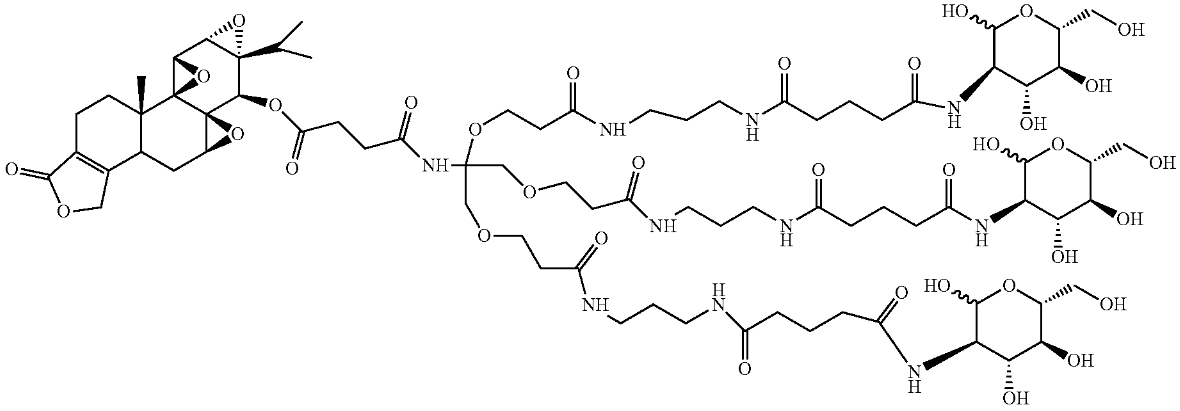 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC(COCCC(=O)NCCCNC(=O)CCCC(=O)N[C@H]1C(O)O[C@H](CO)[C@@H](O)[C@@H]1O)(COCCC(=O)NCCCNC(=O)CCCC(=O)N[C@H]1C(O)O[C@H](CO)[C@@H](O)[C@@H]1O)OCCC(=O)NCCCNC(=O)CCCC(=O)N[C@H]1C(O)O[C@H](CO)[C@@H](O)[C@@H]1O]
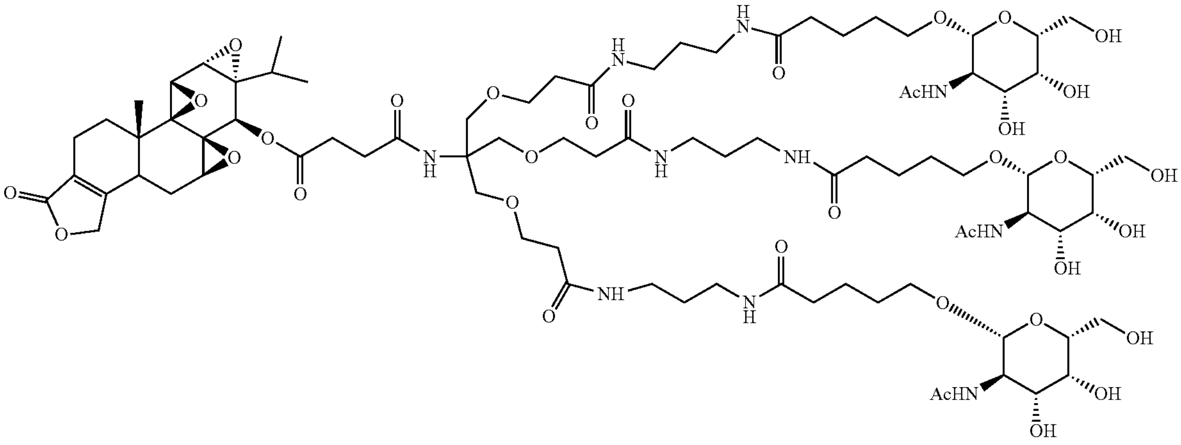 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]

TABLE 2-continued
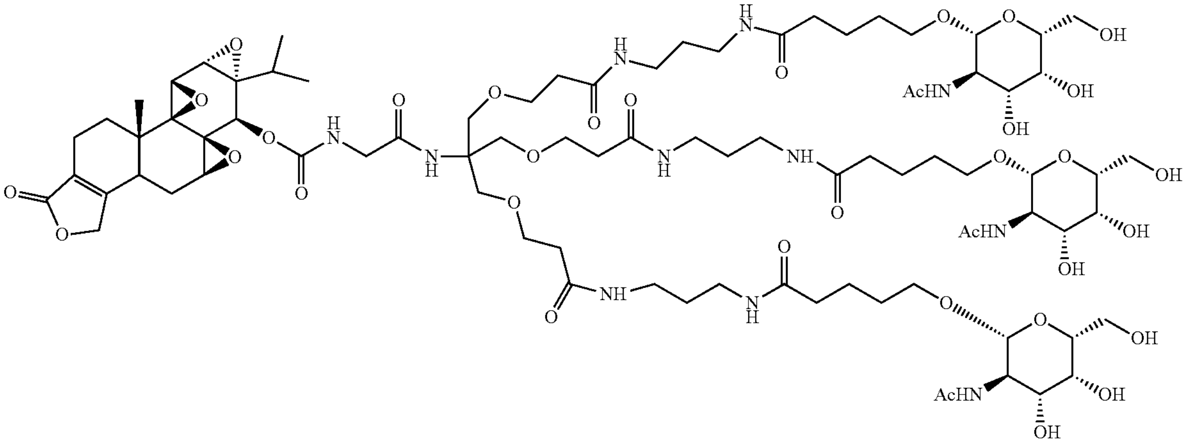 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CNC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]
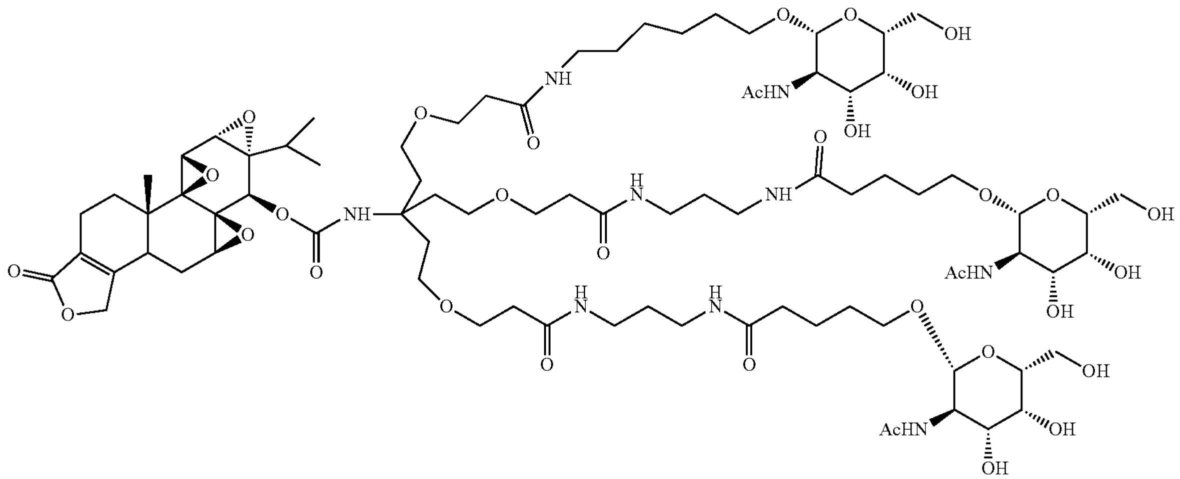 [SMILES: CC(=O)N[C@H]1[C@H](OCCCCCCNC(=O)CCOCCC(CCOCCC(=O)NCCCNC(=O)CCCCO[C@@H]2O[C@H](CO)[C@H](O)[C@H](O)[C@H]2NC(C)=O)(CCOCCC(=O)NCCCNC(=O)CCCCO[C@@H]2O[C@H](CO)[C@H](O)[C@H](O)[C@H]2NC(C)=O)NC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]
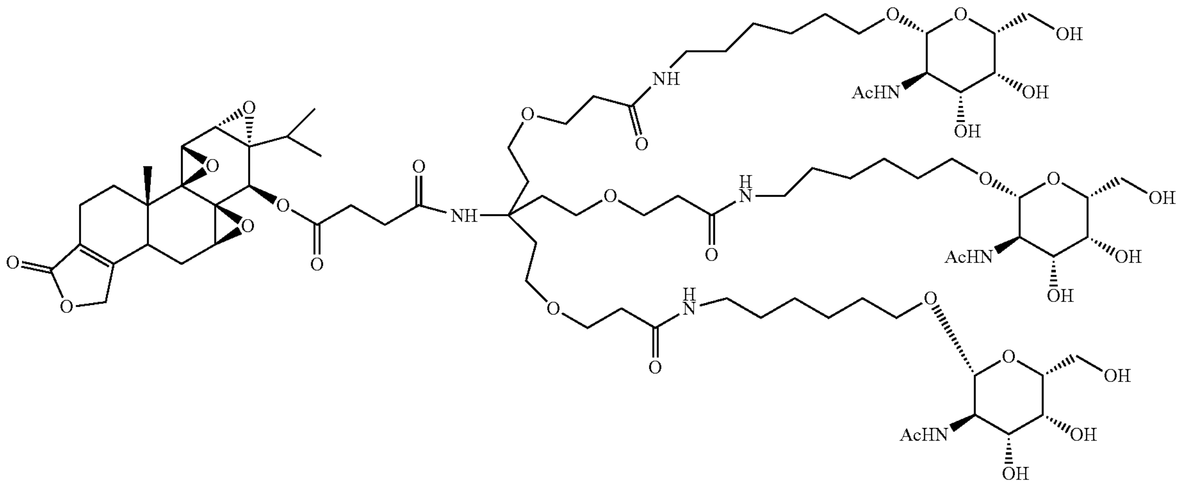 [SMILES: CC(=O)N[C@H]1[C@H](OCCCCCCNC(=O)CCOCCC(CCOCCC(=O)NCCCCCCO[C@@H]2O[C@H](CO)[C@H](O)[C@H](O)[C@H]2NC(C)=O)(CCOCCC(=O)NCCCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]

TABLE 2-continued
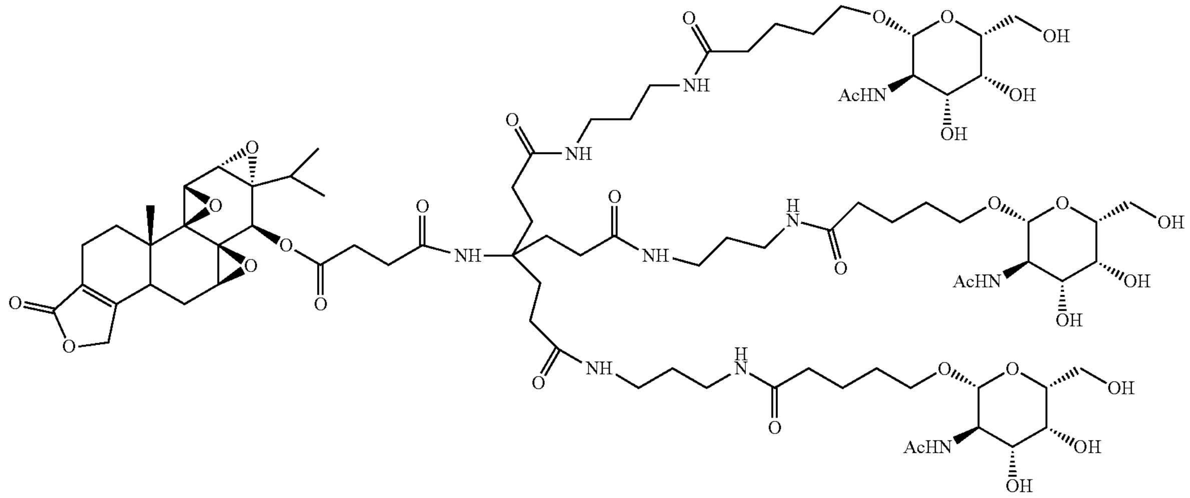 [SMILES: CC(=O)N[C@H]1[C@H](OCCCCC(=O)NCCCNC(=O)CCC(CCC(=O)NCCCNC(=O)CCCCO[C@@H]2O[C@H](CO)[C@H](O)[C@H](O)[C@H]2NC(C)=O)(CCC(=O)NCCCNC(=O)CCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]
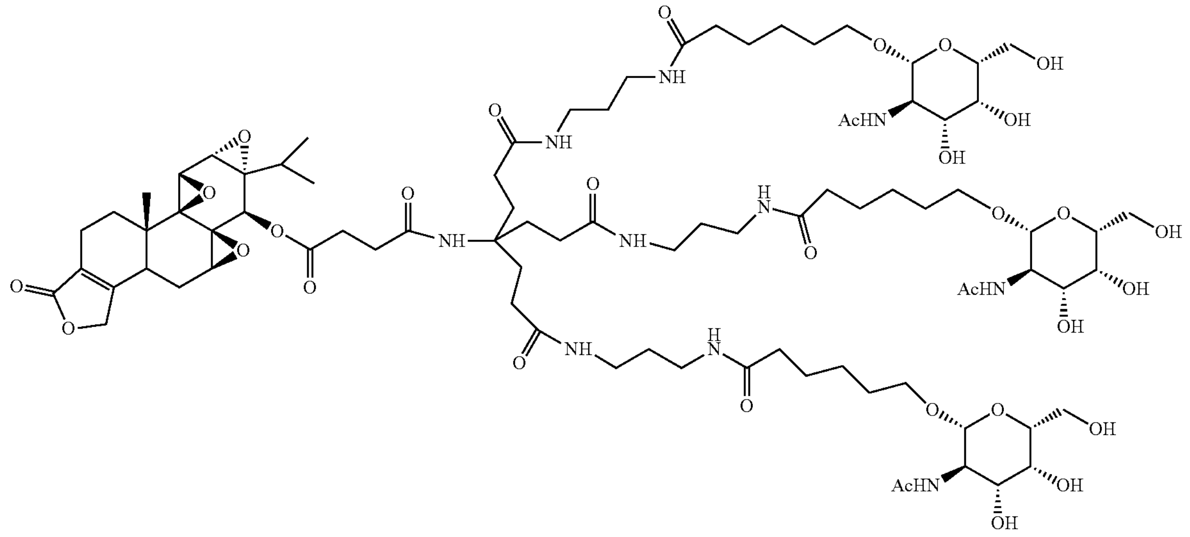 [SMILES: CC(=O)N[C@H]1[C@H](OCCCCCC(=O)NCCCNC(=O)CCC(CCC(=O)NCCCNC(=O)CCCCCO[C@@H]2O[C@H](CO)[C@H](O)[C@H](O)[C@H]2NC(C)=O)(CCC(=O)NCCCNC(=O)CCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]

TABLE 2-continued
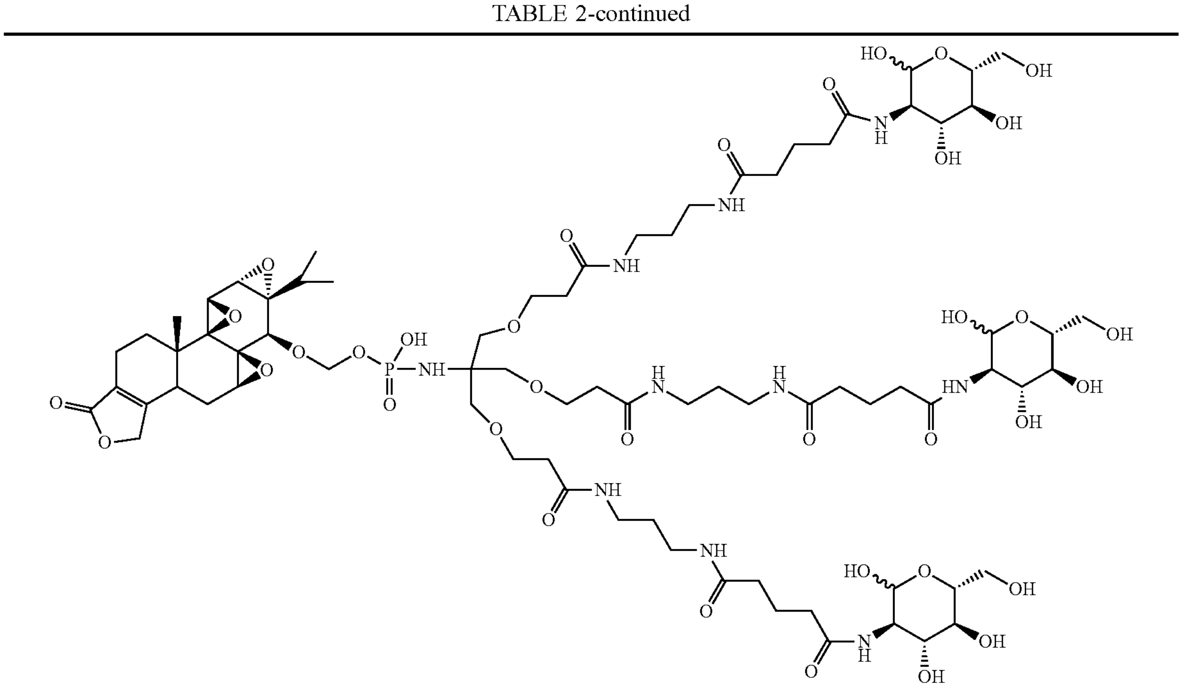
TABLE 3
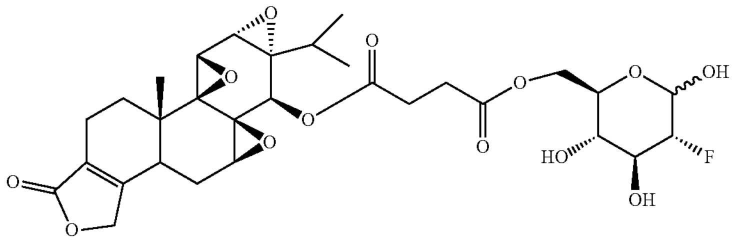 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)OC[C@H]1OC(O)[C@H](F)[C@@H](O)[C@@H]1O]
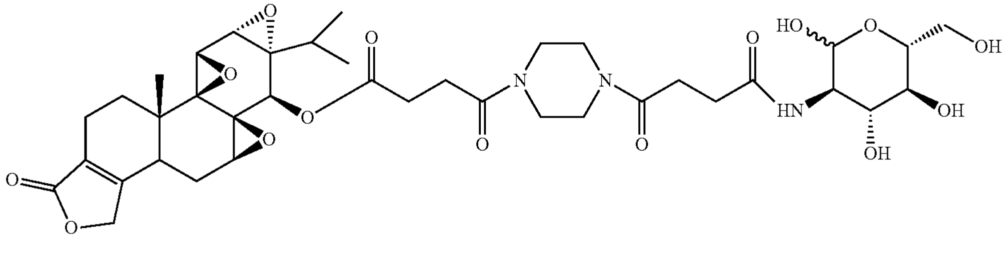 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)N1CCN(C(=O)CCC(=O)N[C@H]2C(O)O[C@H](CO)[C@@H](O)[C@@H]2O)CC1]
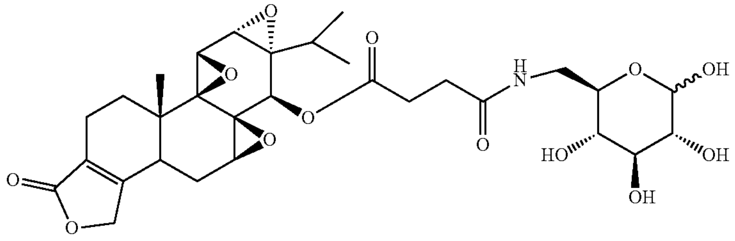 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC[C@H]1OC(O)[C@H](O)[C@@H](O)[C@@H]1O]

TABLE 3-continued
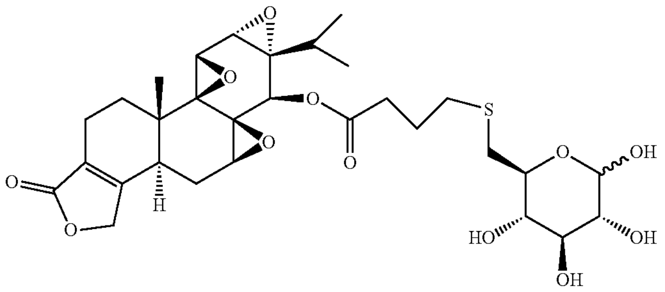 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCCSC[C@H]1OC(O)[C@H](O)[C@@H](O)[C@@H]1O]
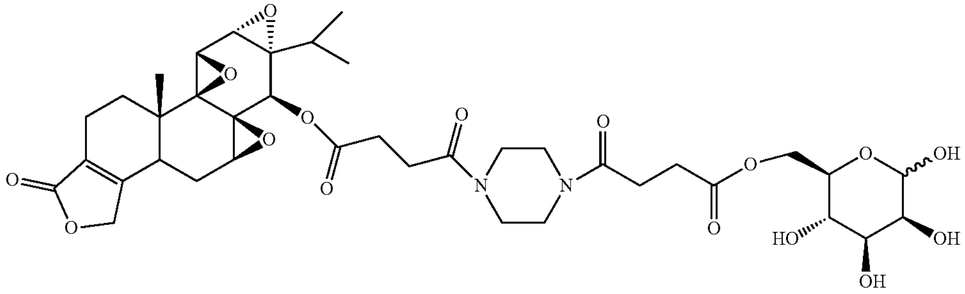 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)N1CCN(C(=O)CCC(=O)OC[C@H]2OC(O)[C@@H](O)[C@@H](O)[C@@H]2O)CC1]
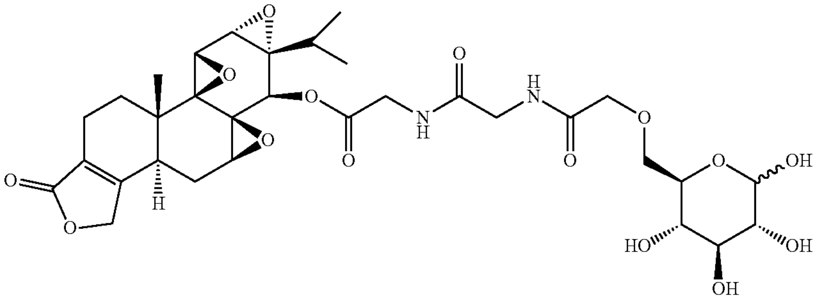 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CNC(=O)CNC(=O)COC[C@H]1OC(O)[C@H](O)[C@@H](O)[C@@H]1O]
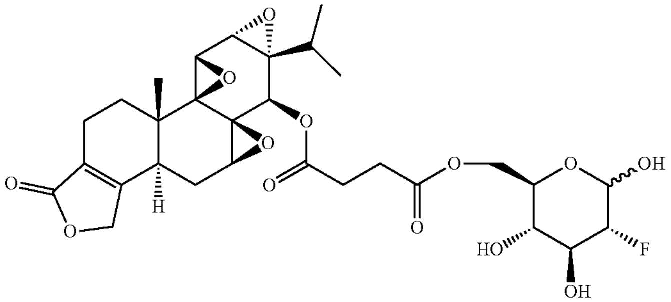 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)OC[C@H]1OC(O)[C@H](F)[C@@H](O)[C@@H]1O]
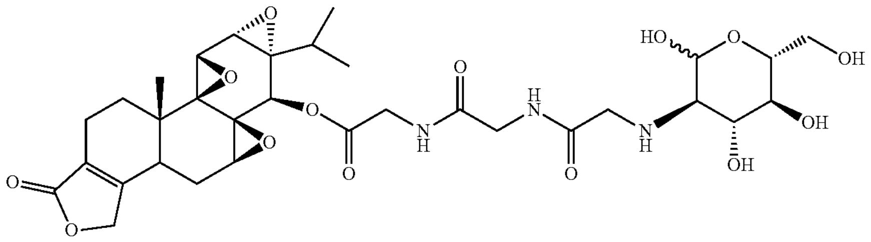 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CNC(=O)CNC(=O)CN[C@H]1C(O)O[C@H](CO)[C@@H](O)[C@@H]1O]

TABLE 3-continued
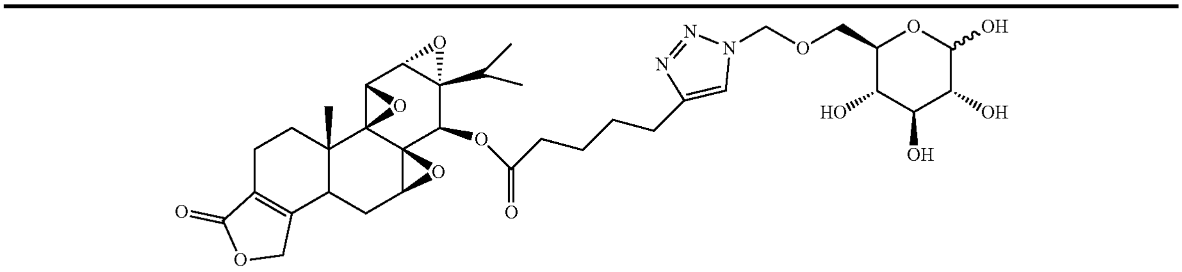
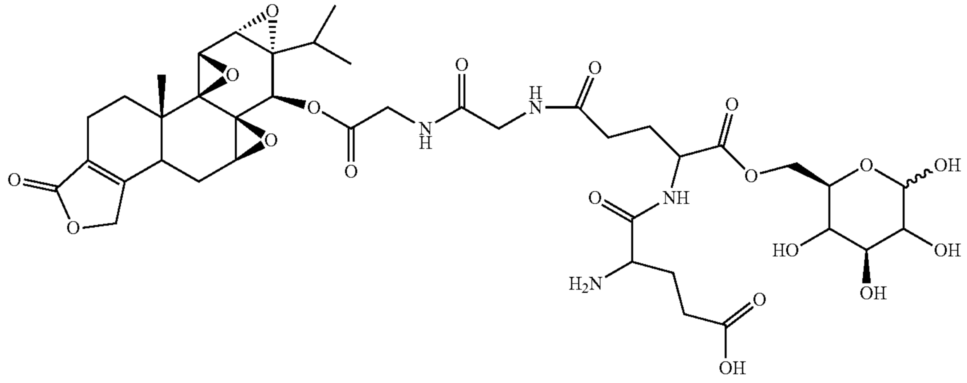 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CNC(=O)CNC(=O)CCC(NC(=O)C(N)CCC(=O)O)C(=O)OC[C@H]1OC(O)C(O)[C@@H](O)C1O]
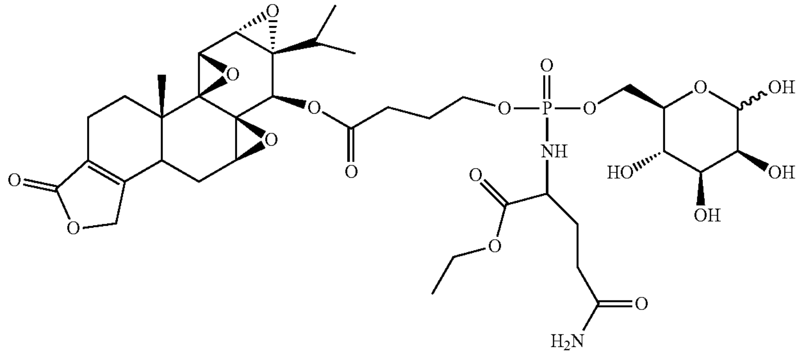 [SMILES: CCOC(=O)C(CCC(N)=O)NP(=O)(OCCCC(=O)O[C@@H]1[C@@]2(C(C)C)O[C@H]2[C@@H]2O[C@]23[C@]12O[C@H]2CC1C2=C(CC[C@@]13C)C(=O)OC2)OC[C@H]1OC(O)[C@@H](O)[C@@H](O)[C@@H]1O]
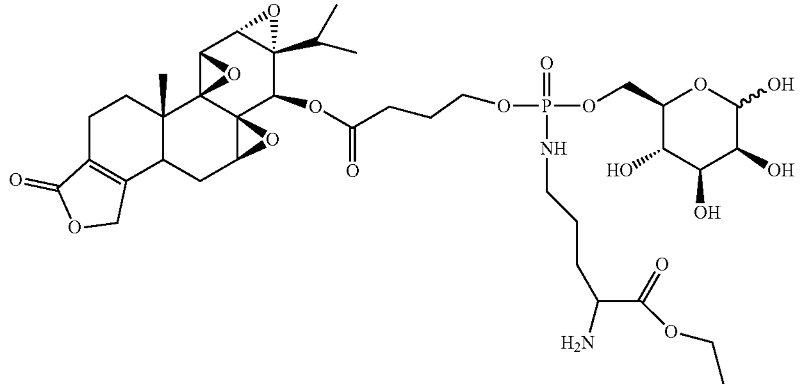 [SMILES: CCOC(=O)C(N)CCCNP(=O)(OCCCC(=O)O[C@@H]1[C@@]2(C(C)C)O[C@H]2[C@@H]2O[C@]23[C@]12O[C@H]2CC1C2=C(CC[C@@]13C)C(=O)OC2)OC[C@H]1OC(O)[C@@H](O)[C@@H](O)[C@@H]1O]
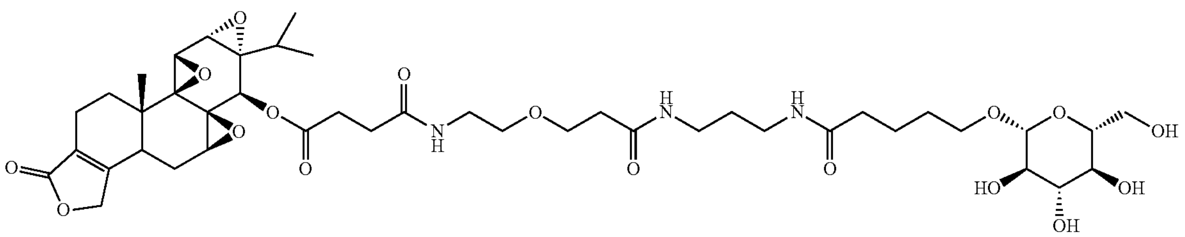 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NCCOCCC(=O)NCCCNC(=O)CCCCO[C@@H]1O[C@H](CO)[C@@H](O)[C@H](O)[C@H]1O]

TABLE 3-continued
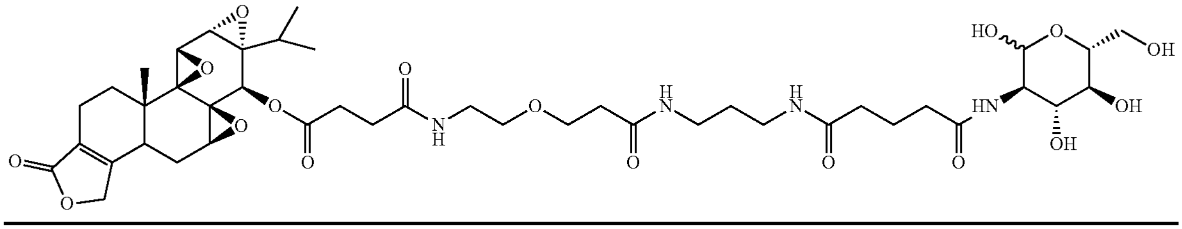
TABLE 4
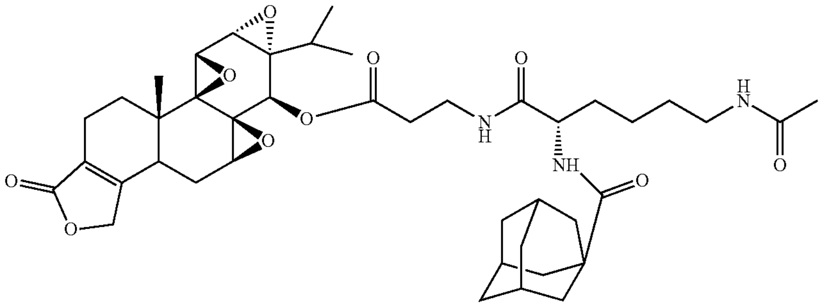 [SMILES: CC(=O)NCCCC[C@H](NC(=O)C12CC3CC(CC(C3)C1)C2)C(=O)NCCC(=O)O[C@@H]1[C@@]2(C(C)C)O[C@H]2[C@@H]2O[C@]23[C@]12O[C@H]2CC1C2=C(CC[C@@]13C)C(=O)OC2]
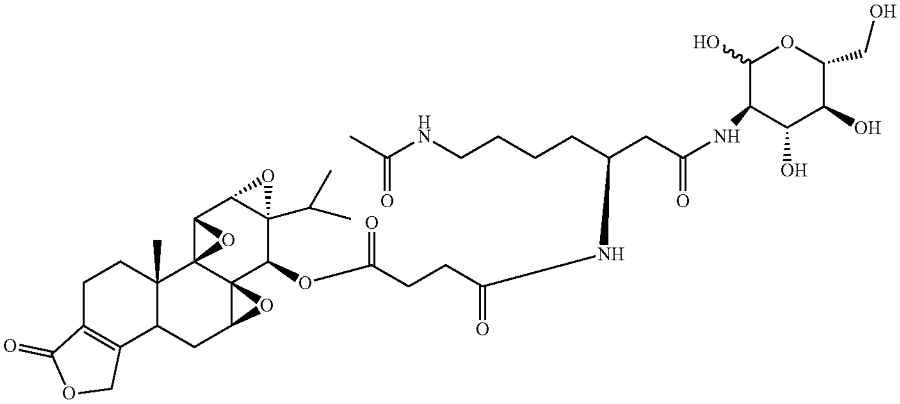 [SMILES: CC(=O)NCCCC[C@@H](CC(=O)N[C@H]1C(O)O[C@H](CO)[C@@H](O)[C@@H]1O)NC(=O)CCC(=O)O[C@@H]1[C@@]2(C(C)C)O[C@H]2[C@@H]2O[C@]23[C@]12O[C@H]2CC1C2=C(CC[C@@]13C)C(=O)OC2]
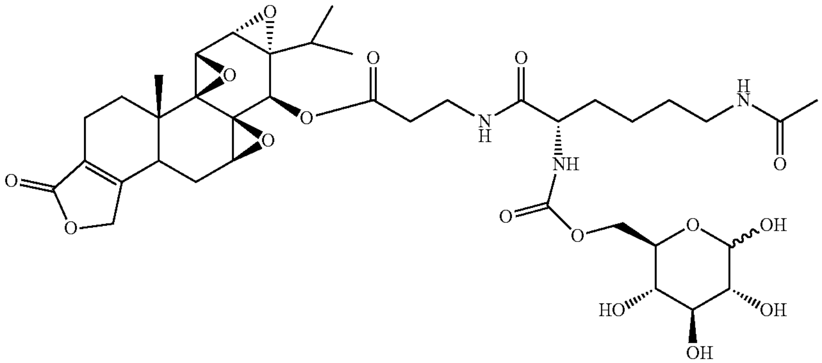 [SMILES: CC(=O)NCCCC[C@H](NC(=O)OC[C@H]1OC(O)[C@H](O)[C@@H](O)[C@@H]1O)C(=O)NCCC(=O)O[C@@H]1[C@@]2(C(C)C)O[C@H]2[C@@H]2O[C@]23[C@]12O[C@H]2CC1C2=C(CC[C@@]13C)C(=O)OC2]

TABLE 4-continued
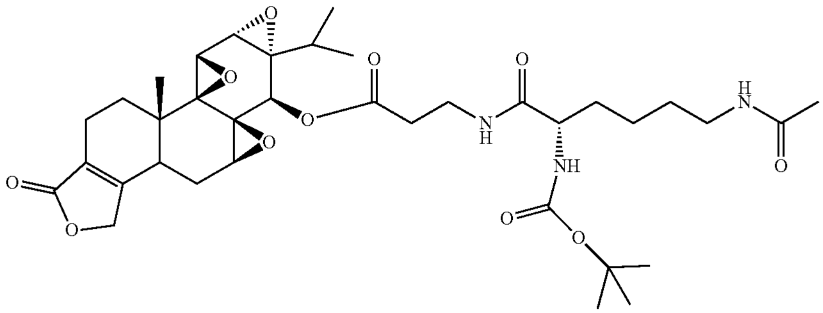 [SMILES: CC(=O)NCCCC[C@H](NC(=O)OC(C)(C)C)C(=O)NCCC(=O)O[C@@H]1[C@@]2(C(C)C)O[C@H]2[C@@H]2O[C@]23[C@]12O[C@H]2CC1C2=C(CC[C@@]13C)C(=O)OC2]
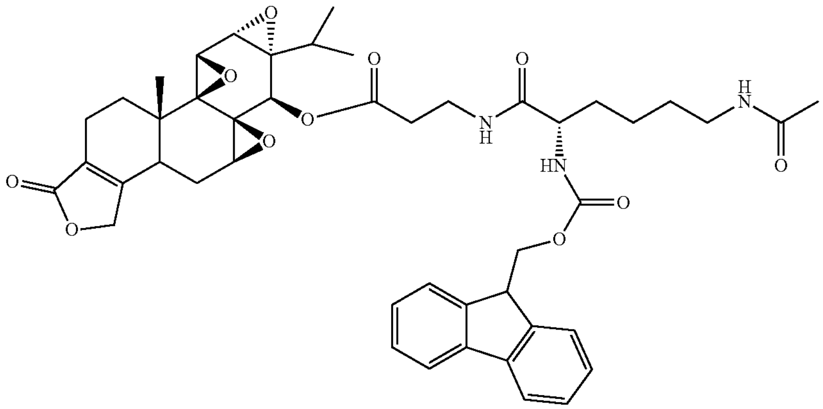 [SMILES: CC(=O)NCCCC[C@H](NC(=O)OCC1c2ccccc2-c2ccccc21)C(=O)NCCC(=O)O[C@@H]1[C@@]2(C(C)C)O[C@H]2[C@@H]2O[C@]23[C@]12O[C@H]2CC1C2=C(CC[C@@]13C)C(=O)OC2]
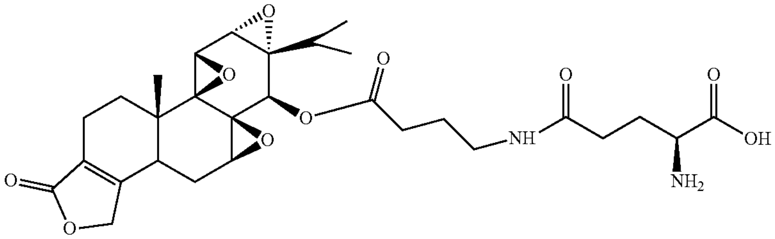 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCCNC(=O)CC[C@H](N)C(=O)O]
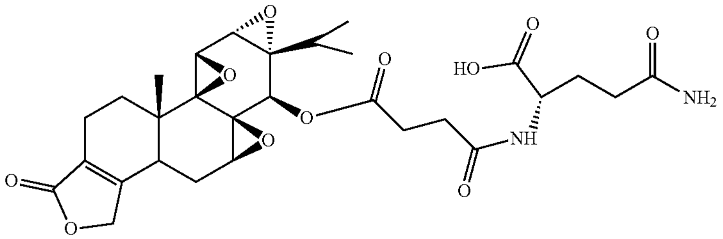 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)N[C@@H](CCC(N)=O)C(=O)O]
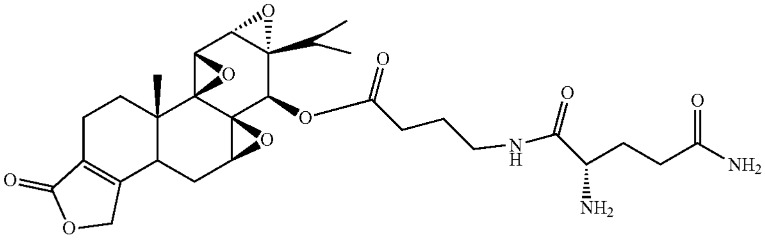 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCCNC(=O)[C@@H](N)CCC(N)=O]

TABLE 4-continued
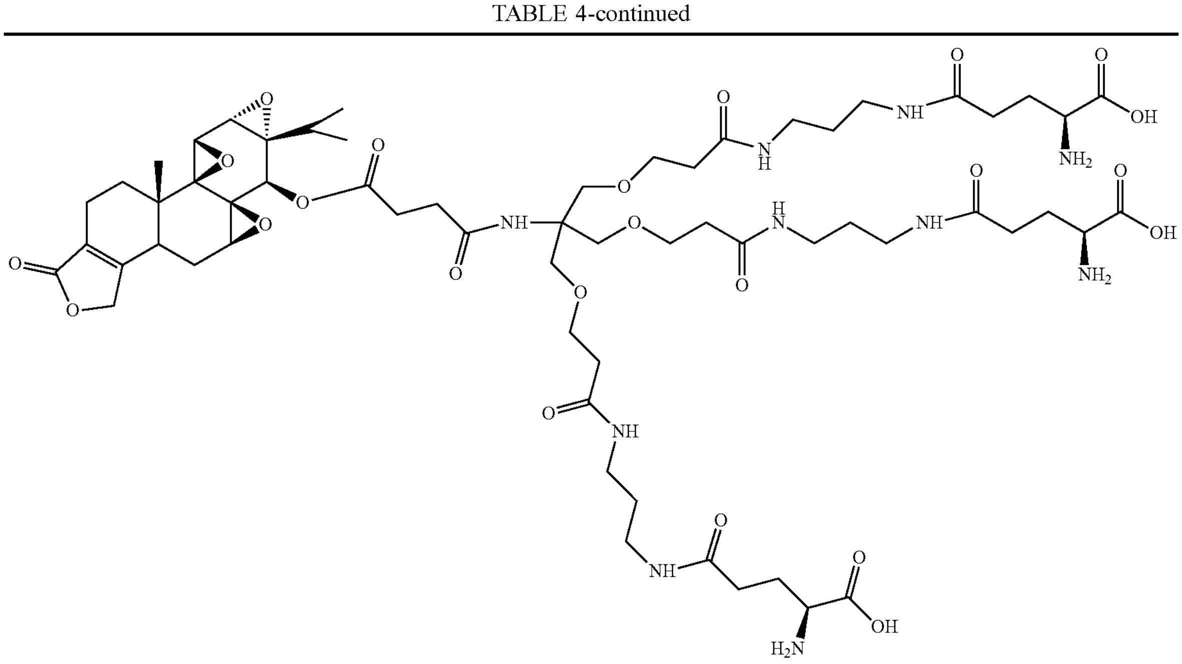
TABLE 5
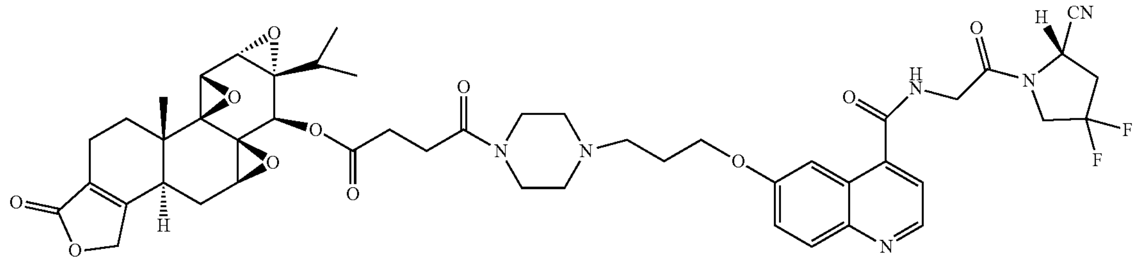 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(CCCOc2ccc3nccc(C(=O)NCC(=O)N4CC(F)(F)C[C@H]4C#N)c3c2)CC1]
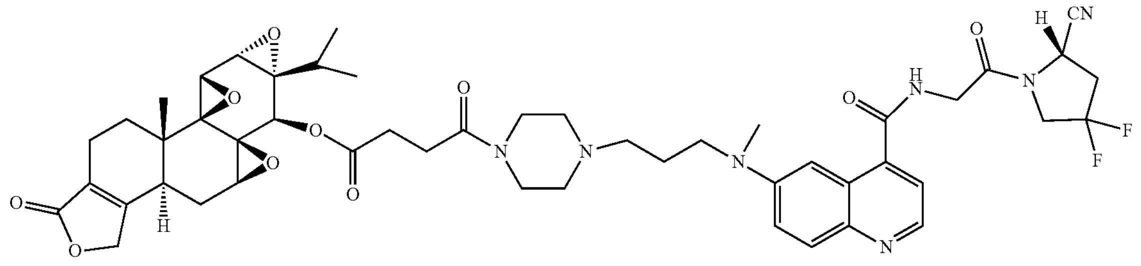 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(CCCN(C)c2ccc3nccc(C(=O)NCC(=O)N4CC(F)(F)C[C@H]4C#N)c3c2)CC1]
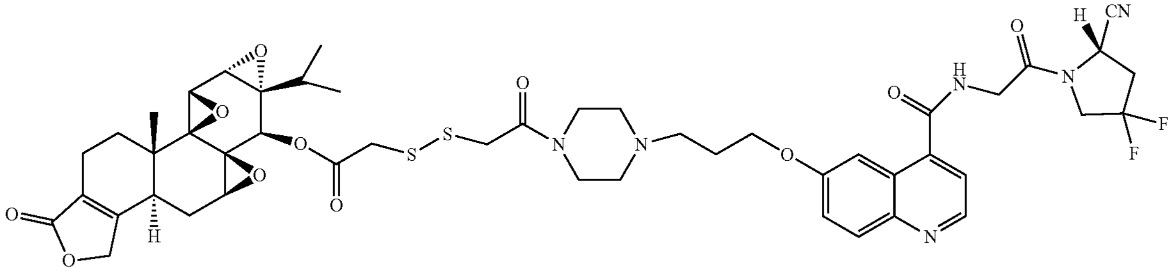 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CSSCC(=O)N1CCN(CCCOc2ccc3nccc(C(=O)NCC(=O)N4CC(F)(F)C[C@H]4C#N)c3c2)CC1]

TABLE 5-continued
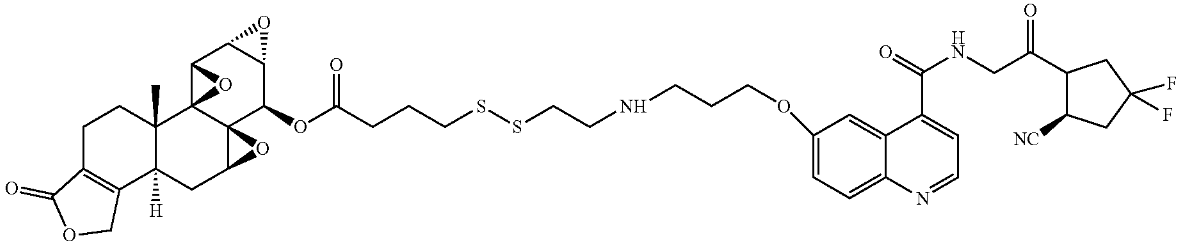 [SMILES: C[C@]12CCC3=C(COC3=O)[C@@H]1C[C@@H]1O[C@@]13[C@H](OC(=O)CCCSSCCNCCCOc1ccc4nccc(C(=O)NCC(=O)C5CC(F)(F)C[C@H]5C#N)c4c1)[C@H]1O[C@H]1[C@@H]1O[C@@]132]
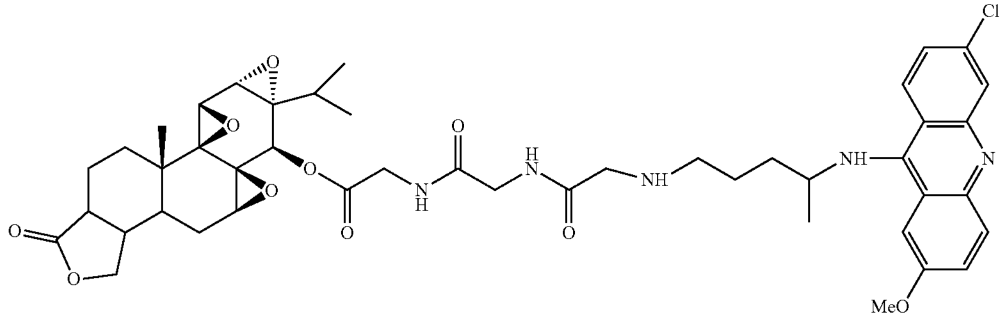 [SMILES: COc1ccc2nc3cc(Cl)ccc3c(NC(C)CCCNCC(=O)NCC(=O)NCC(=O)O[C@@H]3[C@@]4(C(C)C)O[C@H]4[C@@H]4O[C@]45[C@]34O[C@H]4CC3C4COC(=O)C4CC[C@@]35C)c2c1]
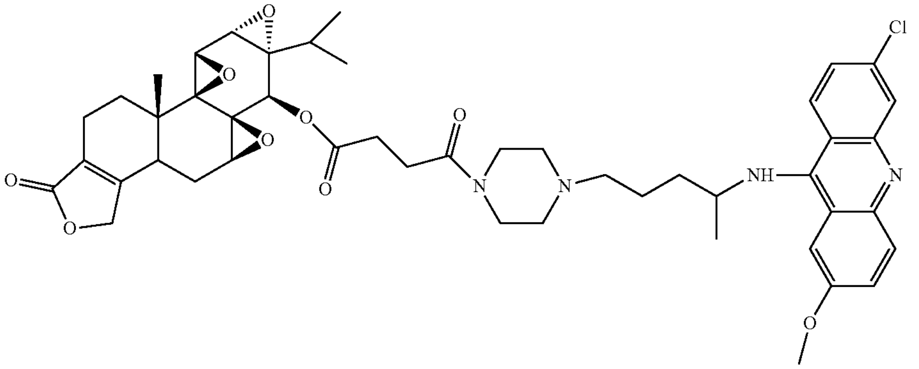 [SMILES: COc1ccc2nc3cc(Cl)ccc3c(NC(C)CCCN3CCN(C(=O)CCC(=O)O[C@@H]4[C@@]5(C(C)C)O[C@H]5[C@@H]5O[C@]56[C@]45O[C@H]5CC4C5=C(CC[C@@]46C)C(=O)OC5)CC3)c2c1]
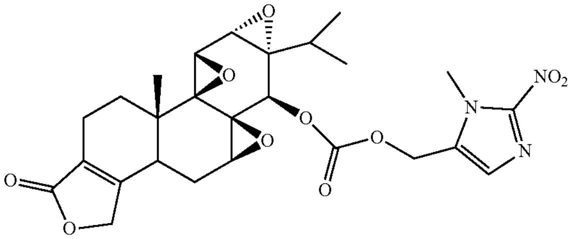 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)OCc1cnc([N+](=O)[O-])n1C]
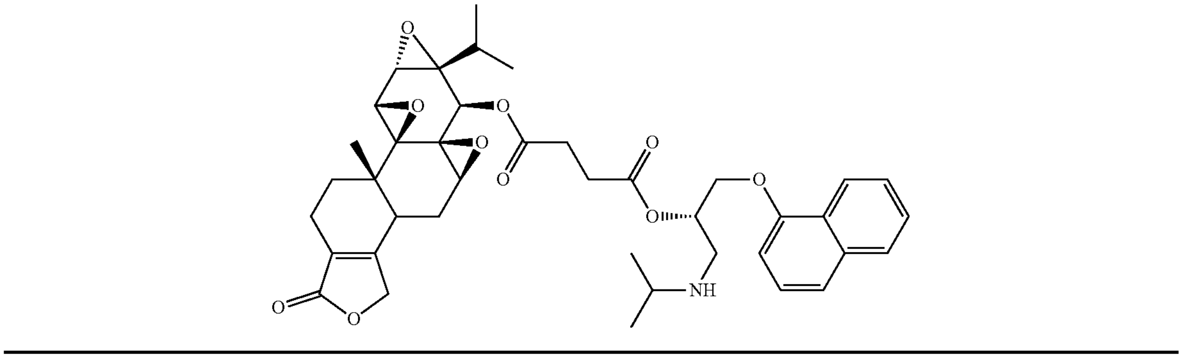

TABLE 6
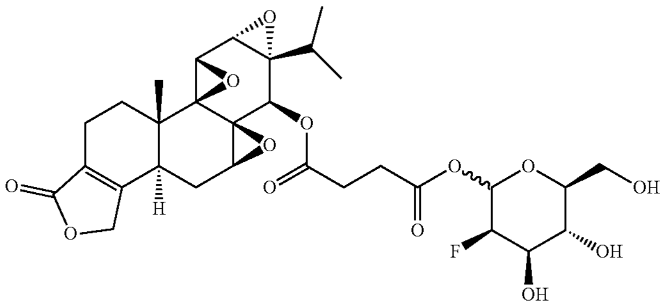 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)OC1O[C@@H](CO)[C@H](O)[C@@H](O)[C@H]1F]
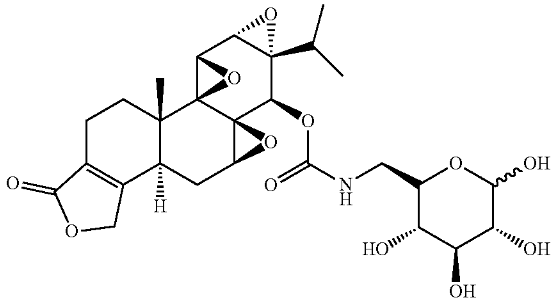
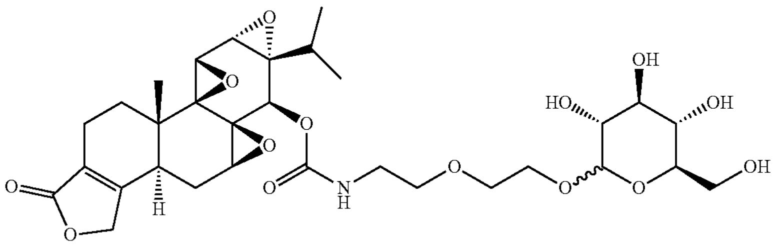 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)NCCOCCOC1O[C@H](CO)[C@@H](O)[C@H](O)[C@H]1O]
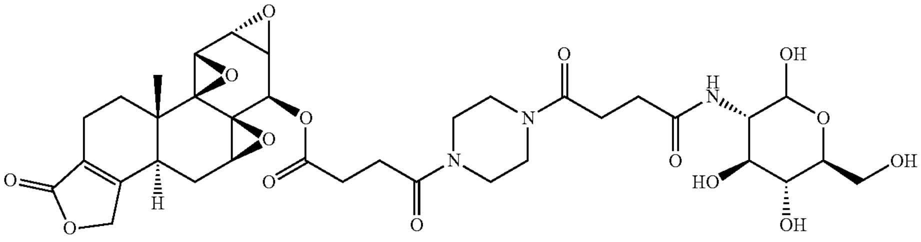
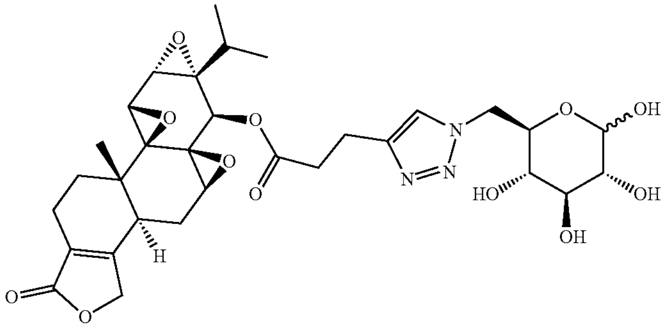 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCc1cn(C[C@H]2OC(O)[C@H](O)[C@@H](O)[C@@H]2O)nn1]

TABLE 6-continued
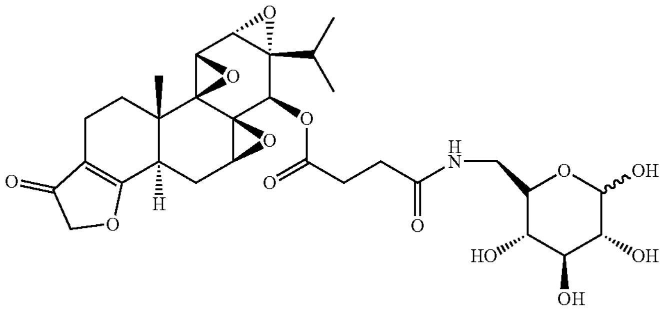
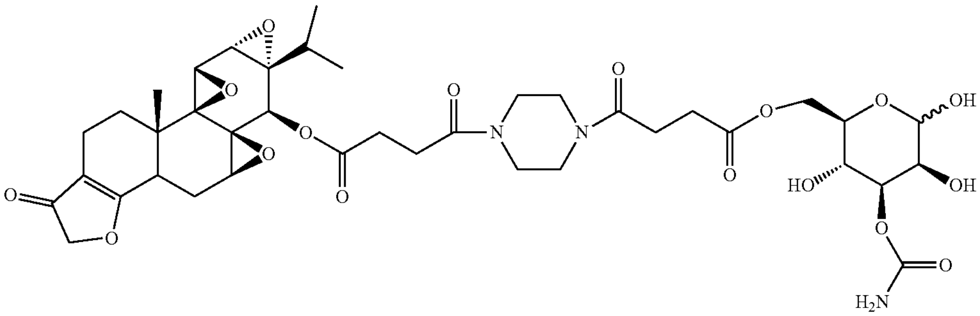 [SMILES: CC(C)[C@]12O[C@H]1[C@@H]1O[C@]13[C@]1(O[C@H]1CC1C4=C(CC[C@@]13C)C(=O)CO4)[C@@H]2OC(=O)CCC(=O)N1CCN(C(=O)CCC(=O)OC[C@H]2OC(O)[C@@H](O)[C@@H](OC(N)=O)[C@@H]2O)CC1]
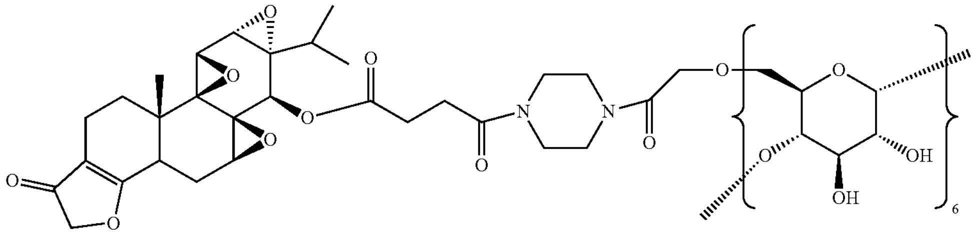
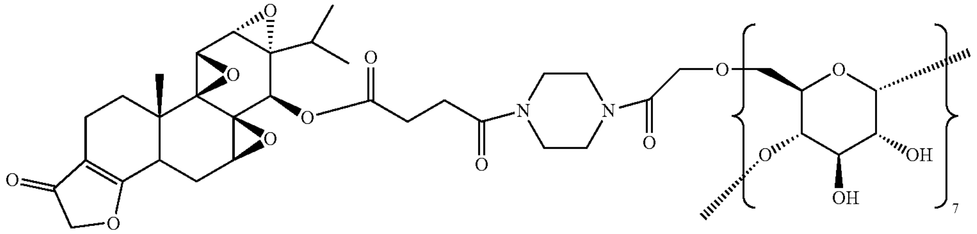
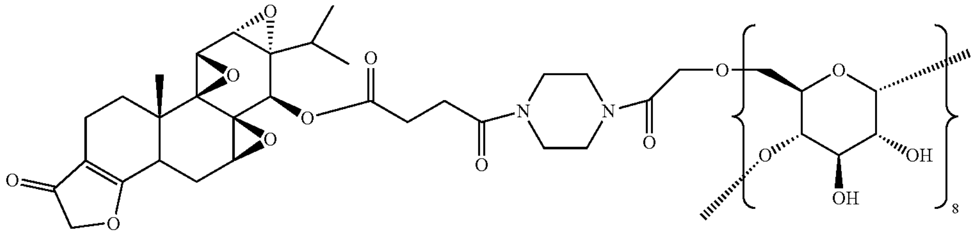

TABLE 6-continued
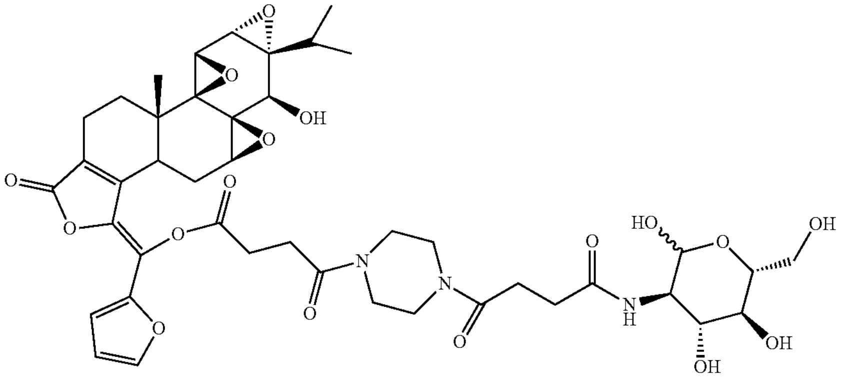 [SMILES: CC(C)[C@]12O[C@H]1[C@@H]1O[C@]13[C@]1(O[C@H]1CC1C4=C(CC[C@@]13C)C(=O)O/C4=C(/OC(=O)CCC(=O)N1CCN(C(=O)CCC(=O)N[C@H]3C(O)O[C@H](CO)[C@@H](O)[C@@H]3O)CC1)c1ccco1)[C@@H]2O]
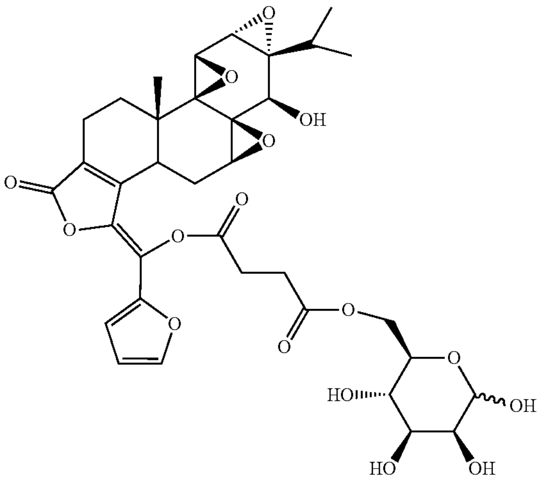 [SMILES: CC(C)[C@]12O[C@H]1[C@@H]1O[C@]13[C@]1(O[C@H]1CC1C4=C(CC[C@@]13C)C(=O)O/C4=C(/OC(=O)CCC(=O)OC[C@H]1OC(O)[C@@H](O)[C@@H](O)[C@@H]1O)c1ccco1)[C@@H]2O]
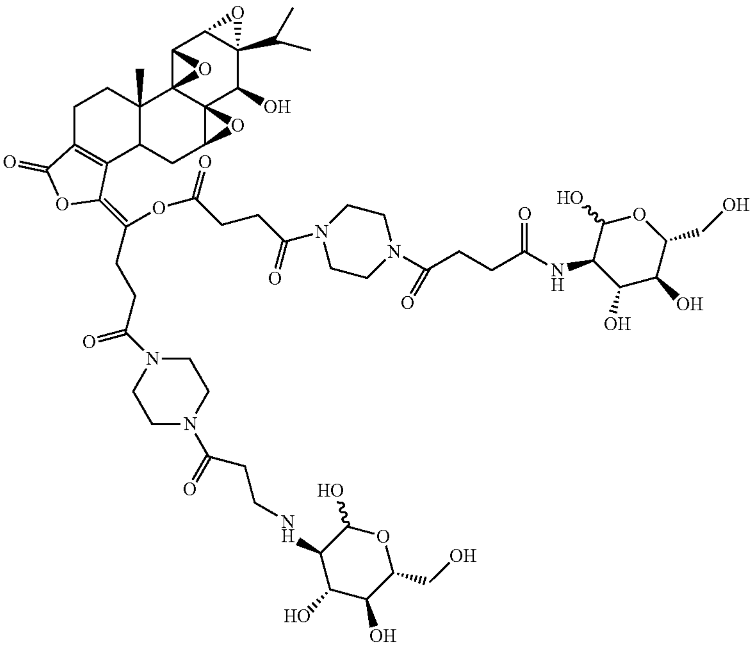 [SMILES: CC(C)[C@]12O[C@H]1[C@@H]1O[C@]13[C@]1(O[C@H]1CC1C4=C(CC[C@@]13C)C(=O)O/C4=C(\CCC(=O)N1CCN(C(=O)CCN[C@H]3C(O)O[C@H](CO)[C@@H](O)[C@@H]3O)CC1)OC(=O)CCC(=O)N1CCN(C(=O)CCC(=O)N[C@H]3C(O)O[C@H](CO)[C@@H](O)[C@@H]3O)CC1)[C@@H]2O]

TABLE 6-continued
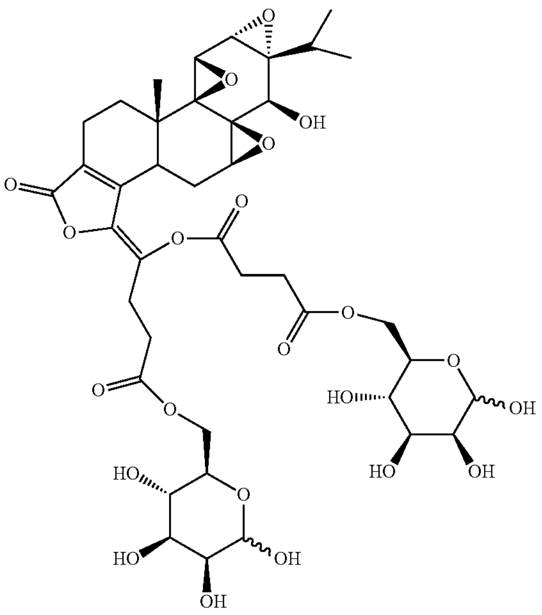 [SMILES: CC(C)[C@]12O[C@H]1[C@@H]1O[C@]13[C@]1(O[C@H]1CC1C4=C(CC[C@@]13C)C(=O)O/C4=C(\CCC(=O)OC[C@H]1OC(O)[C@@H](O)[C@@H](O)[C@@H]1O)OC(=O)CCC(=O)OC[C@H]1OC(O)[C@@H](O)[C@@H](O)[C@@H]1O)[C@@H]2O]
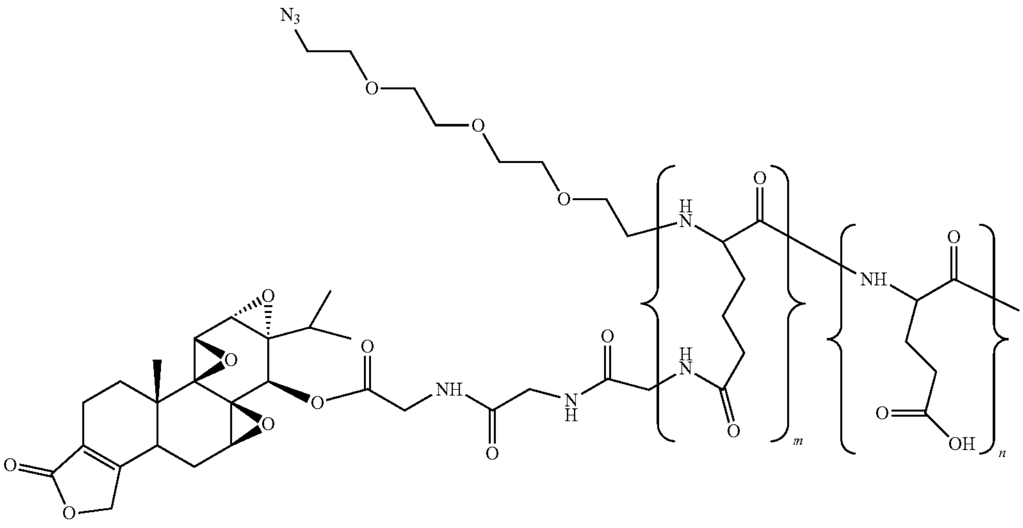

TABLE 6-continued

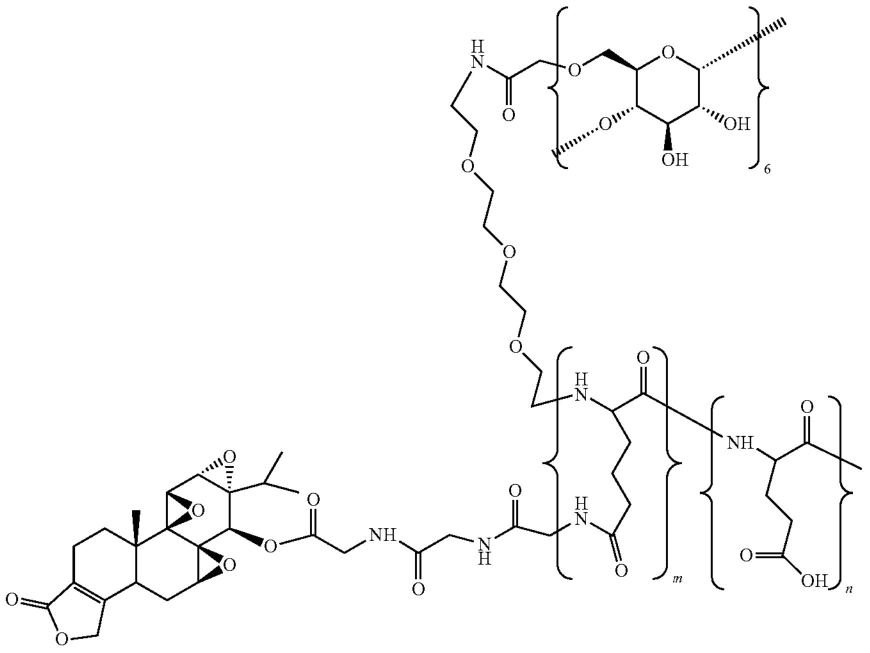

In some embodiments, provided herein is an enantiomer, an enantiomeric mixture, a diastereomer, a diastereomeric mixture, or a pharmaceutically acceptable salt of a compound that is described in any one of the tables disclosed herein.

In one aspect, compounds described herein are in the form of pharmaceutically acceptable salts. As well, active metabolites of these compounds having the same type of activity are included in the scope of the present disclosure.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques known to one of skilled in the art. Alternative reaction conditions for the synthetic transformations described herein may be employed such as variation of solvent, reaction temperature, reaction time, as well as different chemical reagents and other reaction conditions. The starting materials are available from commercial sources or are readily prepared The compounds described herein can prepared by the general synthetic routes described in the below schemes. Schemes A1-A4 each show a non-limiting general synthetic route for the preparation of compounds described herein.

Scheme A1

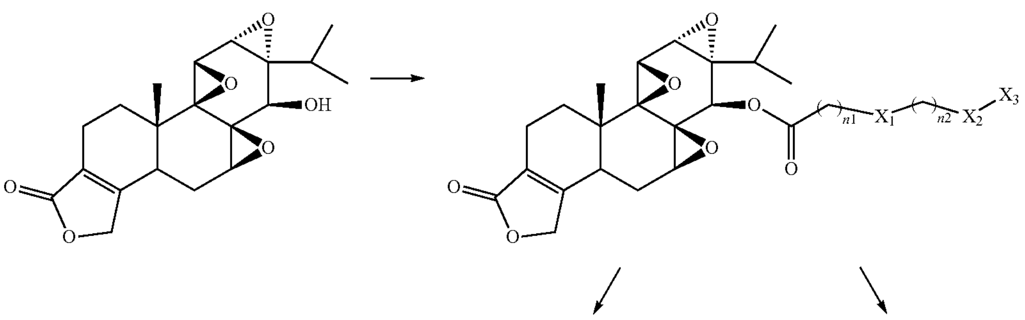

-continued
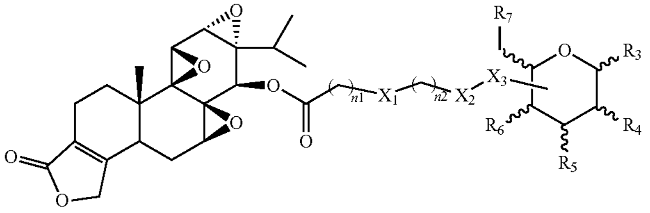
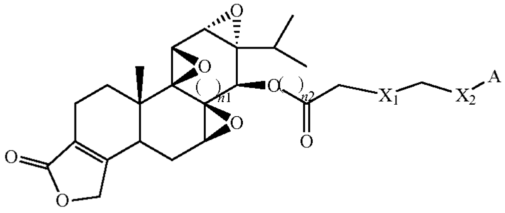
Scheme A2
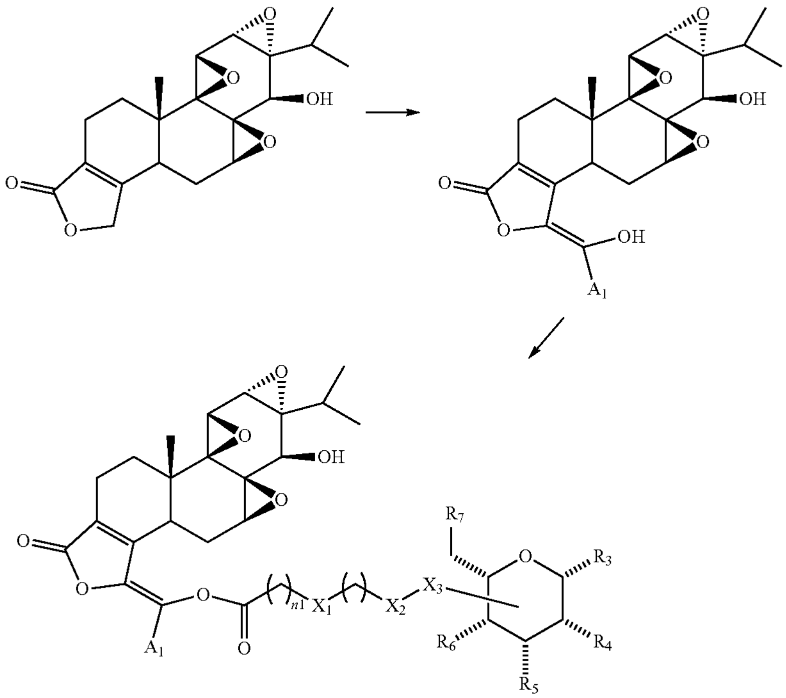
Scheme A3
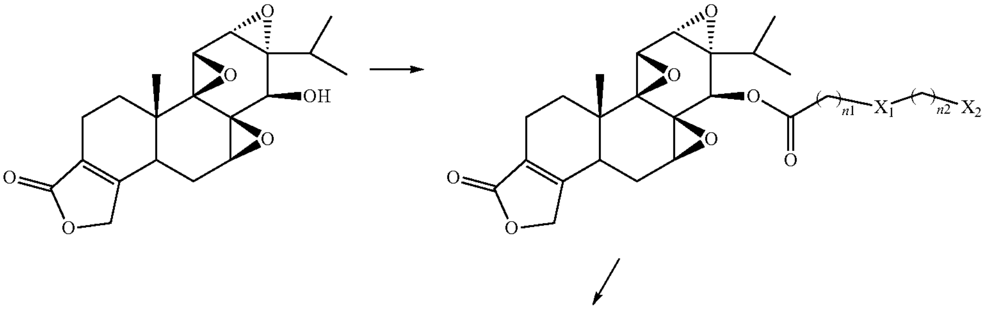

-continued

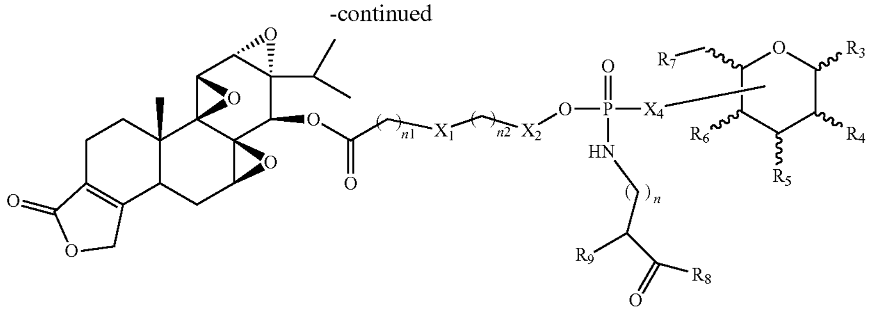

Scheme A4

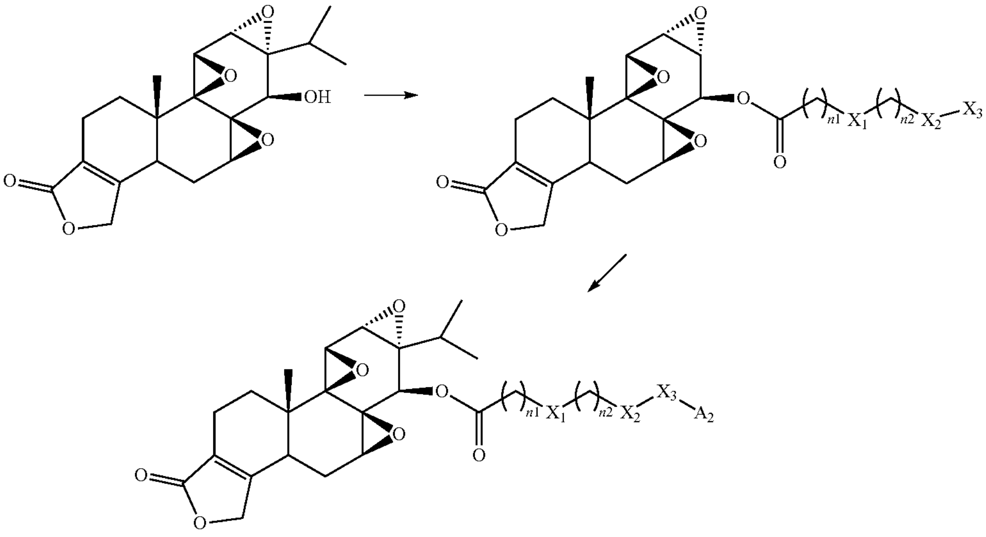

Pharmaceutical Compositions

In one aspect, described herein is a pharmaceutical composition comprising a compound described herein, or an enantiomer, an enantiomeric mixture, a diastereomer, a diastereomeric mixture, or a pharmaceutically acceptable salt thereof, and at least one pharmaceutically acceptable excipient and/or carrier. Examples of a pharmaceutically acceptable excipient, include but are not limited to, a binding agent a flavor agent, a lubricating agent, a disintegration agent, a delay agent, an organic solvent, a suspending agent an isotonicity agent, a buffer, an emulsifier, stabilizer and a preservative.

In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration.

In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Methods of Treatment

Also provided herein is a method for treating cancer in a subject in need thereof, comprising administering to the subject a therapeutically effective amount of any one of the compounds disclosed herein, an enantiomer, an enantiomeric mixture, a diastereomer, a diastereomeric mixture, or a pharmaceutically acceptable salt.

In some embodiments, the cancer is heptacellular carcinoma (HCC), lung cancer, breast cancer, pancreatic cancer, biliary tract cancer, colorectal cancer, or glioblastoma. In some embodiments, the cancer is heptacellular carcinoma (HCC). In some embodiments, the cancer is lung cancer. In some embodiments, the cancer is breast cancer. In some embodiments, the cancer is pancreatic cancer. In some embodiments, the cancer is biliary tract cancer. In some embodiments, the cancer is colorectal cancer. In some embodiments, the cancer is glioblastoma.

The term "cancer" shall refer to a proliferation of tumor cells having the unique trait of loss of normal controls, resulting in unregulated growth, lack of differentiation, local tissue invasion, and/or metastasis. As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of dysplasia, or loss of differentiation and orientation of cells, and have the properties of invasion and metastasis. The term cancer also within context, includes drug resistant cancers, including multiple drug resistant cancers. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocyte leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. Contemplated cancers also include but not limited to ovarian cancer, breast cancer, colon cancer, head and neck cancer, medulloblastoma, and B-cell lymphoma.

Also provided herein is a method for treating a disease or disorder is related to immunomodulation and/or inflammation in a subject in need thereof, comprising administering to the subject a therapeutically effective amount of any one of the compounds disclosed herein, an enantiomer, an enantiomeric mixture, a diastereomer, a diastereomeric mixture, or a pharmaceutically acceptable salt.

In some embodiments, the disease or disorder is related to inflammatory and/or autoimmune diseases. Examples of such diseases or disorders related to inflammation and/or inflammation include, but are not limited to, membranous nephropathy (MN), lupus nephritis, systemic lupus erythematosus, kidney transplantation, renal fibrosis, inflammatory bowel disease, Crohn's disease, intestinal fibrosis, liver fibrosis, asthma, acute lung injury, pulmonary arterial hypertension, pulmonary fibrosis, diabetic nephropathy, diabetic cardiomyopathy, rheumatoid arthritis, and psoriasis. In some embodiments, the disease or disorder related to inflammation and/or inflammation is any one of membranous nephropathy (MN), lupus nephritis, systemic lupus erythematosus, kidney transplantation, renal fibrosis, inflammatory bowel disease, Crohn's disease, intestinal fibrosis, liver fibrosis, asthma, acute lung injury, pulmonary arterial hypertension, pulmonary fibrosis, diabetic nephropathy, diabetic cardiomyopathy, rheumatoid arthritis, or psoriasis.

DEFINITIONS

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

An "alkyl" group by itself or as part of another molecule refers to an aliphatic hydrocarbon group. The alkyl group is branched or straight chain. In some embodiments, the "alkyl" group has 1 to 20 carbon atoms, i.e. a $C_1$-$C_{20}$alkyl. Whenever it appears herein, a numerical range such as "1 to 20" refers to each integer in the given range; e.g., "1 to 20 carbon atoms" means that the alkyl group consist of 1 carbon atom, 2 carbon atoms, 3 carbon atoms, 4 carbon atoms, 5 carbon atoms, 6 carbon atoms, etc., up to and including 20 carbon atoms, although the present definition also covers the occurrence of the term "alkyl" where no numerical range is designated. In some embodiments, an alkyl is a $C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_{20}$ alkylene. In other embodiments, an alkylene is a $C_1$-$C_{10}$ alkylene. In other embodiments, an alkylene is a $C_1$-$C_6$ alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, $—CH_2—$, $—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like.

The term "alkenyl" refers to a type of alkyl group in which at least one carbon-carbon double bond is present. In one embodiment, an alkenyl group has the formula $—C(R)=CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include $—CH=CH_2$, $—C(CH_3)=CH_2$, $—CH=CHCH_3$, $—C(CH_3)=CHCH_3$, and $—CH_2CH=CH_2$.

The term "alkynyl" refers to a type of alkyl group in which at least one carbon-carbon triple bond is present. In one embodiment, an alkynyl group has the formula $—C≡C—R$, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include $—C≡CH$, $—C≡CCH_3$, $—C≡CCH_2CH_3$, and $—CH_2C≡CH$.

An "alkoxy" group refers to a —O(alkyl) group, where alkyl is as defined herein.

The term "alkylamine" refers to the $—N(alkyl)_xH_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$ cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

"Carbocyclylalkyl" refers to a radical of the formula $—R^c$-carbocyclyl where $R^c$ is an alkylene chain as defined above. The alkylene chain and the carbocyclyl radical is optionally substituted as defined above.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$ fluoroalkyl.

The term "fluoroalkyl" refers to an alkyl in which one or more hydrogen atoms are replaced by a fluorine atom. In one aspect, a fluoroalkyl is a $C_1$-$C_6$ fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$ heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 20 or 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms or 3 to 20 in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The term “heterocyclyl” refers to any univalent radical formed by removing a hydrogen atom from any ring atom of a heterocyclic compound as defined herein. Depending on the structure, an heterocyclyl group is a monoradical or a diradical (i.e., an heterocyclylene group).

The terms “heteroaryl” or, alternatively, “heteroaromatic” refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_{10}$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, bicyclic heteroaryl is a $C_6$-$C_9$ heteroaryl. Depending on the structure, an heteroaryl group is a monoradical or a diradical (i.e., an heteroarylene group).

A “heterocycloalkyl” or “heteroalicyclic” group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_1$-$C_{20}$ heterocycloalkyl. In one aspect, a heterocycloalkyl is a $C_1$-$C_{14}$ heterocycloalkyl. In one aspect, a heterocycloalkyl is a $C_1$-$C_{10}$ heterocycloalkyl. In one aspect, a heterocycloalkyl is a $C_2$-$C_{14}$ heterocycloalkyl. In one aspect, a heterocycloalkyl is a $C_2$-$C_{10}$ heterocycloalkyl. In another aspect, a heterocycloalkyl is a $C_4$-$C_{10}$ heterocycloalkyl. In another aspect, a heterocycloalkyl is a $C_5$-$C_{10}$ heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring. Depending on the structure, an heteroaryl group is a monoradical or a diradical (i.e., an heteroarylene group).

“Heterocyclylalkyl” refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

The term “bond” or “single bond” refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term “moiety” refers to a specific segment or functional group of a molecule. Chemical moieties are often recognized chemical entities embedded in or appended to a molecule.

The term “optionally substituted” or “substituted” means that the referenced group is optionally substituted with one or more additional group(s) individually and independently selected from D, halogen, —CN, —$NH_2$, —NH(alkyl), —$N(alkyl)_2$, —OH, —$CO_2H$, —$CO_2$alkyl, —C(=O)$NH_2$, —C(=O)NH(alkyl), —C(=O)$N(alkyl)_2$, —S(=$O)_2NH_2$, —S(=$O)_2$NH(alkyl), —S(=$O)_2N(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —$NH_2$, —NH($CH_3$), —$N(CH_3)_2$, —OH, —$CO_2H$, —$CO_2$($C_1$-$C_4$alkyl), —C(=O)$NH_2$, —C(=O)NH($C_1$-$C_4$alkyl), —C(=O)N($C_1$-$C_4$alkyl)$_2$, —S(=$O)_2NH_2$, —S(=$O)_2$NH($C_1$-$C_4$alkyl), —S(=$O)_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=$O)_2C_1$-$C_4$alkyl. In some embodiments, optional substituents are independently selected from D, halogen, —CN, —$NH_2$, —OH, —NH($CH_3$), —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "inhibit" as used herein refers to the partial or complete elimination of a potential effect, while inhibitors are compounds that have the ability to inhibit.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The present invention, thus generally described, will be understood more readily by reference to the following examples, which are provided by way of illustration and are not intended to be limiting of the present invention.

As used above, and throughout the description of the invention, the following abbreviations, unless otherwise indicated, shall be understood to have the following meanings:

Ac acetyl
AcOH acetic acid
Bn benzyl
DCC dicyclohexyl carbodiimide
DCE dichloroethane
DCM dichloromethane
DIPEA or DIEA diisopropylethylamine
DMAP 4-(N,N-dimethylamino)pyridine
DMF dimethylformamide
DMSO dimethylsulfoxide
Et ethyl
EtOAc or EA ethyl acetate
HATU (1-[Bis(dimethylamino)methylene]-1H-1,2,3-triazolo[4,5-b]pyridinium 3-oxide hexafluorophosphate
HPLC high performance liquid chromatography
Me methyl
MeOH methanol
MS mass spectroscopy
NMR nuclear magnetic resonance
PE petroleum ether
rt. room temperature
TFA trifluoroacetic acid
TEA triethylamine
THF tetrahydrofuran

EXAMPLES

Example 1—Synthesis of ((2R,3S,4S,5R)-5-fluoro-3,4,6-trihydroxytetrahydro-2H-pyran-2-yl)methyl ((5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2''',3''':8a,9]phenanthro[1,2-c]furan-8-yl) succinate (Compound 1)

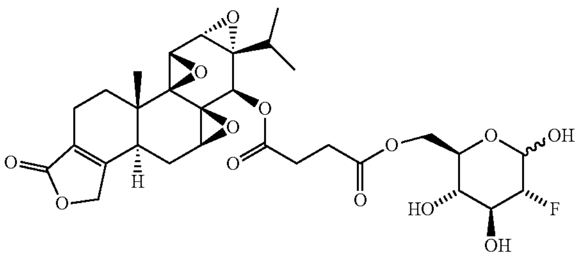 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)OC[C@H]1OC(O)[C@H](F)[C@@H](O)[C@@H]1O]

The following schemes show the synthetic route used to prepare the title compound.

Scheme 1.

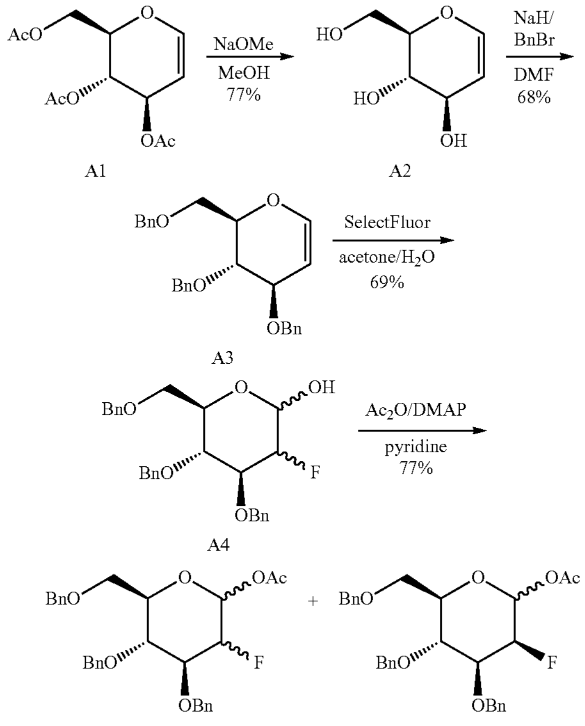

A1 A2 A3 A4 A5 + A6

Scheme 2.

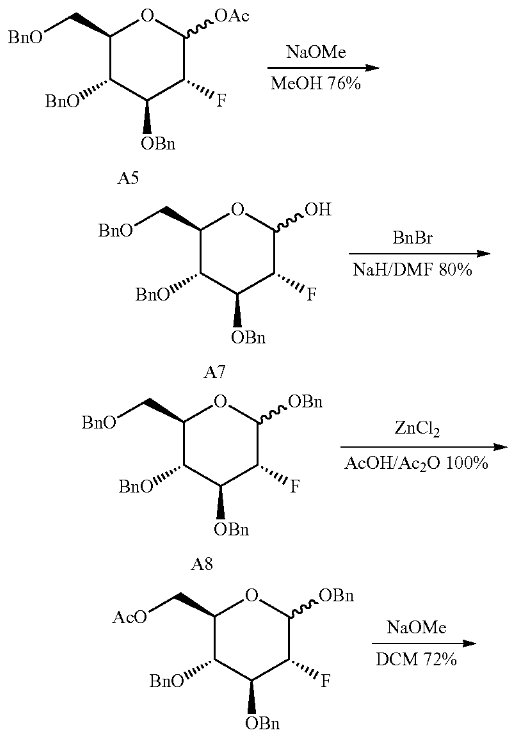

A5 A7 A8 A9

-continued

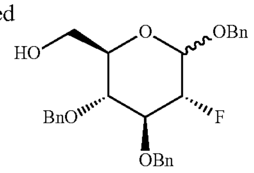

A10

Preparation of (2R,3S,4R)-3,4-bis(benzyloxy)-2-((benzyloxy)methyl)-3,4-dihydro-2H-pyran (A3)

To a stirred solution of compound A2 (1.5 g, 10.0 mmol, 1.0 equiv) in DMF (50 mL) was added NaH (1.8 g, 45 mmol, 4.5 equiv) at 0° C., and the mixture was stirred at rt. for 1 h. BnBr (7.7 g, 45.0 mmol, 4.5 equiv) was added and the mixture was stirred at rt. overnight. The reaction was quenched with $NH_4Cl$ (aq.), then concentrated, the residue was taken up with EA, washed with water and brine, dried Scheme 3.

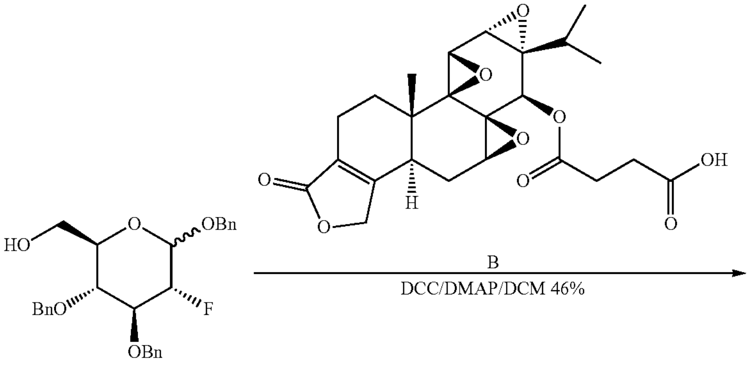

A10

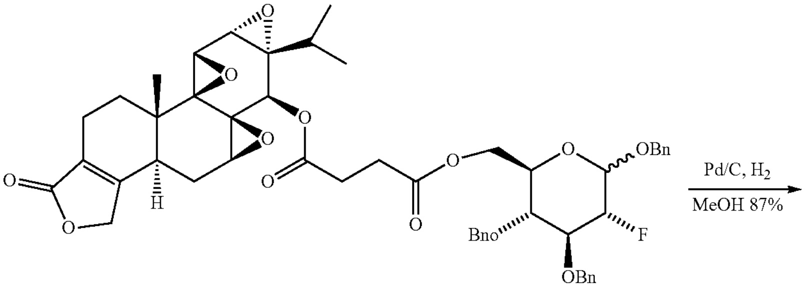

A11

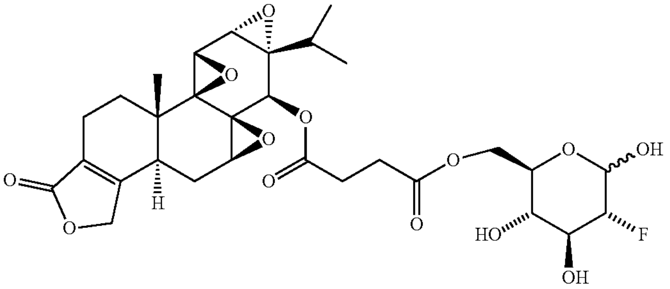

Compound 1

Preparation of (2R,3S,4R)-2-(hydroxymethyl)-3,4-dihydro-2H-pyran-3,4-diol (A2)

To a stirred solution of compound A1 (2.72 g, 10.0 mmol, 1.0 equiv) in MeOH (20 mL) was added NaOMe (216 mg, 4.0 mmol, 0.4 equiv) at 0° C., and the mixture was stirred at rt. for 2 h. The reaction was quenched with $NH_4Cl$ (aq.), then concentrated, the residue was taken up with EA, washed with water and brine, dried over $Na_2SO_4$. Concentration and purification by silica gel (PE-PE:EA=5:1-DCM:MeOH=20:1) provided compound A2 as a colorless oil (1.5 g, yield: 100%).

over $Na_2SO_4$. Concentration and purification by silica gel (PE-PE:EA=40:1-30:1) provided compound A3 as a white solid (2.81 g, yield: 68%).

Preparation of (4S,5R,6R)-4,5-bis(benzyloxy)-6-((benzyloxy)methyl)-3-fluorotetrahydro-2H-pyran-2-ol (A4)

SelectFluor (2.44 g, 6.9 mmol, 1.2 equiv) was added to a solution of compound A3 (2.39 g, 5.75 mmol, 1.0 equiv) in acetone (25 mL), and water (5 mL) and the resulting mixture was stirred at rt. overnight under $N_2$ atmosphere. The reaction was quenched with $NH_4Cl$ (aq.), then concentrated. The residue was taken up with EA, washed with water and brine, dried over $Na_2SO_4$. Concentration and purification by silica gel (PE-PE:EA=20:1-10:1) provided compound A4 as a colorless oil (2.1 g, yield: 69%).

Preparation of (3R,4S,5R,6R)-4,5-bis(benzyloxy)-6-((benzyloxy)methyl)-3-fluorotetrahydro-2H-pyran-2-yl acetate (A6)

To a solution of compound A4 (2.1 g, 4.64 mmol, 1.0 equiv) and DMAP (57 mg, 0.46 mmol, 0.1 equiv) in pyridine (25 mL) was added $Ac_2O$ (1.9 g, 18.6 mmol, 4.0 equiv) at 0° C. The mixture was stirred at rt. for 18 h. The mixture was diluted with EA, washed with water and brine, dried over $Na_2SO_4$. Concentration and purification by silica gel (PE-PE:EA=20:1-10:1) provided compound A6 as a colorless oil (560 mg, yield: total 77%).

Preparation of (3R,4S,5R,6R)-4,5-bis(benzyloxy)-6-((benzyloxy)methyl)-3-fluorotetrahydro-2H-pyran-2-ol (A7)

To a stirred solution of compound A6 (560 Mg, 1.13 mmol, 1.0 equiv) in MeOH (12 mL) was added NaOMe (10 mg, 0.17 mmol, 0.15 equiv) at 0° C., and the mixture was stirred at rt. for 2 h. The reaction was quenched with $NH_4Cl$ (aq.), then concentrated, the residue was taken up with EA, washed with water and brine, dried over $Na_2SO_4$. Concentration and purification by silica gel (PE-PE:EA=5:1) provided compound A7 as a white solid (390 mg, yield: 76%).

Preparation of (3R,4S,5R,6R)-2,4,5-tris(benzyloxy)-6-((benzyloxy)methyl)-3-fluorotetrahydro-2H-pyran (A8)

To a stirred solution of compound A7 (700 mg, 1.55 mmol, 1.0 equiv) in DMF (10 mL) was added NaH (87 mg, 2.17 mmol, 1.4 equiv) at 0° C., and the mixture was stirred at rt. for 1 h. BnBr (371 mg, 2.17 mmol, 1.4 equiv) was added and the mixture was stirred at rt. overnight. The reaction was quenched with $NH_4Cl$ (aq.), then concentrated, the residue was taken up with EA, washed with water and brine, dried over $Na_2SO_4$. Concentration and purification by silica gel (PE-PE:EA=50:1-40:1) provided compound A8 as a yellow solid (670 mg, yield: 80%).

Preparation of ((2R,3R,4S,5R)-3,4,5,6-tetrakis(benzyloxy)tetrahydro-2H-pyran-2-yl)methyl acetate (A9)

To a freshly fused $ZnCl_2$ (1.01 g, 7.41 mmol, 1.0 equiv) was added 1:5 $HOAc/Ac_2O$ 12 mL). The mixture was cooled to 0° C. A solution of compound A8 (630 mg, 1.23 mmol, 1.0 equiv) in 1:5 $HOAc/Ac_2O$ (6 mL) was added dropwise and the mixture was stirred at rt. for 1.5 h. Water was added and the precipitate was collected by filtration. The filtrate was then dissolved in EA, washed with water and brine, dried over $Na_2SO_4$. Concentration and purification by silica gel (PE-PE:EA=40:1-30:1) provided compound A9 as a pale-yellow solid (610 mg, yield: 100%).

Preparation of ((2R,3R,4S,5R)-3,4,6-tris(benzyloxy)-5-fluorotetrahydro-2H-pyran-2-yl)methanol (A10)

To a stirred solution of compound A9 (610 mg, 1.23 mmol, 1.0 equiv) in MeOH (20 mL) was added NaOMe (13 mg, 0.25 mmol, 0.2 equiv) at 0° C., and the mixture was stirred at rt. for 2 h. The reaction was quenched with $NH_4Cl$ (aq.), then concentrated, the residue was taken up with EA, washed with water and brine, dried over $Na_2SO_4$. Concentration and purification by silica gel (PE-PE:EA=5:1-DCM:MeOH=20:1) provided compound A10 as a colorless oil (400 mg, yield: 72%).

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2''',3''':8a,9]phenanthro[1,2-c]furan-8-yl (((2R,3R,4S,5R)-3,4,6-tris(benzyloxy)-5-fluorotetrahydro-2H-pyran-2-yl)methyl) succinate (A11)

To a solution of compound A10 (100 mg, 0.2174 mmol, 1.0 equiv) and compound B (100 mg, 0.2174 mmol, 1.0 equiv) in dry DCM (10 mL) was added DCC (50 mg, 0.239 mmol, 1.1 equiv) and DMAP (30 mg, 0.239 mmol, 1.51 equiv) at 0° C. The mixture was stirred at rt. for 18 h. The mixture was diluted with DCM, washed with water and brine, dried over $Na_2SO_4$. Concentration and purification by prep-HPLC to provide compound A11 as a white solid (90 mg, yield: 46%).

Preparation of ((2R,3S,4S,5R)-5-fluoro-3,4,6-trihydroxytetrahydro-2H-pyran-2-yl)methyl ((5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2''',3''':6,7,2''',3''':8a,9]phenanthro[1,2-c]furan-8-yl) succinate (Compound 1)

A mixture of compound A11 (90 mg, 0.112 mmol, 1.0 equiv) and Pd/C (10%, 50 mg) in MeOH (10 mL) was stirred at rt. overnight under $H_2$ atmosphere. The mixture was filtered and concentrated, the residue was purified by prep-HPLC to provide Compound 1 as a white solid (55 mg, yield: 87%).

Compound 1: $^1H$ NMR ($CD_3OD$, 400 MHz): 0.82 (d, J=7.2 Hz 3H), 0.93 (d, J=6.8 Hz 3H), 1.03 (s, 3H), 1.32-1.34 (m, 1H), 1.48-1.52 (m, 1H), 1.86-1.93 (m, 2H), 2.03-2.10 (m, 1H), 2.22-2.29 (m, 2H), 2.68-2.78 (m, 5H), 3.33-3.35 (m, 1H), 3.45 (d, J=5.6 Hz, 1H), 3.58-3.62 (m, 2H), 3.85-3.98 (m, 2.3H), 4.18-4.22 (m, 1.4H), 4.35-4.42 (m, 0.8H), 4.69-4.71 (m, 0.5H), 4.79-4.84 (m, 1.5H), 5.06 (s, 1H), 5.25 (d J=3.6 Hz, 0.6H). MS (ESI) calcd [$C_{30}H_{37}FO_{13}$] (m/z) for 624.22, found 625.1, [M+H]+.

Example 2—Synthesis of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 4-axo-4-(4-(4-axo-4-(((3S,4S,5R,6S)-2,4,5-trihydroxy-6-(hydroxymethyl)tetrahydro-2H-pyran-3-yl)amino)butanoyl)piperazin-1-yl)butanoate (Compound 2)

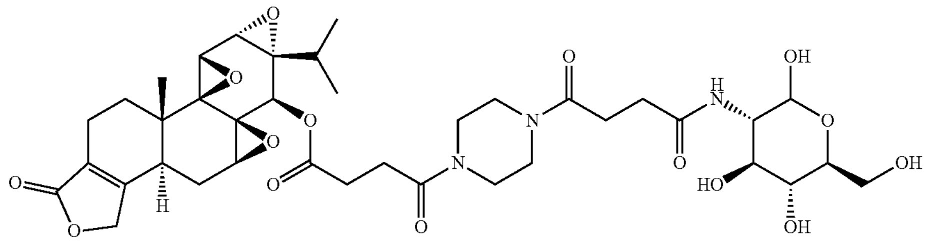 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(C(=O)CCC(=O)N[C@@H]2C(O)O[C@@H](CO)[C@H](O)[C@H]2O)CC1]

The following schemes show the synthetic route used to prepare the title compound.

Scheme 4.

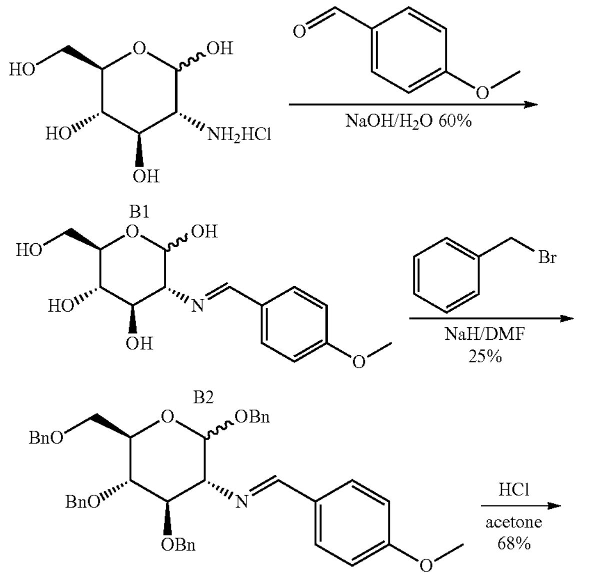

B1

B2

B3

-continued

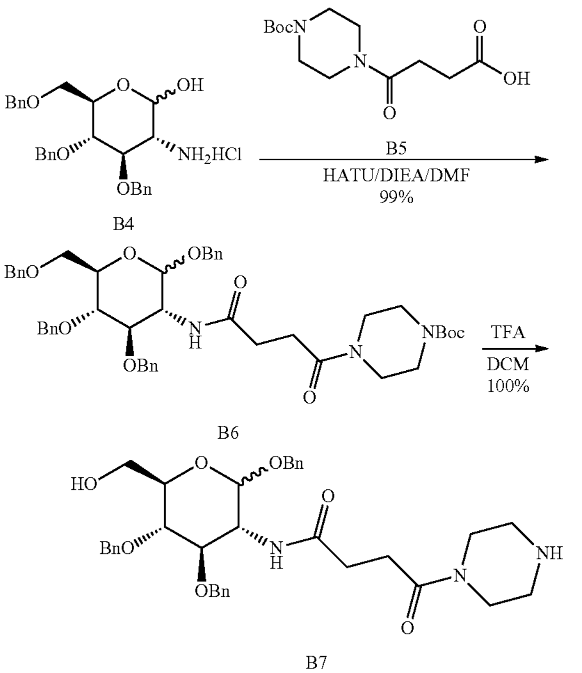

B4

B6

B7

Scheme 5.

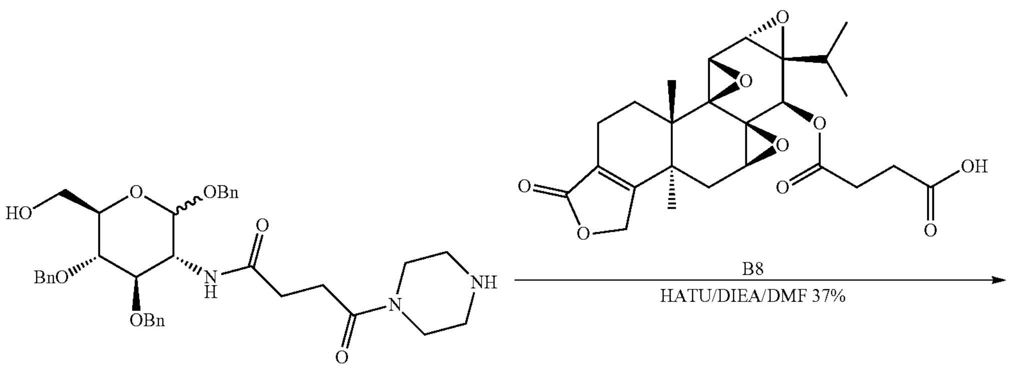

B7

-continued

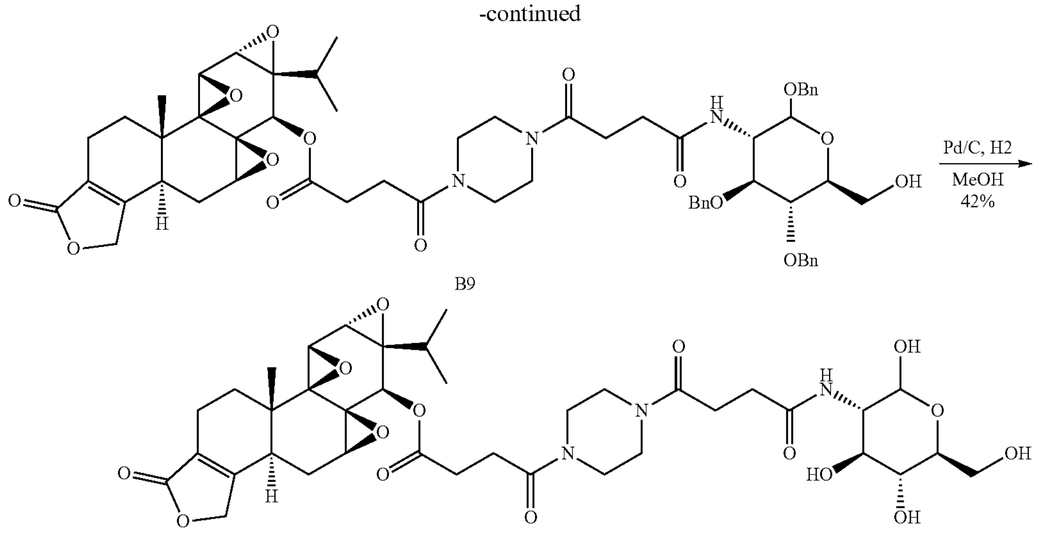

B9

Compound 2

Preparation of (3R,4R,5S,6R)-6-(hydroxymethyl)-3-((E)-(4-methoxybenzylidene)amino)tetrahydro-2H-pyran-2,4,5-triol (B2)

To a stirred solution of compound B1 (1.08 g, 5.0 mmol, 1. equiv) in water (8 mL) was added NaOH (200 mg, 5 mmol, 1.0 equiv) at 0° C., and the mixture was stirred at rt. for 15 min. 4-methoxybenzaldehyde (681 mg, 5 mmol, 1.0 equiv) was added and the resulting mixture was stirred at rt. for 1 h. The reaction was filtered and dried to afford compound B2 as a white solid (900 mg, yield: 60%).

Preparation of (3R,4R,5S,6R,E)-2,4,5-tris(benzyloxy)-6-((benzyloxy)methyl)-N-(4-methoxybenzylidene)tetrahydro-2H-pyran-3-amine (B3)

To a stirred solution of compound B2 (900 mg, 3.03 mmol, 1. equiv) in dry DMF (25 mL) was added NaH (605 mg, 15.13 mmol, 5.0 equiv) in portions at 0° C., and the mixture was stirred at rt. for 30 min. (bromomethyl)benzene (2.18 g, 12.73 mmol, 4.2 equiv) was added and the resulting mixture was stirred at rt. for 18 h. The reaction was quenched with NaCl, concentrated, the residue was purified by silica gel (PE-PE:EA=50:1-30:1) to afford compound B3 as a pale-yellow oil (500 mg, yield: 25%).

Preparation of (3R,4R,5S,6R)-2,4,5-tris(benzyloxy)-6-((benzyloxy)methyl)tetrahydro-2H-pyran-3-amine hydrochloride (B4)

A mixture of compound B3 (500 mg, 0.76 mmol, 1.0 equiv) and 5 N HCl (2 mL) in acetone (12 mL) was refluxed for 20 min. The mixture was cooled and the precipitate was collected by filtration and dried to afford compound B4 as a white solid (300 mg, yield: 68%).

Preparation of tert-butyl 4-(4-oxo-4-(((3R,4R,5S,6R)-2,4,5-tris(benzyloxy)-6-((benzyloxy)methyl)tetrahydro-2H-pyran-3-yl)amino)butanoyl)piperazine-1-carboxylate (B6)

To a solution of compound B4 (115 mg, 0.2 mmol, 1.0 equiv) and compound B5 (57 mg, 0.2 mmol, 1.0 equiv) in dry DMF (5 mL) was added HATU (99 mg, 0.26 mmol, 1.3 equiv) and DIEA (78 mg, 0.6 mmol, 3 equiv) at 0° C. The mixture was stirred at rt. for 18 h. The mixture was concentrated, the residue was taken up with EA, washed with water and brine, dried over $Na_2SO_4$. Concentration and purification by silica gel (PE-PE:EA=20:1-10:1) afforded compound B6 as a white solid (160 mg, yield: 99%).

Preparation of 4-oxo-4-(piperazin-1-yl)-N-((3R,4R,5S,6R)-2,4,5-tris(benzyloxy)-6-(hydroxymethyl)tetrahydro-2H-pyran-3-yl)butanamide (B7)

To a solution of compound B6 (160 mg, 0.198 mmol, 1.0 equiv) in dry DCM (10 mL) was added TFA (1 mL), and the mixture was stirred at rt. for 18 h. The mixture was concentrated to afford compound B7 as a yellow oil (123 mg, yield: 100%).

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2"',3"':8a,9]phenanthro[1,2-c]furan-8-yl 4-oxo-4-(4-(4-oxo-4-(((3S,4S,5R,6S)-2,4,5-tris(benzyloxy)-6-(hydroxymethyl)tetrahydro-2H-pyran-3-yl)amino)butanoyl)piperazin-1-yl)butanoate (B9)

To a solution of compound B7 (123 mg, 0.2 mmol, 1.0 equiv) and compound B8 (92 mg, 0.2 mmol, 1.0 equiv) in dry DMF (5 mL) was added HATU (99 mg, 0.26 mmol, 1.3 equiv) and DIEA (78 mg, 0.6 mmol, 3 equiv) at 0° C. The mixture was stirred at rt. for 18 h. The mixture was concentrated, the residue was taken up with EA, washed with water and brine, dried over $Na_2SO_4$. Concentration and purification by silica gel (PE-PE:EA=20:1-5:1) to afford compound B9 as a white solid (80 mg, yield: 37%).

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2''',3''':8a,9]phenanthro[1,2-c]furan-8-yl 4-oxo-4-(4-(4-oxo-4-(((3S,4S,5R,6S)-2,4,5-trihydroxy-6-(hydroxymethyl)tetrahydro-2H-pyran-3-yl)amino)butanoyl)piperazin-1-yl)butanoate (Compound 2)

A mixture of compound B9 (80 mg, 0.0755 mmol, 1.0 equiv) and Pd/C (10%, 20 mg) in MeOH (5 mL) was stirred at rt. overnight under $H_2$ atmosphere. The mixture was filtered and concentrated, the residue was purified by prep-HPLC to give Compound 2 as a white solid (25 mg, yield: 42%).

Compound 2: $^1$H NMR ($CD_3OD$, 400 MHz): 0.81 (d, J=6.8 Hz 3H), 0.93 (d, J=7.2 Hz 3H), 1.02 (s, 3H), 1.31-1.37 (m, 2H), 1.47-1.51 (m, 1H), 1.85-1.97 (m, 2H), 2.03-2.07 (m, 1H), 2.22-2.29 (m, 2H), 2.55-2.58 (m, 2H), 2.70-2.75 (m, 7H), 3.34-3.38 (m, 1H), 3.44-3.48 (m, 1.5H), 3.57-3.74 (m, 11H), 3.78-3.86 (m, 2.4H), 3.95 (d, J=3.2 Hz, 1H), 4.58-4.60 (m, 0.4H), 4.79-4.81 (m, 1.6H), 5.05 (s, 1H), 5.07 (d J=3.6 Hz, 1H). MS (ESI) calcd [$C_{38}H_{51}N_3O_{15}$] (m/z) for 789.33, found 790.2, [M+H]+.

Example 3. Synthesis of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2''',3''':8a,9]phenanthro[1,2-c]furan-8-yl 4-oxo-4-(4-(4-oxo-4-(((2R,3S,4S,5R)-3,4,5,6-tetrahydroxytetrahydro-2H-pyran-2-yl)methoxy)butanoyl)piperazin-1-yl)butanoate (Compound 3)

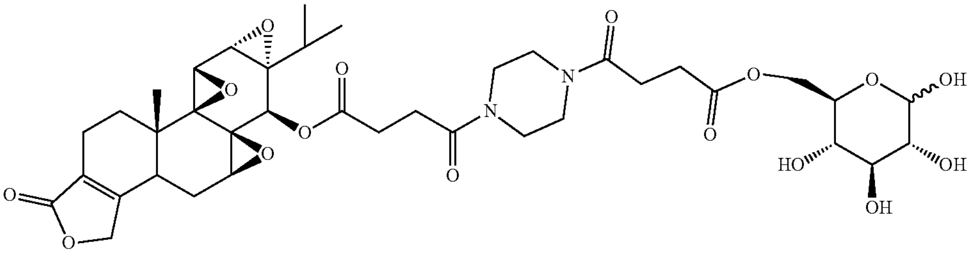 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)N1CCN(C(=O)CCC(=O)OC[C@H]2OC(O)[C@H](O)[C@@H](O)[C@@H]2O)CC1]

The following schemes show the synthetic route used to prepare the title compound.

Scheme 6.

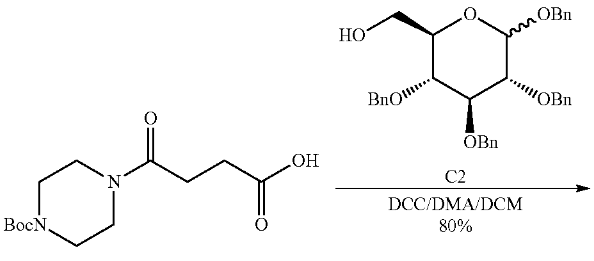

C1

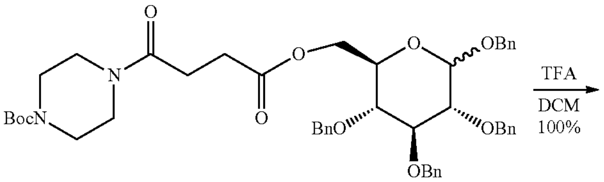

C3

-continued

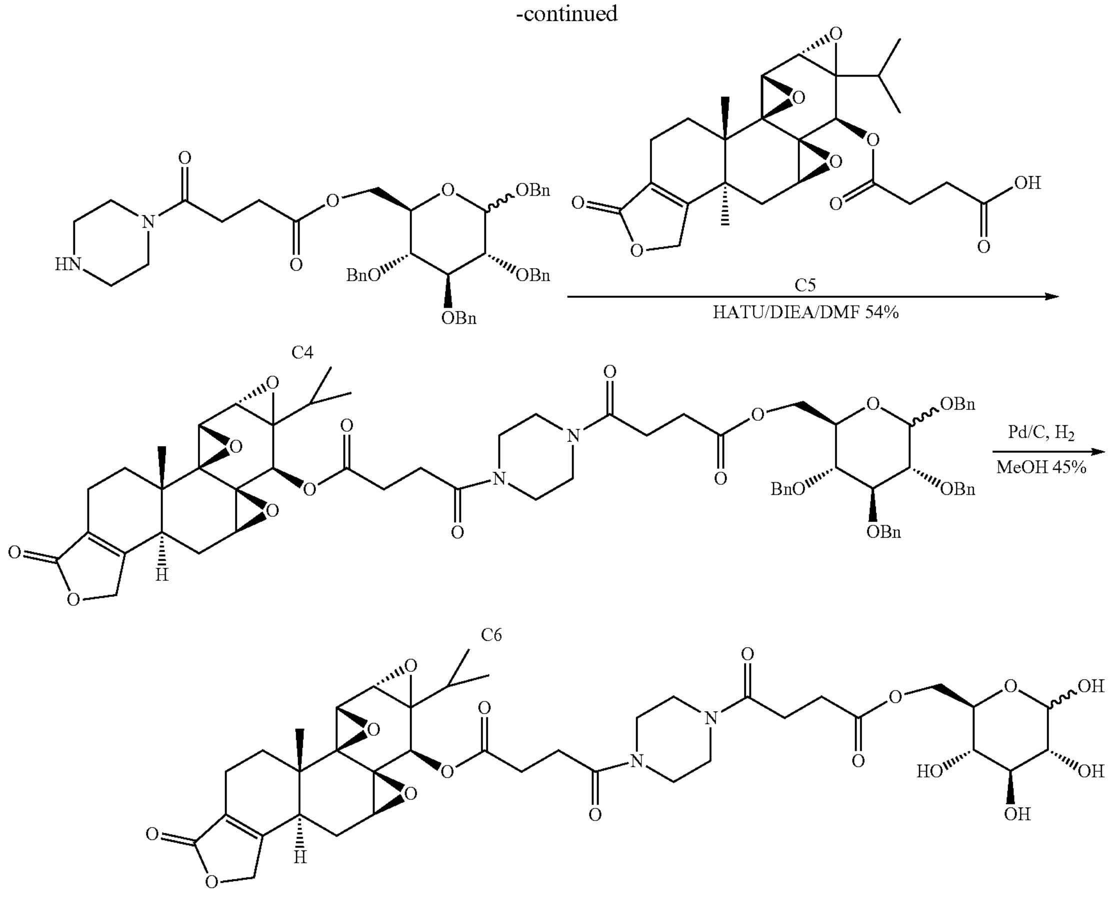

C5

C4

C6

Compound 3

Preparation of tert-butyl 4-(4-oxo-4-(((2R,3R,4S,5R)-3,4,5,6-tetrakis(benzyloxy)tetrahydro-2H-pyran-2-yl)methoxy)butanoyl)piperazine-1-carboxylate (C3)

To a solution of compound C1 (58 mg, 0.2 mmol, 1.0 eq.) and compound C2 (108 mg, 0.2 mmol, 1.0 eq.) in dry DCM (5 mL) was added DCC (45 mg, 0.22 mmol, 1.1 eq.) and DMAP (27 mg, 0.22 mmol, 1.1 eq.) at 0° C. The mixture was stirred at rt. for 18 h and diluted with EA, washed with water then brine, dried over $Na_2SO_4$. After concentration and purification by silica gel (PE-PE:EA=20:1) to give compound C3 as a white solid (130 mg, yield: 80%).

Preparation of ((2R,3R,4S,5R)-3,4,5,6-tetrakis(benzyloxy)tetrahydro-2H-pyran-2-yl)methyl 4-oxo-4-(piperazin-1-yl)butanoate (C4)

To a solution of compound C3 (130 mg, 0.16 mmol, 1.0 eq.) in dry DCM (5 mL) was added TFA (0.1 mL) and the mixture was stirred at rt. for 18 h. The mixture was concentrated to give compound C4 as a yellow oil (113 mg, yield: 100%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 4-oxo-4-(4-(4-oxo-4-(((2R,3R,4S,5R)-3,4,5,6-tetrakis(benzyloxy)tetrahydro-2H-pyran-2-yl)methoxy)butanoyl)piperazin-1-yl)butanoate (C6)

To a solution of compound C4 (113 mg, 0.16 mmol, 1.0 eq.) and compound C5 (74 mg, 0.16 mmol, 1.0 eq.) in dry DMF (5 mL) was added HATU (91 mg, 0.24 mmol, 1.5 eq.) and DIEA (62 mg, 0.48 mmol, 3 eq.) at 0° C. The mixture was stirred at rt. for 18 h and concentrated to give a residue which was taken up with EA, washed with water and brine, dried over $Na_2SO_4$. After concentration and purification by silica gel (PE-PE:EA=20:1-10:1) to give compound C6 as a white solid (100 mg, yield: 54%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2"',3"':8a,9]phenanthro[1,2-c]furan-8-yl 4-oxo-4-(4-(4-oxo-4-(((2R,3S,4S,5R)-3,4,5,6-tetrahydroxytetrahydro-2H-pyran-2-yl)methoxy)butanoyl)piperazin-1-yl)butanoate (Compound 3)

A mixture of compound C6 (80 mg, 0.0695 mmol, 1.0 eq.) and Pd/C (10%, 40 mg) in MeOH (5 mL) was stirred at rt. overnight under $H_2$ atmosphere. The mixture was filtered and concentrated, then purified by pre-HPLC to give the title compound as a white solid (25 mg, yield: 45%). MS (ESI) calcd. [$C_{38}H_{50}N_2O_{16}$] (m/z) for 790.32, found 791.2, $[M+H]^+$. HPLC: 214 nm, 9.845/9.941, 100%; 254 nm, 9.847/9.945 min, 100%.

Example 4. Synthesis of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2'",3'":8a,9]phenanthro[1,2-c]furan-8-yl 2-(2-(2-(((2R,3R,4S,5R)-3,4,5,6-tetrakis(benzyloxy)tetrahydro-2H-pyran-2-yl)methoxy)acetamido)acetamido)acetate (Compound 4)

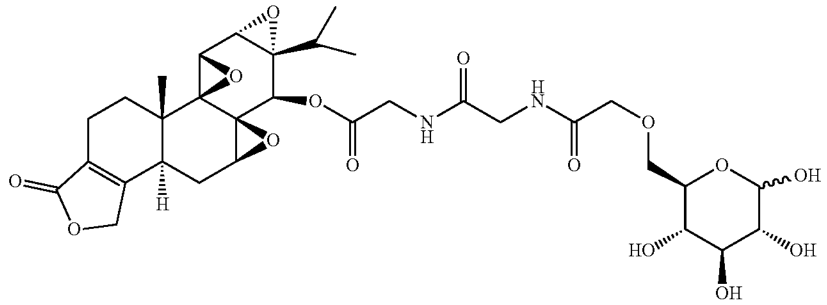 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CNC(=O)CNC(=O)COC[C@H]1OC(O)[C@H](O)[C@@H](O)[C@@H]1O]

The following schemes show the synthetic route used to prepare the title compound.

Scheme 7.

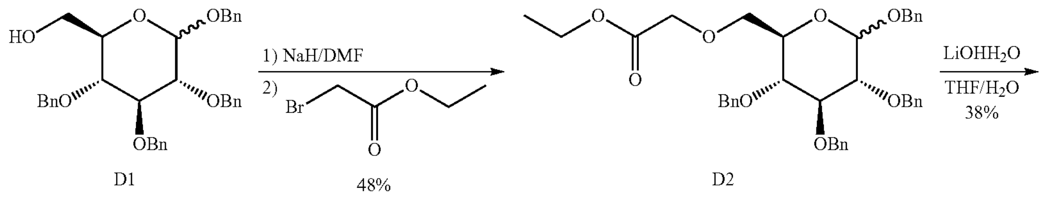

D1

D2

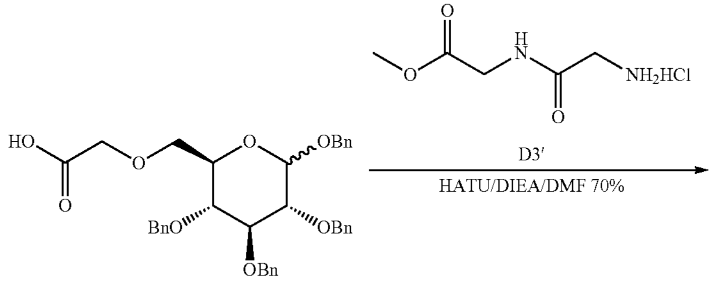

D3

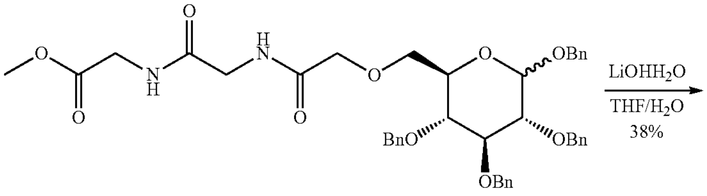

D4

-continued

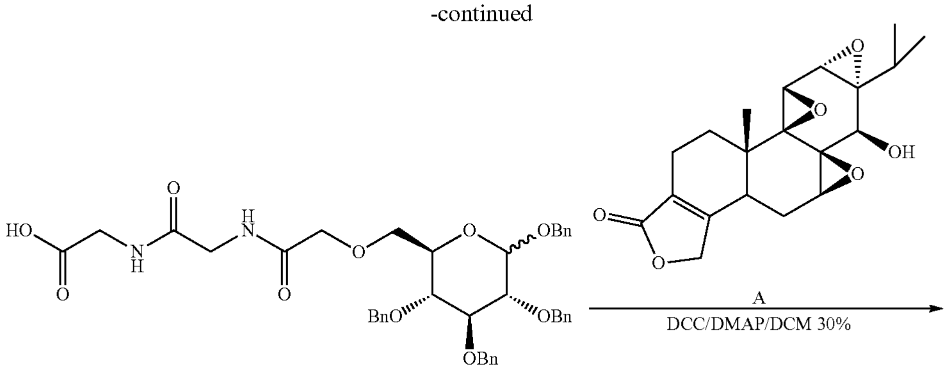

D5

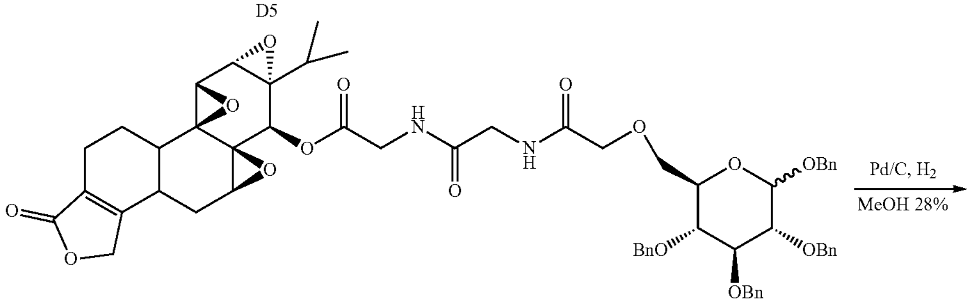

D6

Compound 4

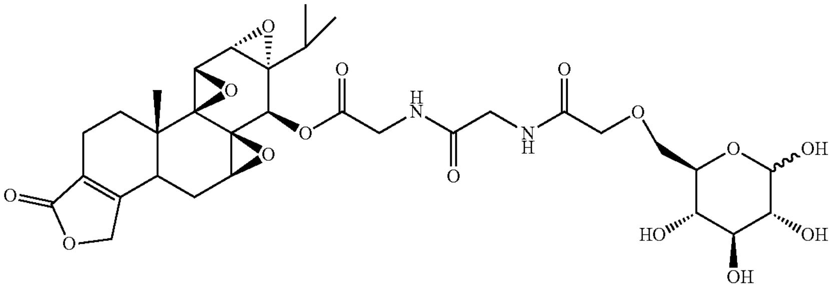

Preparation of ethyl 2-(((2R,3R,4S,5R)-3,4,5,6-tetrakis(benzyloxy)tetrahydro-2H-pyran-2-yl)methoxy) acetate (D2)

To a solution of compound D1 (540 mg, 1.0 mmol, 1.0 equiv) in dry DMF (40 mL) was added NaH (48 mg, 1.2 mmol, 1.2 equiv) in portions. The mixture was stirred at rt. for 0.5 h under $N_2$ atmosphere. Ethyl 2-bromoacetate (200 mg, 1.2 mmol, 1.2 equiv) was added and the resulting mixture was stirred at rt. overnight. The reaction mixture quenched with brine, concentrated, and the residue was taken up with EA, washed with water, dried over $Na_2SO_4$. Concentrated, the residue was purified with column chromatography on silica gel (PE~EA:50:1) to give compound D2 as a colorless oil (300 mg, yield: 48%).

Preparation of 2-(((2R,3R,4S,5R)-3,4,5,6-tetrakis (benzyloxy)tetrahydro-2H-pyran-2-yl)methoxy)acetic acid (D3)

To a solution of compound D2 (300 mg, 0.48 mmol, 1.0 equiv) in THF (6 mL) and water (2 mL) was added $LiOHH_2O$ (101 mg, 2.4 mmol, 5.0 equiv), the mixture was stirred at rt. overnight under $N_2$ atmosphere. The mixture was concentrated and the residue was acidified by 2 N HCl to pH=4~5, extracted with EA and washed with water, dried over $Na_2SO_4$. Concentrated, the residue was purified with column chromatography on silica gel (PE~EA=2:1) to give compound D3 as a colorless oil (mg, yield: 38%).

Preparation of methyl 2-(2-(2-(((2R,3R,4S,5R)-3,4,5,6-tetrakis(benzyloxy)tetrahydro-2H-pyran-2-yl) methoxy)acetamido)acetamido)acetate (D4)

To a solution of compound D3 (110 mg, 0.18 mmol, 1.0 equiv), compound 3' (34 mg, 0.18 mmol, 1.0 equiv) and HATU (90 mg, 0.234 mmol, 1.3 equiv) in dry DMF (5 mL) was added DIEA (77 mg, 0.6 mmol, 3.3 equiv) at 0° C. and the resulting mixture was stirred at rt. overnight under $N_2$ atmosphere. The reaction mixture was quenched with water, concentrated, and the residue was diluted with EA, then washed with water, dried over $Na_2SO_4$. After concentration, the residue was purified with column chromatography on silica gel (PE~EA=5:1) to give compound D4 as a white solid (165 mg, yield: 70%).

Preparation of 2-(2-(2-(((2R,3R,4S,5R)-3,4,5,6-tetrakis(benzyloxy)tetrahydro-2H-pyran-2-yl)methoxy)acetamido)acetamido)acetic acid (D5)

To a solution of compound D4 (165 mg, 0.227 mmol, 1.0 equiv) in THF (6 mL) and water (2 mL) was added $LiOHH_2O$ (48 mg, 1.14 mmol, 5.0 equiv), the mixture was stirred at rt. overnight under $N_2$ atmosphere. The mixture was concentrated, the residue was acidified by 2 N HCl to pH=4~5, extracted with EA and washed with water, dried over $Na_2SO_4$. After concentration, the residue was purified with column chromatography on silica gel (PE~EA=2:1) to give compound D5 as a white solid (160 mg, yield: 99%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 2-(2-(2-(((2R,3R,4S,5R)-3,4,5,6-tetrakis(benzyloxy)tetrahydro-2H-pyran-2-yl)methoxy)acetamido)acetamido)acetate (D6)

To a solution of compound D5 (160 mg, 0.23 mmol, 1.0 equiv) and compound A (82 mg, 0.23 mmol, 1.0 equiv) in dry DCM (5 mL) was added DCC (56 mg, 0.27 mmol, 1.2 equiv) and DMAP(cat.) at 0° C. and the resulting mixture was stirred overnight at rt. under $N_2$ atmosphere. The reaction mixture was filtered, the filtrate was concentrated, and purified by pre-HPLC to give compound D6 as a white solid (72 mg, yield: 30%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 2-(2-(2-(((2R,3R,4S,5R)-3,4,5,6-tetrakis(benzyloxy)tetrahydro-2H-pyran-2-yl)methoxy)acetamido)acetamido)acetate (Compound 4)

To a solution of compound D6 (72 mg, 0.068 mmol, 1.0 equiv) in MeOH (6 mL) was added Pd/C (36 mg, 10%), the mixture was stirred for 6 h at rt. under $H_2$ atmosphere. The mixture was filtered and the filtrate was concentrated and purified by pre-HPLC to give the title compound as a white solid (13 mg, yield: 28%). MS (ESI) calcd. $[C_{32}H_{42}N_2O_{15}]$ (m/z) for 694.26 found 695.4, $[M+H]^+$. HPLC: 220 nm, 8.904 min, 100%; 254 nm, 8.906 min, 100%.

Example 5. Synthesis of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 4-(4-(4-((6-chloro-2-methoxyacridin-9-yl)amino)pentyl)piperazin-1-yl)-4-oxobutanoate (Compound 5)

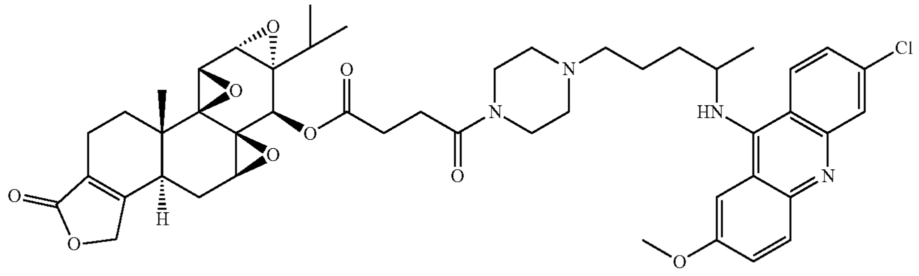 [SMILES: COc1ccc2nc3cc(Cl)ccc3c(NC(C)CCCN3CCN(C(=O)CCC(=O)O[C@@H]4[C@@]5(C(C)C)O[C@H]5[C@@H]5O[C@]56[C@]45O[C@H]5C[C@H]4C5=C(CC[C@@]46C)C(=O)OC5)CC3)c2c1]

The following schemes show the synthetic route used to prepare the title compound.

Scheme 8.

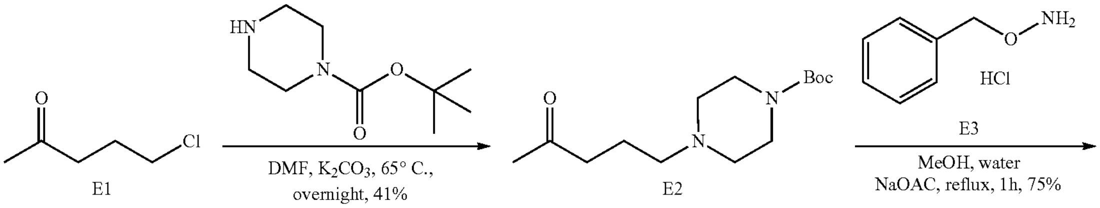

E1 E2

-continued

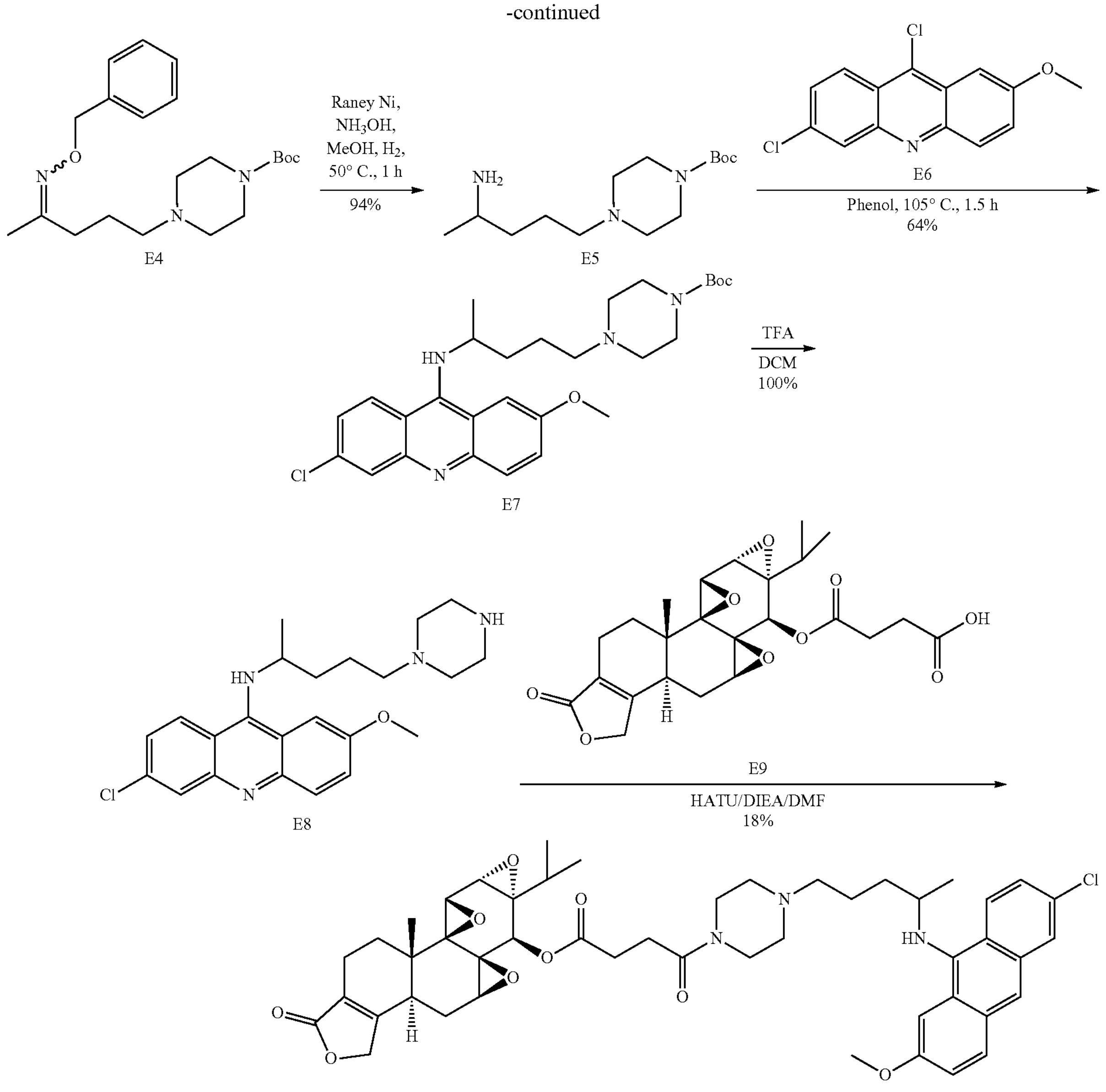

Compound 5

Preparation of tert-butyl 4-(4-oxopentyl)piperazine-1-carboxylate (E2)

$K_2CO_3$ (3.7 g, 26.9 mmol, 1.3 eq) was added to a stirred solution of compound E1 (2.5 g, 20.7 mmol, 1.0 eq) and tert-butyl piperazine-1-carboxylate (7.7 g, 41.4 mmol, 2.0 eq) in DMF (30 mL) at rt. After stirring at 65° C. overnight, the mixture was poured into ice-water (200 mL), extracted by EtOAc (200 mL×3), all the EA layer were combined and washed with brine (200 mL×3), dried over $Na_2SO_4$ and concentrated. The residue was purified by silica gel column (DCM:MeOH=20:1 to 10:1) gave the product E2 as yellow oil (2.3 g, yield: 41%).

Preparation of tert-butyl 4-(4-((benzyloxy)imino) pentyl)piperazine-1-carboxylate (E4)

To a stirred mixture of E2 (2.3 g, 8.5 mmol, 1.0 eq) and O-Benzylhydroxylamine hydrochloride (1.5 g, 9.4 mmol, 1.05 eq) in MeOH (10 mL) was added NaOAc (3.5 g, 42.5 mmol, 5.0 eq), followed by addition of water (20 ml) at rt. After stirring at 100° C. (oil bath) for 1 h, the mixture was concentrated to remove the organic solvent, then diluted with EtOAc (200 mL), the aq layer was further extracted by EtOAc (200 ml×2), all the EA layer were combined and washed with brine (200 mL), dried over $Na_2SO_4$ and concentrated. A yellow solid was formed while concentration, the solid was collected by filtration gave the 1st part of product (E4, 1.91 g, yield: 59%), and the filtrate was concentrated and purified by silica gel column (PE:EA=4:1; 1:1, then DCM:MeOH=10:1) to give the 2nd part of product as yellow oil (500 mg, yield: 16%), totally 2.4 g of product was obtained, yield 75%.

Preparation of tert-butyl 4-(4-aminopentyl)piperazine-1-carboxylate (E5)

To a mixture of E4 (1.91 g, 5.08 mmol) and $NH_{30}H$ (2 mL) in MeOH (20 mL) was added Raney Ni (about 5 mL in water). After stirring at 50° C. under $H_2$ for 5.5 h, the mixture was filtrated. The filtrate was concentrated and diluted with water (100 mL), extracted with EtOAc, all the EA layer were combined and washed with brine, dried over $Na_2SO_4$ and concentrated to give the product as yellow oil (E5, 1.3 g, yield: 94%), which was used to next step without further purification.

Preparation of tert-butyl 4-(4-((6-chloro-2-methoxy-acridin-9-yl)amino)pentyl)piperazine-J-carboxylate (E7)

E6 (500 mg, 1.8 mmol, 1.0 eq) was mixed with Phenol (2.0 g) in a 25 mL flask, then the mixture was stirred at 105° C. (oil bath) for 0.5 h. E5 (635 mg, 2.34 mmol, 1.3 eq) was added to the above mixture and kept stirring for additional 1.0 h. After cooling to rt, the mixture was diluted with DCM (5 mL) and subjected to a silica gel column (Biotage, 25 g, MeOH in DCM, 0-50%, 254 nm), collected the part of product, concentrated to give the product as yellow solid (E7, 597 mg, 64% yield).

Preparation of 6-chloro-2-methoxy-N-(5-(piperazin-1-yl)pentan-2-yl)acridin-9-amine (E8)

A mixture of E7 (100 mg, 0.195 mmol) and TFA (0.2 mL) in DCM (5 mL) was stirred at rt. for 18 h. The mixture was concentrated to give crude E8 as a yellow solid (100 mg).

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2"',3"':8a,9]phenanthro[1,2-c]furan-8-yl 4-(4-(4-((6-chloro-2-methoxyacridin-9-yl)amino)pentyl)piperazin-1-yl)-4-oxobutanoate (Compound 5)

To a solution of E8 (100 mg, 0.195 mmol, 1.0 equiv) and E9 (90 mg, 0.195 mmol, 1.0 equiv) in dry DMF (5 mL) was added HATU (97 mg, 0.254 mmol, 1.3 equiv) and DIEA (63 mg, 0.488 mmol, 2.5 equiv) at 0° C. The mixture was stirred at rt. for 18 h. The mixture was concentrated, and the residue was purified by pre-HPLC to give Compound 5 as a yellow solid (30 mg, yield: 18%). MS (ESI) calcd. [$C_{47}H_{55}ClN_4O_9$] (m/z) for 854.37, found 428.6, [½M+H]+. HPLC: 220 nm, 9.948, 100%; 254 nm, 9.95 min, 100%.

Example 6. Synthesis of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 3-((S)-6-acetamido-2-((tert-butoxycarbonyl)amino)hexanamido)propanoate (Compound 6)

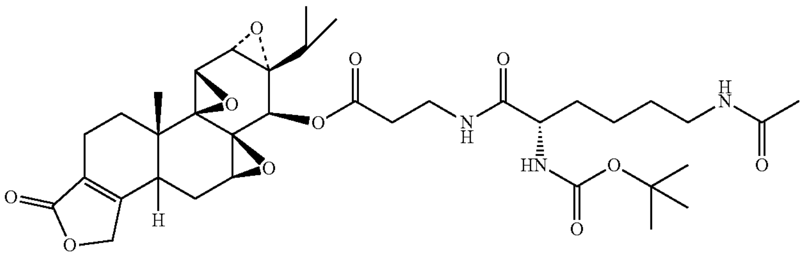

The following schemes show the synthetic route used to prepare the title compound.

Scheme 9.

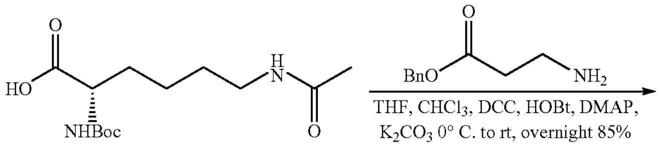

F1

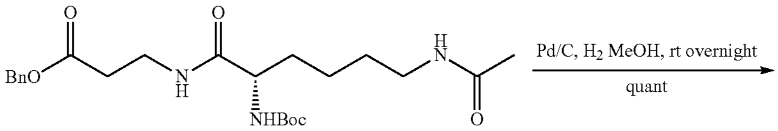

F2

-continued

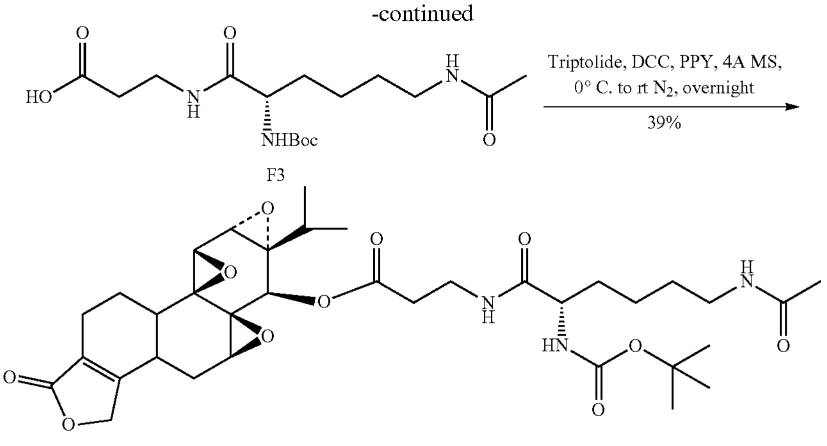

F3

Compound 6

Preparation of (S)-benzyl 3-(6-acetamido-2-((tert-butoxycarbonyl)amino)hexanamido) propanoate (F2)

Step 1: 3-aminopropanoic acid (1.8 g, 20.0 mmol, 1.0 eq), BnOH (4.3 g, 40.0 mmol, 2.0 eq) and PTSA (4.2 g, 22.0 mmol, 1.1 eq) in Toluene (50 mL) was stirred at reflux overnight, then removed the solvent under vacuum, diluted by EA/PE (about 1/10, v/v, 100 mL), the solid was collected by filtration and dried under vacuum to give benzyl 3-aminopropanoate (PTSA salt) as pale yellow solid (6.8 g, 97% yield).

Step 2: (S)-6-acetamido-2-((tert-butoxycarbonyl)amino) hexanoic acid (Compound F1, 576 mg, 2.0 mmol, 1.0 eq) in THF (10 mL), added HOBt (405 mg, 3.0 mmol, 1.5 eq) under ice-water bath. After stirring for 10 min, DMAP (244 mg, 2.0 mmol, 1.0 eq) added, followed by DCC (824 mg, 4.0 mmol, 2.0 eq) in $CHCl_3$ (10 mL), then stirred for another 15 min. $K_2CO_3$ (414 mg, 3.0 mmol, 1.5 eq) and benzyl 3-aminopropanoate (PTSA salt) (843 mg, 2.4 mmol, 1.2 eq) were added. The resulting mixture was allowed stirred at rt overnight. The unsoluble white solid was filtrated off, the filtrate was concentrated and partioned between EA (200 mL) and water (200 mL), the aq layer was further extracted by EA (200 mL), all the EA layer was combined and washed by brine (200 mL), dried over $Na_2SO_4$, filtrated and concentrated. The residue was purified by flash column (MeOH in DCM, 0-20%) to give the product as pale-yellow oil (F2,768 mg, yield 85%).

Preparation of(S)-3-(6-acetamido-2-((tert-butoxycarbonyl)amino)hexanamido) propanoic acid (F3)

A mixture of Pd/C (5%, 80 mg) and F2 (220 mg, 0.50 mmol) in MeOH (10 mL) was stirred at rt under $H_2$ overnight. Filtrated off the catalyst and the filtrate were concentrated to give the product as white foam solid (F3, 177 mg, quant).

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2'',3'':6,7;2''',3''':8a,9]phenanthro[1,2-c]furan-8-yl 3-((S)-6-acetamido-2-((tert-butoxycarbonyl)amino)hexanamido)propanoate (Compound 6)

To a white cloudy mixture of F3 (45 mg, 0.125 mmol, 2.0 eq) in $CHCl_3$/THF (1/1, 4 mL) was added 4 Å MS (about 800 mg), and stirred at rt under $N_2$ for 0.5 h. The mixture was cooled under ice-water bath, and DCC (29 mg, 0.138 mmol, 2.2 eq) in $CHCl_3$ (0.5 mL) added, followed by addition of PPY (4-Pyrrolidinopyridine, 20 mg, 0.138 mmol, 2.2 eq). After stirring at the same temperature for 0.5 h, Triptolide (22 mg 0.062 mmol, 1.0 eq) was added. Kept stirring and gently warmed up to rt overnight. The mixture was diluted with DCM/EA (about 20 mL), filtrated, the filtrate was concentrated and purified by flash column (0-10% MeOH in DCM), collected the parts of product and give a crude product, which was further purified by Pre-HPLC (ODS, ACN in water, 20-95%, 214 nm), followed by concentration and freezing-drying to give the desired product as white solid (Compound 6) and the unreacted triptolide was recovered. $^1H$ NMR ($CDCl_3$, 400 MHz) δ 0.91 (d, 3H, J=7.2 Hz), 1.01 (d, 3H, J=6.8 Hz), 1.088 (s, 3H), 1.24-1.32 (m, 2H), 1.38-1.44 (m, 1H), 1.47 (s, 9H), 1.57-1.72 (m, 4H), 1.81-1.94 (m, 2H), 2.01 (s, 3H), 2.16-2.27 (m, 2H), 2.36-2.40 (m, 1H), 3.66-2.76 (m, 3H), 3.28 (bs, 2H), 3.56-3.65 (m, 4H), 3.98 (s, 1H), 4.24 (m, 1H), 4.73 (s, 2H), 5.14 (s, 1H), 5.33 (d, 1H, J=7.2 Hz), 5.89 (bs, 1H), 7.07 (bs, 1H). MS (ESI) calcd. for $[M+H]^+$ (m/z): 702.3, found: 702.3.

Example 7. Synthesis of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2'',3'':6,7;2''',3''':8a,9]phenanthro[1,2-c]furan-8-yl((1-methyl-2-nitro-1H-imidazol-5-yl)methyl) carbonate (Compound 7)

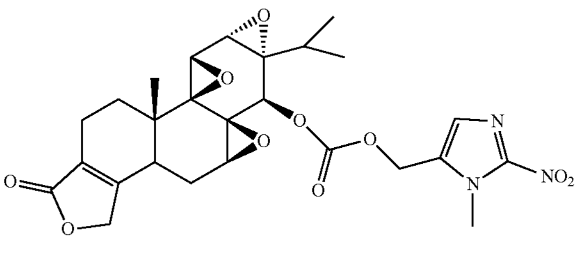 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)OCc1cnc([N+](=O)[O-])n1C]

The following schemes show the synthetic route used to prepare the title compound.

Scheme

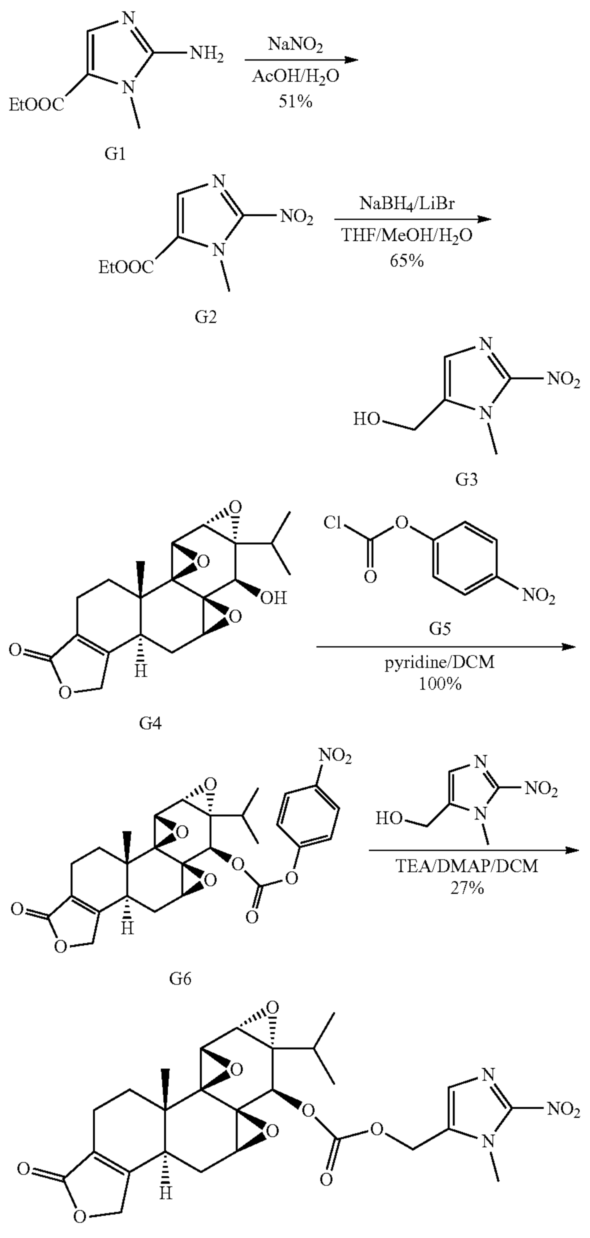

G1 G2 G3 G4 G5 G6 Compound 7

Preparation of ethyl 1-methyl-2-nitro-1H-imidazole-5-carboxylate (G2)

To a solution of $NaNO_2$ (1713 mg, 24.85 mmol, 7.0 equiv) in $H_2O$ (5 mL) was added dropwise a solution of G1 (600 mg, 3.55 mmol, 1.0 equiv) in AcOH (4 mL) at −5° C. under $N_2$ atmosphere. The mixture was warmed to rt for overnight. the reaction mixture was extracted with DCM, dried over $Na_2SO_4$. Concentrated and purified with column chromatography on silica gel (PE:EA=20:1) to give compound G2 as a yellow crystals (360 mg, yield: 51%).

Preparation of (1-methyl-2-nitro-1H-imidazol-5-yl) methanol (G3)

To a solution of compound G2 (405 mg, 2.03 mmol, 1.0 equiv) in THF/MeOH (8 mL/2 mL) and cooled to 0° C., then $NaBH_4$ (231 mg, 6.09 mmol, 3.0 equiv) and LiBr (530 mg, 6.09 mmol, 3.0 equiv) in $THF/H_2O$ (4 mL/2 mL) was added dropwise at below 10° C. The mixture was stirred at rt overnight under $N_2$ atmosphere. The $NH_4Cl$ was added at 0° C. and stirring was prolonged for 30 min, the precipitate was filtrated and washed with THF, the filtrate was concentrated, the residue was taken up in a mixture of EA/MeOH (98/2, V/V) and the resulting solution was passed through a pad of silica gel to give compound G3 as a pale yellow to orange crystals (263 mg, yield: 65%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl (4-nitrophenyl) carbonate (G6)

To a solution of compound G4 (36 mg, 0.1 mmol, 1.0 equiv) in dry DCM (2 mL) was added dry pyridine (17 uL, 0.15 mmol, 1.5 equiv) at 0° C. under $N_2$ atmosphere. The compound G5 (30 mg, 0.15 mmol, 1.5 equiv) was added and the mixture was stirred at r.t for overnight under $N_2$ atmosphere. The mixture was quenched with 1N HCl, extracted with DCM, washed with brine, dried over $Na_2SO_4$. Concentrated in vacuum to give compound G6 as a white solid (52 mg, yield: 100%), which was used directly in the next step without further purification.

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2,3':4b,5;2",3":6,7,2"',3"':8a,9]phenanthro[1,2-c]furan-8-yl ((1-methyl-2-nitro-1H-imidazol-5-yl)methyl) carbonate (Compound 7)

To a solution of compound G6 (52 mg, 0.1 mmol, 1.0 equiv) and compound G3 (19 mg, 0.12 mmol, 1.2 equiv) in dry DCM (5 mL) was added $Et_3N$ (31 mg, 0.3 mmol, 3.0 equiv) and DMAP (3 mg, 0.02 mmol, 0.2 equiv) at 0° C. under $N_2$ atmosphere. The mixture was stirred at rt overnight. The mixture was quenched with Sat.$NH_4Cl$, extracted with DCM, washed with brine, dried over $Na_2SO_4$. After concentration, the residue was purified by Prep-HPLC to give the title compound as a white solid (Compound 7, 15 mg, yield: 27%). $^1$H-NMR ($CDCl_3$, 400 MHz): 0.85 (d, J=6.8 Hz, 3H), 0.97 (d, J=7.2 Hz, 3H), 1.05 (s, 3H), 1.19-1.25 (m, 1H), 1.55-1.60 (m, 1H), 1.88-1.95 (m, 2H), 2.13-2.22 (m, 2H), 2.30-2.35 (m, 1H), 2.67-2.71 (m, 1H), 3.49 (d, J=5.6 Hz, 1H), 3.55 (s, 1H), 3.84 (d, J=3.2 Hz, 1H), 4.06 (s, 3H), 4.68 (s, 2H), 4.82 (s, 1H), 5.21-5.29 (m, 2H), 7.27 (s, 1H). MS (ESI) calcd. [$C_{26}H_{29}N_3O_{10}$] (m/z) for 543.52 found 544.1, $[M+H]^+$. HPLC: 220 nm, 12.204 min, 99.97%; 254 nm, 12.205 min, 99.94%.

Example 8. Synthesis of the Conjugate of Triptolide with Tri-Glucosamine (Compound 8)
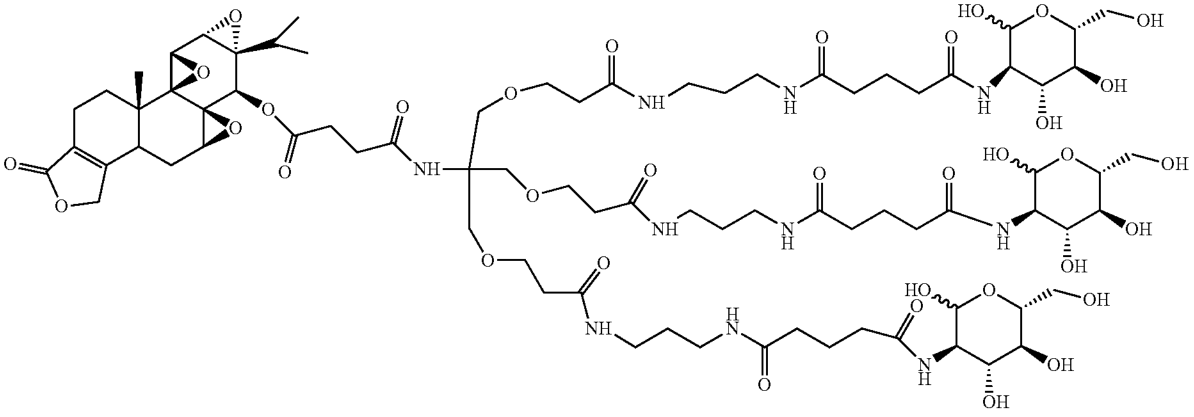 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC(COCCC(=O)NCCCNC(=O)CCCC(=O)N[C@H]1C(O)O[C@H](CO)[C@@H](O)[C@@H]1O)(COCCC(=O)NCCCNC(=O)CCCC(=O)N[C@H]1C(O)O[C@H](CO)[C@@H](O)[C@@H]1O)COCCC(=O)NCCCNC(=O)CCCC(=O)N[C@H]1C(O)O[C@H](CO)[C@@H](O)[C@@H]1O]
The following schemes show the synthetic route used to prepare the title compound.
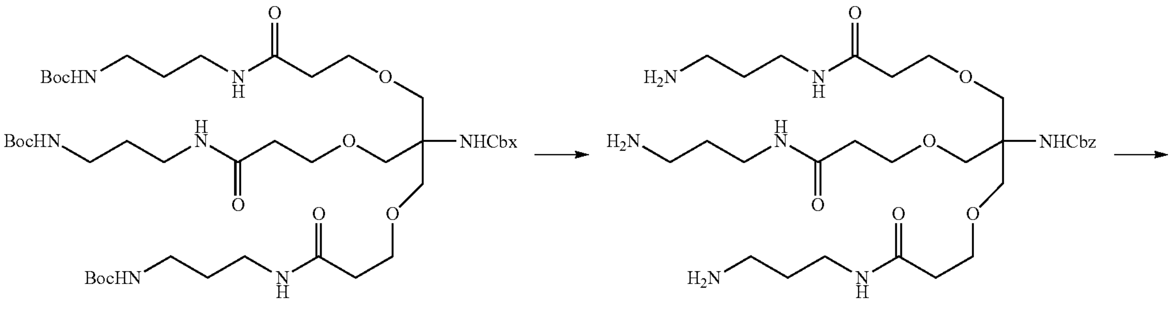
H1 H2
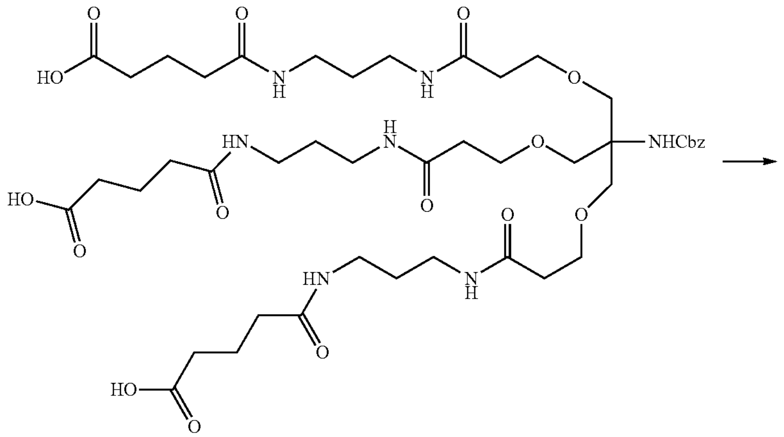
H3

-continued

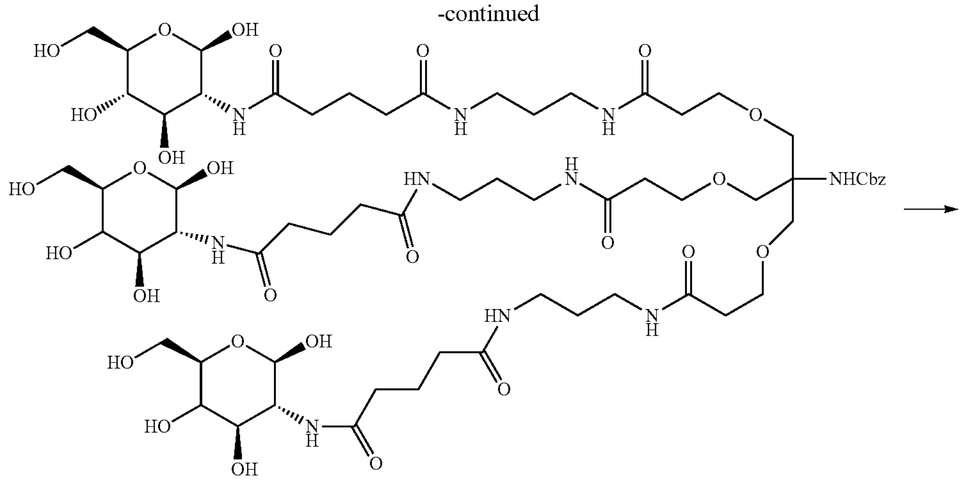

H4

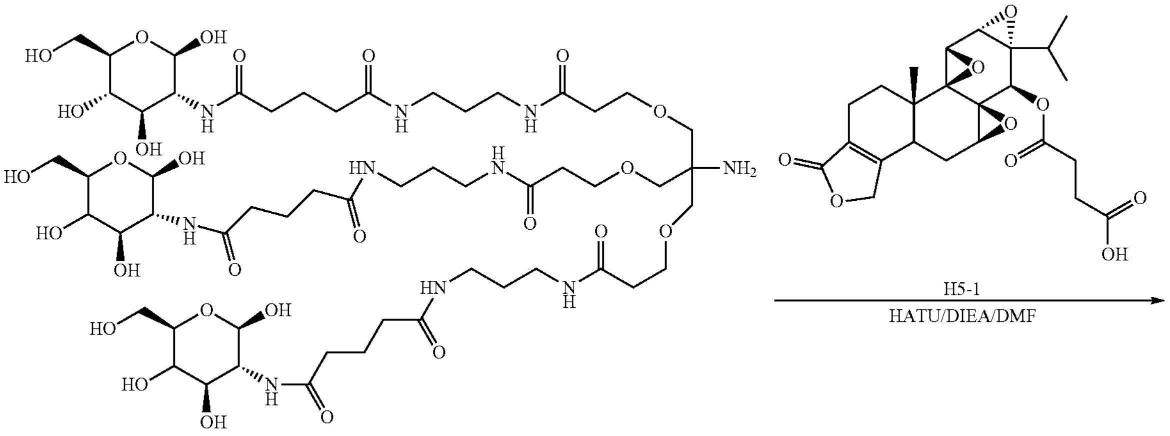

H5

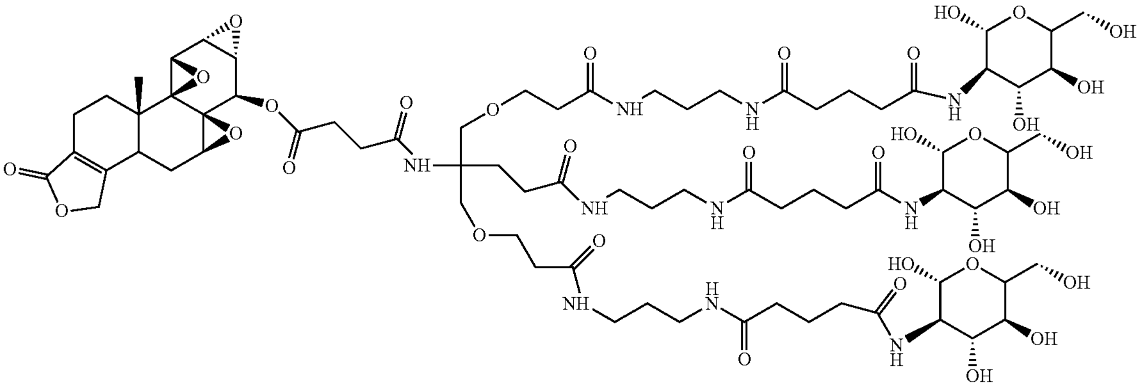

Compound B

Preparation of Compound H2

The solution of H1 (1.0 g, 1.0638 mmol, 1.0 equiv) in TFA (10 mL) and was stirred at r.t for 1 hrs, then was diluted with toluene and concentrated, the residue was co-evaporated with toluene and dried under reduced pressure using a high vacuum pump to get H2 as the TFA salt, which was used for the next reaction without any further purification (1.0 g, yield: 100%)

Preparation of Compound H3

To a solution of H2 (1.0 g, 1.0638 mmol, 1.0 eq.) in pyridine (10 mL) was added dihydro-2H-pyran-2,6(3H)-dione (728 mg, 6.3830 mmol, 6.0 eq.). The solution was stirred at room temperature overnight. LC-MS showed the reaction was complete. It was concentrated and the residue was purified by Prep-HPLC to get H3 as a white solid (710 mg, yield: 68.3% for two steps).

Preparation of Compound H4

To a solution of H3 (660 mg, 0.5110 mmol, 1.0 equiv) and in DMF (20 mL) was added (2R,3R,4R,5S,6R)-3-amino-6-(hydroxymethyl)tetrahydro-2H-pyran-2,4,5-triol hydrochloride (661 mg, 3.0658 mmol, 6.0 equiv) and DIPEA (785 mg, 6.1316 mmol, 12 equiv) at 0° C. under $N_2$ atmosphere. It was stirred for 5 min and then HATU (971 mg, 2.5550 mmol, 5.0 equiv) was added and stirred for another 18 hours. LCMS showed the reaction was completed. $H_2O$ (5.0 ml) was added and stirred for 30 min. Then the reaction mixture was concentrated, the residue was purified by Prep-HPLC to give H4 as a white solid (628 mg, yield: 84%).

Preparation of Compound H5

To a solution of H4 (828 mg, 0.5653 mmol, 1.0 equiv) in MeOH/$H_2O$ (30/5 mL) was added Pd/C, 10% (160 mg, cat.) and stirred under $H_2$ overnight. LCMS showed the reaction was completed. It was filtered and the filtrate was concentrated to give compound H5 as a white solid (676 mg, yield: 90%).

Preparation of Compound 8

To a solution of compound H5-1 (100 mg, 0.2173 mmol, 1.0 equiv) and in DMF (6 mL) was added H5 (347 mg, 0.2608 mmol, 1.2 equiv) and DIPEA (83 mg, 0.6519 mmol, 3.0 equiv) at 0° C. under $N_2$ atmosphere. The mixture was stirred for 5 min. Then HATU (107 mg, 0.2825 mmol, 1.3 equiv) was added to the mixture and was stirred for another two hours. LCMS showed the reaction was completed. Water (3.0 ml) was added and stirred for 30 min. Then the mixture was concentrated and the residue was purified by Prep-HPLC to give the triptolide tri-glucosamine conjugate (Compound 8) as a white solid (105 mg, yield: 27%).

Example 9. Synthesis of the Conjugate of Triptolide with Tri-Glucose (Compound 9)

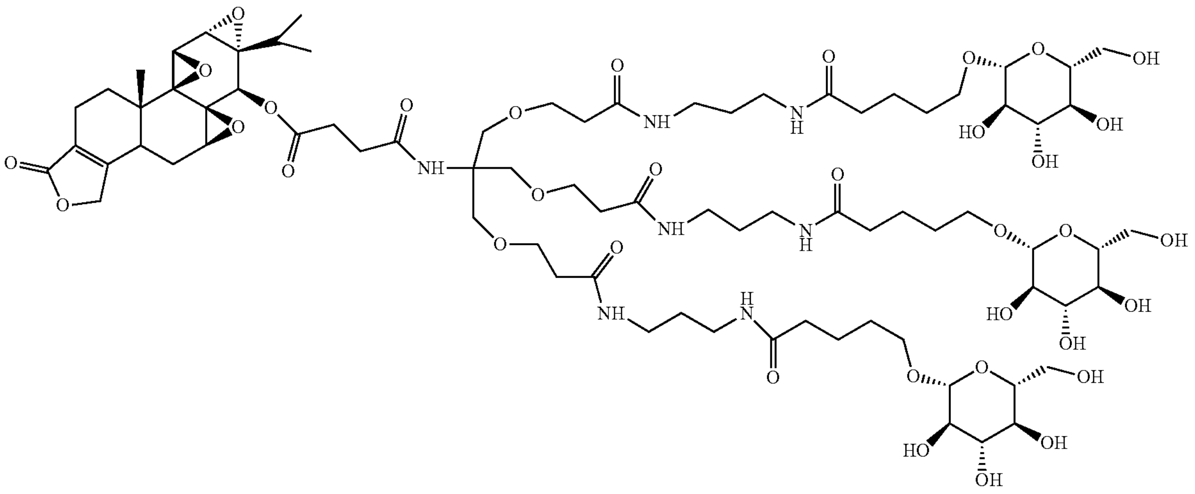 [SMILES: CC(C)[C@]12O[C@H]1[C@@H]1O[C@]13[C@]1(O[C@H]1CC1C4=C(CC[C@@]13C)C(=O)OC4)[C@@H]2OC(=O)CCC(=O)NC(COCCC(=O)NCCCNC(=O)CCCCO[C@@H]1O[C@H](CO)[C@@H](O)[C@H](O)[C@H]1O)(COCCC(=O)NCCCNC(=O)CCCCO[C@@H]1O[C@H](CO)[C@@H](O)[C@H](O)[C@H]1O)COCCC(=O)NCCCNC(=O)CCCCO[C@@H]1O[C@H](CO)[C@@H](O)[C@H](O)[C@H]1O]

The following schemes show the synthetic route used to prepare the title compound.

Scheme 12.

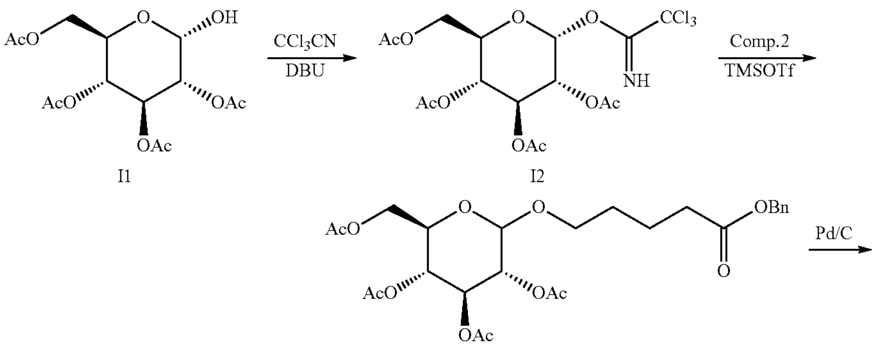

I1 I2 I3

-continued
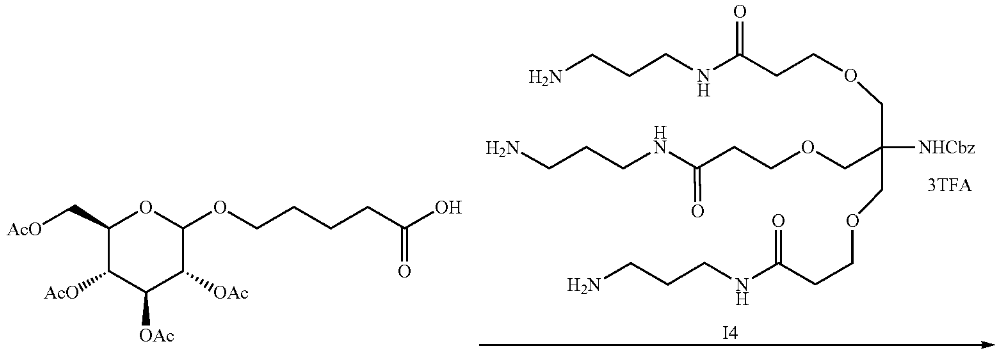
I4
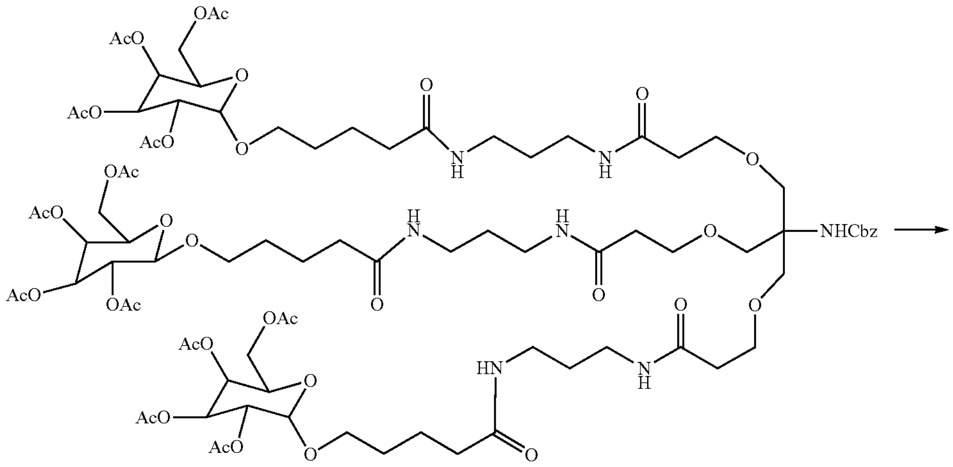
I4
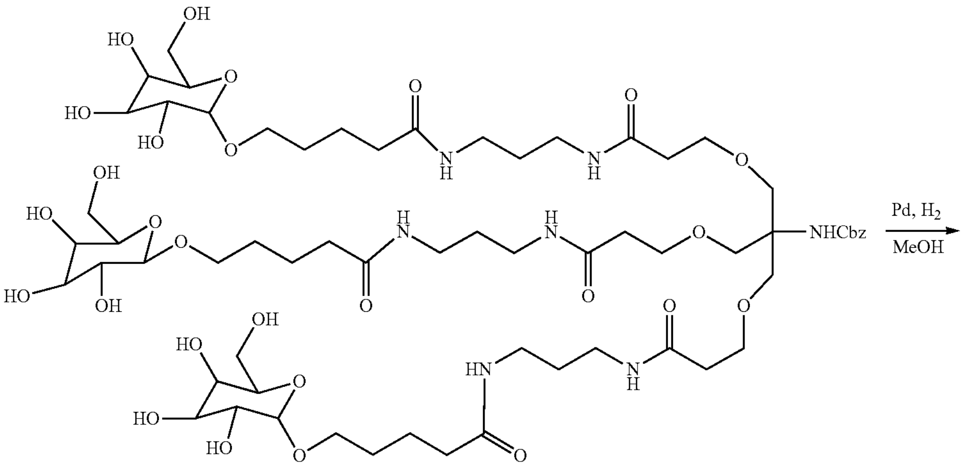
I6

-continued

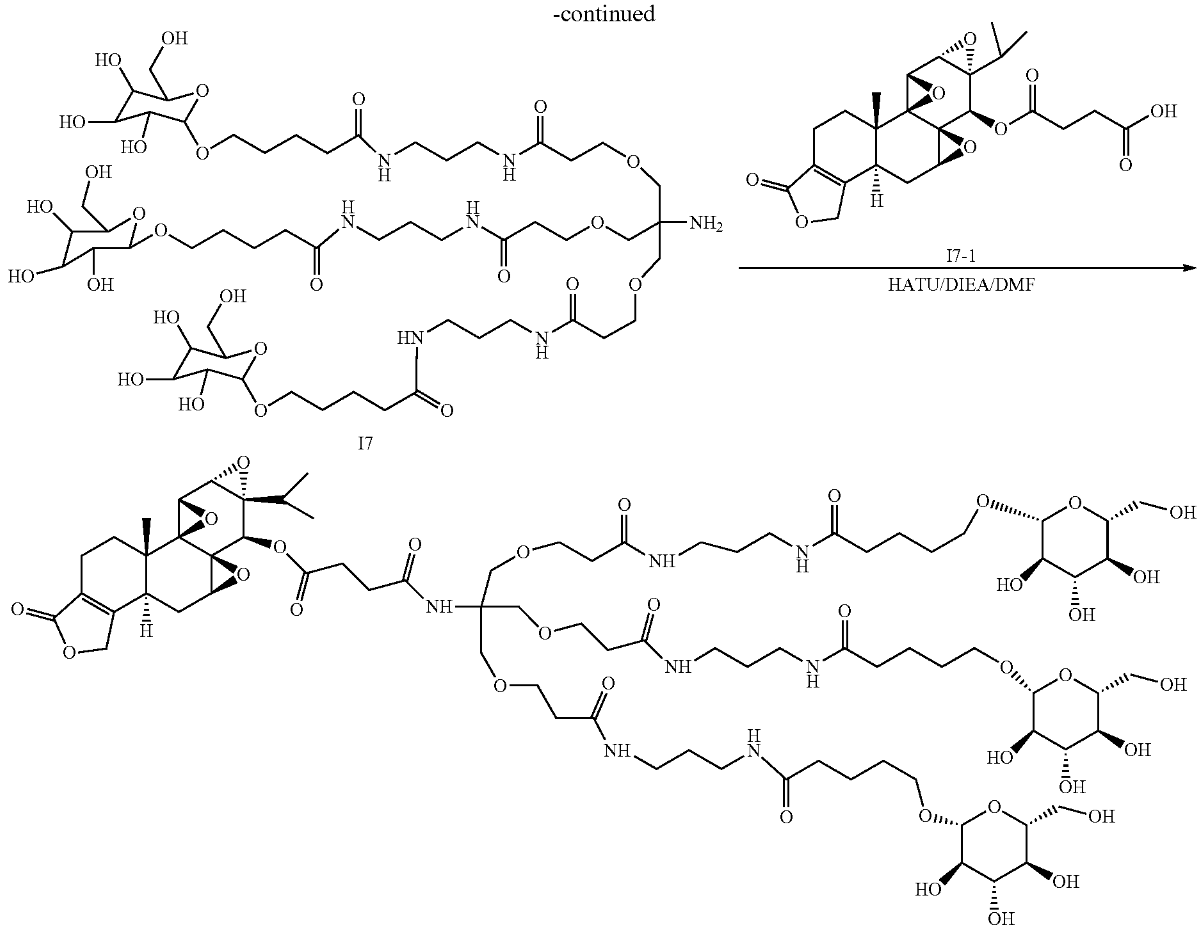

I7

Compound 9

Preparation of Compound I2

To a solution of compound I1 (1.044 g, 3.0 mmol, 1.0 equiv) in DCM (20 mL) was added DBU (228 mg, 1.5 mmol, 0.5 eq.) and Trichloroacetonitrile (2.59 g, 18 mmol, 6.0 eq.) at 0° C. Then it was warmed to room temperature and stirred overnight. TLC showed the reaction was completed. It was concentrated and the residue was purified by a flash column to get 1.3 g of the desired product Compound I2.

Preparation of Compound I3

To a solution of compound I2 (1.3 g, 2.6477 mmol, 1.0 equiv) in DCM (15 mL) was added benzyl 5-hydroxypentanoate (826 mg, 3.9716 mmol, 1.5 eq.) and TMSOTf (118 mg, 0.5295 mmol, 0.2 eq.) at 0° C. The solution was stirred for 3 hours. Then TEA (0.5 ml) was added and stirred for another 30 min. LCMS showed the reaction was complete. It was quenched with water, extracted with DCM. The organic phase was dried, filtered and concentrated. The residue was purified by Prep-HPLC to get compound I3 as a colorless oil (500 mg, yield: 35% for two steps).

Preparation of Compound I4

To a solution of compound I3 (500 mg, 0.9294 mmol, 1.0 equiv) in MeOH (10 ml) was added Pd/C (10%, 80 mg). The mixture was stirred under $H_2$ for 5 hours. LCMS showed the reaction was completed. It was filtered and concentrated to get the desired product as a white solid (I4, 380 mg, yield: 91%).

Preparation of Compound I5

To a solution of compound I4 (380 mg, 0.8482 mmol, 3.3 equiv) in DMF (8.0 mL) was added compound I4-1 (240 mg, 0.2570 mmol, 1.0 eq.), DIEA (329 mg, 2.57 mmol, 10 eq.) and HATU (488 mg, 1.285 mmol, 5.0 eq.). Then it was stirred overnight. LCMS showed the reaction was completed. It was quenched with water and stirred for 30 min. The solution was concentrated and the residue was dissolved in water and extracted with DCM. The organic phase was dried, filtered and concentrated. The residue was purified by Prep-HPLC to give compound I5 as a white solid (380 mg, yield: 76%).

Preparation of Compound I6

To a solution of compound I5 (380 mg, 0.1969 mmol, 1.0 equiv) in MeOH (8.0 mL) was added MeONa (21 mg, 0.3938 mmol, 2.0 eq.). It was stirred for 5 hours. LCMS showed the reaction was completed. It was concentrated and the residue was purified by Prep-HPLC to give compound I6 as a white solid (220 mg, yield: 79%).

Preparation of Compound I7

To a solution of compound I6 (220 mg, 0.1543 mmol, 1.0 equiv) in MeOH (10.0 mL) was added Pd/C (10%, 40 mg, cat.). It was stirred under $H_2$ for 5 hours. LCMS showed the reaction was completed. It was concentrated give compound I7 as a white solid (200 mg, yield: 100%). Exact Mass: 1291.67.

Preparation of Compound 9

To a solution of compound I7 (200 mg, 0.1548 mmol, 1.0 eq.) and in DMF (6 mL) was added compound I7-1 (71 mg, 0.1548 mmol, 1.0 eq.) and DIPEA (40 mg, 0.3096 mmol, 2.0 eq.) at 0° C. under $N_2$ atmosphere. The mixture was stirred for 5 min. Then HATU (88 mg, 0.2322 mmol, 1.5 eq.) was added and it was stirred for another two hours. LCMS showed the reaction was completed. Water (3.0 ml) was added and stirred for 30 min. Then the mixture was concentrated, and the residue was purified by Prep-HPLC to give Compound 9 as a white solid (120 mg, yield: 45%). $^1$H-NMR (DMSO-d6, 400 MHz): 0.75 (d, J=6.6 Hz, 3H), 0.86 (d, J=6.6 Hz, 3H), 0.91 (s, 3H), 1.27-1.33 (m, 2H), 1.41-1.44 (m, 6H), 1.47-1.52 (m, 13H), 1.80 (s, 9H), 1.86-1.90 (m, 2H), 2.04 (t, J=7.2 Hz, 1H), 2.28 (t, J=6.6 Hz, 1H), 3.01-3.06 (m, 13H), 3.29 (t, J=6.0 Hz, 1H), 3.41-3.44 (m, 3H), 3.47-3.55 (m, 20H), 3.64-3.65 (m, 3H), 3.67-3.72 (m, 7H), 3.95 (s, 1H), 4.23 (d, J=8.4 Hz, 3H), 4.46 (d, J=4.2 Hz, 3H), 4.54 (d, J=6.0 Hz, 3H), 4.57 (t, J=5.4 Hz, 3H), 4.76-4.87 (m, 2H), 4.96 (s, 1H), 7.26 (s, 1H), 7.73 (t, J=5.4 Hz, 3H), 7.83 (t, J=5.4 Hz, 3H).

Example 10. Synthesis of the Conjugate of Triptolide with Tri-GalNHAc (Compound 10)

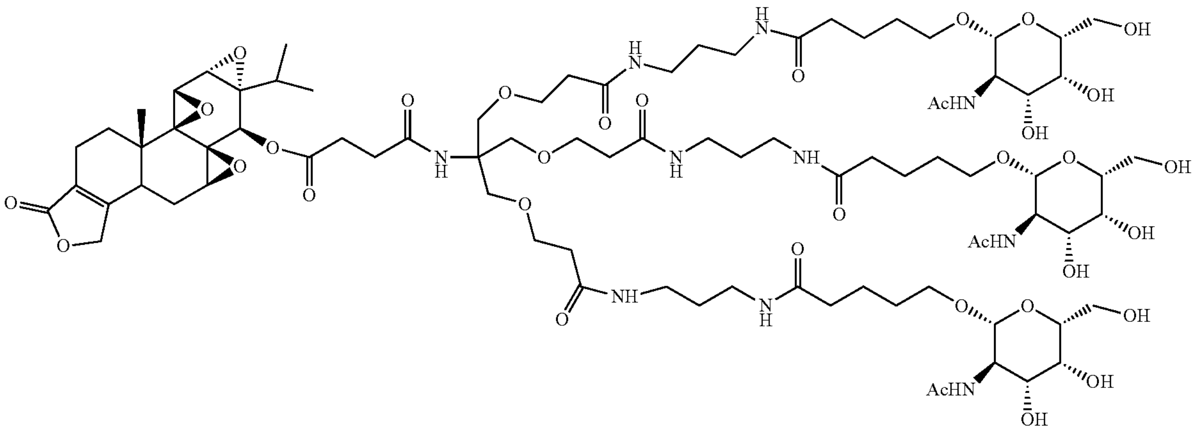 [SMILES: CC(=O)N[C@H]1[C@H](OCCCCC(=O)NCCCNC(=O)CCOCC(COCCC(=O)NCCCNC(=O)CCCCO[C@@H]2O[C@H](CO)[C@H](O)[C@H](O)[C@H]2NC(C)=O)(COCCC(=O)NCCCNC(=O)CCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]

The following schemes show the synthetic route used to prepare the title compound.

Scheme 13.

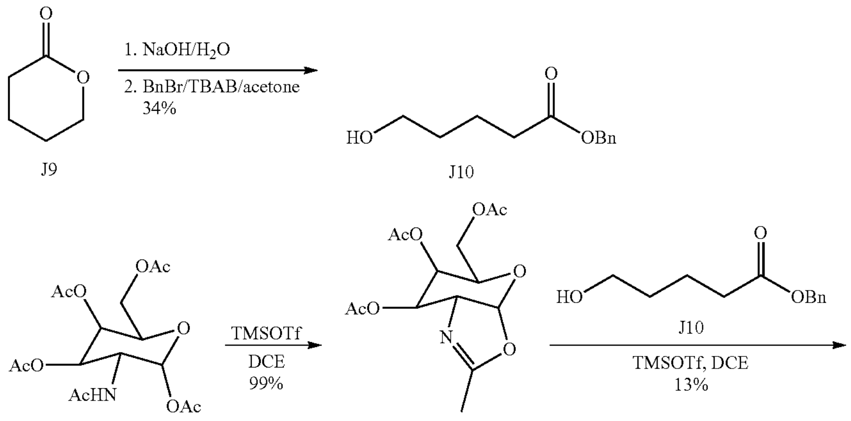

J9 J10 J11 J12

-continued
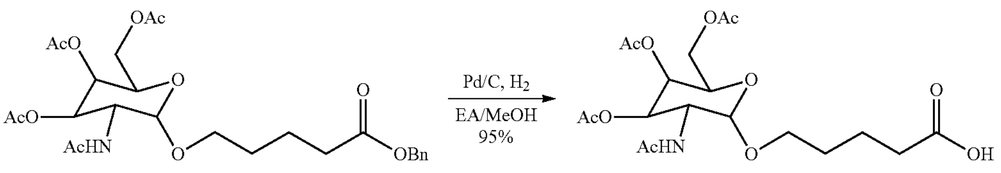
J13 J14
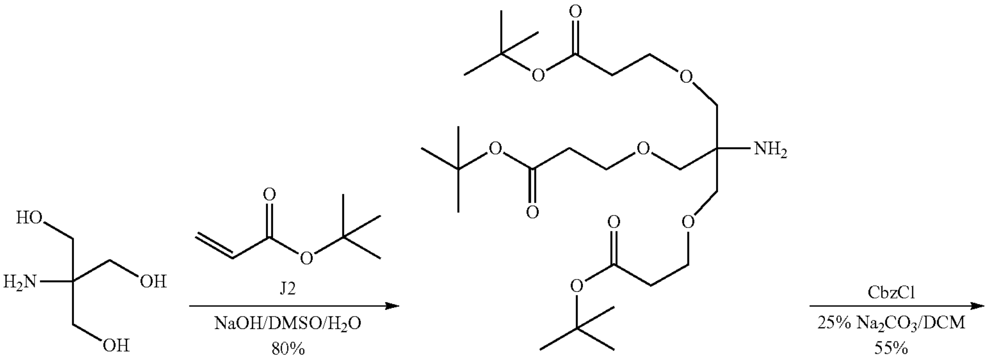
J1 J3
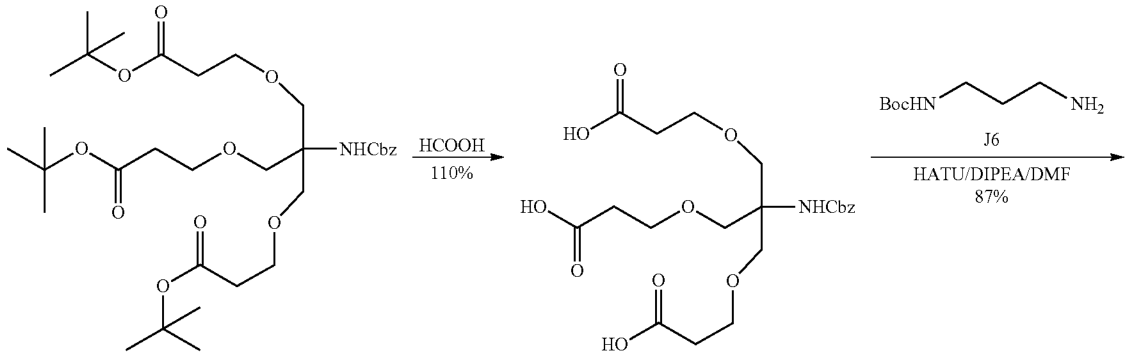
J4 J5
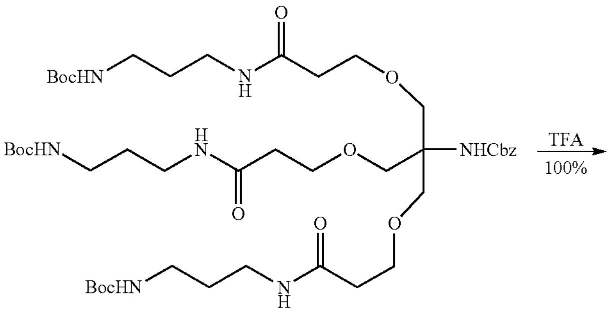
J7
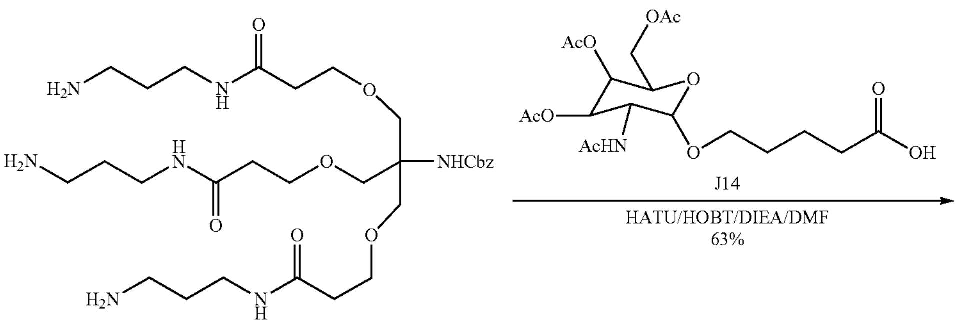
J8

-continued
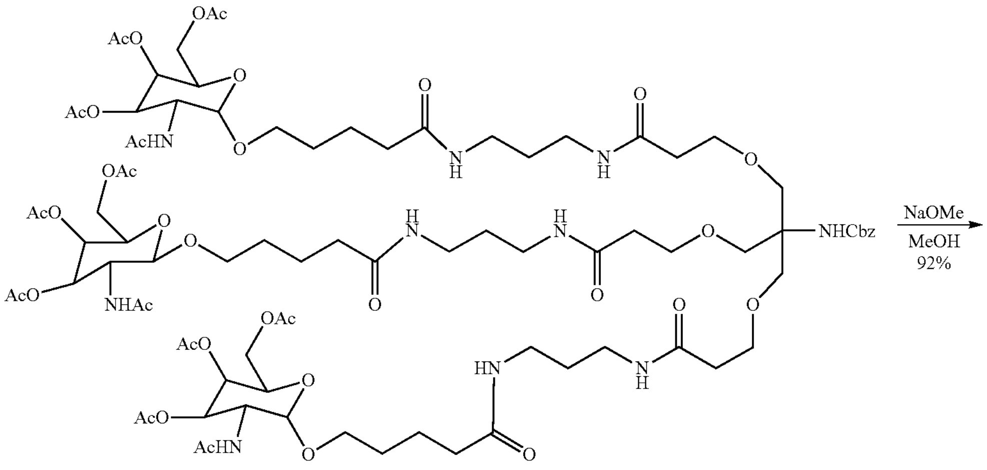
J15
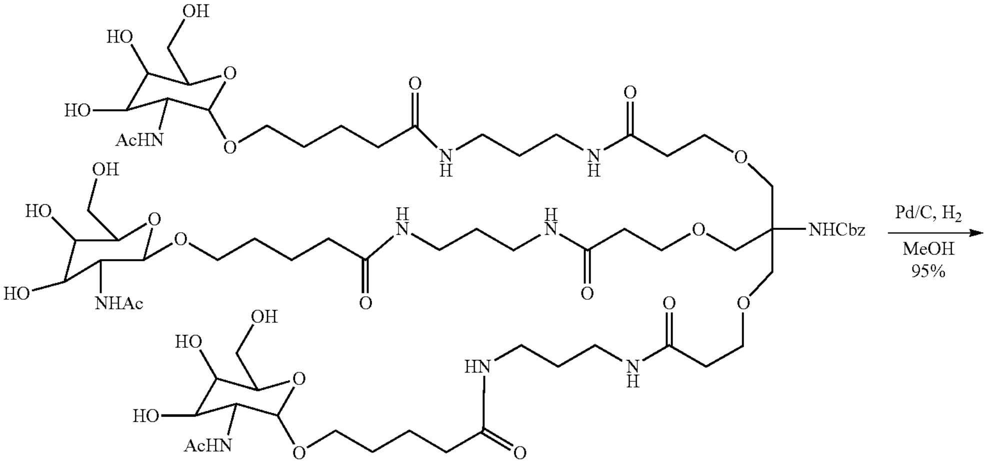
J16
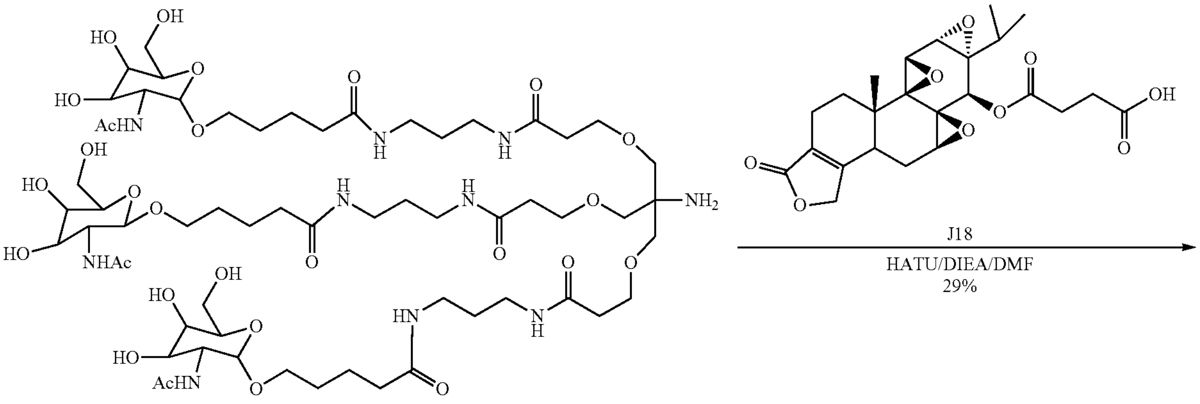
J17

-continued

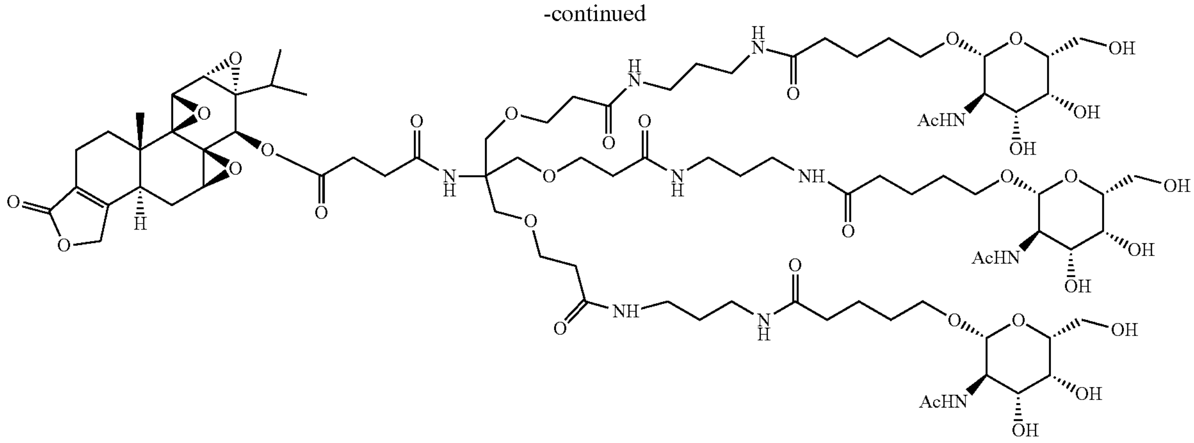

Compound 10

Preparation of di-tert-butyl 3,3'-((2-amino-2-((3-(tert-butoxy)-3-oxopropoxy)methyl)propane-1,3-diyl)bis(oxy))dipropanoate (J3)

To a solution of compound J1 (1.21 g, 10 mmol, 1.0 equiv) in DMSO (2 ML) was added 5M NaOH (0.2 mL, 1.0 mmol, 0.1 equiv) at below 15 under $N_2$ atmosphere, followed by the compound J2 (4.36 g, 34 mmol, 3.4 equiv) which was injected dropwise. The mixture was allowed to reach r.t for 24 hrs under $N_2$ atmosphere. The reaction mixture was cooled to 0° C. and diluted with water, extracted with EA, washed with brine, dried over $Na_2SO_4$, concentrated to give compound J3 as a light-yellow oil, which was used for next step without any further purification (4.0 g).

Preparation of di-tert-butyl 3,3'-((2-(((benzyloxy)carbonyl)amino)-2-((3-(tert-butoxy)-3-oxopropoxy)methyl)propane-1,3-diyl)bis(oxy))dipropanoate (J4)

To a solution of compound J3 (4.0 g, 7.91 mmol, 1.0 equiv) in DCM (40 mL) was added 25% $Na_2CO_3$ (16.8 g, 39.55 mmol, 5.0 equiv) at 0° C. under $N_2$ atmosphere, then CbzCl (2.7 g, 15.82 mmol, 2.0 equiv) was added dropwise and the mixture was stirred at r.t for overnight. The mixture was diluted with DCM and quenched with water, washed with brine, dried over $Na_2SO_4$, concentrated and purified with column chromatography on silica gel (PE:EA=10:1~7:1) to give compound J4 as a colorless oil (2.8 g, yield: 55%).

Preparation of 3,3'-((2-(((benzyloxy)carbonyl)amino)-2-((2-carboxyethoxy)methyl) propane-1,3-diyl)bis(oxy))dipropanoic acid (J5)

To a solution of compound J4 (2.8 g, 4.37 mmol, 1.0 equiv) in HCOOH (40 mL) and was stirred at r.t for overnight. The mixture was concentrated and dried under vacuum to give compound J5 as a yellow oil, which was used without further purification (2.27 g)

Preparation of Compound J7

To a solution of compound J5 (1.8 g, 3.82 mmol, 1.0 equiv) and compound J6 (2.7 g, 15.28 mmol, 4.0 equiv) in DMF (30 mL) was added HATU (5.1 g, 13.37 mmol, 3.5 equiv) and DIPEA (3.0 g, 22.92 mmol, 6.0 equiv) at 0° C. under $N_2$ atmosphere. The mixture was stirred at r.t for overnight. the reaction was quenched with cooled water, extracted with DCM, washed with Sat.$NaHCO_3$ and brine, dried over $Na_2SO_4$, concentrated and purified by Prep-HPLC to give compound J7 as a white solid (3.12 g, yield: 87%).

Preparation of benzyl (1,19-diamino-J0-((3-((3-aminopropyl)amino)-3-oxopropoxy)methyl)-5,15-dioxo-8,12-dioxa-4,16-diazanonadecan-10-yl)carbamate (J8)

To a solution of compound J7 (870 mg, 0.925 mmol, 1.0 equiv) in TFA (5 mL) and was stirred at r.t for 1 hrs. The mixture was diluted with toluene and concentrated, The residue was co-evaporated with toluene and dried under reduced pressure using a high vacuum pump to yield J8 as the TFA salt, which was used for the next reaction without any further purification (591 mg, yield: 100%)

Preparation of benzyl 5-hydroxypentanoate (J10)

To a solution of compound J9 (5.0 g, 50 mmol, 1.0 equiv) and NaOH (2.0 g, 50 mmol, 1.0 equiv) in $H_2O$ (50 mL) and was stirred at 70° C. for overnight. The mixture was cooled to r.t and concentrated, the residue was suspended in acetone (50 mL) and was added TBAB (0.8 g, 2.5 mmol, 0.05 equiv) and BnBr (10.2 g, 60 mmol, 1.2 equiv), the mixture was heated to reflux for overnight. acetone was removed in vacuo to give an oily residue, which was dissolved in EA and washed with Sat.$NaHCO_3$ and brine, dried over $Na_2SO_4$, concentrated and purified with column chromatography on silica gel (PE:EA=5:1~1:1) to give compound J10 as a colorless oil (3.6 g, yield: 34%).

Preparation of (3aR,5R,6R,7R,7aR)-5-(acetoxymethyl)-2-methyl-5,6,7,7a-tetrahydro-3aH-pyrano[3,2-d]oxazole-6,7-diyl diacetate (J12)

To a solution of compound J11 (1557 mg, 4.0 mmol, 1.0 equiv) in DCE (5 mL) was added TMSOTf (1333 mg, 6.0 mmol, 1.5 equiv) and stirred at 55° C. for 2 hrs, then the mixture was stirred at r.t for overnight. The mixture was poured into the ice cold Sat.$NaHCO_3$, extracted with DCM, washed with water and brine, dried over $Na_2SO_4$, concentrated to give compound J12 as a dark gum, which was used for the next step without any further purification (1.3 g, yield: 99%).

Preparation of (3aR,5R,6R,7R,7aR)-5-(acetoxymethyl)-2-methyl-5,6,7,7a-tetrahydro-3aH-pyrano[3,2-d]oxazole-6,7-diyl diacetate (J13)

To a solution of compound J12 (1.3 g, 3.95 mmol, 1.0 equiv) and compound J10 (1.23 g, 5.92 mmol, 1.5 equiv) in DCE (15 mL) was added 4 A power molecular sieves and was stirred at r.t for 30 min under $N_2$ atmosphere, the TMSOTf (0.44 g, 1.98 mmol, 0.5 equiv) was added to the reaction and the mixture was stirred at r.t for 12 hours. The mixture was poured into the ice cold Sat.$NaHCO_3$, extracted with DCM, washed with water and brine, dried over $Na_2SO_4$, concentrated, the residue purified by Prep-HPLC to give compound J13 as a colorless oil (358 mg, yield: 13%).

Preparation of 5-(((2S,3R,4R,5R,6R)-3-acetamido-4,5-diacetoxy-6-(acetoxymethyl)tetra hydro-2H-pyran-2-yl)oxy)pentanoic acid (J14)

To a solution of compound J13 (358 mg, 0.67 mmol, 1.0 equiv) in MeOH (1 mL) and EA (5 ml) was added 10% Pd/C (36 mg) and stirred at r.t for overnight under $H_2$ atmosphere. The mixture was filtered, the filtrate was concentrated and dried under reduced pressure using a high vacuum pump to yield J14 as a colorless oil, which was used for the next step without any further purification (285 mg, yield: 95%).

Preparation of Compound J15

To a solution of compound J14 (240 mg, 0.54 mmol, 3.5 equiv) and in DMF (5 mL) was added HATU (233 mg, 0.61 mmol, 4.0 equiv) and DIPEA (198 mg, 1.53 mmol, 10.0 equiv) at 0° C. under $N_2$ atmosphere. The mixture was stirred at r.t for 30 min, then a solution of compound J8 (100 mg, 0.153 mmol, 1.0 equiv) in DMF (2 mL) was added and stirred at r.t for 3 hrs. The reaction mixture was concentrated, and water was added to the residue, extracted with DCM, washed with Sat.$NaHCO_3$ and brine, dried over $Na_2SO_4$. After concentration and purification by Prep-HPLC to give compound J15 as a white solid (185 mg, yield: 63%).

Preparation of benzyl (1-(((2R,3R,4R,5R,6R)-3-acetamido-4,5-dihydroxy-6-(hydroxymethyl)tetrahydro-2H-pyran-2-yl)oxy)-31-(((2S,3R,4R,5R,6R)-3-acetamido-4,5-dihydroxy-6-(hydroxymethyl) tetrahydro-2H-pyran-2-yl)oxy)-16-((3-((3-(5-(((2S,3R,4R,5R,6R)-3-acetamido-4,5-dihydroxy-6-(hydroxymethyl)tetrahydro-2H-pyran-2-yl)oxy) pentanamido)propyl)amino)-3-oxopropoxy)methyl)-5,11,21,27-tetraoxo-14,18-dioxa-6,10,22,26-tetraazahentriacontan-16-yl)carbamate (J16)

To a solution of compound J15 (175 mg, 0.091 mmol, 1.0 equiv) in MeOH (5 mL) was added NaOMe (95 mg, 1.759 mmol, 20 equiv) and stirred at r.t for 2 hrs. The mixture was concentrated, the residue purified by Prep-HPLC to give compound J16 as a white solid (126 mg, yield: 92%).

Preparation of (R,R,R,S,R)-N,N'-(10-((3-((3-(5-(((2R,3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)methyl)-10-amino-5,15-dioxo-8,12-dioxa-4,16-diazanonadecane-1,19-diyl)bis(5-(((2S,3R,4R,5R,6R)-3-acetamido-4,5-dihydroxy-6-(hydroxymethyl) tetrahydro-2H-pyran-2-yl)oxy)pentanamide) (J17)

To a solution of compound J16 (126 mg, 0.081 mmol, 1.0 equiv) in MeOH (5 mL) and DMF (2.5 mL) was added 10% Pd/C (15 mg) and stirred at r.t for overnight under $H_2$ atmosphere. The mixture was filtered, the filtrate was concentrated and dried under reduced pressure using a high vacuum pump to yield J17 as a yellow oil, which was used for the next step without any further purification (110 mg)

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2'",3'":8a,9]phenanthro[1,2-c]furan-8-yl 21-(((2R,3R,4R,5R,6R)-3-acetamido-4,5-dihydroxy-6-(hydroxymethyl)tetrahydro-2H-pyran-2-yl)oxy)-6,6-bis((3-((3-(5-(((2S,3R,4R,5R,6R)-3-acetamido-4,5-dihydroxy-6-(hydroxymethyl)tetrahydro-2H-pyran-2-yl)oxy)pentanamido)propyl)amino)-3-oxopropoxy)methyl)-4,11,17-trioxo-8-oxa-5,12,16-triazahenicosan-1-oate (J18)

To a solution of compound J18 (40 mg, 0.086 mmol, 1.1 equiv) and in DMF (5 mL) was added HATU (39 mg, 0.101 mmol, 1.3 equiv) and DIPEA (31 mg, 0.234 mmol, 3.0 equiv) at 0° C. under $N_2$ atmosphere, The mixture was stirred at r.t for 1 hrs. Then a solution of compound 17 (110 mg, 0.078 mmol, 1.0 equiv) in DMF (2 mL) was added and stirred at r.t for 3 hrs. the reaction mixture was concentrated and purified by Prep-HPLC to give the title compound (Compound 10) as a white solid (40 mg, yield: 29%).

$^1$H-NMR (DMSO-d6, 600 MHz): 0.75 (d, J=6.6 Hz, 3H), 0.86 (d, J=6.6 Hz, 3H), 0.91 (s, 3H), 1.27-1.33 (m, 2H), 1.41-1.44 (m, 6H), 1.47-1.52 (m, 13H), 1.80 (s, 9H), 1.86-1.90 (m, 2H), 2.04 (t, J=7.2 Hz, 1H), 2.28 (t, J=6.6 Hz, 1H), 3.01-3.06 (m, 13H), 3.29 (t, J=6.0 Hz, 1H), 3.41-3.44 (m, 3H), 3.47-3.55 (m, 20H), 3.64-3.65 (m, 3H), 3.67-3.72 (m, 7H), 3.95 (s, 1H), 4.23 (d, J=8.4 Hz, 3H), 4.46 (d, J=4.2 Hz, 3H), 4.54 (d, J=6.0 Hz, 3H), 4.57 (t, J=5.4 Hz, 3H), 4.76-4.87 (m, 2H), 4.96 (s, 1H), 7.20 (s, 1H), 7.62 (d, J=9.0 Hz, 3H), 7.73 (t, J=5.4 Hz, 3H), 7.83 (t, J=5.4 Hz, 3H). MS (ESI) calcd [$C_{85}H_{136}N_{10}O_{35}$] (m/z) for 1856.92 found 1858.3, $[M+H]^+$. HPLC: 220 nm, 15.981 min, 91.23%; 254 nm, 15.984 min, 85.11%.

Example 11. Synthesis of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2''',3''':8a,9]phenanthro[1,2-c]furan-8-yl 3-((S)-6-acetamido-2-(adamantane-1-carboxamido)hexanamido)propanoate (Compound 11)
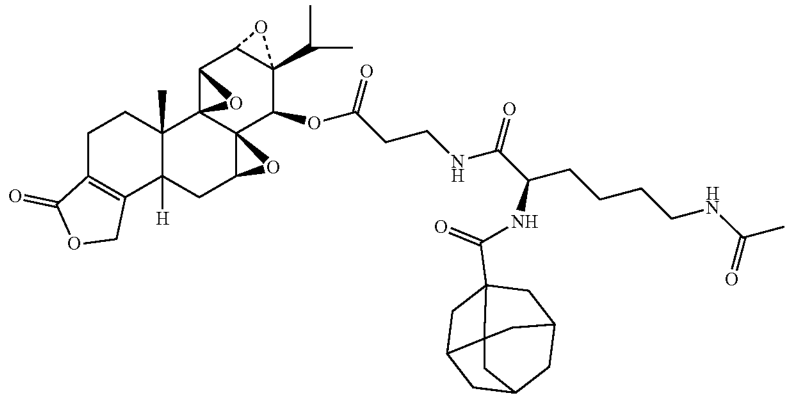
The following schemes show the synthetic route used to prepare the title compound.
Scheme 14.
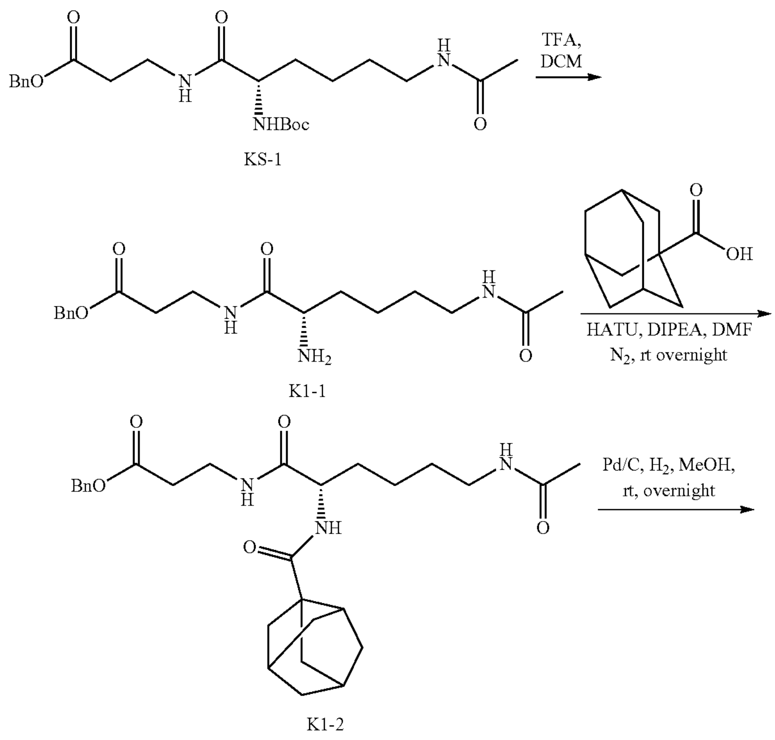

-continued

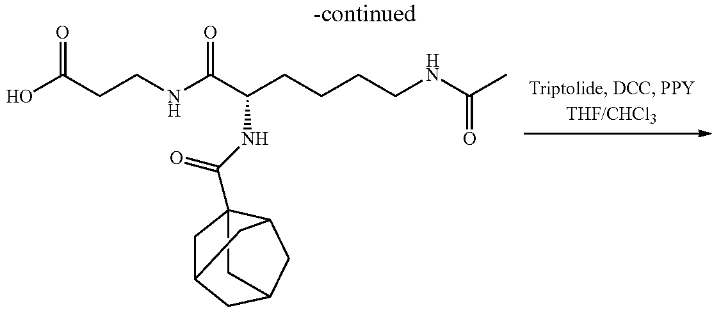

K1-3

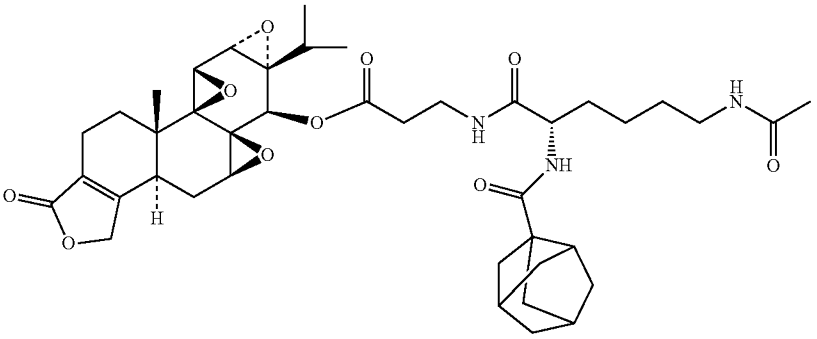

Compound 11

Preparation of (S)-benzyl 3-(6-acetamido-2-aminohexanamido)propanoate (K1-1)

(S)-benzyl 3-(6-acetamido-2-((tert-butoxycarbonyl)amino)hexanamido)propanoate (KS-1, 240 mg, 0.54 mmol, 1.0 eq) in DCM (5.0 mL) was added TFA (0.5 mL) and stirred 0° C. under $N_2$ overnight, LC-MS showed reaction complete and detected the desired product. Removed off the solvent to give the crude product (S)-benzyl 3-(6-acetamido-2-aminohexanamido)propanoate (K1-1, 186 mg, yield: theoretical) as a light yellow oil used directly for the next step. MS (ESI) calcd. for Chemical Formula: $[C_{18}H_{28}N_3O_4]^+$ [m/z]: 350.2, found: 350.2 $(M+H)^+$.

Preparation of (S)-benzyl 3-(6-acetamido-2-(adamantane-1-carboxamido) hexanamido)propanoate (K1-2)

To a solution of adamantane-1-carboxylic acid (97 mg, 0.54 mmol, 1.0 eq) in DMF (5.0 mL) was added DIEA (346 mg, 2.675 mmol, 3.0 eq) and HATU (244 mg, 0.641 mmol, 1.2 eq) at 0° C. After stirring for 0.5 h, (S)-benzyl 3-(6-acetamido-2-aminohexanamido)propanoate (K1-1,186 mg, 0.54 mmol, 1.0 eq) in DMF (1.0 mL) was added dropwise and the mixture was stirred at r.t under $N_2$ overnight. LC-MS showed the reaction was completed and detected the desired product. After concentration, the residue was purified by Prep-HPLC to give the desired product (S)-benzyl 3-(6-acetamido-2-(adamantane-1-carboxamido)hexanamido) propanoate (K1-2, 273 mg, yield: theoretical) as a light yellow oil. MS (ESI) calcd for Chemical Formula: $[C_{29}H_{41}N_3O_5]^+$ [m/z]: 512.3, found: 512.3 $(M+H)^+$.

Preparation of (S)-3-(6-acetamido-2-(adamantane-1-carboxamido)hexanamido) propanoic acid (K1-3)

(S)-benzyl 3-(6-acetamido-2-(adamantane-1-carboxamido)hexanamido) propanoate (K1-2, 273 mg, 0.54 mmol, 1.0 eq) in MeOH (20.0 mL) was added Pd/C (30 mg) and stirred r.t under $H_2$ overnight, LC-MS showed the reaction was completed and the desired product was formed. Removed off the solvent and the residue was purified by Prep-HPLC to give the desired product (S)-3-(6-acetamido-2-(adamantane-1-carboxamido)hexanamido)propanoic acid (K1-3, 144 mg, yield: 64.0%) as a light yellow oil. MS (ESI) calcd. for Chemical Formula: $[C_{22}H_{36}N_3O_5]^+$ [m/z]: 422.3, found: 422.3 $(M+H)^+$.

Preparation of (5bS,6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2"',3"':8a,9]phenanthro[1,2-c]furan-8-yl 3-((S)-6-acetamido-2-(adamantane-1-carboxamido)hexanamido)propanoate (Compound 11)

A solution of (S)-3-(6-acetamido-2-(adamantane-1-carboxamido)hexanamido) propanoic acid (K1-3, 110 mg, 0.261 mmol, 2.0 eq) in $THF/CHCl_3$ (0.5/0.5 mL) was added DCC (60 mg, 0.287 mmol, 2.2 eq) and PPY (43 mg, 0.287 mmol, 2.2 eq) at 0° C. and stirred at 0° C. under $N_2$ for 15 mins, Triptolide (47 mg, 0.130 mmol, 1.0 eq) in $THF/CHCl_3$ (0.5/0.5 mL) was added dropwise and stirred at 0° C. to room temperature under $N_2$ overnight. LC-MS showed the reaction was complete and detected the desired product. Removed off the solvent and the residue was purified by FLASH and Prep-HPLC to give the desired product as white solid (Compound 11, 68 mg, yield: 69%). $^1H$ NMR (400 MHz, $CDCl_3$) δ (ppm): 0.92 (d, 3H, J=6.4 Hz), 1.02 (d, 3H, J=6.8 Hz), 1.08 (s, 3H), 1.20-1.45 (m, 6H), 1.50-1.68 (m, 4H), 1.72-1.80 (m, 8H), 1.86-1.92 (m, 6H), 1.92-2.02 (m, 2H), 2.03 (s, 3H), 2.09 (s, 3H), 2.14-2.50 (m, 3H), 2.60-2.70 (m, 2H), 2.70-2.80 (m, 1H), 3.10-3.40 (m, 2H), 3.57 (d, 2H, J=5.2 Hz), 3.60-3.74 (m, 3H), 3.99 (d, 2H, J=2.8 Hz), 4.54-4.64 (m, 1H), 4.73 (s, 2H), 5.15 (s, 1H), 6.00-6.20 (m, 1H), 6.53 (d, 1H, J=7.6 Hz), 7.09 (t, 1H, J=5.6 Hz). MS (ESI) calcd. for Chemical Formula: $[C_{42}H_{55}N_3O_{10}]^+$ [m/z]: 764.4, found: 764.4 $(M+H)^+$.

Example 12. Synthesis of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7;2'",3'":8a,9]phenanthro[1,2-c]furan-8-yl 4-(4-(3-((4-((2-((S)-2-cyano-4,4-difluoropyrrolidin-1-yl)-2-oxoethyl)carbamoyl)quinolin-6-yl)oxy)propyl)piperazin-1-yl)-4-oxobutanoate (Compound 12)

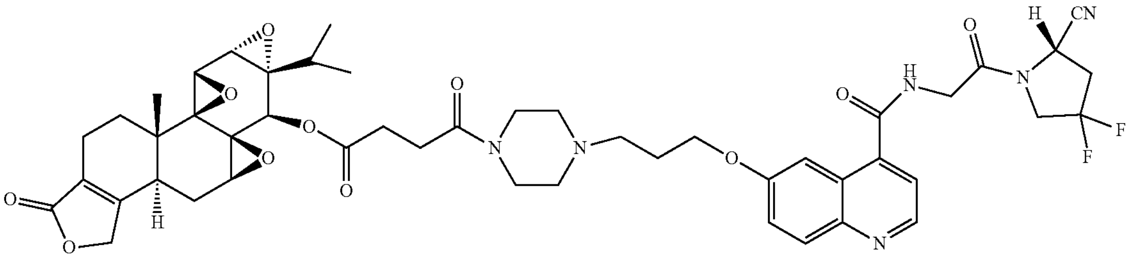 [SMILES: CC(C)[C@]12O[C@H]1[C@@H]1O[C@]13[C@]1(O[C@H]1C[C@H]1C4=C(CC[C@@]13C)C(=O)OC4)[C@@H]2OC(=O)CCC(=O)N1CCN(CCCOc2ccc3nccc(C(=O)NCC(=O)N4CC(F)(F)C[C@H]4C#N)c3c2)CC1]

The following schemes show the synthetic route used to prepare the title compound.

Scheme 15.

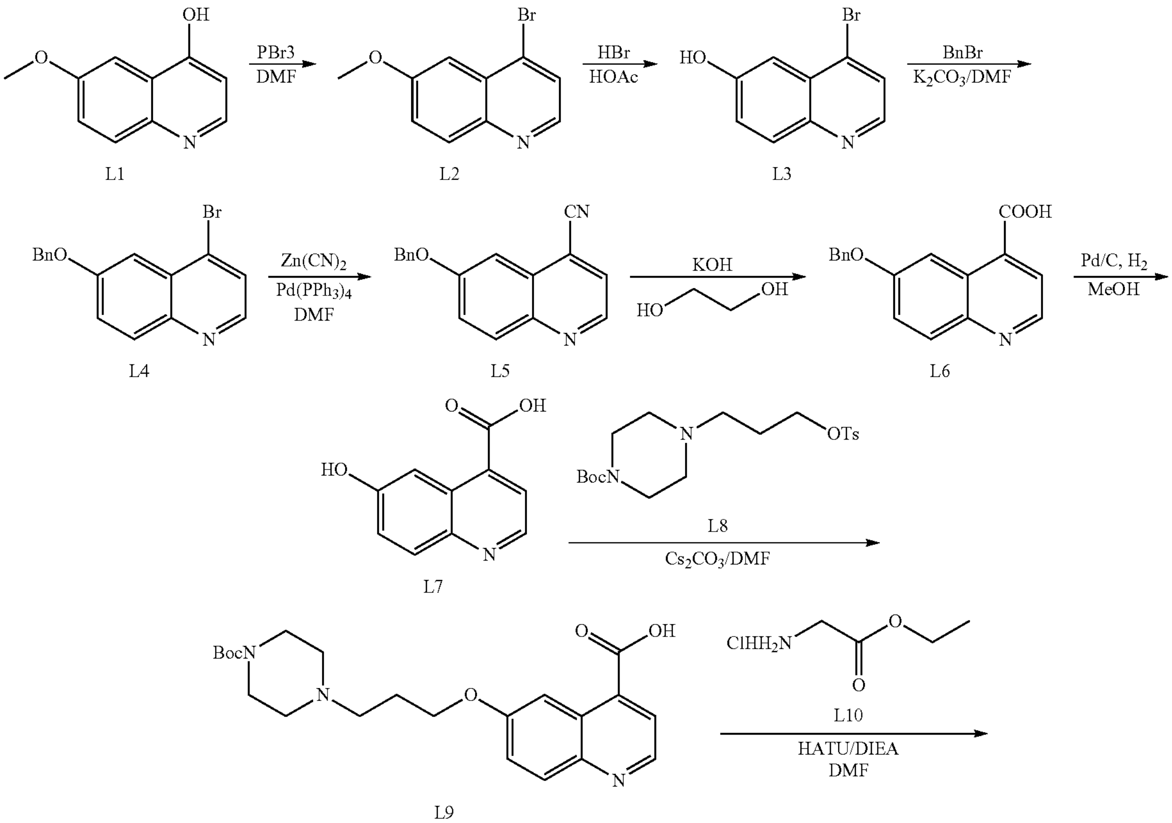

-continued
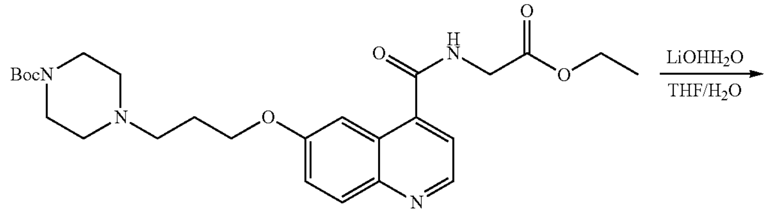
L11
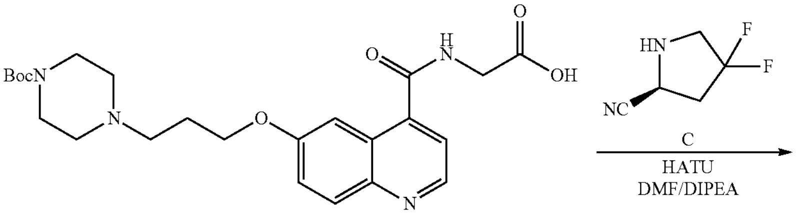
L12
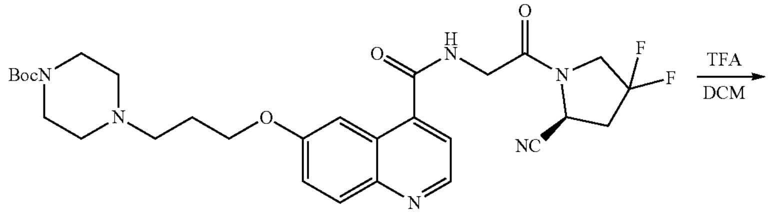
L13
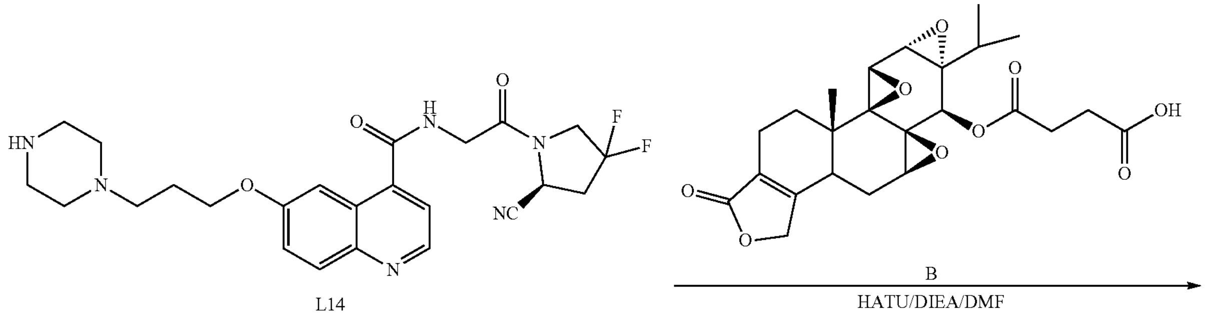
L14
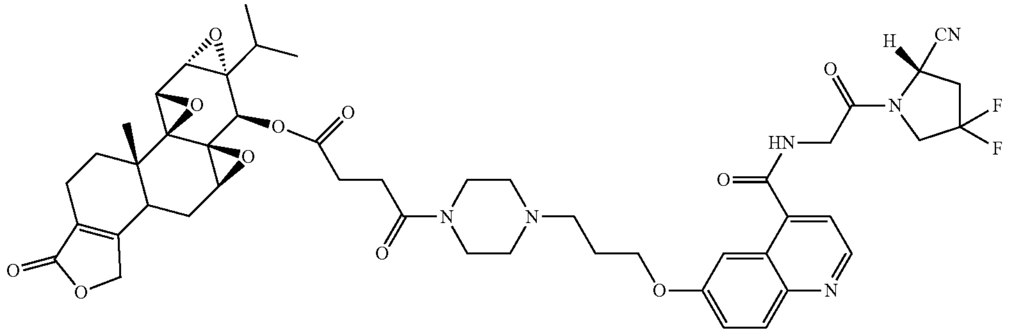
Compound 12
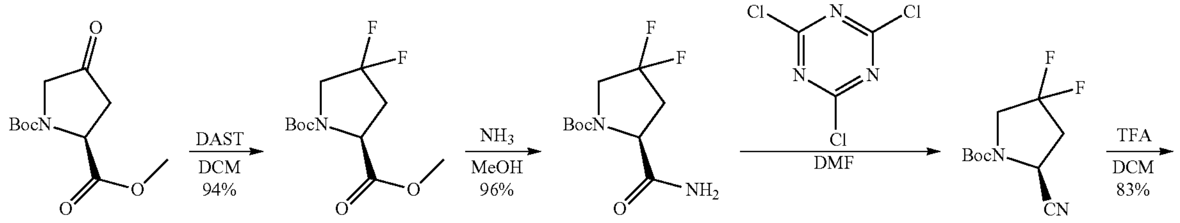
L15 L16 L17 L18

-continued

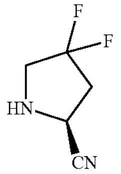

C

Preparation of 4-bromo-6-methoxyquinoline (L2)

To a solution of compound L1 (1.75 g, 10.0 mmol, 1.0 equiv) in DMF (25 mL) was added $PBr_3$ (2.98 g, 11.0 mmol, 1.1 equiv) in portions, the mixture was stirred at rt. under $N_2$ atmosphere for 18 h. The mixture was treated with $NaHCO_3$ (aq.) until pH-8-9, extracted with EA. The combined extracts were washed with water and brine, dried over $Na_2SO_4$. Concentrated and purified by silica gel (PE:EA=5:1) to give compound L2 as a white solid (1.75 g, yield: 74%).

Preparation of 4-bromoquinolin-6-ol (L3)

To a solution of compound L2 (1.67 g, 7.0 mmol, 1.0 equiv) in HOAc (20 mL) was added HBr (10 mL) and the resulting mixture was refluxed overnight under $N_2$ atmosphere. The reaction mixture was concentrated to give crude compound L3 as a yellow solid, 1.4 g, yield: 89%).

Preparation of 6-(benzyloxy)-4-bromoquinoline (L4)

To a solution of compound L3 (448 mg, 2 mmol, 1.0 equiv) in DMF (10 mL) was added $K_2CO_3$ (690 mg, 5 mmol, 2.5 equiv) followed by BnBr (359 mg, 2.1 mmol, 1.05 equiv), the mixture was stirred at rt. under $N_2$ atmosphere for 18 h. The mixture was concentrated and purified by silica gel (PE:EA=5:1) to give crude compound L4 as a yellow solid (400 mg, yield: 64%).

Preparation of 6-(benzyloxy)quinoline-4-carbonitrile (L5)

A mixture of compound L4 (1.45 g, 4.62 mmol, 1.0 equiv), $Zn(CN)_2$ (813 mg, 6.92 mmol, 1.5 equiv) and $Pd(PPh_3)_4$ (320 mg, 0.77 mmol, 0.06 equiv) in dry DMF (25 mL) was stirred at 100° C. overnight under $N_2$ atmosphere. The reaction mixture was concentrated, the residue was diluted with EA and washed with water, dried over $Na_2SO_4$. Concentrated, the residue purified by silica gel (PE:EA=5:1) to give compound L5 as a yellow solid (1.27 g, yield: 83%).

Preparation of 6-(benzyloxy)quinoline-4-carboxylic acid (L6)

To a solution of compound L5 (300 mg, 1.15 mmol, 1.0 equiv) in ethane-1,2-diol (8 mL) was added KOH (258 mg, 4.61 mmol, 4.0 equiv), the mixture was stirred at 130° C. under $N_2$ atmosphere overnight. The mixture was acidified by 2 N HCl until pH-4-5, the precipitate was filtered and dried to give compound L6 as a off-white solid (300 mg, yield: 93%).

Preparation of 6-hydroxyquinoline-4-carboxylic acid (L7)

To a solution of compound L6 (200 mg, 0.716 mmol, 1.0 equiv) in MeOH (10 mL) was added Pd/C (20 mg, 10%), the mixture was stirred at rt. for 6 h under $H_2$ atmosphere. The mixture was filtered, the filtrate was concentrated to give compound L7 as an off-white solid (135 mg, yield: 100%).

Preparation of 6-(3-(4-(tert-butoxycarbonyl)piperazin-1-yl)propoxy)quinoline-4-carboxylic acid (L9)

A mixture of compound L7 (135 mg, 0.716 mmol, 1.0 equiv), compound L8 (257 mg, 0.6454 mmol, 0.9 equiv) and $CS_2CO_3$ (700 mg, 2.148 mmol, 3.0 equiv) in dry DMF (20 mL) was stirred at 60° C. overnight under $N_2$ atmosphere. This mixture containing L9 was used for the next step without treating.

Preparation of tert-butyl 4-(3-((4-((2-ethoxy-2-oxoethyl)carbamoyl)quinolin-6-yl)oxy)propyl)piperazine-1-carboxylate (L11)

To the reaction mixture of compound L9 was added compound L10 (100 mg, 0.716 mmol, 1.0 equiv), HATU (360 mg, 0.947 mmol, 1.3 equiv) and DIEA (0.5 mL) and the resulting mixture was stirred at rt. overnight under $N_2$ atmosphere. The mixture was concentrated, the residue was purified by silica gel (DCM:MeOH=50:1) to give compound L11 as a yellow solid (175 mg, yield: 49%).

Preparation of 2-(6-(3-(4-(tert-butoxycarbonyl)piperazin-1-yl)propoxy)quinoline-4-carboxamido)acetic acid (L12)

To a solution of compound L11 (175 mg, 0.35 mmol, 1.0 equiv) in THF (6 mL) and water (6 mL) was added $LiOHH_2O$ (44 mg, 1.05 mmol, 3.0 equiv), the mixture was stirred at RT. under $N_2$ atmosphere overnight. The mixture was acidified by 2 N HCl until pH-4-5, then concentrated to give crude compound L12 as an off-white solid.

Preparation of (S)-1-tert-butyl 2-methyl 4,4-difluoropyrrolidine-1,2-dicarboxylate (L16)

To a solution of compound L15 (1.95 g, 8.01 mmol, 1.0 equiv) in DCM (30 mL) was stirred at 0° C., then DAST (3.36 g, 20.84 mmol, 2.6 equiv) in DCM (10 mL) was added. The resulting mixture was stirred at r.t. under $N_2$ overnight. The solution was added to ice water, concentrated and the residue was diluted with EA, washed with water (20 mL×3) and brine (20 mL×3), dried over $Na_2SO_4$. Concentrated in vacuo and purified by flash chromatography on silica gel (PE:EA=20:1-4:1) to give compound L16 as a yellow oil. (2.0 g, yield: 94%).

Preparation of (S)-tert-butyl 2-carbamoyl-4,4-difluoropyrrolidine-1-carboxylate (L17)

To a solution of compound L16 (2.0 g, 7.547 mmol, 1.0 equiv) in MeOH (30 mL) was added $NH_3$. The resulting mixture was stirred at 50° C. overnight. The reaction was concentrated in vacuo and purified by flash chromatography on silica gel (PE:EA=12:1-4:1) to give compound L17 as a yellow solid. (1.82 g, yield: 96%).

Preparation of (S)-tert-butyl 2-cyano-4,4-difluoro-pyrrolidine-1-carboxylate (L18)

To a solution of compound L17 (1.7 g, 6.8 mmol, 1.0 equiv) in DMF (20 mL) was added 2,4,6-trichloro-1,3,5-triazine (1.87 g, 10.2 mmol, 1.5 equiv) at 0° C. The resulting mixture was stirred at r.t. under $N_2$ for 1 h. The solution was added ice water, concentrated and the residue was diluted with EA, washed with water (20 mL×3) and brine (20 mL×3), dried over $Na_2SO_4$. Concentrated in vacuo and purified by flash chromatography on silica gel (PE:EA=50:1-20:1) to give compound L18 as a white solid. (1.4 g, yield: 83%).

Preparation of (S)-4,4-difluoropyrrolidine-2-carbonitrile (C)

To a solution of compound L18 (81 mg, 0.35 mmol, 1.0 equiv) in DCM (4 mL) was added TFA (0.1 mL) at 0° C. The resulting mixture was stirred at r.t. under $N_2$ for 6 h. The mixture was concentrated to give crude compound C as a brown oil (100 mg, yield: 100%).

Preparation of (S)-tert-butyl 4-(3-((4-((2-(2-cyano-4,4-difluoropyrrolidin-1-yl)-2-oxoethyl)carbamoyl)quinolin-6-yl)oxy)propyl)piperazine-J-carboxylate (L13)

To the reaction mixture of crude compound L12 was added compound C (100 mg), HATU (172 mg, 0.45 mmol, 1.3 equiv) and DIEA (0.5 mL) and the resulting mixture was stirred at rt. overnight under $N_2$ atmosphere. The mixture was concentrated, the residue was purified by silica gel (DCM:MeOH=50:1) to give compound L13 as a yellow solid (70 mg).

Preparation of tert-butyl 4-(3-((4-((2-((2R)-2-cyano-4,4-difluorocyclopentyl)-2-oxoethyl)carbamoyl)quinolin-6-yl)oxy)propyl)piperazine-J-carboxylate (L14)

To a solution of compound L13 (70 mg) in DCM (4 mL) was added TFA (0.1 mL) at 0° C. The resulting mixture was stirred at r.t. under $N_2$ for 6 h. The mixture was concentrated to give crude compound L14 as a yellow solid (60 mg, yield: 100%).

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2",3":6,7,2"',3"':8a,9]phenanthro[1,2-c]furan-8-yl 4-(4-(3-((4-((2-((S)-2-cyano-4,4-difluoropyrrolidin-1-yl)-2-oxoethyl)carbamoyl)quinolin-6-yl)oxy)propyl)piperazin-1-yl)-4-oxobutanoate (Compound 12)

To the reaction mixture of crude compound L14 was added compound B (28 mg, 0.06 mmol, 1.0 equiv), HATU (30 mg, 0.078 mmol, 1.3 equiv) and DIEA (0.1 mL) and the resulting mixture was stirred at rt. overnight under $N_2$ atmosphere. The mixture was concentrated, the residue was purified by pre-HPLC to give the title compound (Compound 12) as a yellow solid (10 mg). $^1$H-NMR ($CD_3OD$, 400 MHz): 0.81 (d, J=4.4 Hz, 3H), 0.93 (d, J=4.8 Hz, 3H), 1.02 (s, 3H), 1.29-1.32 (m, 4H) 1.46 (m, 2H), 1.88-1.90 (m, 1H), 1.93-1.97 (m, 1H), 2.08-2.11 (m, 2H), 2.19-2.26 (m, 2H), 2.48-2.53 (m, 2H), 2.58-2.60 (m, 2H), 2.65-2.67 (m, 2H), 2.70-2.75 (m, 6H), 2.87-2.95 (m, 1H), 3.44 (d, J=4.0 Hz, 1H), 3.59-3.62 (m, 4H), 3.94 (d, J=1.6 Hz, 1H), 4.10-4.17 (m, 1H), 4.28-4.35 (m, 3H), 4.78-4.81 (m, 2H), 5.05 (s, 1H), 5.11-5.13 (m, 1H), 7.45-7.47 (m, 1H), 7.56-7.57 (m, 1H), 7.95-7.98 (m, 2H), 8.74-8.75 (m, 2H). MS (ESI) calcd. [$C_{48}H_{54}F_2N_6O_{11}$] (m/z) for 928.38 found 929.3, $[M+H]^+$. HPLC: 214 nm, 11.762 min, 98.726%; 254 nm, 11.764 min, 98.896%.

Example 13. Synthesis of the Conjugate of Triptolide with Tri-GalNHAc (Compound 13)

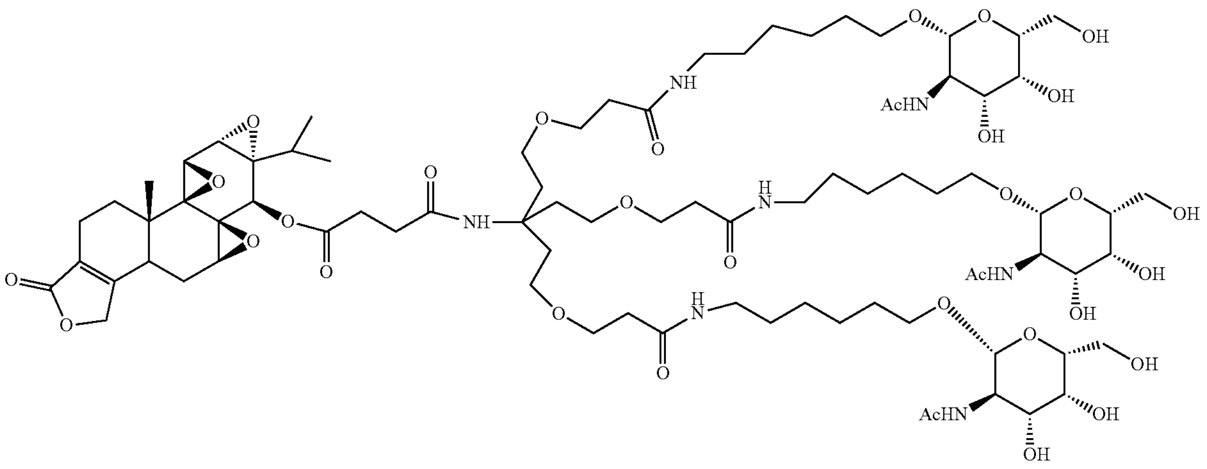 [SMILES: CC(=O)N[C@H]1[C@H](OCCCCCCNC(=O)CCOCCC(CCOCCC(=O)NCCCCCCO[C@@H]2O[C@H](CO)[C@H](O)[C@H](O)[C@H]2NC(C)=O)(CCOCCC(=O)NCCCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]

The following schemes show the synthetic route used to prepare the title compound.
Scheme 16.
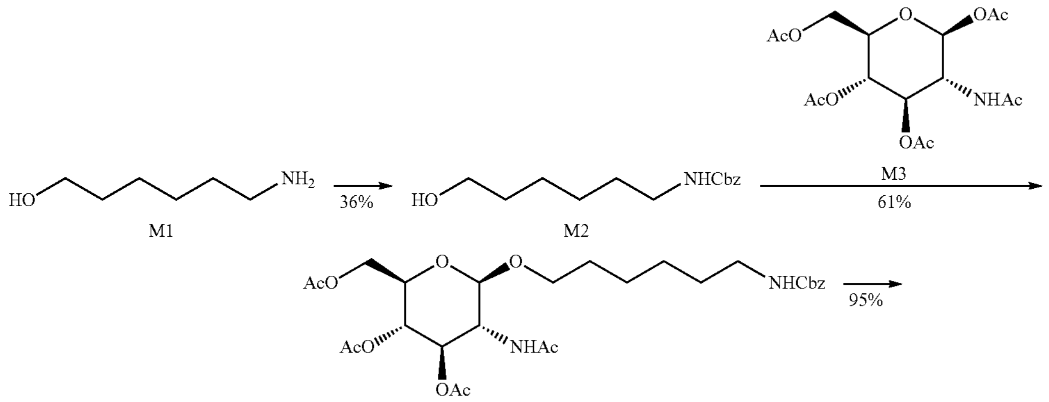
M1
M2
M4
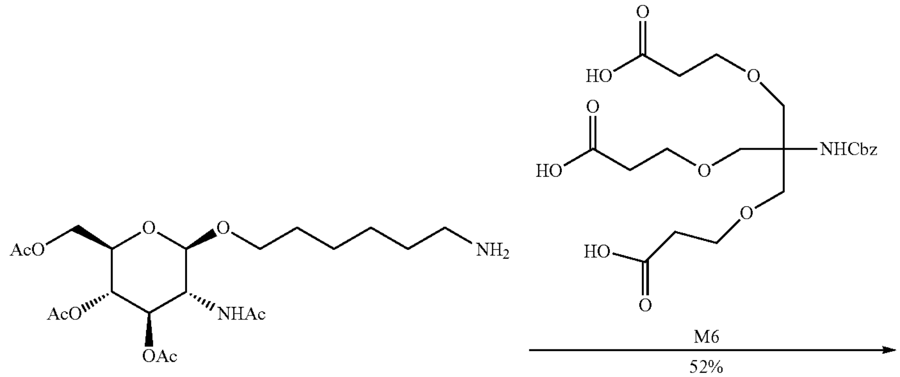
M5
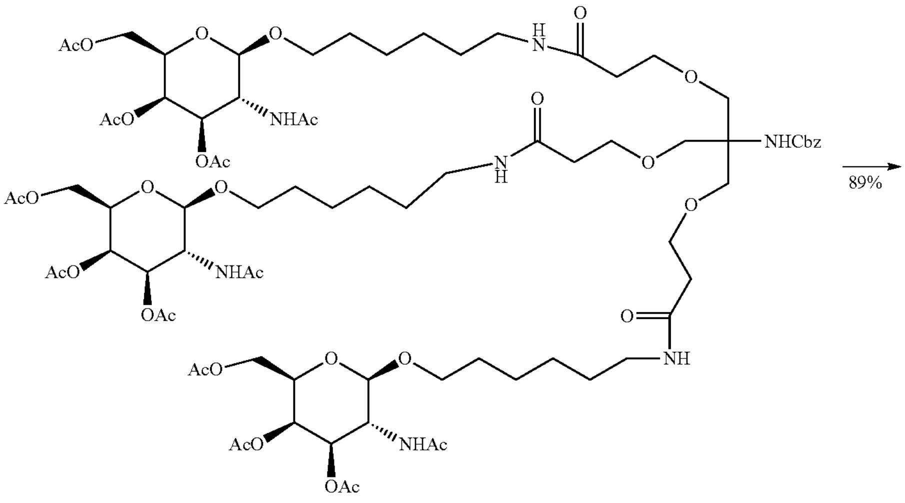
M7

-continued

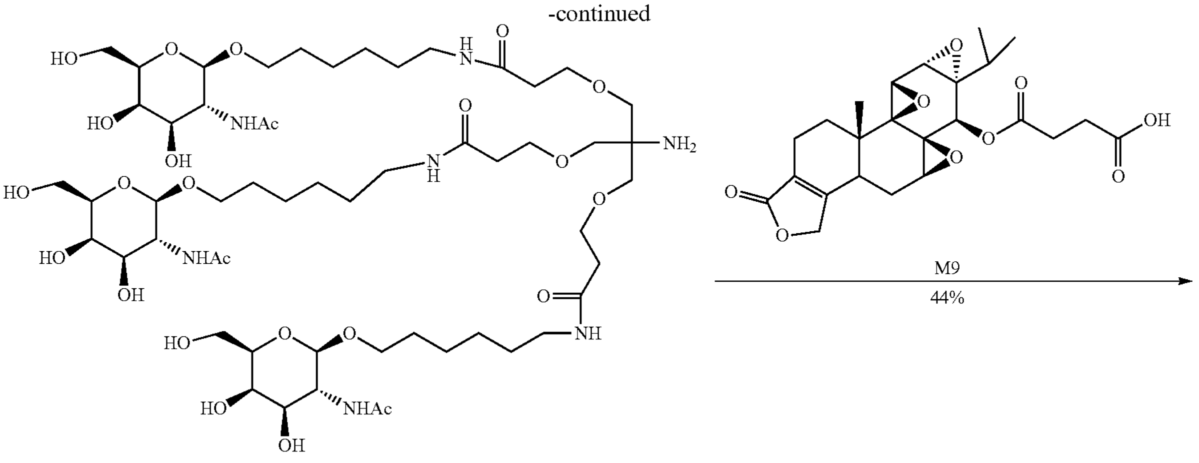

M8

Compound 13

Preparation of benzyl (6-hydroxyhexyl)carbamate (M2)

To a solution of compound M1 (860 mg, 7.33 mmol, 1.0 equiv) and in DCM (10 mL) was added $Et_3N$ (2.22 g, 21.99 mmol, 3.0 equiv), then Cbz-Cl (1.12 g, 6.60 mmol, 0.9 equiv) was added. The resulting mixture was stirred at r.t. under $N_2$ overnight. Water was added, concentrated in vacuo and then purified by flash chromatography on silica gel (PE:EA=20:1-4:1) to give compound M2 as a white solid. (660 mg, yield: 37%).

Preparation of (2R,3R,4R,5R,6R)-5-acetamido-2-(acetoxymethyl)-6-((6-(((benzyloxy)carbonyl)amino)hexyl)oxy)tetrahydro-2H-pyran-3,4-diyl diacetate (M4)

To a solution of compound M2 (500 mg, 1.99 mmol, 1.0 equiv) and compound M3 (775 mg, 1.99 mmol, 1.0 equiv) in DCE (15 mL) was added $Sc(OTf)_3$ (98 mg, 0.199 mmol, 0.1 equiv). The resulting mixture was stirred at 90° C. under $N_2$ overnight. The reaction was quenched by $NaHCO_{3(aq.)}$ (10 mL), concentrated and the residue was diluted with water, extracted with EA (15 mL×3). The combined organic layer was washed with water (20 mL×3) and brine (20 mL×3) respectively, dried over $Na_2SO_4$. After Concentration in vacuo and purification by flash chromatography on silica gel (PE:EA=50:1-8:1) to give compound M4 as a colorless oil. (700 mg, yield: 61%).

Preparation of (2R,3R,4R,5R,6R)-5-acetamido-2-(acetoxymethyl)-6-((6-aminohexyl)oxy)tetrahydro-2H-pyran-3,4-diyl diacetate (MS)

To a solution of compound M4 (700 mg, 1.20 mmol, 1.0 equiv) in MeOH (10 mL) was added Pd/C (80 mg, 10%). The resulting mixture was stirred at r.t. under $H_2$ for 1 h. Filtered and the filtrate was concentrated in vacuo to give crude compound M5 (530 mg, yield: 95%) as a white solid.

Preparation of Compound M7

To a solution of compound M5 (530 mg, 1.188 mmol, 3.5 equiv) and compound M6 (160 mg, 0.339 mmol, 1.0 equiv) in DMF (8 mL) was added HATU (515 mg, 1.356 mmol, 4.0 equiv) and followed by DIEA (437 mg, 3.39 mmol, 10.0 equiv) at 0° C. The resulting mixture was stirred at 0° C. under $N_2$ overnight. The reaction was quenched with water (10 mL), concentrated in vacuo and purified by HPLC to give compound M7 as a white solid. (310 mg, yield: 52%).

Preparation of Compound M8

To a solution of compound M7 (310 mg, 0.569 mmol, 1.0 equiv) in MeOH (8 mL) was added NaOMe (30 mg). The resulting mixture was stirred at r.t. under $N_2$ overnight, then concentrated in vacuo and purified by HPLC to give a white solid. (230 mg, yield: 94%).

The fresh prepared white solid (230 mg, 0.167 mmol, 1.0 equiv) in MeOH (8 mL) was added Pd/C (50 mg, 10%). The resulting mixture was stirred at r.t. under $H_2$ for 1 h. Filtered and the filtrate was concentrated in vacuo to give crude compound M8 (200 mg, yield: 95%) as a white solid.

Preparation of Compound 13

To a solution of compound M8 (200 mg, 0.161 mmol, 1.0 equiv) and compound M9 (74 mg, 0.161 mmol, 1.0 equiv) in DMF (8 mL) was added DIEA (62 mg, 0.483 mmol, 3.0 equiv), and followed by HATU (92 mg, 0.241 mmol, 1.5 equiv) at 0° C. The resulting mixture was stirred at 0° C. under $N_2$ overnight. The reaction was quenched water (10 mL), concentrated in vacuo and purified by HPLC to give Compound 13 as a white solid. (120 mg, yield: 44%). MS (ESI) calcd $[C_{78}H_{125}N_7O_{33}]^+$ (m/z) for 1687.83 found 1687, 1688 [M+H]+. HPLC: 254 nm, No absorption; 220 nm, 9.946 min, 99.73%.
Example 14. Synthesis of the Conjugate of Triptolide with Tri-GalNHAc (Compound 14)
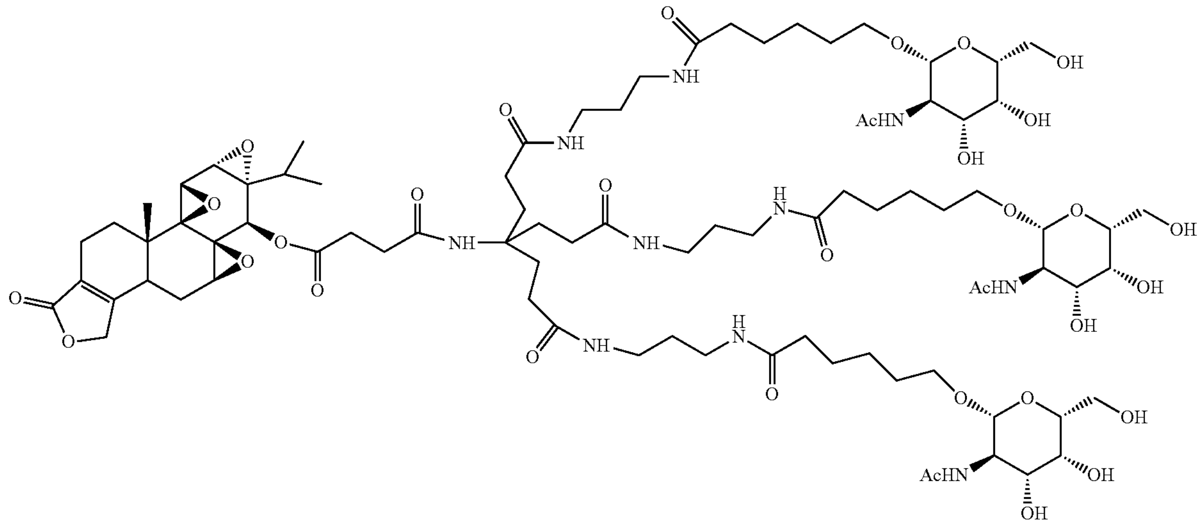 [SMILES: CC(=O)N[C@H]1[C@H](OCCCCCC(=O)NCCCNC(=O)CCC(CCC(=O)NCCCNC(=O)CCCCCO[C@@H]2O[C@H](CO)[C@H](O)[C@H](O)[C@H]2NC(C)=O)(CCC(=O)NCCCNC(=O)CCCCCO[C@@H]2O[C@H](CO)[C@H](O)[C@H](O)[C@H]2NC(C)=O)NC(=O)CCC(=O)O[C@@H]2[C@@]3(C(C)C)O[C@H]3[C@@H]3O[C@]34[C@]23O[C@H]3CC2C3=C(CC[C@@]24C)C(=O)OC3)O[C@H](CO)[C@H](O)[C@@H]1O]
The following schemes show the synthetic route used to prepare the title compound.
Scheme 17.
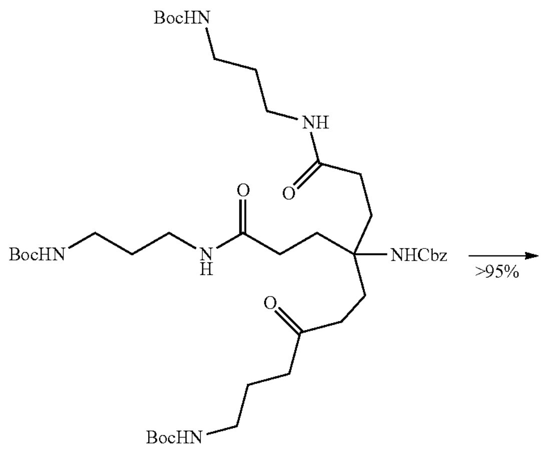
N1

-continued
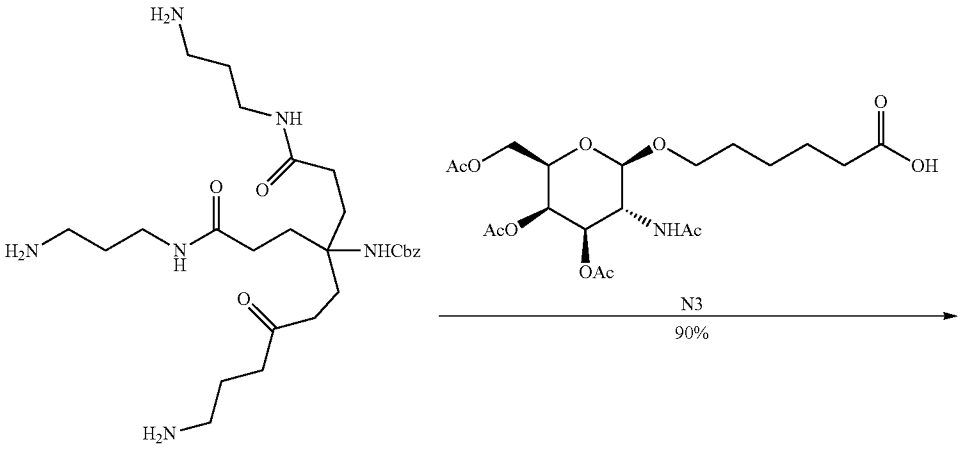
N2
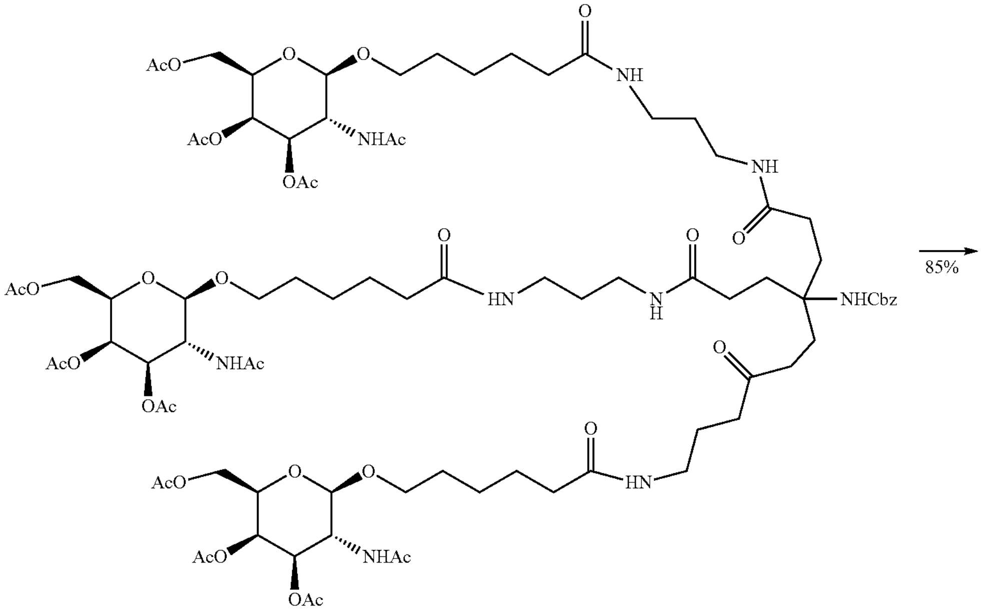
N4
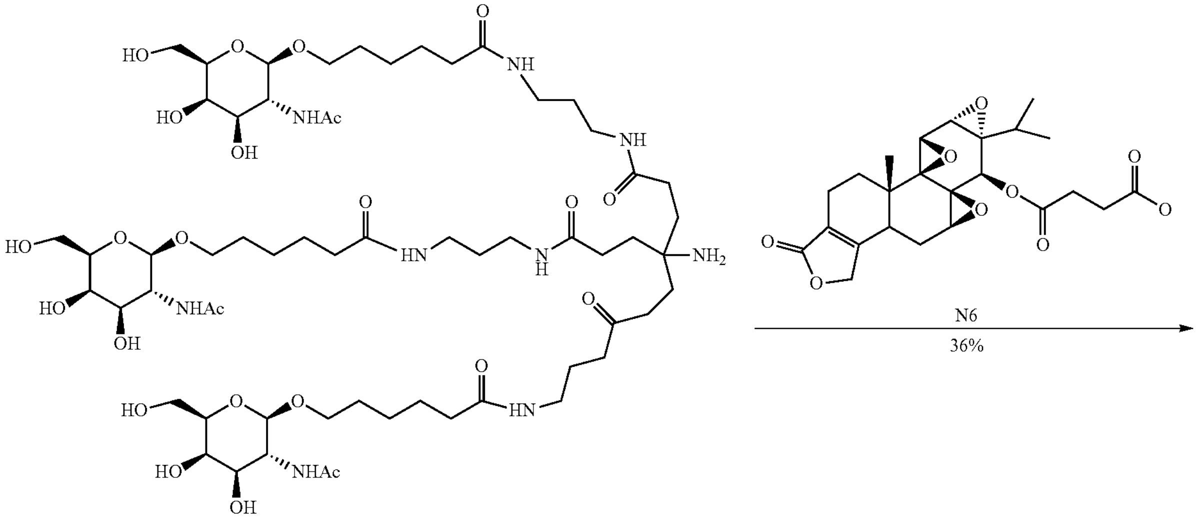
N5

-continued

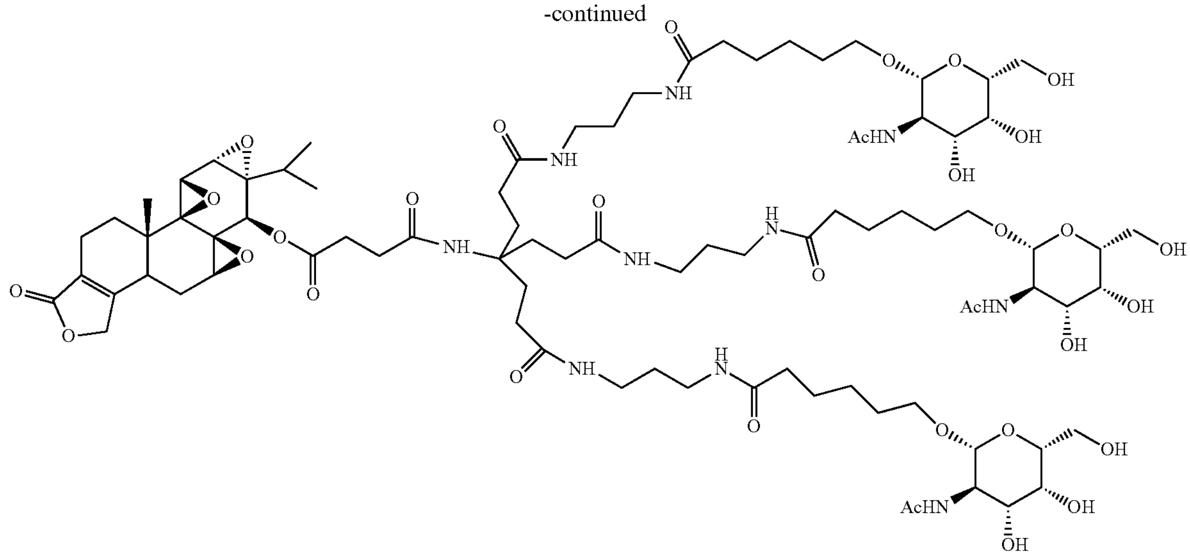

Compound 14

Preparation of benzyl (1,7-bis((3-aminopropyl) amino)-4-(3-((3-aminopropyl)amino)-3-oxopropyl)-1,7-dioxoheptan-4-yl)carbamate (N2)

To a solution of compound N1 (500 mg, 0.59 mmol, 1.0 equiv) in DCM (2 mL) was added TFA (5 mL) at 0° C. and was stirred at r.t for 2 hrs. The mixture was diluted with toluene and concentrated. The residue was co-evaporated with toluene and dried under reduced pressure using a high vacuum pump to yield N2 as the TFA salt, which was used for the next reaction without any further purification (323 g, yield over 95%).

Preparation of N4

To a solution of compound N3 (950 mg, 2.06 mmol, 3.5 equiv) in DMF (10 mL) was added HATU (894 mg, 2.35 mmol, 4.0 equiv) and DIPEA (760 mg, 5.88 mmol, 10.0 equiv) at 0° C. under $N_2$ atmosphere. The mixture was stirred at r.t for 30 min, then a solution of compound N2 (323 mg, 0.59 mmol, 1.0 equiv) in DMF (2 mL) was added and stirred at r.t for overnight. The reaction mixture was concentrated and the residue was quenched with cooled water. After extraction with DCM, the organic phase was washed with Sat.$NaHCO_3$, water and brine respectively, dried over $Na_2SO_4$. and concentrated. The residue was purified by C18 column to give compound N4 as a white solid (1.0 g, yield: 90%).

Preparation of N1,N7-bis(3-(6-(((2S,3R,4R,5R,6R)-3-acetamido-4,5-dihydroxy-6-(hydroxymethyl)tetrahydro-2H-pyran-2-yl)oxy)hexanamido)propyl)-4-(3-((3-(6-(((2S,3R,4R,5R,6R)-3-acetamido-4,5-dihydroxy-6-(hydroxymethyl)tetrahydro-2H-pyran-2-yl)oxy)hexanamido)propyl)amino)-3-oxopropyl)-4-aminoheptanediamide (N5)

To a solution of compound N4 (1.0 g, 0.53 mmol, 1.0 equiv) in MeOH (10 mL) was added NaOMe (29 mg, 0.53 mmol, 1.0 equiv) and stirred at r.t for 2 hrs under $N_2$ atmosphere. The mixture was concentrated, the residue purified by Prep-HPLC (20%~40% ACN in water) to give compound a white solid (760 mg, yield: 96%).

To a solution of the fresh prepared solid (410 mg, 0.27 mmol, 1.0 equiv) in MeOH (10 mL) was added 10% Pd/C (15 mg) and stirred at r.t under $H_2$ atmosphere for 2 hrs. The mixture was filtered and concentrated to yield N5 as a white solid, which was used for the next step without any further purification (335 mg, yield: 89%)

Preparation of (6aS,7aR,8R,8aS,9aS,9bS,10aS,10bS)-8a-isopropyl-10b-methyl-3-oxo-1,2,3,5,5b,6,6a,8,8a,9a,9b,10b-dodecahydrotris(oxireno)[2',3':4b,5;2'',3'':6,7,2''',3''':8a,9]phenanthro[1,2-c]furan-8-yl 14-((1,29-bis(((2S,3R,4R,5R,6R)-3-acetamido-4,5-dihydroxy-6-(hydroxymethyl)tetrahydro-2H-pyran-2-yl)oxy)-15-(3-((3-(6-(((2S,3R,4R,5R,6R)-3-acetamido-4,5-dihydroxy-6-(hydroxymethyl)tetrahydro-2H-pyran-2-yl)oxy)hexanamido)propyl)amino)-3-oxopropyl)-6,12,18,24-tetraoxo-7,11,19,23-tetraazanonacosan-15-yl)amino)-4-oxobutanoate (Compound 14)

To a solution of compound N5 (335 mg, 0.25 mmol, 1.0 equiv) and compound N6 (124 mg, 0.27 mmol, 1.1 equiv) in DMF (10 mL) was added HATU (121 mg, 0.32 mmol, 1.3 equiv) and DIPEA (95 mg, 0.74 mmol, 3.0 equiv) at 0° C. under $N_2$ atmosphere. The mixture was stirred at r.t for 2 hrs. The reaction mixture was concentrated and purified by Prep-HPLC (18%-38% ACN in water) to give Compound 14 as a white solid (170 mg, yield: 36%). $^1$H-NMR (DMSO-d6, 400 MHz): 0.72 (d, J=6.8 Hz, 3H), 0.83 (d, J=6.8 Hz, 3H), 0.91 (s, 3H), 1.20-1.31 (m, 9H), 1.41-1.50 (m, 19H), 1.80 (s, 9H), 1.86-1.90 (m, 2H), 2.04 (t, J=7.2 Hz, 1H), 2.28 (t, J=6.6 Hz, 1H), 3.01-3.06 (m, 13H), 3.29 (t, J=6.0 Hz, 1H), 3.41-3.44 (m, 3H), 3.47-3.55 (m, 20H), 3.64-3.65 (m, 3H), 3.67-3.72 (m, 7H), 3.95 (s, 1H), 4.23 (d, J=8.4 Hz, 3H), 4.47 (d, J=4.2 Hz, 3H), 4.54-4.60 (m, 6H), 4.74-4.87 (m, 2H), 4.96 (s, 1H), 7.29 (s, 1H), 7.62 (d, J=9.2 Hz, 3H), 7.75 (t, J=5.6 Hz, 6H). MS (ESI) calcd [$C_{85}H_{136}N_{10}O_{32}$] (m/z) for 1808.92 found 1809.3, $[M+H]^+$. HPLC: 220 nm, 9.042 min, 99.36%; 254 nm, 9.043 min, 100%.

Example 15—In Vivo Anti-Cancer Evaluation

Huh-7 HCC Animal Model

To evaluate the antitumor efficacy of the triptolide conjugates disclosed herein against solid tumors, huh-7 cells (~$10\times10^6$ cells) were injected into the right flank of male nude mice. When the tumors reached a volume of ~150 $mm^3$, the mice were randomly divided into 4 groups with 7 or 8 mice per group and were treated as below indicated. Tumor volumes were measured twice per week and estimated by using the formula: Tumor volume (V)=(L×W×W) ÷2, W is tumor width, L is tumor length.

1. Group 1 was the control group in which the mice were administered daily the vehicle (0.5% CMC-Na/carboxymethylcellulose sodium, i.p.) for 3 weeks;
2. Group 2 was the test group in which the mice were administered daily Compound 1 (2.0 mg/kg, i.p.) for 3 weeks;
3. Group 3 was the test group in which the mice were administered daily Compound 2 (2.0 mg/kg, i.p.) for 3 weeks; and
4. Group 4 was the positive control group in which the mice where administered daily Lenvatinib (5.0 mg/kg, oral) for 3 weeks.

Figure 2:
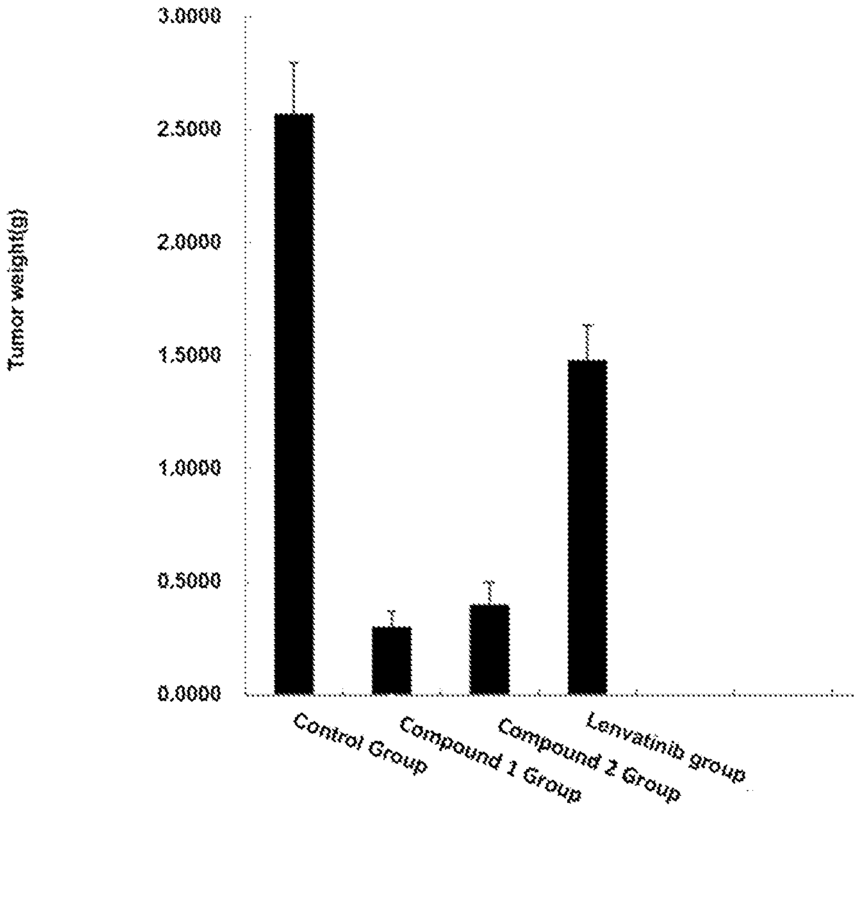
FIG. 2 shows the average tumor weights for each mice group after 21 days of treatment: Group 1 (control group; i.p. 0.5% CMC-Na; once daily); Group 2 (Compound 1; 2.0 mg/kg, i.p.; once daily); Group 3 (Compound 2; 2.0 mg/kg, i.p.; once daily); and Group 4 (Lenvatinib; 5.0 mg/kg, oral; once daily).

The tumor growth-time of treatment curve is shown in FIG. 1, indicating that as early as 4 days after treatment, both the triptolide conjugate groups (V=245 $mm^3$ for Compound 1 treated group and 315 $mm^3$ for Compound 2 treated group) and Lenvatinib group (V=381 $mm^3$) showed a significant decrease in tumor growth as compared with the control group (V=598 $mm^3$). The significant tumor growth inhibition lasted to the end of the experiment. By the end of the treatment, the average tumor volume of the control group and Lenvatinib group increased up to 15 and 9 times, respectively, as compared to those before the treatment, while the average tumor volume of the triptolide conjugate treatment groups only increased up to 2.0 and 2.7 times, respectively, as compared to those before the treatment. The tumor inhibition rate of the treated groups were 88.3% for the Compound 1 treated group, 84.4% for the Compound 2 treated group, and 42.3% for the Lenvatinib treated group, based on the average tumor weights after 21 days treatment shown in FIG. 2.

HepG-2 HCC Animal Model

To evaluate the antitumor efficacy of the novel triptolide-conjugate against solid tumors, HepG-2 cells (~$10\times10^6$ cells) were injected into the right flank of male nude mice. when the tumors were reached a volume of ~150 $mm^3$, mice were randomly divided into 5 groups with 8 mice per group and treated as below indicated. Tumor volumes were measured twice per week and estimated by using the formula: Tumor volume (V)=(L×W×W) 2, W is tumor width, L is tumor length.

Figure 3:
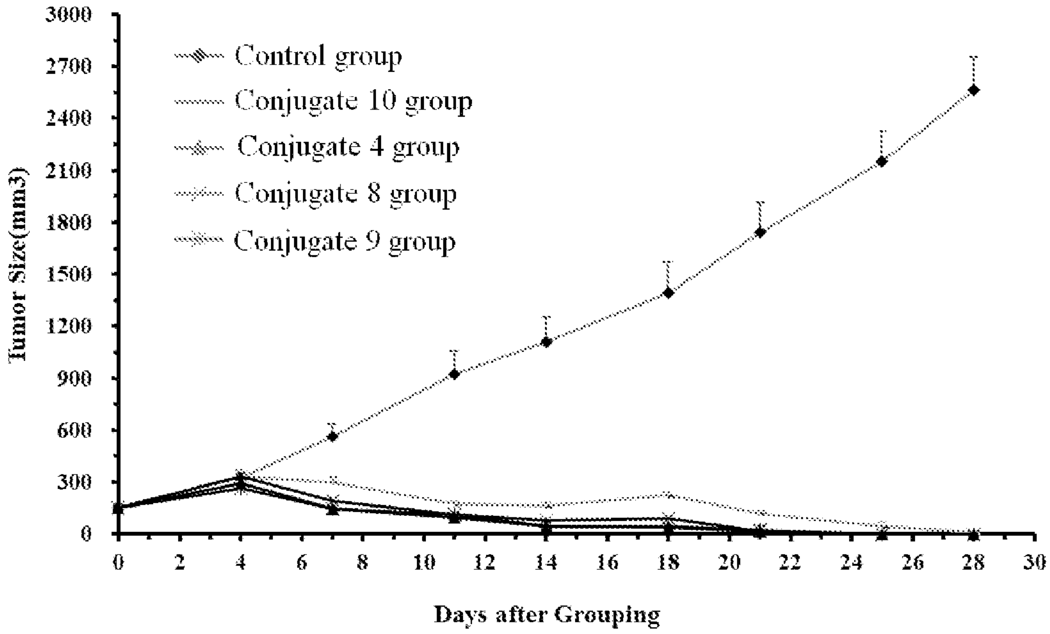
FIG. 3 shows the tumor growth-time of treatment curve for mice that were treated over a four-week period: Group 1 (control group; i.p. brine; once daily); Group 2 (Conjugate 4; 2.0 mg/kg, i.p.; once daily); Group 3 (Conjugate 8; 6.0 mg/kg, i.p.; once daily); Group 4 (Conjugate 9; 6.0 mg/kg, i.p.; once daily); and Group 5 (Conjugate 10; 6.0 mg/kg, i.p.; once daily).
Figure 4:
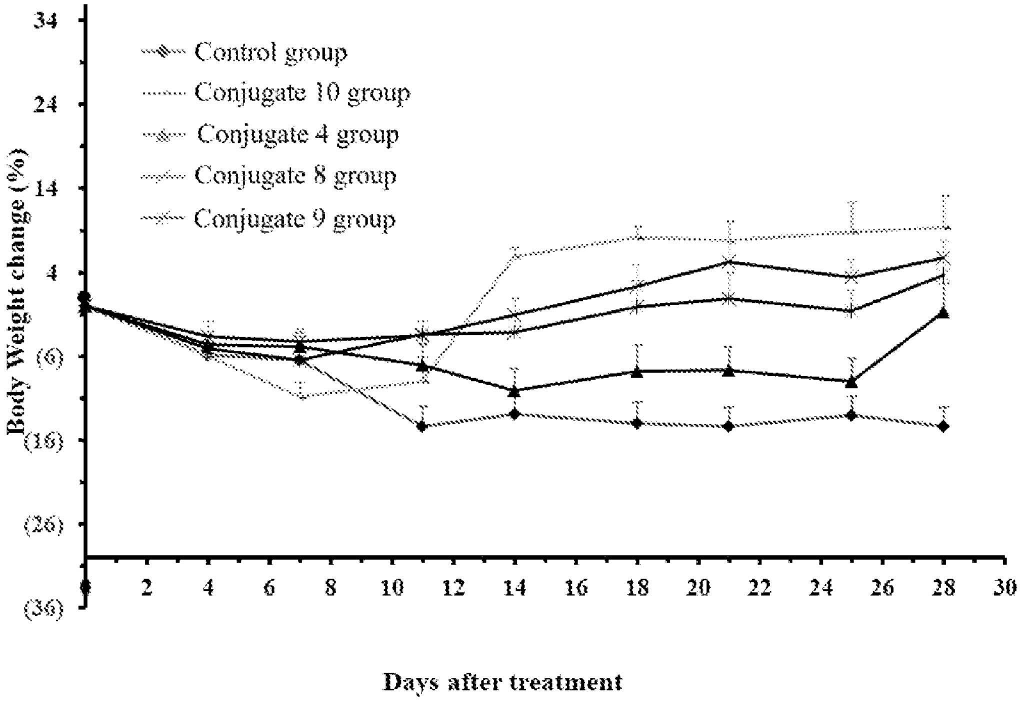
FIG. 4 shows the average tumor weights for each mice group after 28 days of treatment: Group 1 (control group; i.p. brine; once daily); Group 2 (Conjugate 4; 2.0 mg/kg, i.p.; once daily); Group 3 (Conjugate 8; 6.0 mg/kg, i.p.; once daily); Group 4 (Conjugate 9; 6.0 mg/kg, i.p.; once daily); and Group 5 (Conjugate 10; 6.0 mg/kg, i.p.; once daily).

1. Group 1 is the control in which the mice were daily administered vehicle (i.p. brine) for 4 weeks;
2. in Group 2, mice were daily administered Conjugate 4 (2.0 mg/kg, i.p.) for 4 weeks;
3. in Group 3, mice were daily administered Conjugate 8 (6.0 mg/kg, i.p.) for 4 weeks;
4. in Group 4, mice were daily administered Conjugate 9 (6.0 mg/kg i.p.) for 4 weeks;
5. in Group 5, mice were daily administered Conjugate 10 (6.0 mg/kg, i.p.) for 4 weeks;

The tumor growth-time of treatment curve is shown in FIG. 3 indicating that after 4-week treatment with the triptolide-conjugates, the tumor in mice begun to shrink. After 28 days treatment, the tumor size in the vehicle group increased to 17.72 times, while the tumor size in all mice treated with triptolide-conjugates (Compounds/Conjugates 4, 8, 9, and 10 respectively) was gradually shrinked to disappear (FIG. 3). The mice body weight change-time of treatment curve is shown in FIG. 4 indicating the triptolide-conjugates do not have significant system toxicity to the mice compared with the vehicle.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound of Formula I, or an enantiomer, an enantiomeric mixture, a diastereomer, a diastereomeric mixture, or a pharmaceutically acceptable salt thereof:

(I)

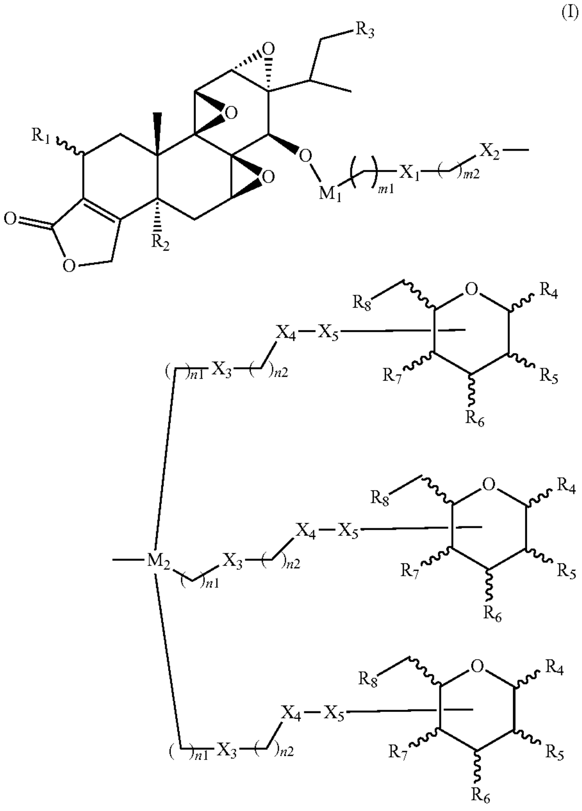

wherein $m_1$, $m_2$, $n_1$, $n_2$ are each independently 0-15;

$R_1$, $R_2$, and $R_3$ each independently OH, H, halo, unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether;

$M_1$ is selected from a bond, —C(═O)—, —$OPO_2$—, —$SO_2$—, —NH(CO)—, —(CO)NH—, —$CH_2OPO_2$—, —$CH_2$—O—C(═O)—, and —$CH_2O$—;

$M_2$ is selected from C and Si;

$X_1$, $X_2$, $X_3$, $X_4$, and $X_5$ are each independently a bond, —C(═O)—, (C═O)-$L_1$-(C═O), (C═O)-$L_1$, $L_1$-(C═O), O(CO), (CO)O, O, S, S—S, Se—Se—, NH, NR, NH(CO), (CO)NH, $L_2$-NH(CO), NH(CO)-$L_2$, $L_2$-(CO)NH, —(CO)NH-$L_2$, (CO)NH-$L_2$-NH(CO), NR-$L_2$-NR, $L_2$-O, O-$L_2$, unsubstituted or substituted $C_1$-$C_{10}$ alkylene, unsubstituted or substituted $C_3$-$C_{10}$ cycloalkylene, unsubstituted or substituted arylene, unsubstituted or substituted heteroarylene, unsubstituted or substituted $C_1$-$C_{10}$ heterocyclylene, or unsubstituted or substituted peptide comprising 1-10 natural amino acids;

each $L_1$ is each independently unsubstituted or substituted arylene, unsubstituted or substituted heteroarylene, unsubstituted or substituted $C_1$-$C_{10}$ heterocyclylene;

each $L_2$ is each independently unsubstituted or substituted $C_1$-$C_{10}$ alkylene;

each R is independently unsubstituted or substituted $C_1$-$C_{10}$ alkyl, unsubstituted or substituted $C_3$-$C_{10}$ cycloalkyl, unsubstituted or substituted $C_1$-$C_{10}$ acyl, unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, or unsubstituted or substituted $C_1$-$C_{10}$ heterocycyl; and $X_5$ is attached to any one of $R_4$, $R_5$, $R_6$, $R_7$, and $R_8$; the remaining $R_4$, $R_5$, $R_6$, $R_7$, and $R_8$ that are not attached to $X_5$ are each independently H, OH, $O(CO)NH_2$, halo, NH($C_1$-$C_{10}$ acyl), unsubstituted or substituted O($C_1$-$C_{10}$ alkyl), unsubstituted or substituted O($C_3$-$C_{10}$ cycloalkyl), unsubstituted or substituted O($C_1$-$C_{10}$ acyl), unsubstituted or substituted $C_1$-$C_{10}$ carboxyl ester, unsubstituted or substituted $C_1$-$C_{10}$ alkyl ketone, or unsubstituted or substituted $C_1$-$C_{10}$ alkyl ether, unsubstituted or substituted aryl, unsubstituted or substituted heteroaryl, unsubstituted or substituted $C_1$-$C_{10}$ heterocycyl, unsubstituted or substituted peptide comprising 1-10 amino acids, or forms a glycosidic bond with a natural monosaccharide.

2. The compound of claim 1, or an enantiomer, an enantiomeric mixture, a diastereomer, a diastereomeric mixture, or a pharmaceutically acceptable salt thereof, wherein $m_1$ and $m_2$ are each independently 0, 1, 2, 3, or 4.

3. The compound of claim 1, or an enantiomer, an enantiomeric mixture, a diastereomer, a diastereomeric mixture, or a pharmaceutically acceptable salt thereof, wherein $n_1$ and $n_2$ are each independently 0, 1, 2, 3, or 4.

4. The compound of claim 1, or an enantiomer, an enantiomeric mixture, a diastereomer, a diastereomeric mixture, or a pharmaceutically acceptable salt thereof, wherein $R_1$, $R_2$, and $R_3$ are each H.

5. The compound of claim 1, or an enantiomer, an enantiomeric mixture, a diastereomer, a diastereomeric mixture, or a pharmaceutically acceptable salt thereof, wherein $M_1$ is —C(═O)—, —NH(CO)—, or —(CO)NH—; and $M_2$ is C.

6. The compound of claim 1, or an enantiomer, an enantiomeric mixture, a diastereomer, a diastereomeric mixture, or a pharmaceutically acceptable salt thereof, wherein $X_1$ is a bond and $X_2$ is NH(CO) or (CO)NH.

7. The compound of claim 1, or an enantiomer, an enantiomeric mixture, a diastereomer, a diastereomeric mixture, or a pharmaceutically acceptable salt thereof, wherein $X_3$ is O; $X_4$ is (CO)NH-$L_2$-NH(CO); and $X_5$ is NH(CO)-$L_2$, $L_2$-(CO)NH, $L_2$-O, or O-$L_2$.

8. The compound of claim 1, or an enantiomer, an enantiomeric mixture, a diastereomer, a diastereomeric mixture, or a pharmaceutically acceptable salt thereof, wherein $X_5$ is attached to $R_4$; and $R_5$, $R_6$, $R_7$, and $R_8$ are each independently OH or NH($C_1$-$C_{10}$ acyl).

9. The compound of claim 1, or an enantiomer, an enantiomeric mixture, a diastereomer, a diastereomeric mixture, or a pharmaceutically acceptable salt thereof, wherein $X_5$ is attached to $R_5$; and $R_4$, $R_6$, $R_7$, and $R_8$ are each independently OH or NH($C_1$-$C_{10}$ acyl).

10. The compound of claim 1, or an enantiomer, an enantiomeric mixture, a diastereomer, a diastereomeric mixture, or a pharmaceutically acceptable salt thereof, wherein $X_5$ is attached to $R_8$; and $R_4$, $R_5$, $R_6$, and $R_7$ are each independently OH or NH($C_1$-$C_{10}$ acyl).

11. The compound of claim 1, or an enantiomer, an enantiomeric mixture, a diastereomer, a diastereomeric mixture, or a pharmaceutically acceptable salt thereof, wherein the compound has a structure selected from any one of the following structures:

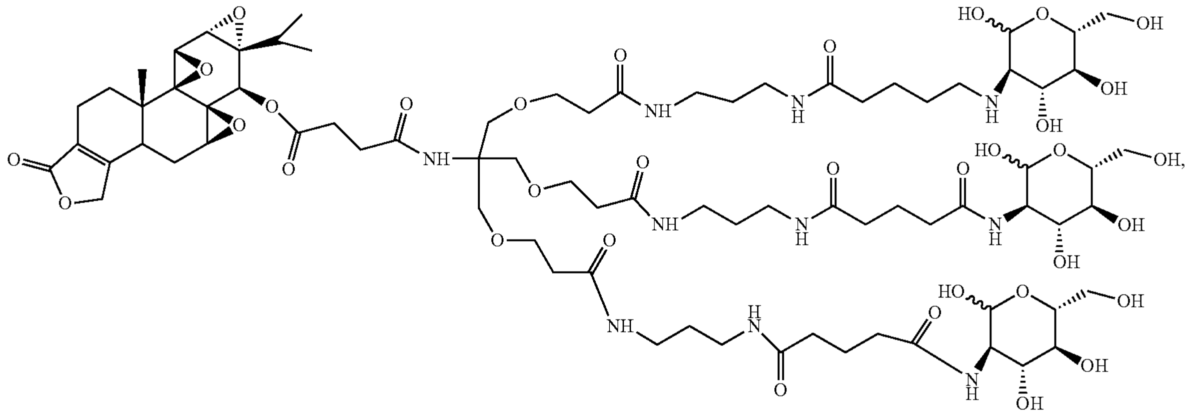

,

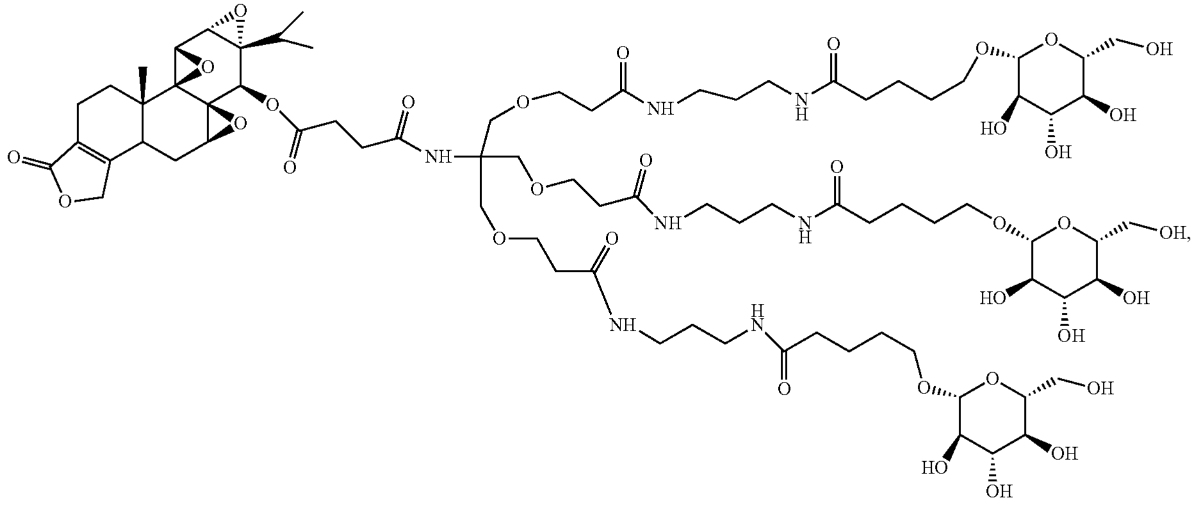

,

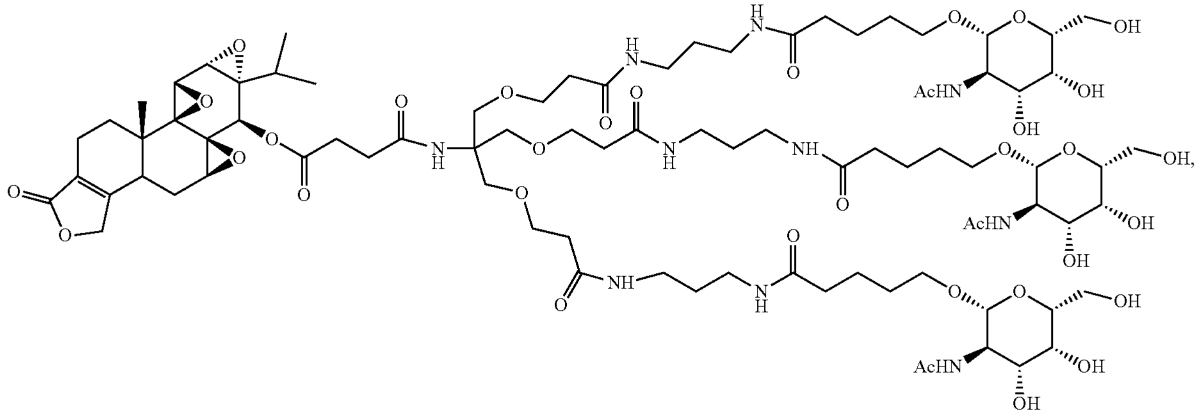

-continued

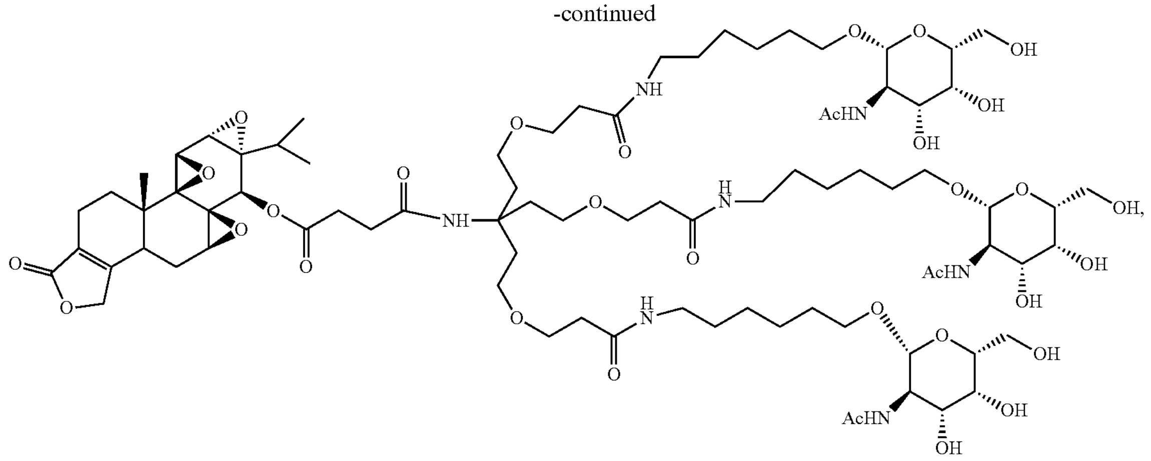

and

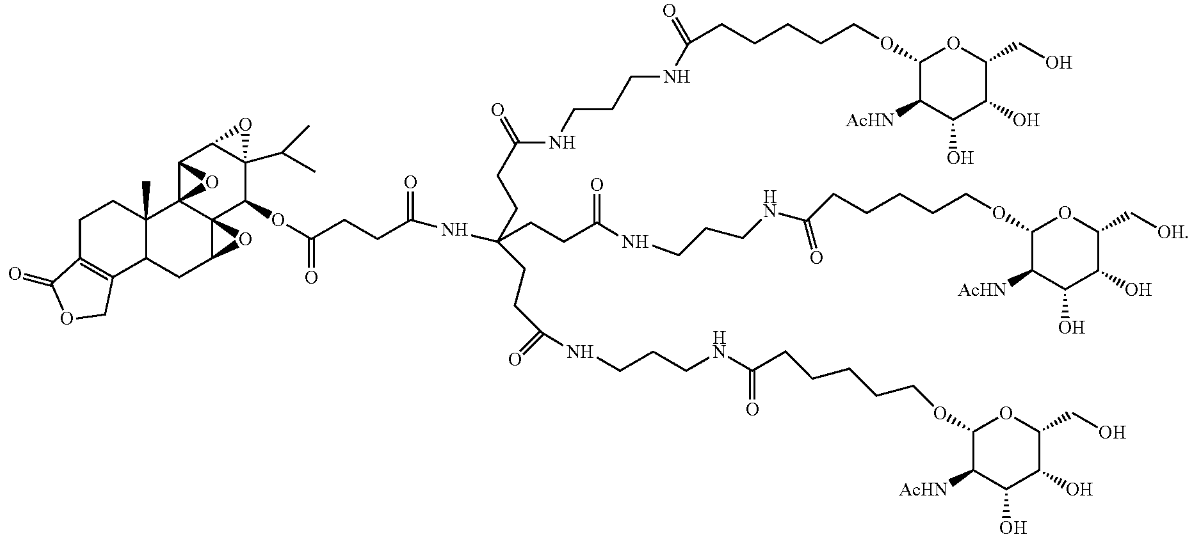

12. A pharmaceutical composition comprising a compound of claim 1, or an enantiomer, an enantiomeric mixture, a diastereomer, a diastereomeric mixture, or a pharmaceutically acceptable salt thereof, and at least one pharmaceutically acceptable excipient.

13. A method for treating a cancer selected from heptacellular carcinoma (HCC), lung cancer, breast cancer, pancreatic cancer, biliary tract cancer, colorectal cancer, and glioblastoma in a subject in need thereof, comprising administering to the subject a therapeutically effective amount of a compound of claim 1, or an enantiomer, an enantiomeric mixture, a diastereomer, a diastereomeric mixture, or a pharmaceutically acceptable salt thereof.

* * * * *